United States Patent
Bae et al.

(10) Patent No.: US 8,053,762 B2
(45) Date of Patent: Nov. 8, 2011

(54) IMIDAZOQUINAZOLINE DERIVATIVE, PROCESS FOR PREPARING THE SAME, AND ORGANIC ELECTRONIC DEVICE USING THE SAME

(75) Inventors: Jae-Soon Bae, Daejeon Metropolitan (KR); Dong-Hoon Lee, Seoul (KR); Dae-Woong Lee, Daejeon Metropolitan (KR); Jun-Gi Jang, Daejeon Metropolitan (KR); Sang-Young Jeon, Daejeon Metropolitan (KR)

(73) Assignee: LG Chem, Ltd., Seoul (KR)

( * ) Notice: Subject to any disclaimer, the term of this patent is extended or adjusted under 35 U.S.C. 154(b) by 733 days.

(21) Appl. No.: 11/637,174

(22) Filed: Dec. 12, 2006

(65) Prior Publication Data

US 2007/0131929 A1    Jun. 14, 2007

(30) Foreign Application Priority Data

Dec. 13, 2005    (KR) .................. 10-2005-0122778

(51) Int. Cl.
*H01L 51/00*    (2006.01)
*H01L 51/46*    (2006.01)
*H01L 51/54*    (2006.01)

(52) U.S. Cl. .......... 257/40; 428/690; 428/917; 313/504; 313/506; 136/263; 544/250; 544/252

(58) Field of Classification Search ................ 428/690, 428/917, 411.1, 336; 136/263; 544/245–247, 544/249–252; 313/502–509; 257/40, 104, 257/E51; 532/1; 540/1; 548/302.1
See application file for complete search history.

(56) References Cited

U.S. PATENT DOCUMENTS

| 4,017,466 | A  | * | 4/1977 | Milligan et al. ............ 528/353 |
| 4,786,729 | A  |   | 11/1988 | Heidenreich et al. |
| 6,551,723 | B1 |   | 4/2003 | Okada et al. |
| 2003/0082405 | A1 | * | 5/2003 | Taguchi .................. 428/690 |
| 2004/0043247 | A1 |   | 3/2004 | Lee et al. |
| 2004/0170863 | A1 |   | 9/2004 | Kim et al. |
| 2005/0045269 | A1 | * | 3/2005 | Tateishi .................. 156/230 |
| 2006/0154105 | A1 |   | 7/2006 | Yamamoto et al. |

FOREIGN PATENT DOCUMENTS

| EP | 0241795 A2 | 10/1987 |
| JP | 2000-063818 | 2/2000 |
| JP | 2004-002297 | 1/2004 |
| JP | 2004-217547 | 8/2004 |

OTHER PUBLICATIONS

Davis, M.; Mann, F. G. J. Chem. Soc. 1962, 945-954.*
Saga, M.; Hachihama, M.; Shono, T. Journal of Polymer Science: Part A-1 vol. 8, 2265-2274 (1970).*

(Continued)

*Primary Examiner* — Angela Ortiz
*Assistant Examiner* — J. L. Yang
(74) *Attorney, Agent, or Firm* — McKenna Long & Aldridge LLP

(57) ABSTRACT

The present invention relates to a novel imidazoquinazoline derivative, a process for preparing the same, and an organic electronic device using the same.
The imidazoquinazoline derivative according to the present invention serves as hole injecting, hole transporting, electron injecting, electron transporting, or a light emitting material in an organic electronic device including an organic light emitting device, and the device according to the present invention exhibits excellent characteristics in efficiency, operating voltage, and stability.

14 Claims, 7 Drawing Sheets

OTHER PUBLICATIONS

Suma, G.; Baehekar, R. H.; Rao, A. R. R. OPPI Briefs vol. 32, No. 1, 2000.*

Frére et al., "Novel 6-substituted benzothiazol-2-yl indolo[1,2-c]qionazolines and benzimidazo[1,2-c]qionazolines", Tetrahedron 59 (2003), pp. 773-779.

Pessoa-Mahana et al., "Solvent-Free Synthesis of 6-Arylbenzimidazo[1,2-c]quinazolines under Microwave Irradiation", Synthesis vol. 3, (2004), pp. 436-440.

El-Brollosy et al., "Synthesis of Novel Quinazole Derivatives for Potential Anticancer Activity", Pharm. Sci., vol. 17(1), (2002), pp. 17-21.

Suma et al., "A Facile Method with Improved Yields in the Synthesis of 6-Arylpyrido[2',3':4,5]Pyrimido[1,6-a] Benzimidazoles", Organic Preparations and Procedures International, vol. 32, No. 1 (2000), pp. 99-101.

Devi K Rama et al.: "Condensation of 2-(3-aminonaphth-2-yl)benzimidazole with carboxylic acids and ketones", Indian Journal of Chemistry. Section B: Organic and Medicinal Chemistry, Council of Scientific and Industrial Research (C S I R), IN, vol. 35B, No. 7, Jan. 1, 1996, pp. 721-723, XP009149040.

Bahekar, R.H.: "Bronchodilation and Structure-Activity Relationship Studies on New 6-Substituted Benzimidazo[1,2-c]quinazolines", Arzneimittel Forschung, vol. 50, No. 8, Aug. 2000, pp. 712-716, XP001525865.

Korshak V V et al.: "A General Method of the Synthesis of Step-Ladder Polymers", Makromolekulare Chemie, Huthig Und Wepf Verlag, Basel, CH, vol. 176, No. 5, Jan. 1, 1975, pp. 1233-1271, XP000952391.

Saga Motoo et al.: "Preparation of some new polybenzimidazoquinazolines" Journal of Polymer Science: Part A-1, Polymer Chemistry, Wiley, US, vol. 8, No. 8, Aug. 1, 1970 pp. 2265-2274, XP008121038.

Padmaja, et al.: "Synthesis and Mass Spectra of 5,6-Dihydro-6, 6-disubstituted-benzimidazo[1,2-c]benzo[h]quinazolines", Indian Journal of chemistry, 1988, vol. 27B, No. 10, p. 909-911.

Rao, et al. "Synthesis of benzimidazo[1,2-c]quinazolines as possible bronchodilators", Indian Journal of chemistry, 1999, vol. 38B, No. 4, p. 434-439.

* cited by examiner

[Figure 1]
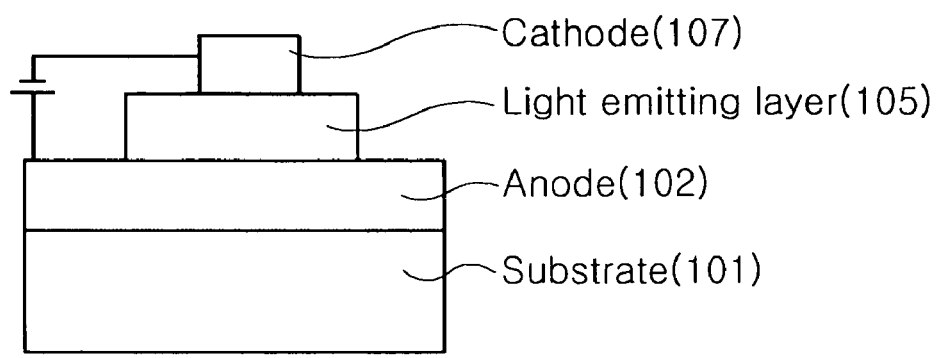
[Figure 2]
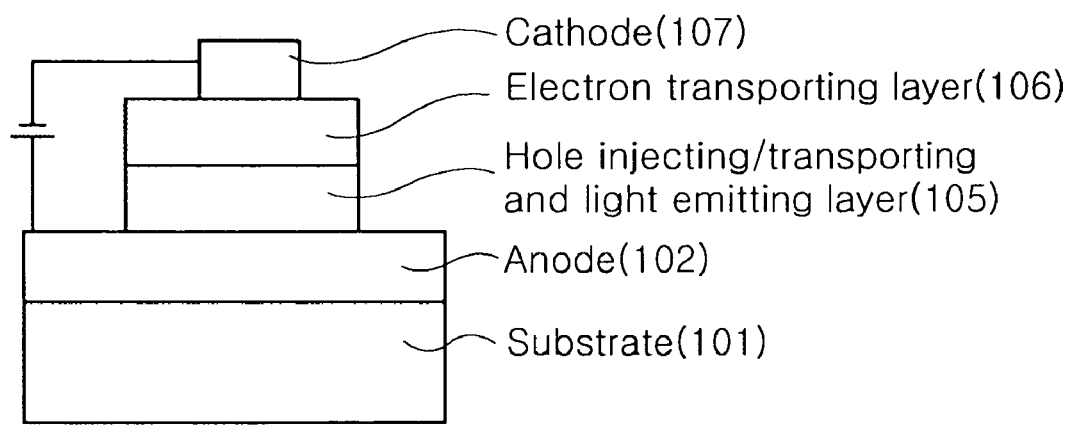

[Figure 3]
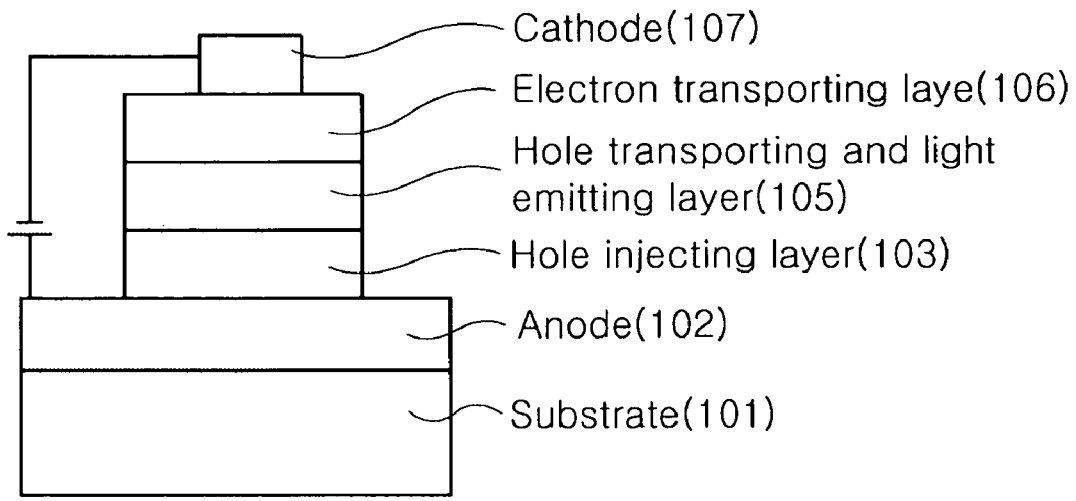
[Figure 4]
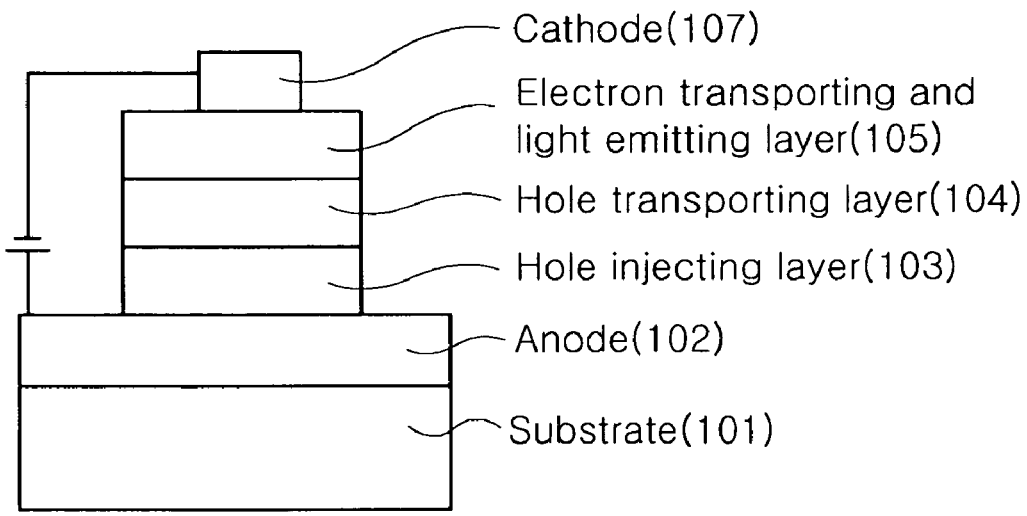

[Figure 5]
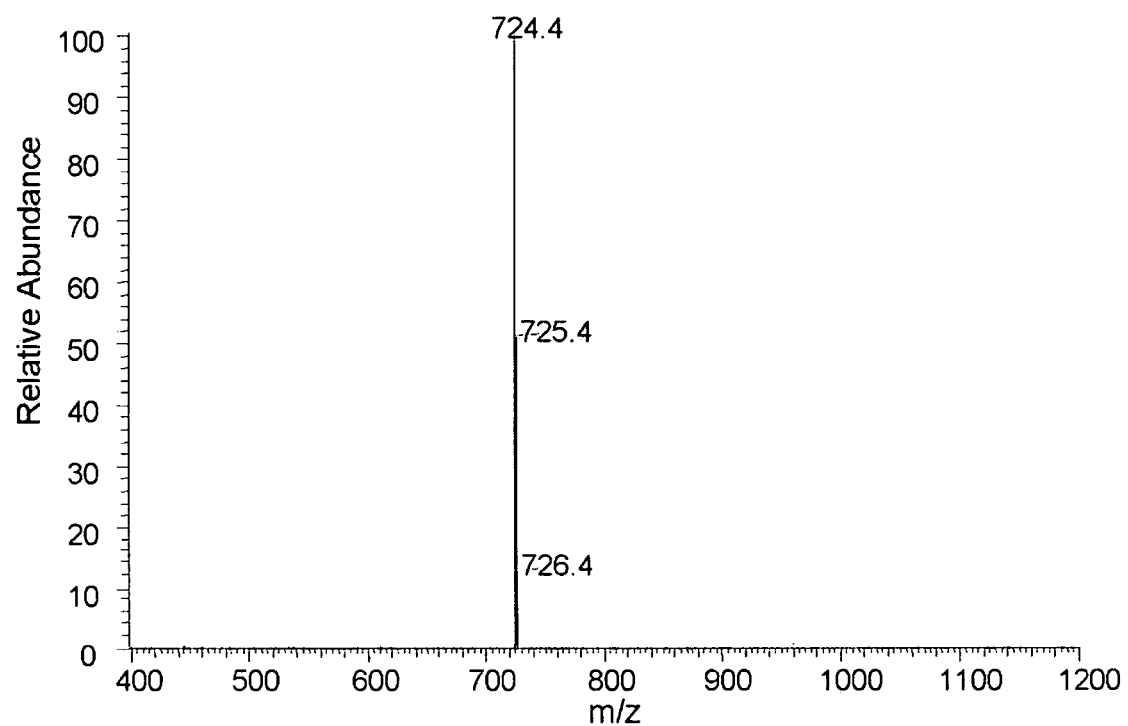

【Figure 6】
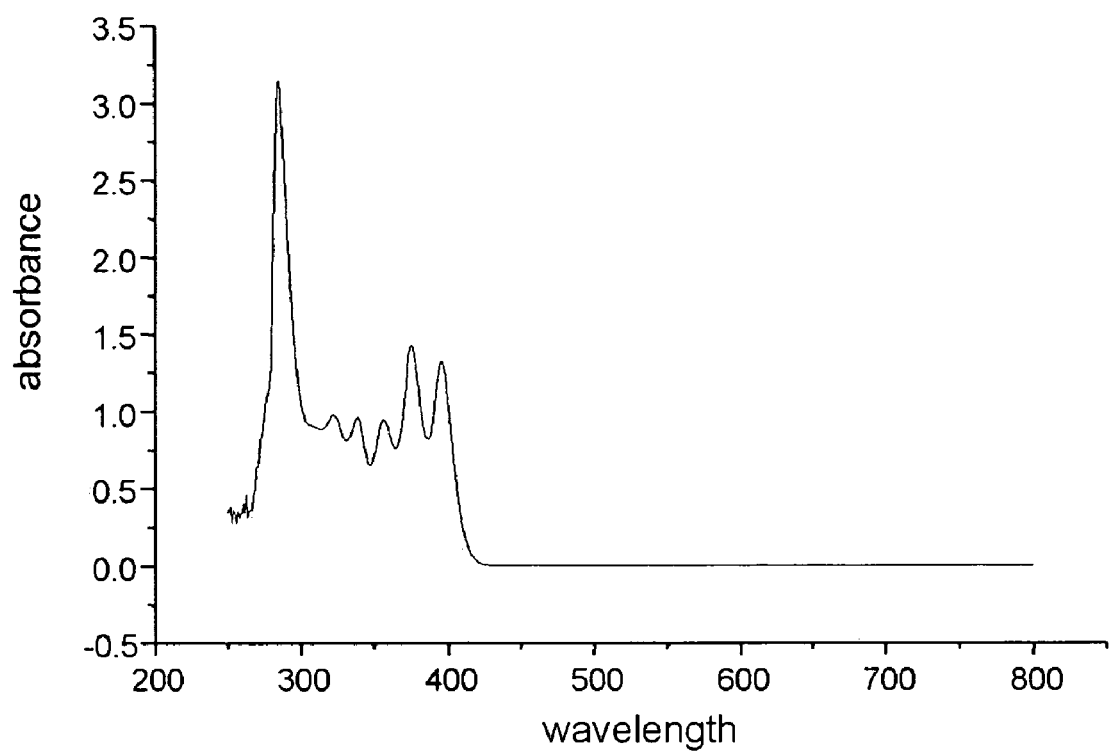

[Figure 7]
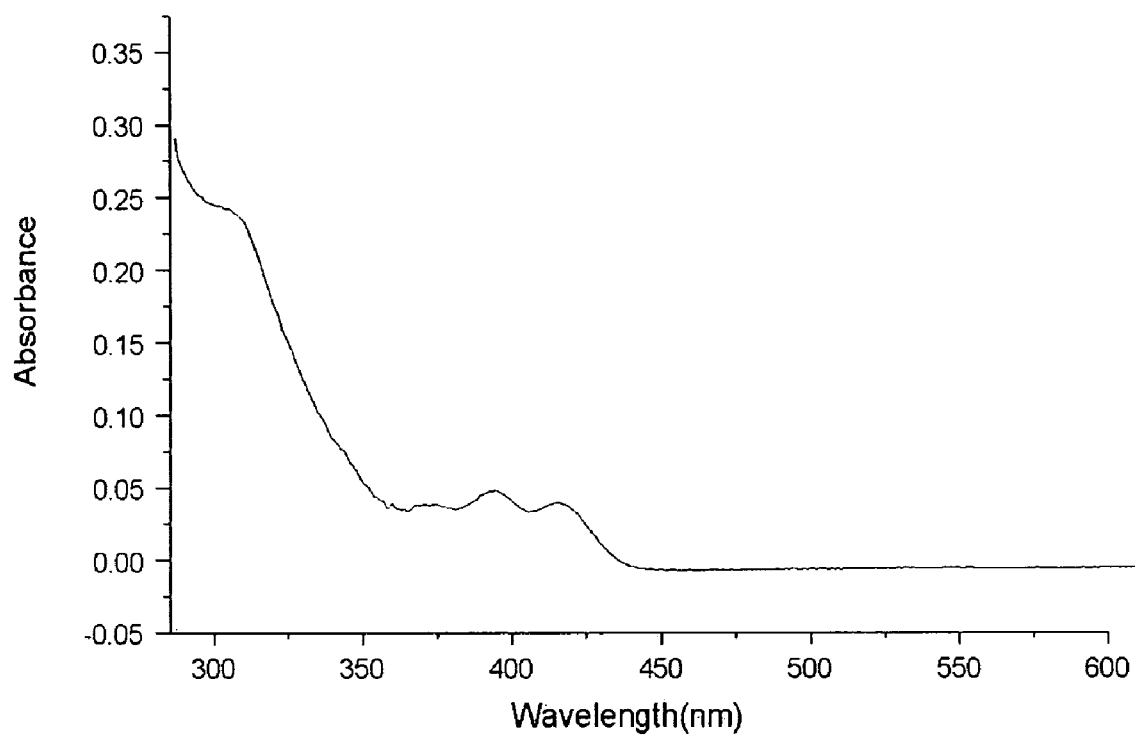

[Figure 8]
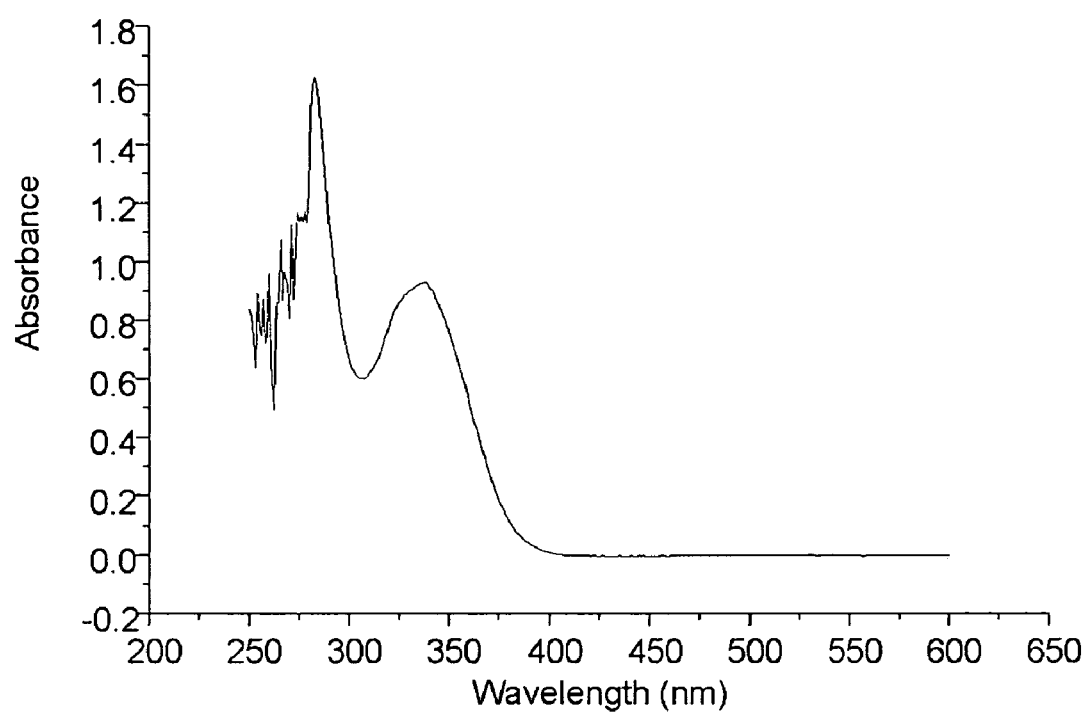

[Figure 9]
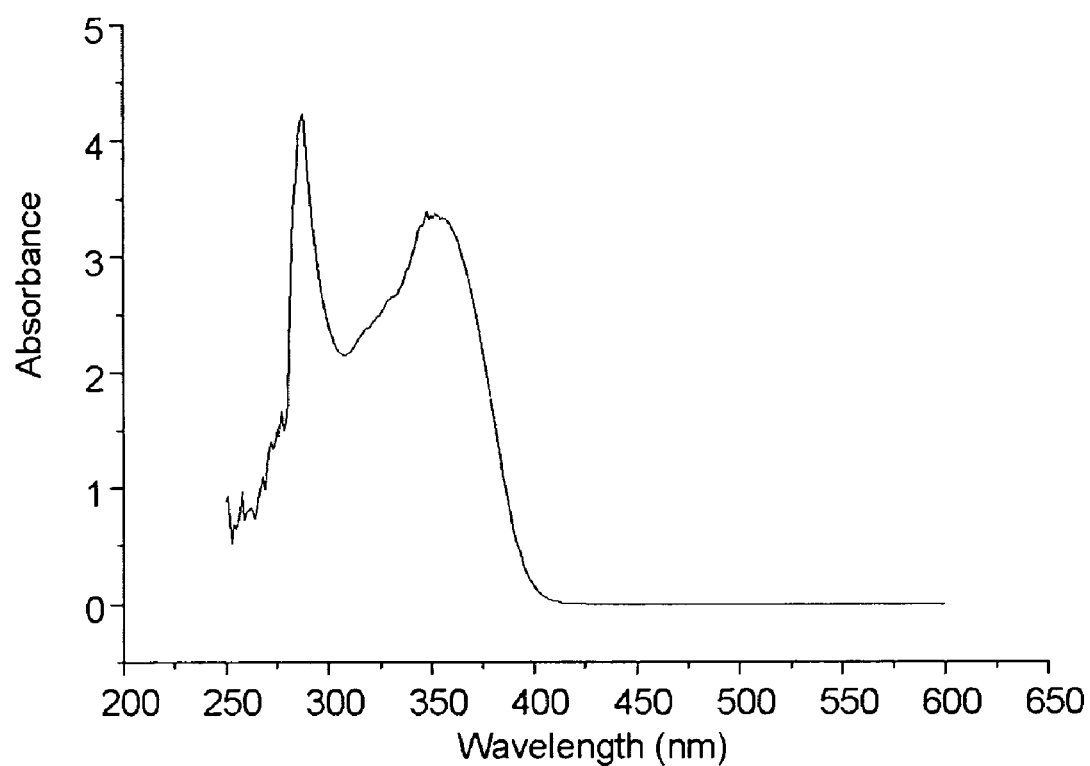

IMIDAZOQUINAZOLINE DERIVATIVE, PROCESS FOR PREPARING THE SAME, AND ORGANIC ELECTRONIC DEVICE USING THE SAME

TECHNICAL FIELD

The present invention relates to a novel imidazoquinazoline derivative, a process for preparing the same, and an organic electronic device using the same.

This application claims priority benefits from Korean Patent Application No. 10-2005-0122778, filed on Dec. 13, 2005, the entire content of which is fully incorporated herein by reference.

BACKGROUND ART

The term "organic electronic device" refers to a device requiring charge exchange between an electrode and an organic material using holes and/or electrons. The organic electronic device can be largely classified into two types according to its operational principle as follows: one type is an electronic device having a configuration in which an exciton is formed in an organic material layer by photons flown from an external light source into the device and the exciton is separated into an electron and a hole, the electron and the hole formed are transported to a different electrode, respectively and used as a current source (voltage source), and the other type is an electronic device having a configuration in which a hole and/or electron are/is injected into an organic material semiconductor forming an interface with an electrode by applying a voltage or current to two or more electrodes to allow the device to operate by means of the injected electron and hole.

Examples of the organic electronic device include an organic light emitting device, an organic solar cell, an organic photoconductor (OPC) drum and an organic transistor, all of which require a hole injecting or hole transporting material, an electron injecting or electron transporting material, or a light emitting material for driving the device. Hereinafter, the organic light emitting device will be mainly and specifically described, but in the above-mentioned organic electronic devices, the hole injecting or hole transporting material, the electron injecting or electron transporting material, or the light emitting material injection functions according to a similar principle.

In general, the term "organic light emitting phenomenon" refers to a phenomenon in which electric energy is converted to light energy by means of an organic material. The organic light emitting device using the organic light emitting phenomenon has a structure usually comprising an anode, a cathode and an organic material layer interposed therebetween. Herein, the organic material layer may be mostly formed in a multilayer structure comprising layers of different materials, for example, the hole injecting layer, the hole transporting layer, the light emitting layer, the electron transporting layer, the electron injecting layer and the like, in order to improve efficiency and stability of the organic light emitting device. In the organic light emitting device having such a structure, when a voltage is applied between two electrodes, holes from the anode and electrons from a cathode are injected into the organic material layer, the holes and the electrons injected are combined together to form excitons. Further, when the excitons drop to a ground state, lights are emitted. Such the organic light emitting device is known to have characteristics such as self-luminescence, high brightness, high efficiency, low drive voltage, wide viewing angle, high contrast and high-speed response.

The materials used for the organic material layer of the organic light emitting device can be classified into a light emitting material and a charge transporting material, for example, a hole injecting material, a hole transporting material, an electron transporting material and an electron injecting material, according to their functions. Further, the light emitting material can be divided into a blue, green or red light emitting material and a yellow or orange light emitting material required for giving more natural color, according to a light emitting color. On the other hand, an efficiency of a device is lowered owing to maximum luminescence wavelength moved to a longer wavelength due to the interaction between the molecules, the deterioration of color purity and the reduction in light emitting efficiency when only one material is used for the light emitting material, and therefore a host/dopant system can be used as the light emitting material for the purpose of enhancing the color purity and the light emitting efficiency through energy transfer.

In order to allow the organic light emitting device to fully exhibit the above-mentioned excellent characteristics, a material constituting the organic material layer in the device, for example, a hole injecting material, a hole transporting material, a light emitting material, an electron transporting material and an electron injecting material should be essentially composed of a stable and efficient material. However, the development of a stable and efficient organic material layer material for the organic light emitting device has not yet been fully realized. Accordingly, the development of new materials is continuously desired. The development of such a material is equally required to the above-mentioned other organic electronic devices.

DISCLOSURE

Technical Problem

The present inventors have synthesized a novel imidazoquinazoline derivative, and then have found that the compound has excellent surfactant characteristics and charge transfer ability when it serves as hole injecting, hole transporting, electron injecting, electron transporting, or a light emitting materials in an organic electronic device, thus completing the present invention.

Technical Solution

Therefore, it is an object of the present invention to provide a novel imidazoquinazoline derivative, a process for preparing the same, and an organic electronic device using the same.

ADVANTAGEOUS EFFECTS

The imidazoquinazoline derivative according to the present invention can serve as hole injecting, hole transporting, electron injecting, electron transporting, or a light emitting materials in an organic electronic device including an organic light emitting device, and the device according to the present invention exhibits excellent characteristics in efficiency, operating voltage, and stability.

DESCRIPTION OF DRAWINGS

FIGS. 1 to 4 are diagrams for illustrating the structures of the organic light emitting devices applicable to the present invention.

FIG. 5 is a mass spectrum of the 1-3-26 compound of Example 12.

FIG. 6 is a UV spectrum of the 1-2-62 compound of Example 3 ($2\times10^{-5}$ M, toluene as a solvent).

FIG. 7 is a UV spectrum of the 1-3-26 compound of Example 12 ($2\times10^{-5}$ M, toluene as a solvent).

FIG. 8 is a UV spectrum of the 1-2-8 compound of Example 18 ($2\times10^{-5}$ M, toluene as a solvent).

FIG. 9 is a UV spectrum of the 1-3-5 compound of Example 24 ($2\times10^{-5}$ M, toluene as a solvent).

BEST MODE

The present invention provides an imidazoquinazoline derivative represented by the following formula 1:

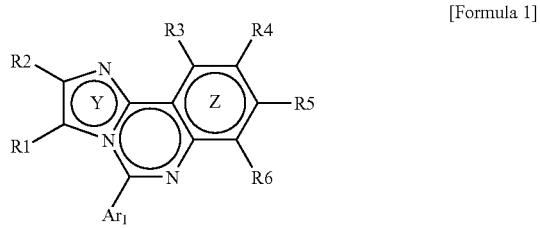

[Formula 1]

wherein R1 and R2 may be each independently the same as or different from each other, a hydrogen atom; a $C_1$ to $C_{30}$ alkyl group which is unsubstituted or substituted with at least one group selected from the group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; a $C_3$ to $C_{30}$ cycloalkyl group which is unsubstituted or substituted with at least one group selected from the group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; a $C_5$ to $C_{30}$ aryl group which is unsubstituted or substituted with at least one group selected from the group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; or a $C_2$ to $C_{30}$ heteroaryl group which is unsubstituted or substituted with at least one group selected from the group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group, and are bonded with an adjacent group to form an aliphatic, aromatic, aliphatic hetero-, or aromatic hetero-condensed ring, or to form a spiro bond;

R3 to R6 may be each independently the same as or different from each other, and each are a hydrogen atom; a $C_1$ to $C_{12}$ alkoxy group which is unsubstituted or substituted with at least one group selected from the group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; a $C_1$ to $C_{12}$ alkylthioxy group which is unsubstituted or substituted with at least one group selected from the group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; a $C_1$ to $C_{30}$ alkylamine group which is unsubstituted or substituted with at least one group selected from the group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; a $C_5$ to $C_{30}$ arylamine group which is unsubstituted or substituted with at least one group selected from the group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; a $C_5$ to $C_{30}$ aryl group which is unsubstituted or substituted with at least one group selected from the group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; a $C_2$ to $C_{30}$ heteroaryl group which is unsubstituted or substituted with at least one group selected from the group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; a silicone group which is unsubstituted or substituted with at least one group selected from the group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; a boron group which is unsubstituted or substituted with at least one group selected from the group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; an amino group; a nitrile group; a nitro group; a halogen group; an amide group; or an ester group, and are bonded with an adjacent group to form an aliphatic, aromatic, aliphatic hetero-, or aromatic hetero-condensed ring, or to form a spiro bond;

Ar1 is a $C_5$ to $C_{30}$ aryl group which is unsubstituted or substituted with at least one group selected from the group consisting of a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; or a $C_2$ to $C_{30}$ heteroaryl group which is unsubstituted or substituted with at least one group selected from the group consisting of a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group;

Y is a heteroaryl group in which at least one ring-constituting carbon atoms is further substituted with nitrogen atom(s); and Z is an aryl group, or a heteroaryl group in which at least one ring-constituting carbon atoms is further substituted with nitrogen atom(s). Examples thereof include the following structures.

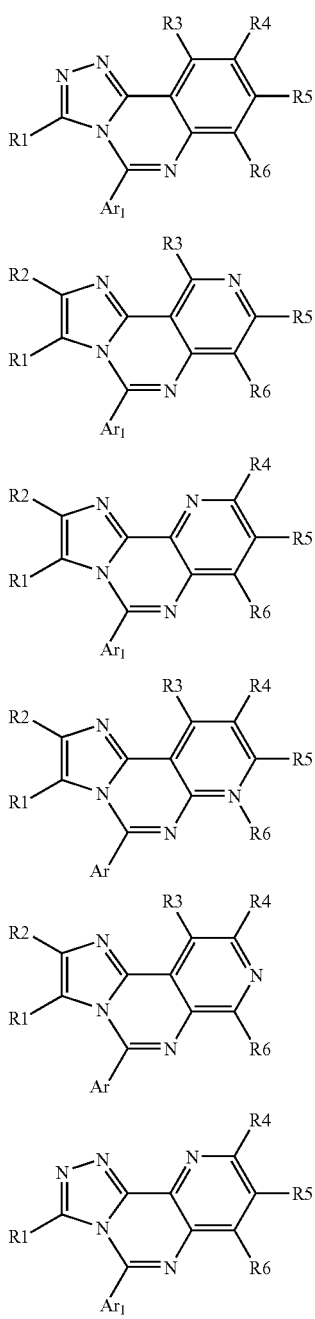

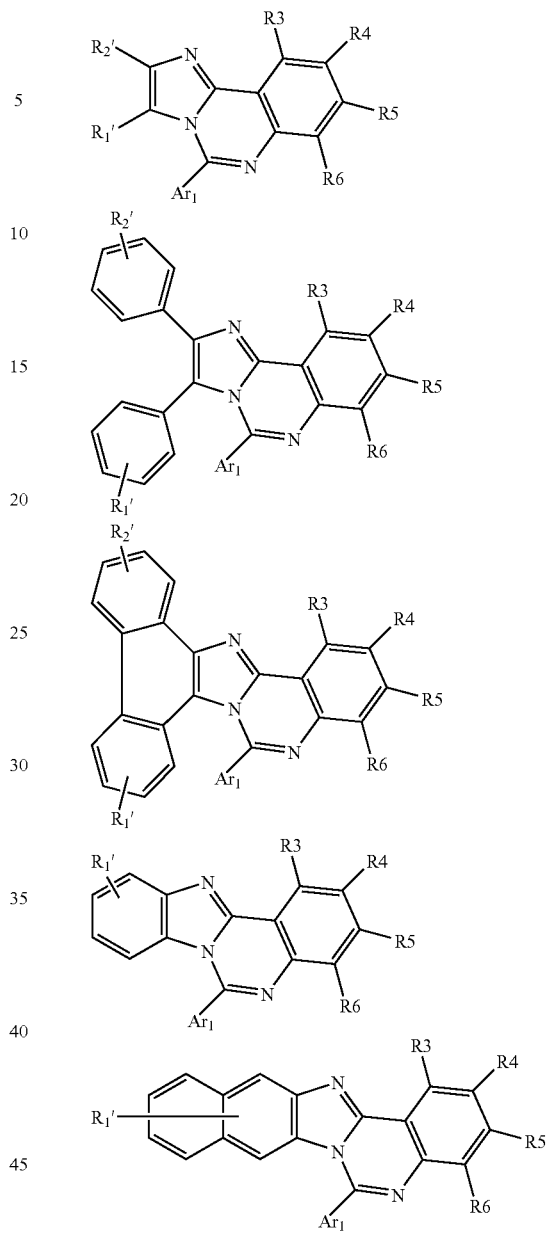

In the structural formulae, R3 to R6, and Ar1 are as defined for the formula 1, and $R_1'$ and $R_2'$ are same as defined for R1 and R2 in the formula 1.

As used in the present invention, the substituents are defined as follows.

The alkyl group preferably has 1 to 30 carbon atoms and does not give steric hindrance. Specific examples thereof include, but not limited thereto, a methyl group, an ethyl group, a propyl group, an isopropyl group, a butyl group, a t-butyl group, a pentyl group, a hexyl group and a heptyl group.

The cycloalkyl group preferably has 3 to 30 carbon atoms and does not give steric hindrance. More preferable specific examples thereof include, but not limited thereto, a cyclopentyl group or a cyclohexyl group.

Examples of the alkoxy group include an alkoxy group having 1 to 30 carbon atoms.

Preferably, in the formula 1,

R1 and R2 may be each independently the same as or different from each other, and each are a phenyl group, a biphenyl group, a naphthyl group, a pyridinyl group, or a methyl- or nitrile-substituted phenyl group.

Further preferably, in the formula 1,

R1 and R2 are bonded with an adjacent group to form an aliphatic, aromatic, aliphatic hetero-, or aromatic hetero-condensed ring, or to form a spiro bond.

Particularly, the compound of the formula 1 can be selected from the group consisting of the following structural formulae, but not limited thereto.

Examples of the alkenyl group include an alkenyl group linked with an aryl group such as a stilbenzyl group and a styrenyl group.

Examples of the aryl group include a phenyl group, a naphthyl group, an anthracenyl group, a biphenyl group, a pyrenyl group, a perylenyl group, and a derivative thereof.

Examples of the arylamine group include a phenylamine group, a naphthyl amine group, a biphenylamine group, an anthracenylamine group, a 3-methyl-phenylamine group, a 4-methyl-naphthyl amine group, a 2-methyl-biphenylamine group, a 9-methyl-anthracenylamine group, a diphenyl amine group, a phenyl naphthyl amine group, a ditolyl amine group, a phenyl tolyl amine group, a carbazole group, and a triphenyl amine group.

Examples of the heteroaryl group include a pyridyl group, a bipyridyl group, a triazine group, an acridyl group, a thiophene group, an imidazole group, an oxazole group, a thiazole group, a triazole group, a quinoliyl group, and an isoquinoline group.

Examples of the halogen group include fluorine, chlorine, bromine, and iodine.

Specific examples of the compound of the formula 1 are as follows, but not limited thereto.

If the structure of the formula 1 is a compound of the following structural formula, Ar1 has a structure as shown in Table 1.

TABLE 1

| No. | Ar1 |
|---|---|
| 1-1-1 | |
| 1-1-2 | |
| 1-1-3 | |

TABLE 1-continued
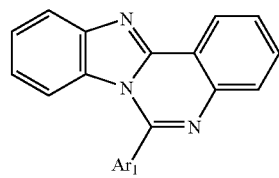
| No. | Ar1 |
| --- | --- |
| 1-1-4 | 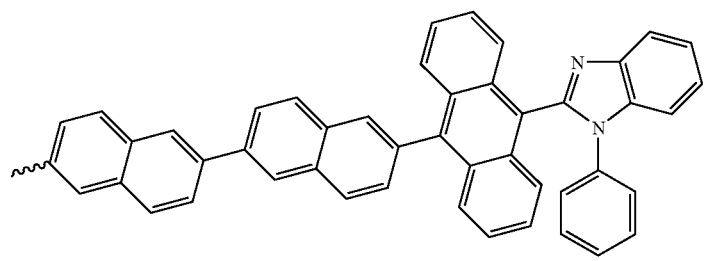 |
| 1-1-5 | 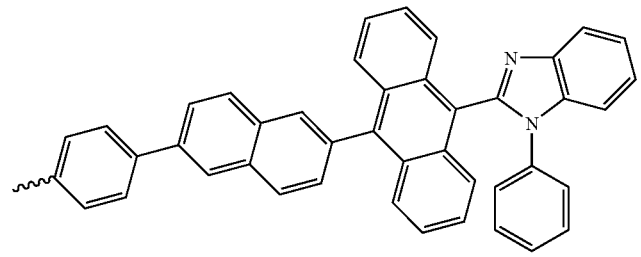 |
| 1-1-6 | 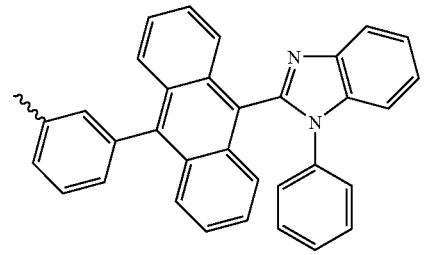 |
| 1-1-7 | 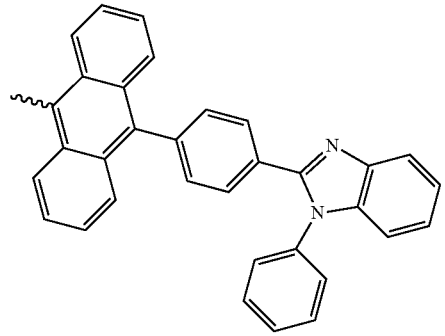 |

TABLE 1-continued
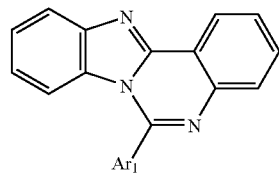
| No. | Ar1 |
|---|---|
| 1-1-8 | 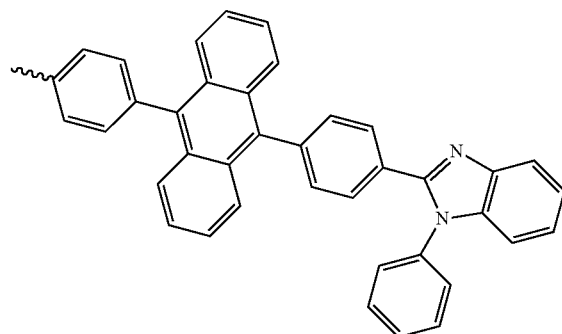 |
| 1-1-9 | 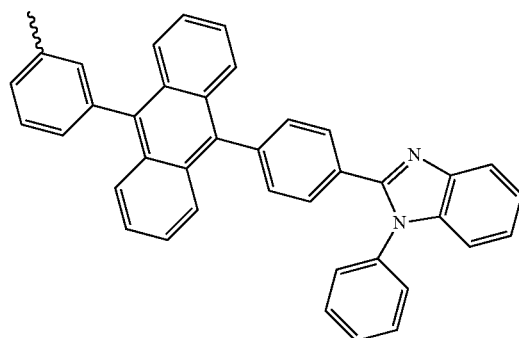 |
| 1-1-10 | 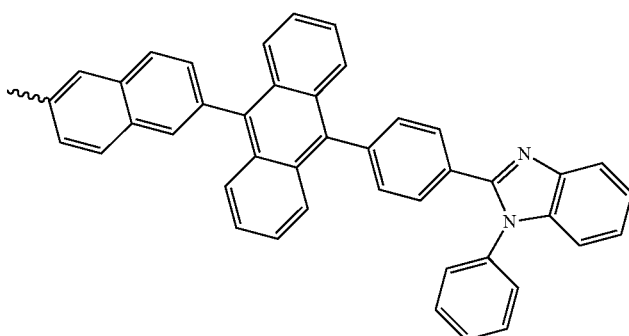 |
| 1-1-11 | 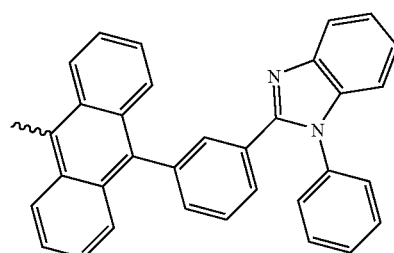 |

TABLE 1-continued
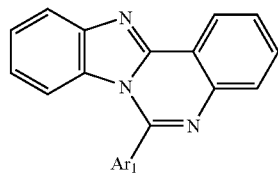
| No. | Ar1 |
|---|---|
| 1-1-12 | 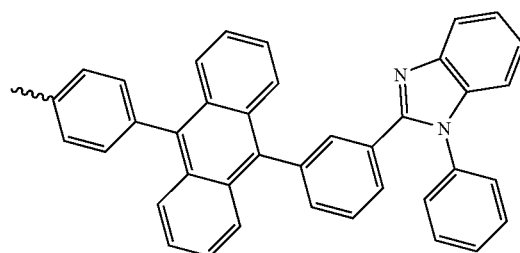 |
| 1-1-13 | 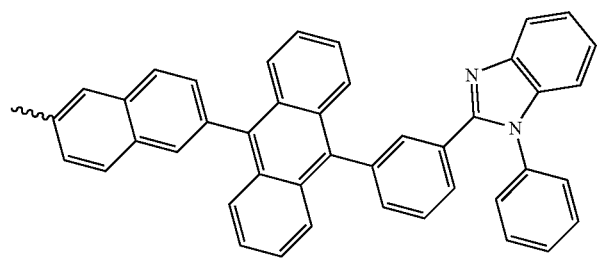 |
| 1-1-14 | 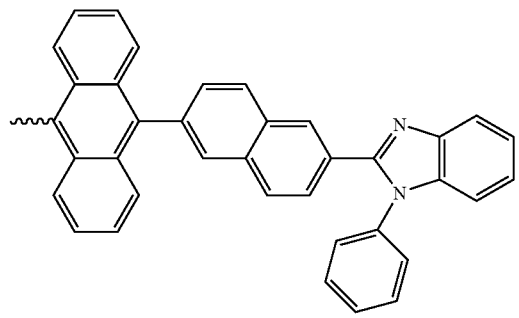 |
| 1-1-15 | 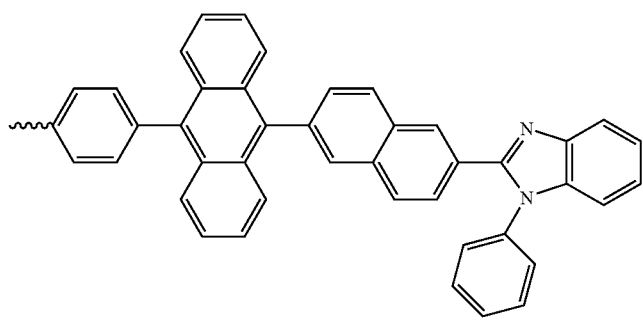 |

TABLE 1-continued
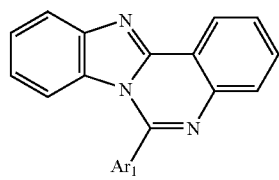
| No. | Ar1 |
|---|---|
| 1-1-16 | 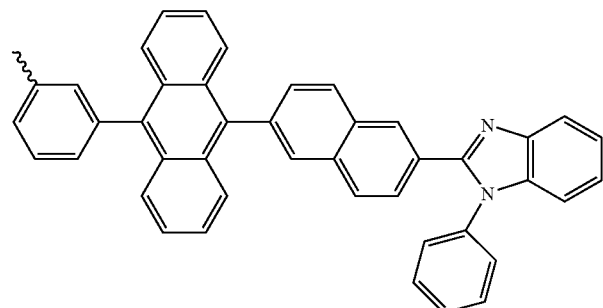 |
| 1-1-17 | 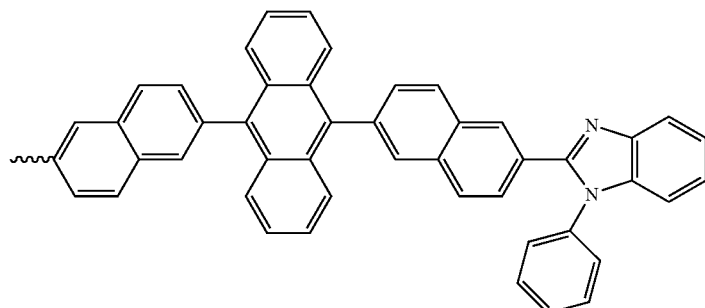 |
| 1-1-18 | 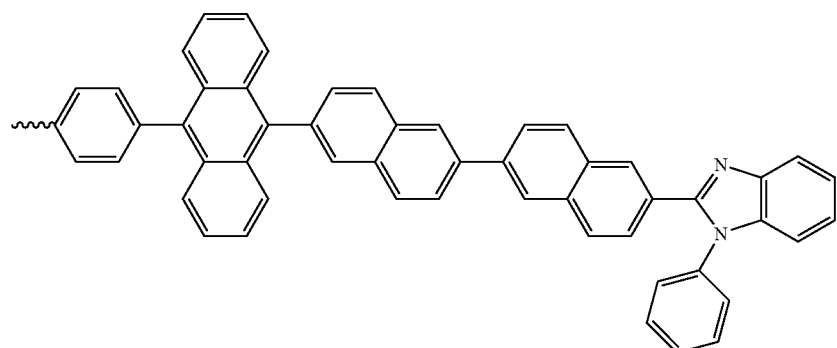 |
| 1-1-19 | 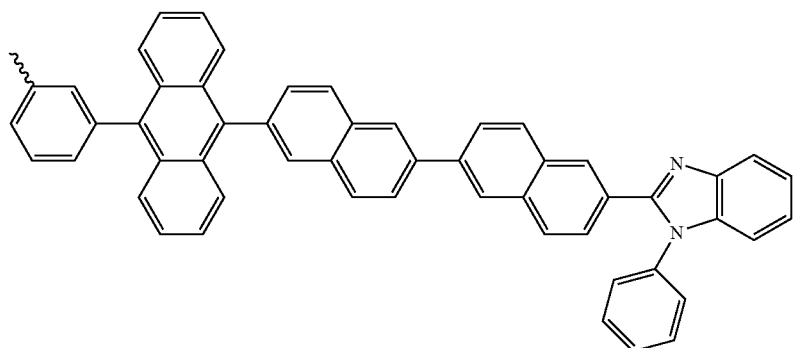 |

TABLE 1-continued
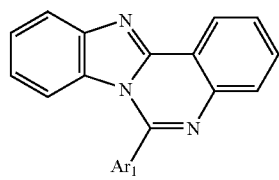
| No. | Ar1 |
|---|---|
| 1-1-20 | 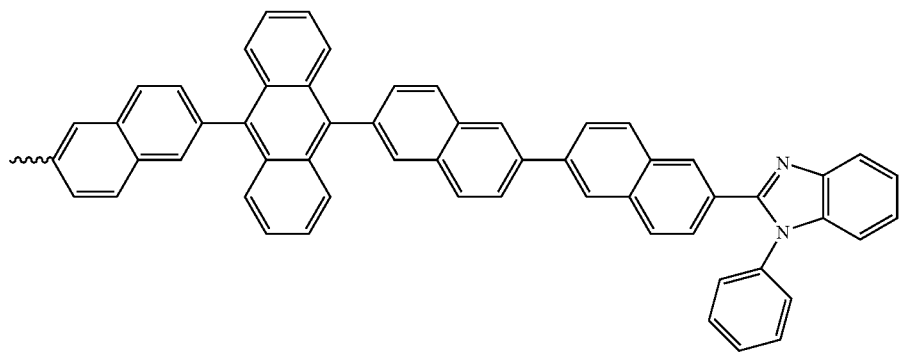 |
| 1-1-21 | 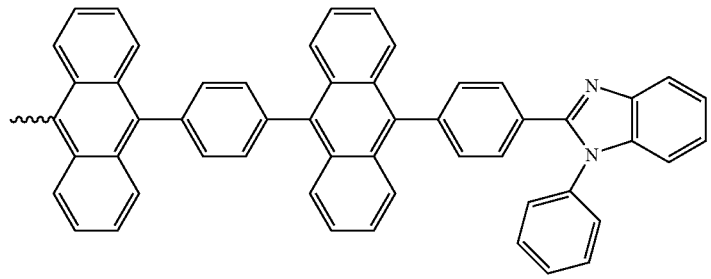 |
| 1-1-22 | 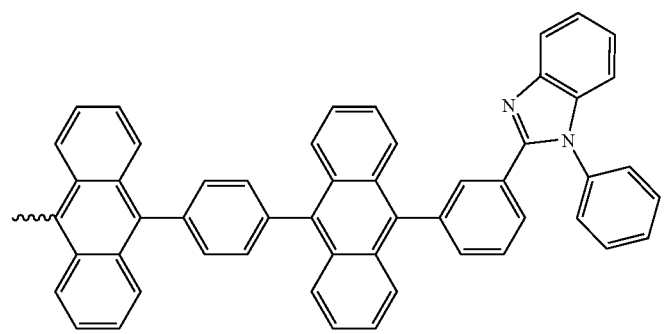 |
| 1-1-23 | 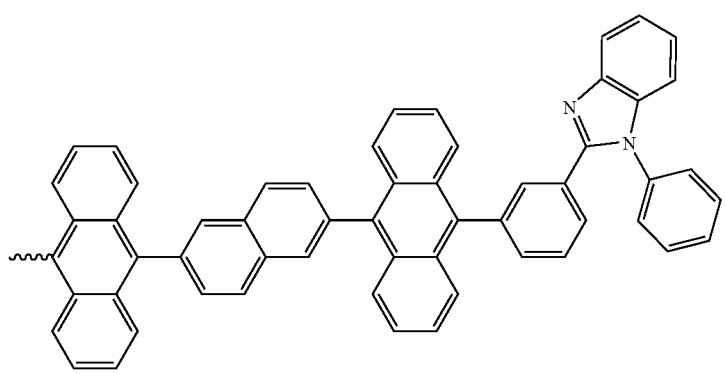 |

TABLE 1-continued
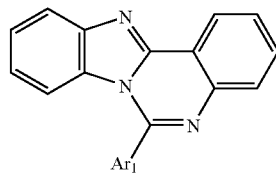
| No. | Ar1 |
| --- | --- |
| 1-1-24 | 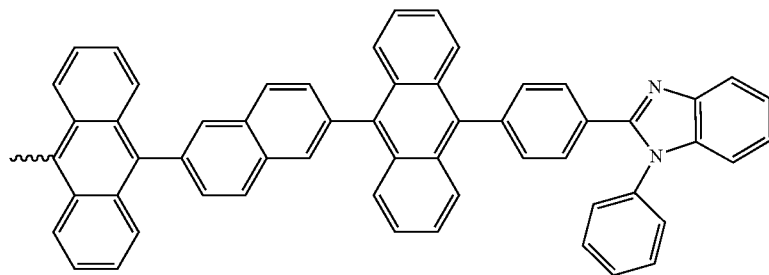 |
| 1-1-25 | 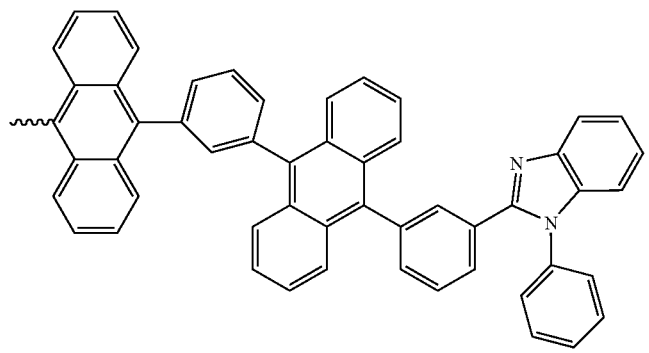 |
| 1-1-26 | 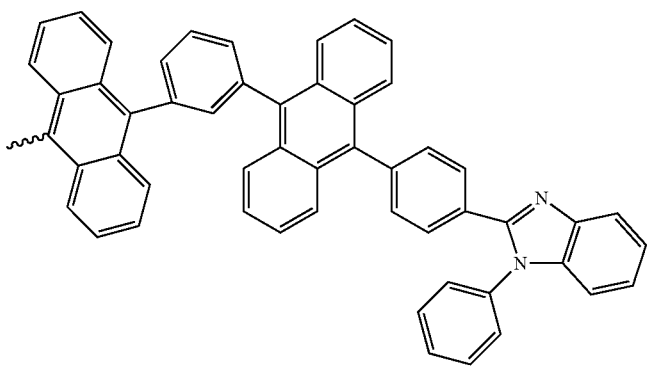 |
| 1-1-27 | 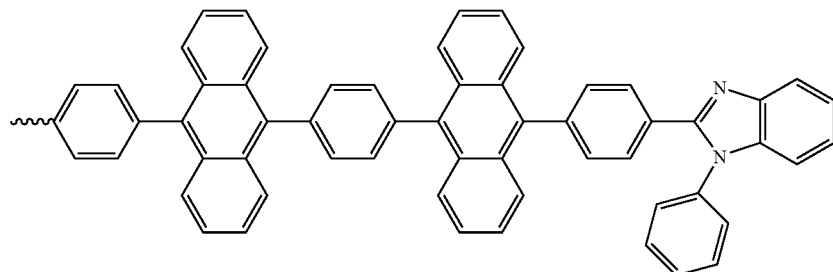 |

TABLE 1-continued
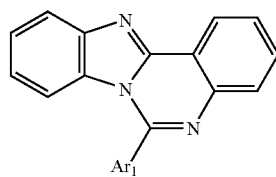
| No. | Ar1 |
|---|---|
| 1-1-28 | 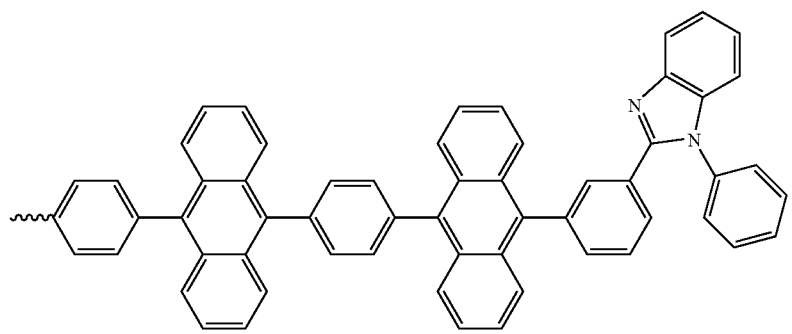 |
| 1-1-29 | 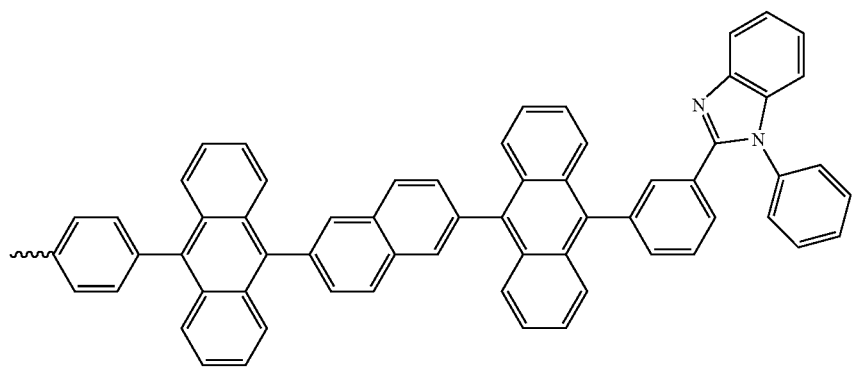 |
| 1-1-30 | 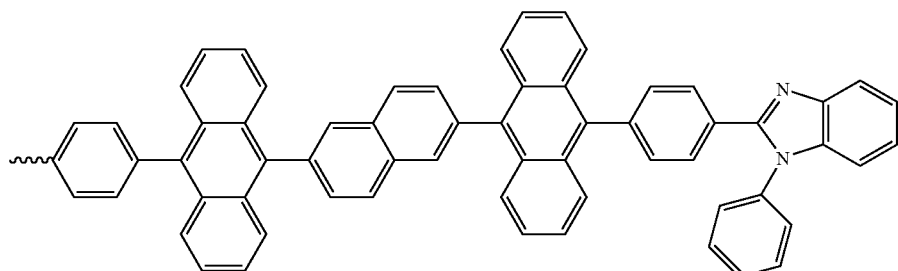 |
| 1-1-31 | 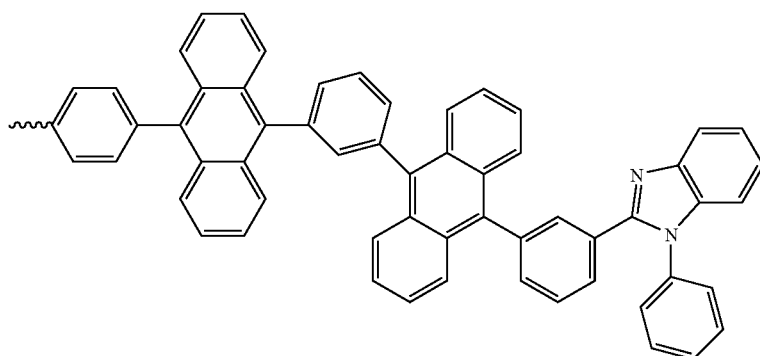 |

TABLE 1-continued
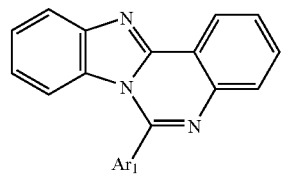
| No. | Ar1 |
|---|---|
| 1-1-32 | 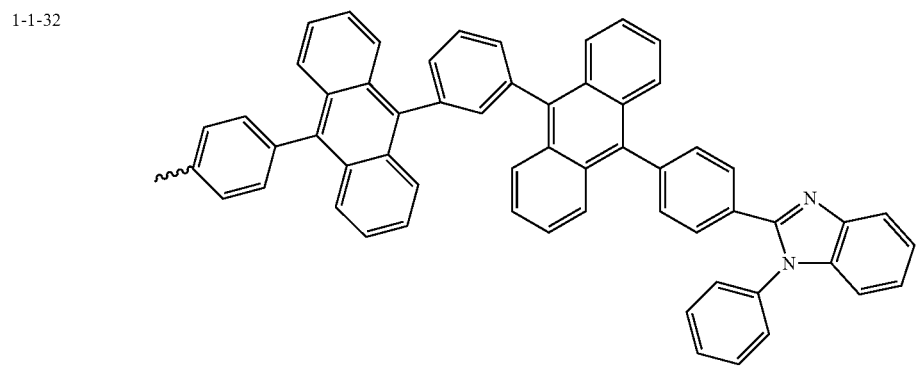 |
| 1-1-33 | 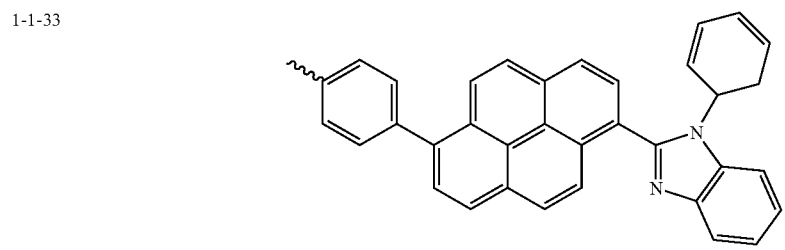 |
| 1-1-34 | 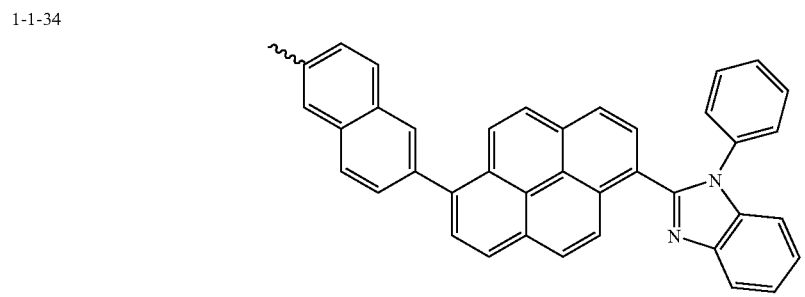 |
| 1-1-35 | 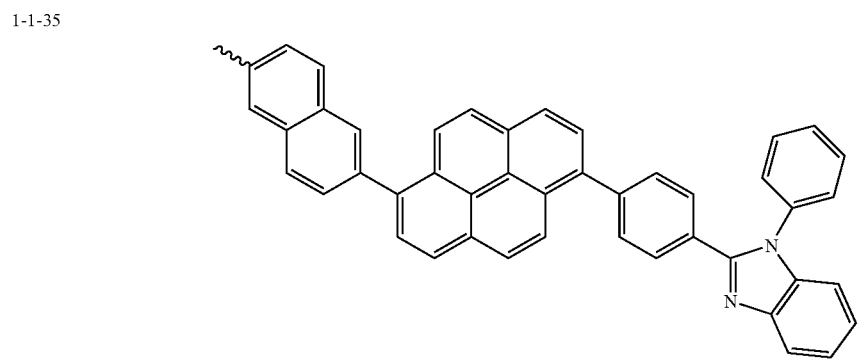 |

TABLE 1-continued

| No. | Ar1 |
|---|---|
| 1-1-36 | |
| 1-1-37 | |
| 1-1-38 | |
| 1-1-39 | |
| 1-1-40 | |

TABLE 1-continued
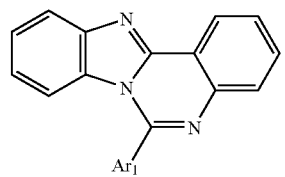
| No. | Ar1 |
| --- | --- |
| 1-1-41 | 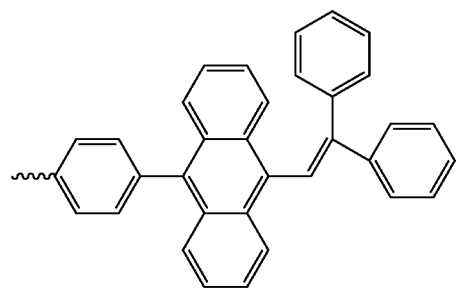 |
| 1-1-42 | 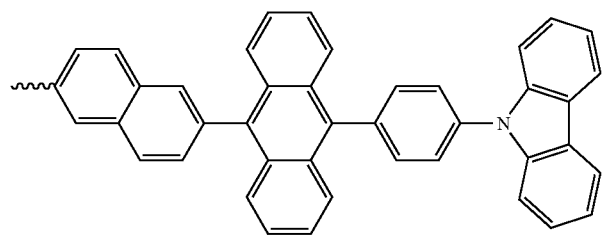 |
| 1-1-43 | 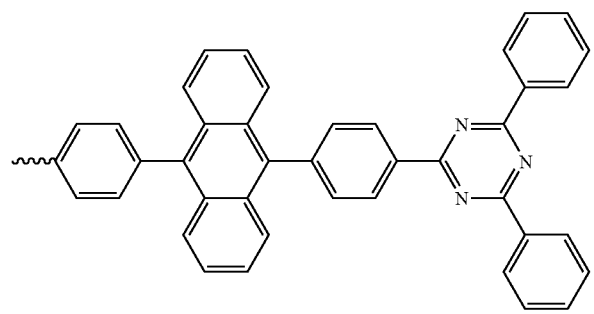 |
| 1-1-44 | 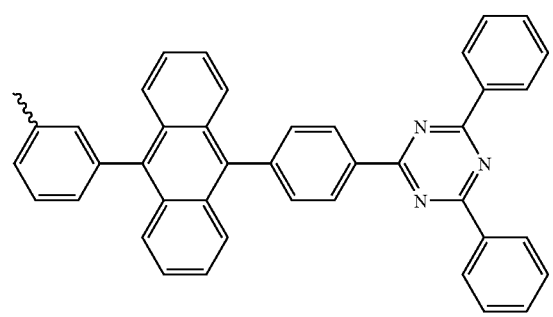 |

TABLE 1-continued
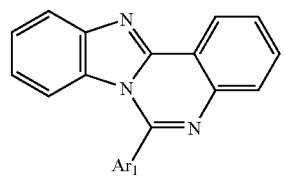
| No. | Ar1 |
|---|---|
| 1-1-45 | 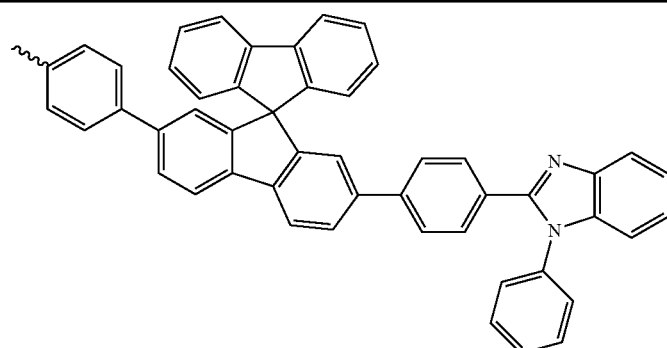 |
| 1-1-46 | 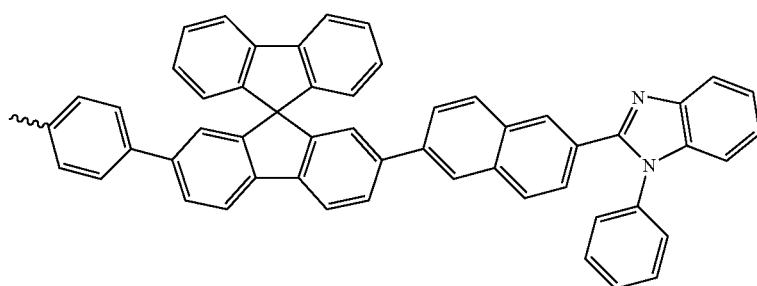 |
| 1-1-47 | 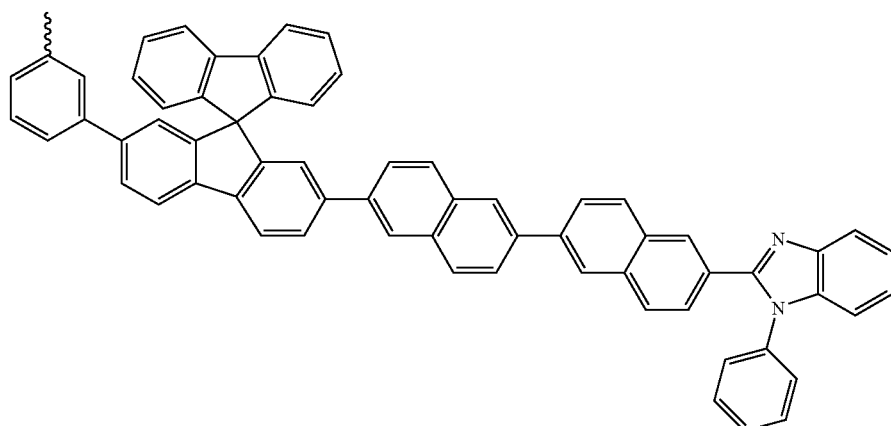 |
| 1-1-48 | 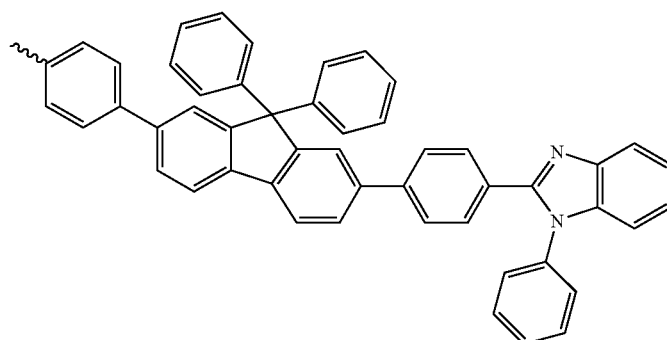 |

TABLE 1-continued
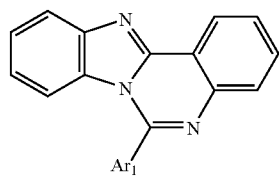
| No. | Ar1 |
|---|---|
| 1-1-49 | 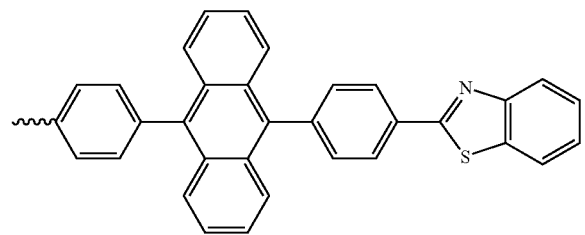 |
| 1-1-50 | 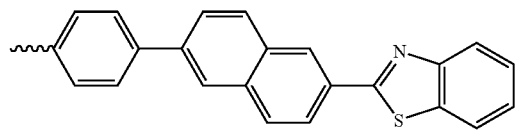 |
| 1-1-51 | 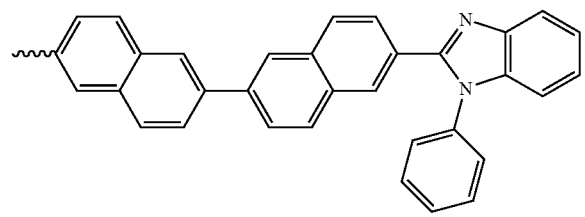 |
| 1-1-52 | 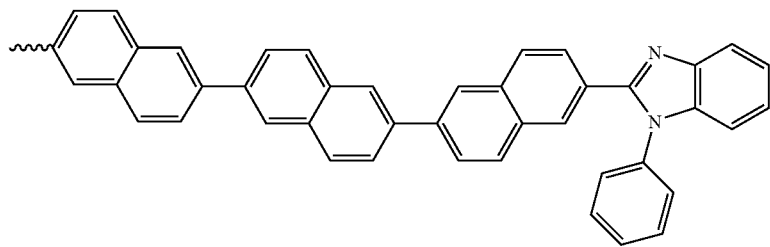 |
| 1-1-53 | 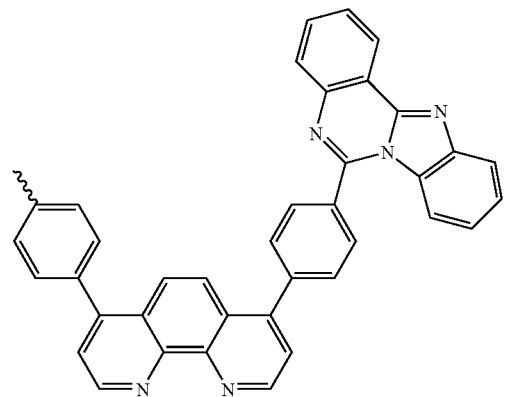 |

TABLE 1-continued
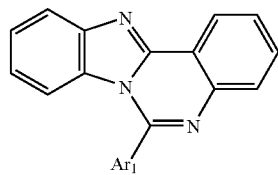
| No. | Ar1 |
| --- | --- |
1-1-54
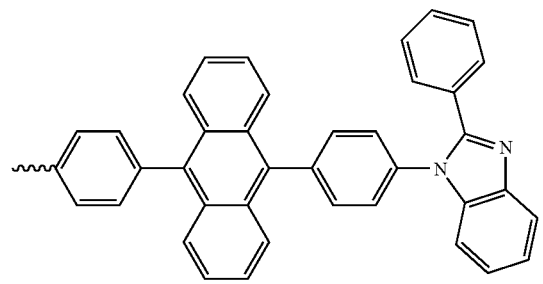
1-1-55
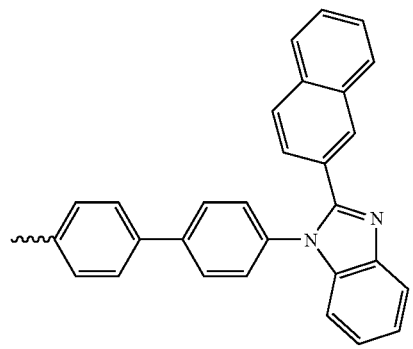
1-1-56
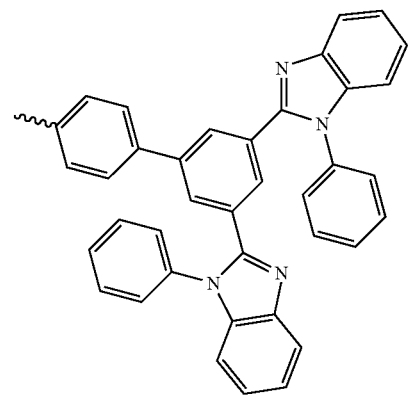

TABLE 1-continued
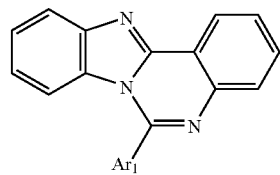
| No. | Ar1 |
| --- | --- |
| 1-1-57 | 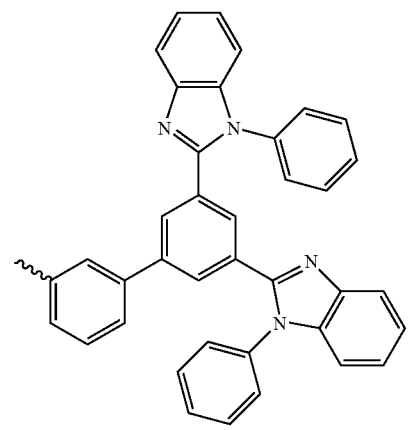 |
| 1-1-58 | 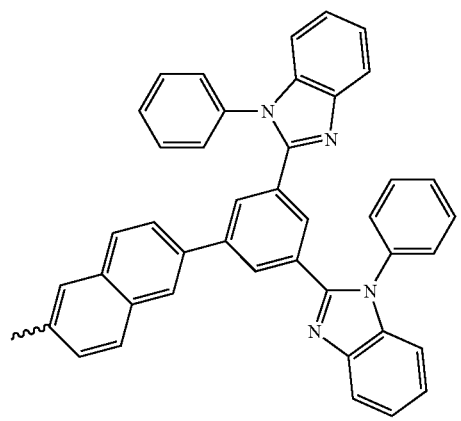 |
| 1-1-59 | 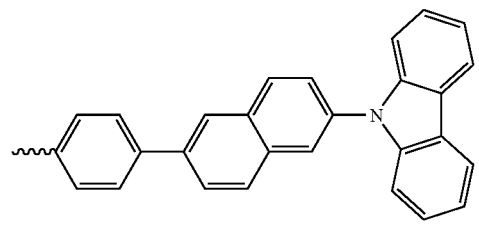 |

TABLE 1-continued
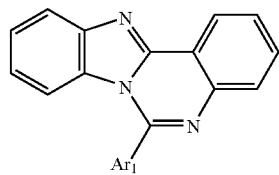
| No. | Ar1 |
|---|---|
| 1-1-60 | 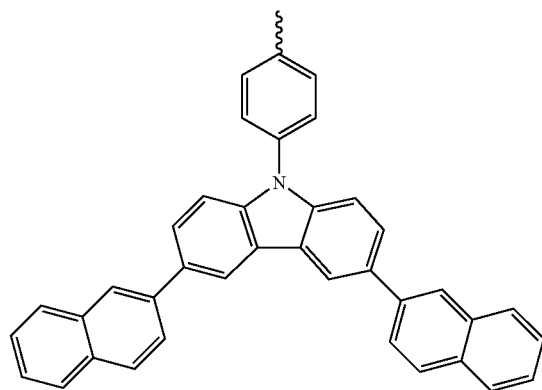 |
| 1-1-61 | 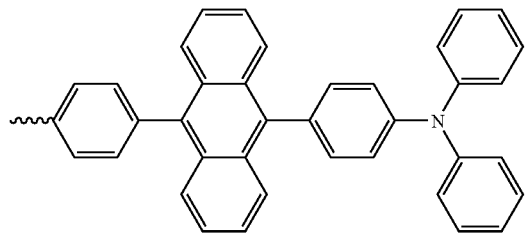 |
| 1-1-62 | 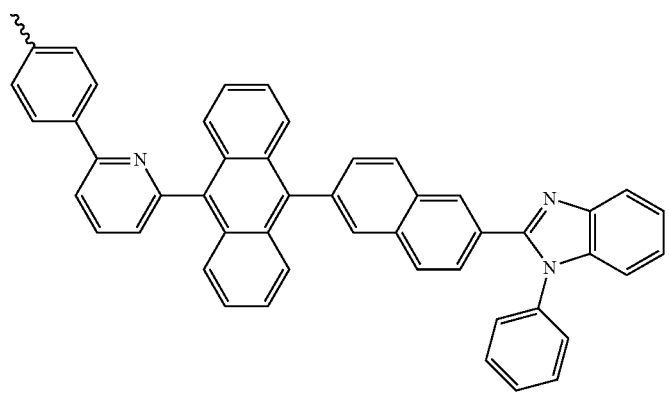 |

TABLE 1-continued
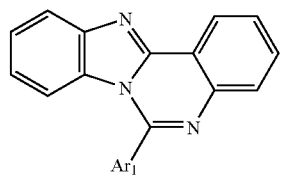
| No. | Ar1 |
| --- | --- |
| 1-1-63 | 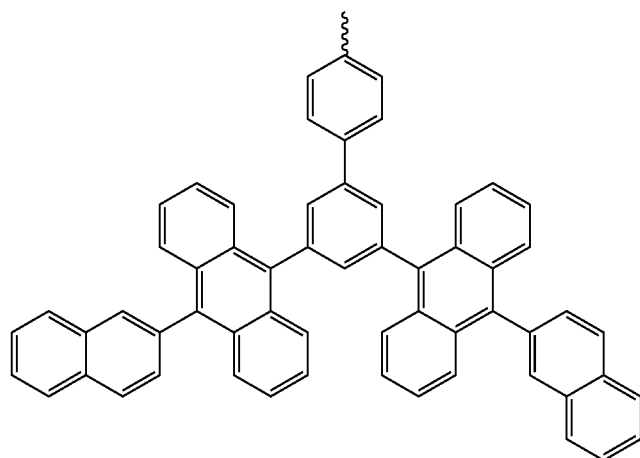 |
| 1-1-64 | 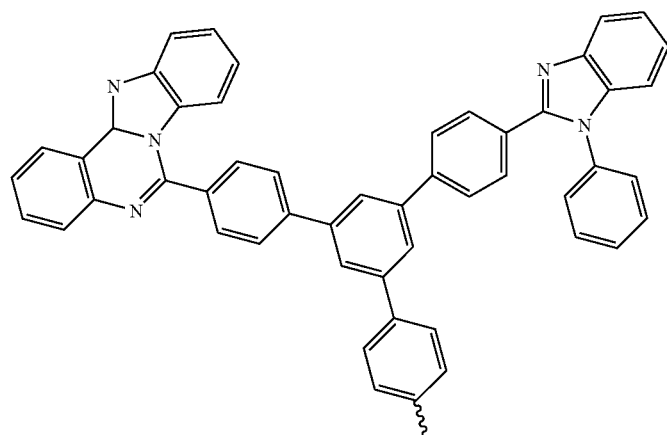 |
| 1-1-65 | 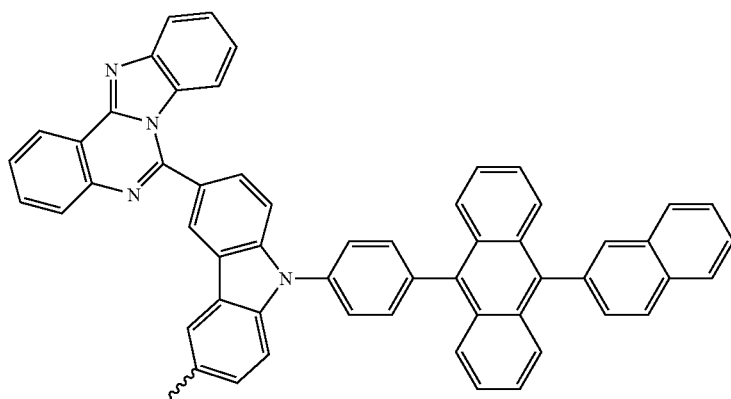 |

TABLE 1-continued
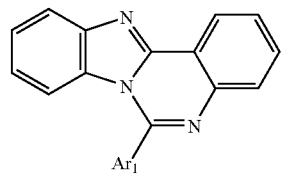
| No. | Ar1 |
|---|---|
| 1-1-66 | 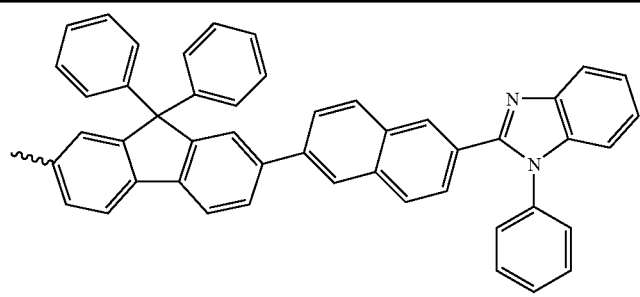 |
| 1-1-67 | 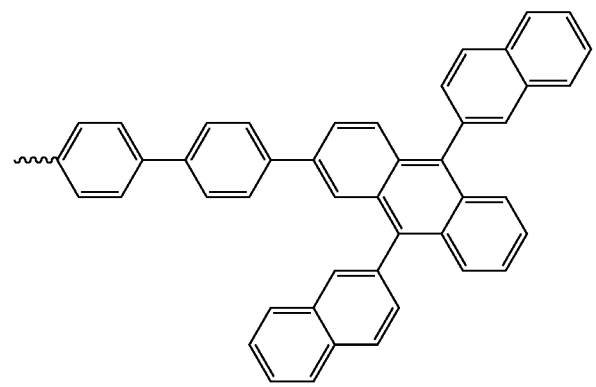 |
| 1-1-68 | 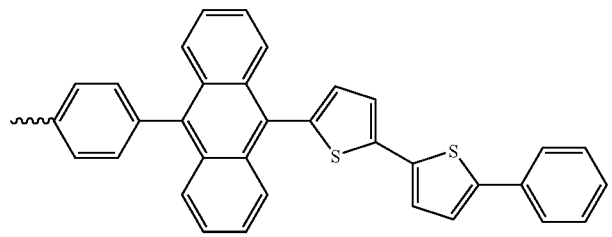 |
| 1-1-69 | 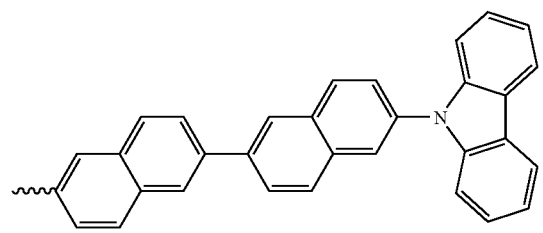 |
| 1-2-1 | 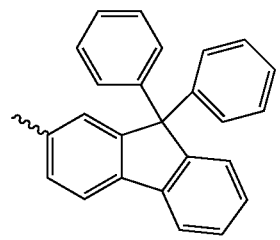 |

TABLE 1-continued

| No. | Ar1 |
|---|---|
| 1-2-2 | |
| 1-2-3 | |
| 1-2-4 | |
| 1-2-5 | |
| 1-2-6 | |

TABLE 1-continued
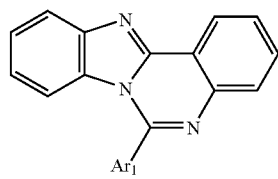
| No. | Ar1 |
|---|---|
| 1-2-7 | 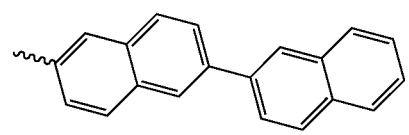 |
| 1-2-8 | 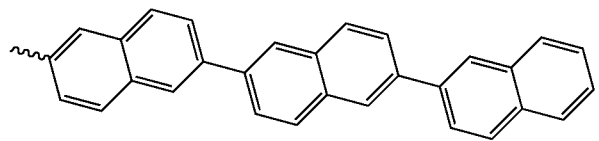 |
| 1-2-9 | 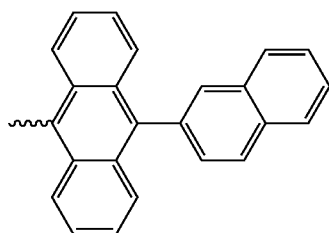 |
| 1-2-10 | 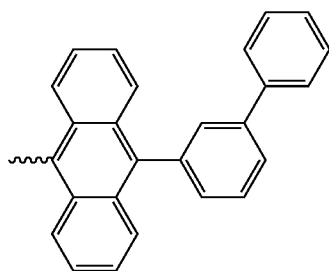 |
| 1-2-11 | 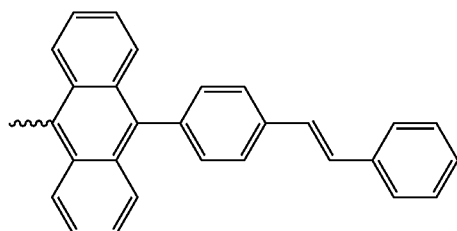 |
| 1-2-12 | 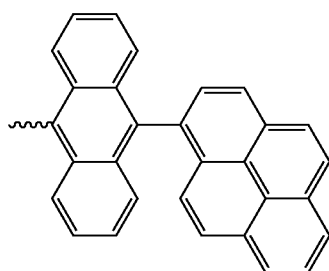 |

TABLE 1-continued
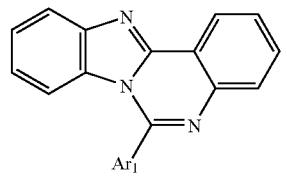
| No. | Ar1 |
|---|---|
| 1-2-13 | 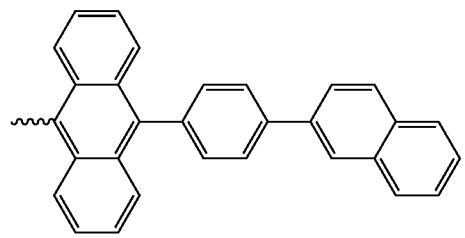 |
| 1-2-14 | 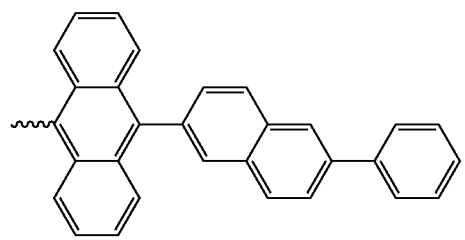 |
| 1-2-15 | 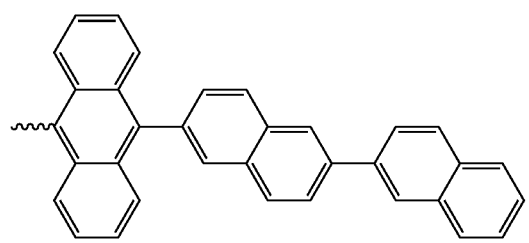 |
| 1-2-16 | 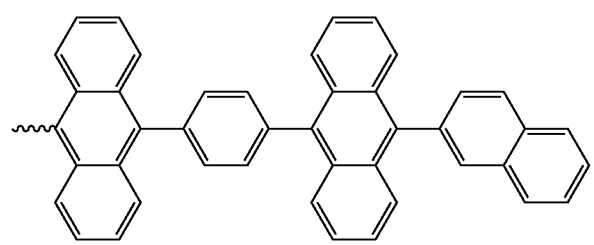 |
| 1-2-17 | 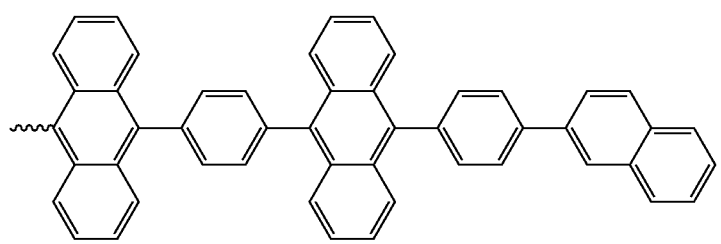 |

TABLE 1-continued
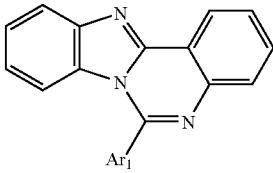
| No. | Ar1 |
|---|---|
| 1-2-18 | 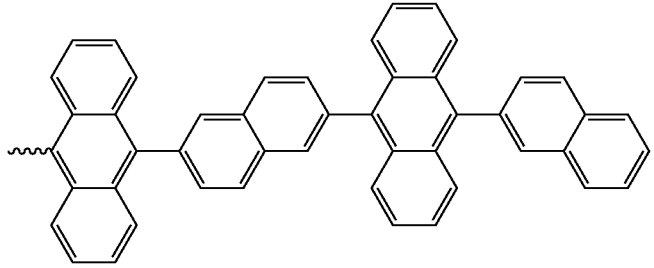 |
| 1-2-19 | 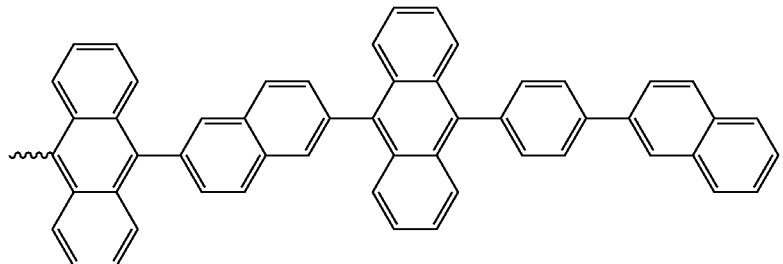 |
| 1-2-20 | 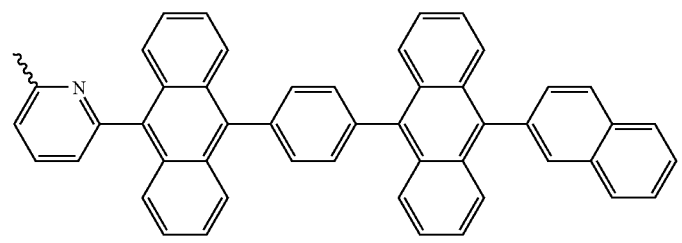 |
| 1-2-21 | 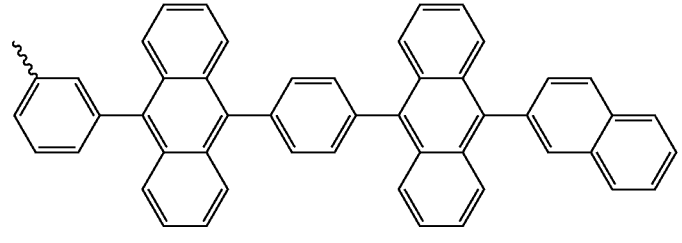 |
| 1-2-22 | 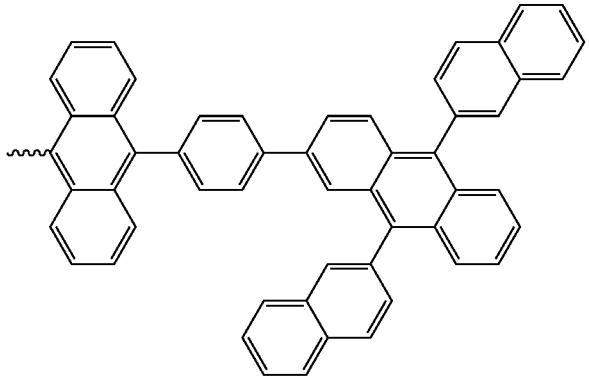 |

TABLE 1-continued
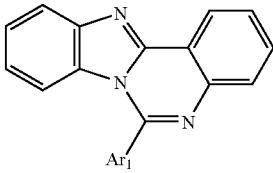
| No. | Ar1 |
|---|---|
| 1-2-23 | 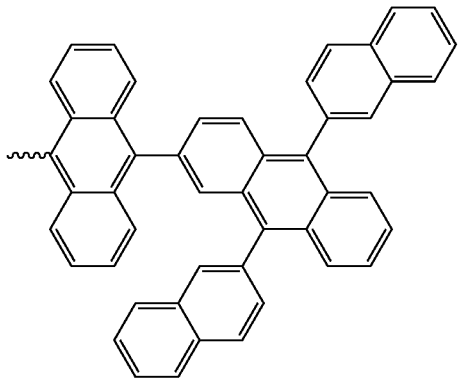 |
| 1-2-24 | 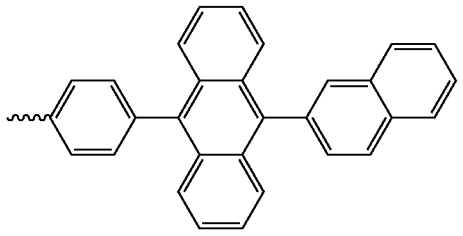 |
| 1-2-25 | 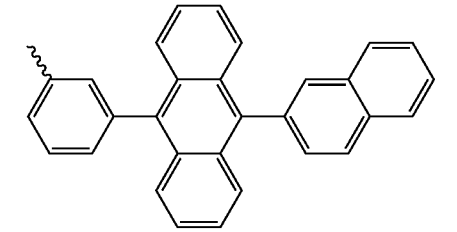 |
| 1-2-26 | 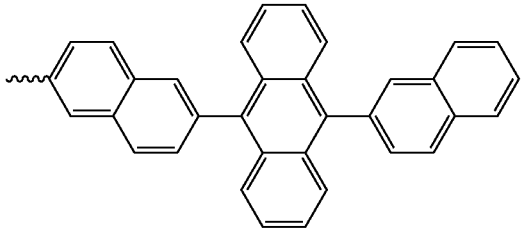 |
| 1-2-27 | 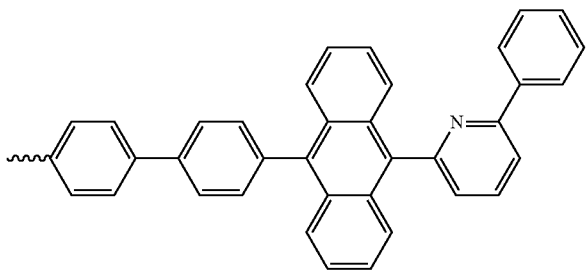 |

TABLE 1-continued
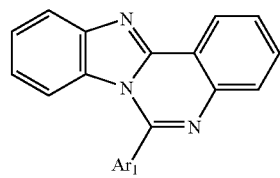
| No. | Ar1 |
|---|---|
| 1-2-28 | 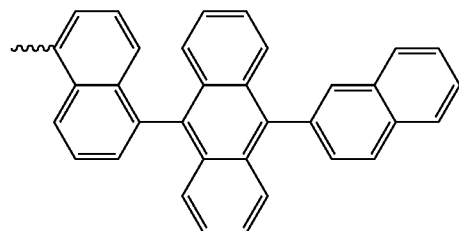 |
| 1-2-29 | 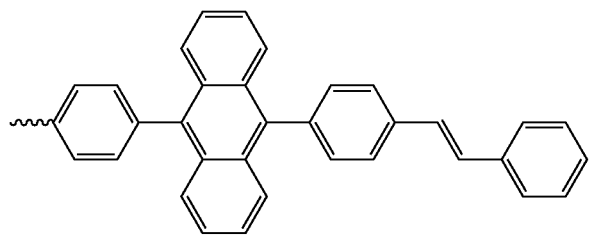 |
| 1-2-30 | 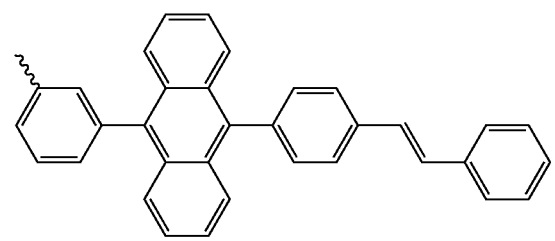 |
| 1-2-31 | 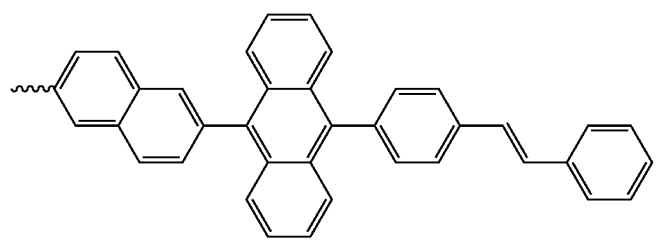 |
| 1-2-32 | 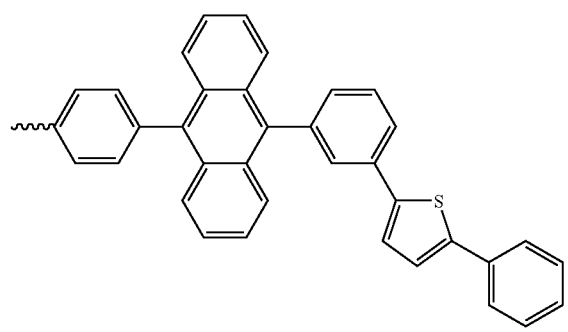 |

TABLE 1-continued
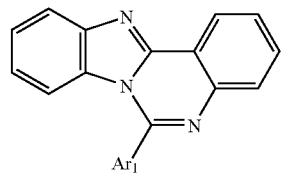
| No. | Ar1 |
|---|---|
| 1-2-33 | 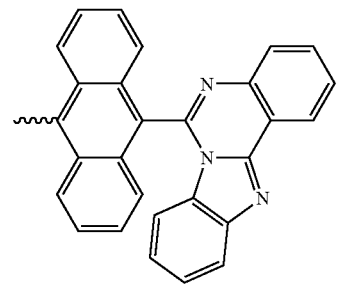 |
| 1-2-34 | 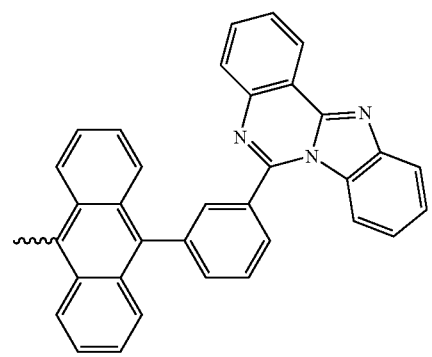 |
| 1-2-35 | 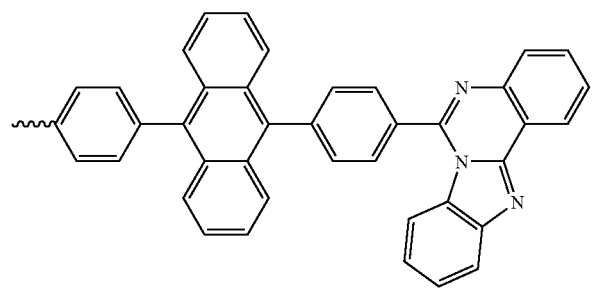 |
| 1-2-36 | 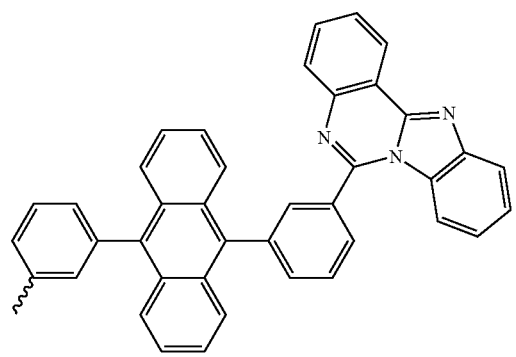 |

TABLE 1-continued
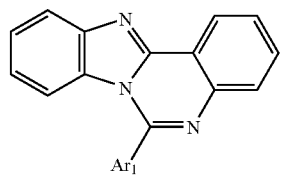
| No. | Ar1 |
|---|---|
| 1-2-37 | 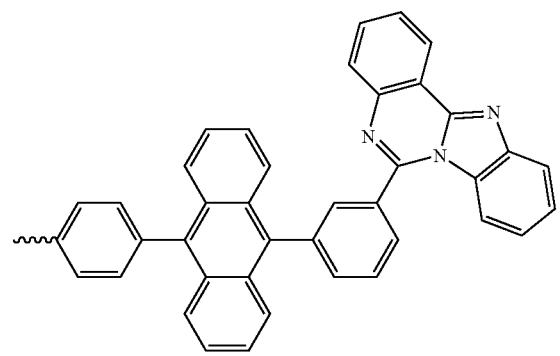 |
| 1-2-38 | 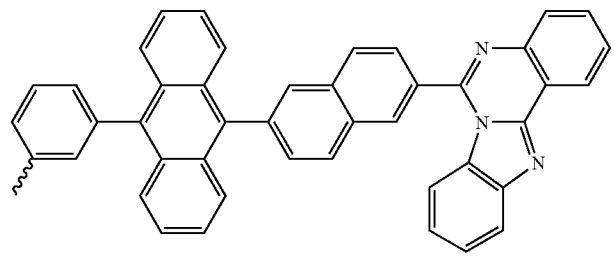 |
| 1-2-39 | 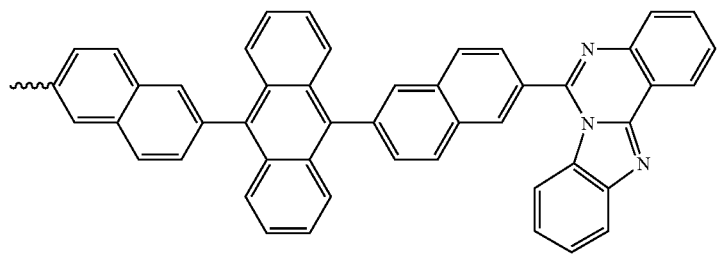 |
| 1-2-40 | 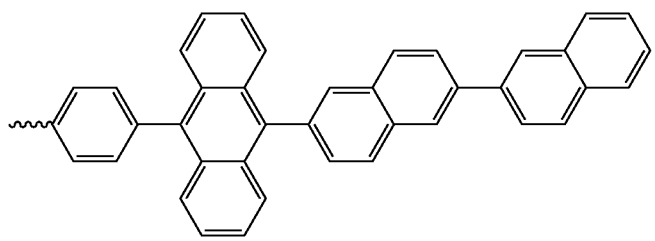 |
| 1-2-41 | 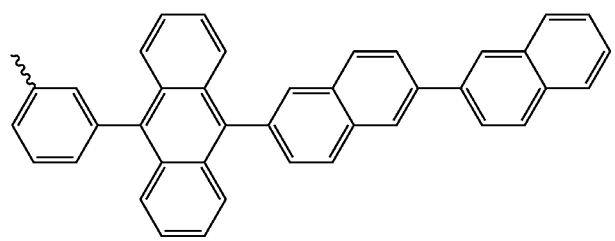 |

TABLE 1-continued
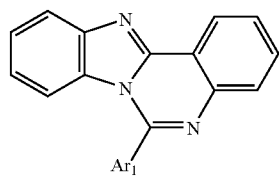
| No. | Ar1 |
|---|---|
| 1-2-42 | 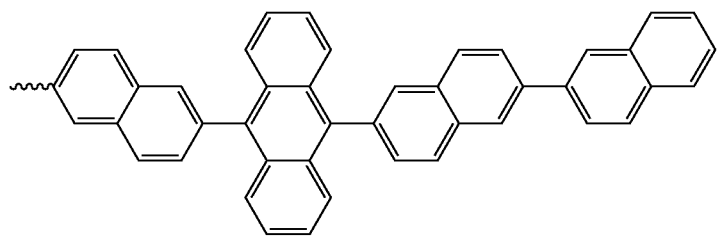 |
| 1-2-43 | 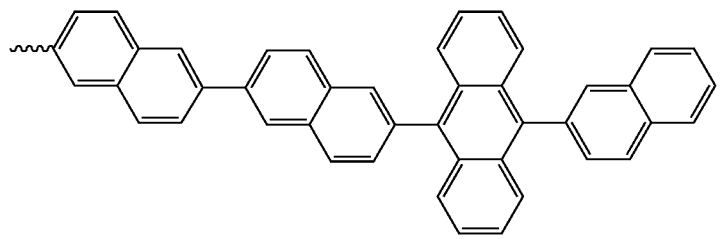 |
| 1-2-44 | 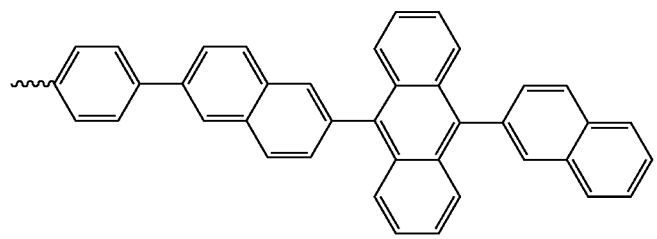 |
| 1-2-45 | 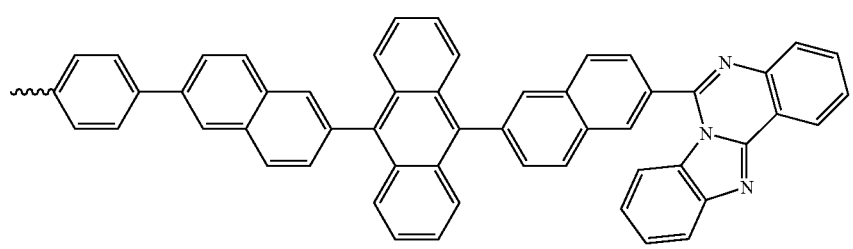 |
| 1-2-46 | 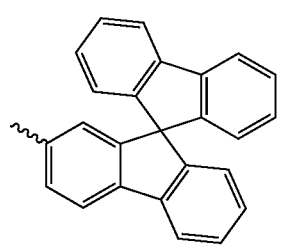 |

TABLE 1-continued
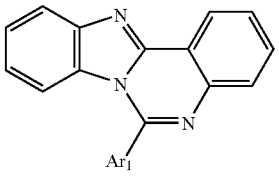
| No. | Ar1 |
|---|---|
| 1-2-47 | 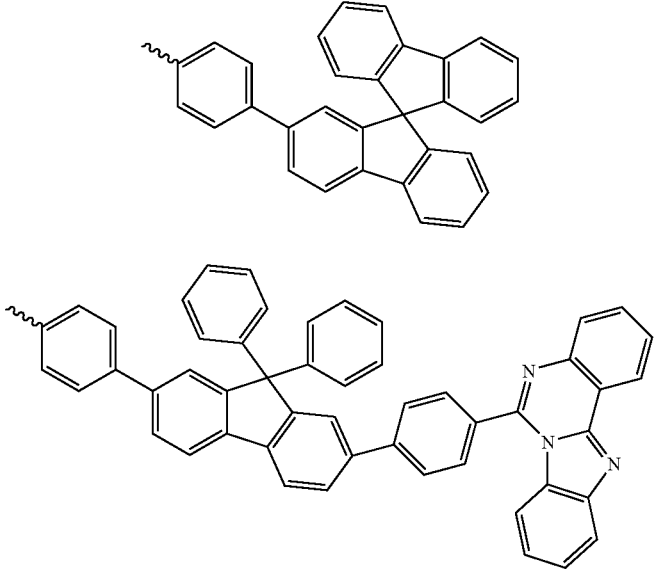 |
| 1-2-48 | 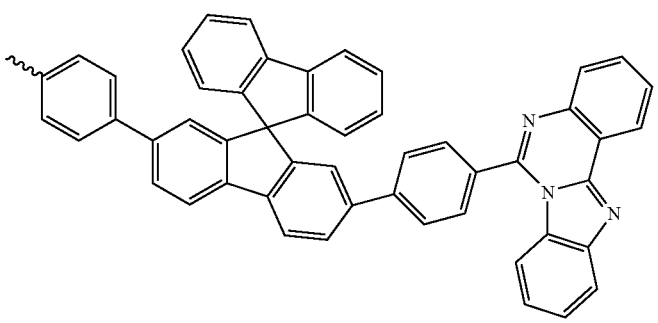 |
| 1-2-49 | 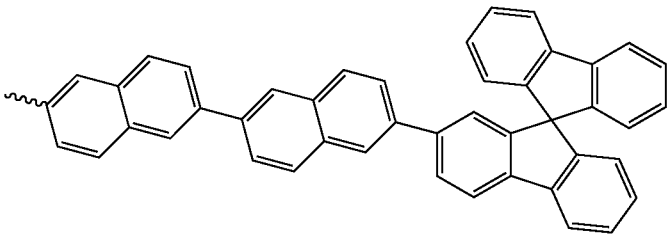 |
| 1-2-50 | 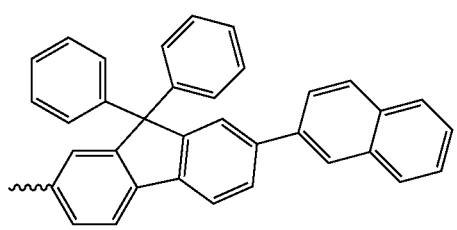 |
| 1-2-51 | |

TABLE 1-continued
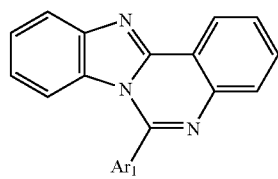
| No. | Ar1 |
|---|---|
| 1-2-52 | 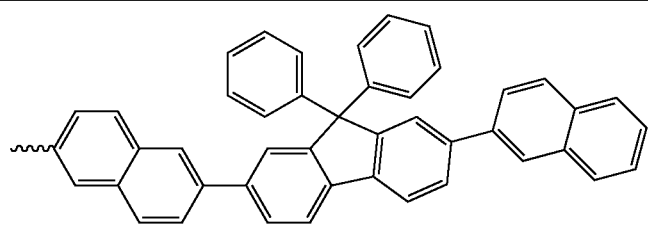 |
| 1-2-53 | 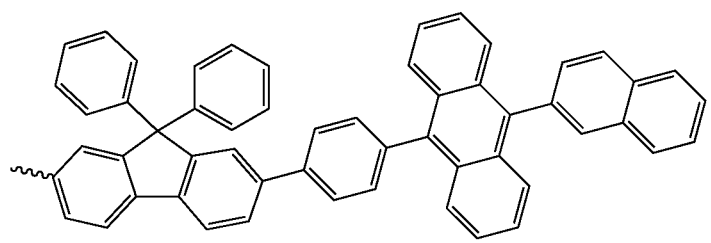 |
| 1-2-54 | 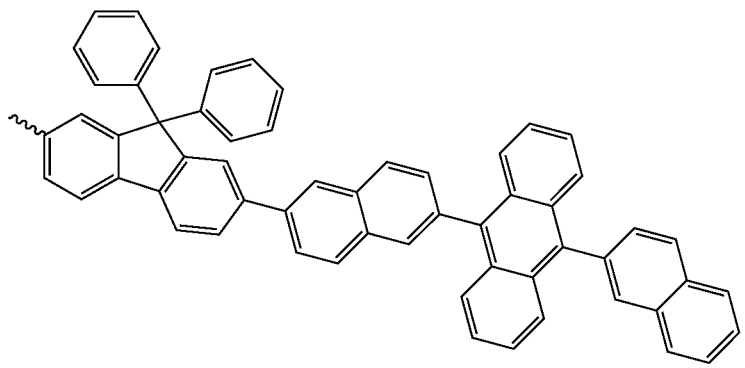 |
| 1-2-55 | 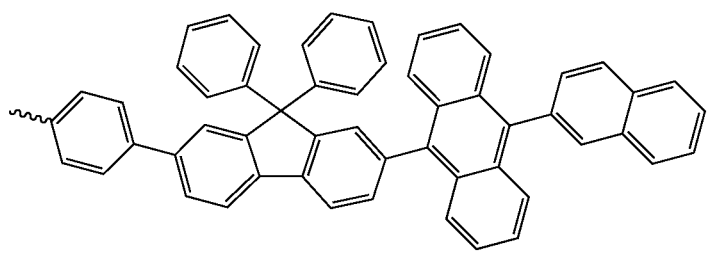 |
| 1-2-56 | 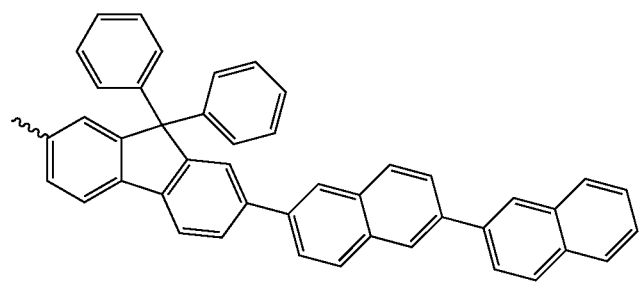 |

TABLE 1-continued
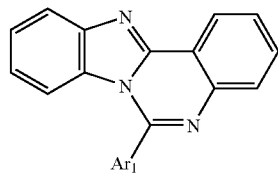
| No. | Ar1 |
|---|---|
| 1-2-57 | 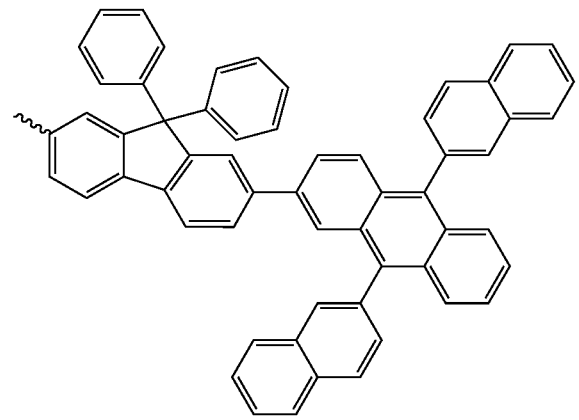 |
| 1-2-58 | 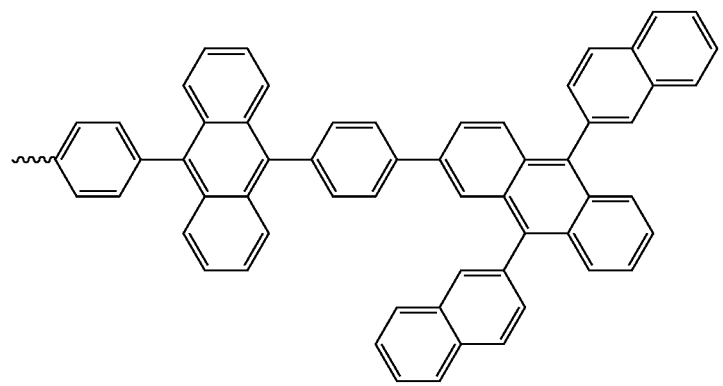 |
| 1-2-59 | 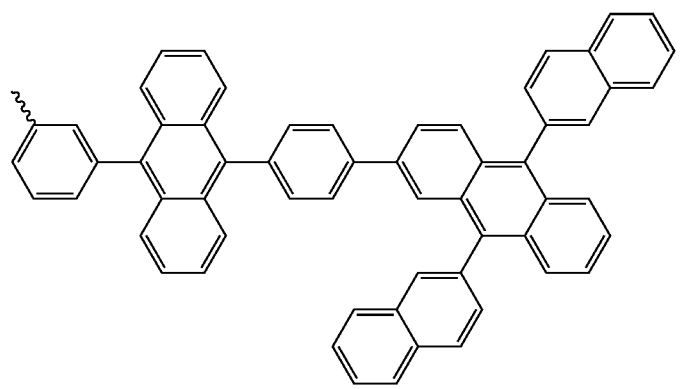 |

TABLE 1-continued
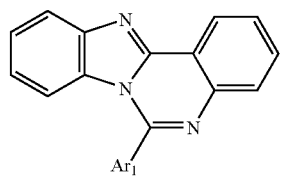
| No. | Ar1 |
|---|---|
| 1-2-60 | 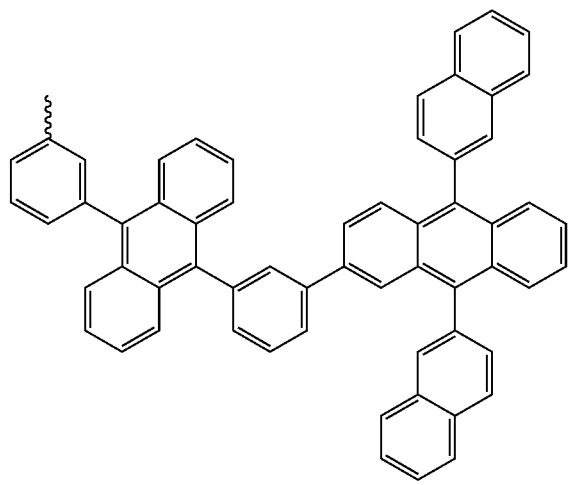 |
| 1-2-61 | 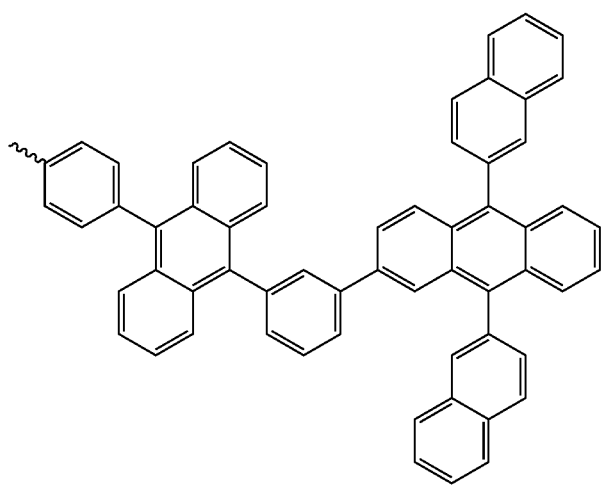 |
| 1-2-62 | 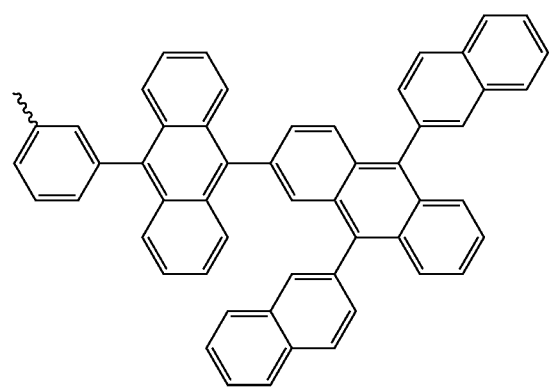 |

TABLE 1-continued
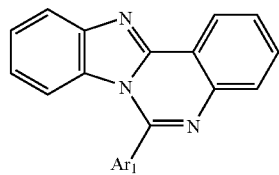
| No. | Ar1 |
|---|---|
| 1-2-63 | 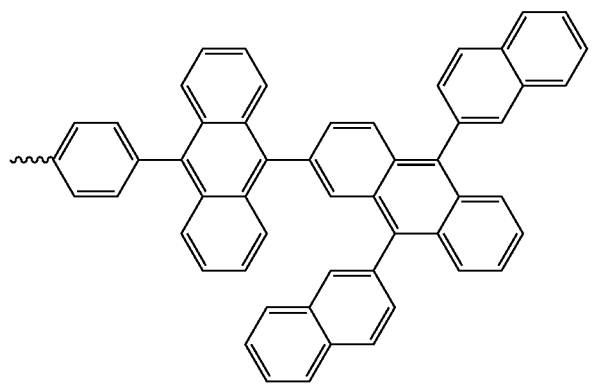 |
| 1-2-64 | 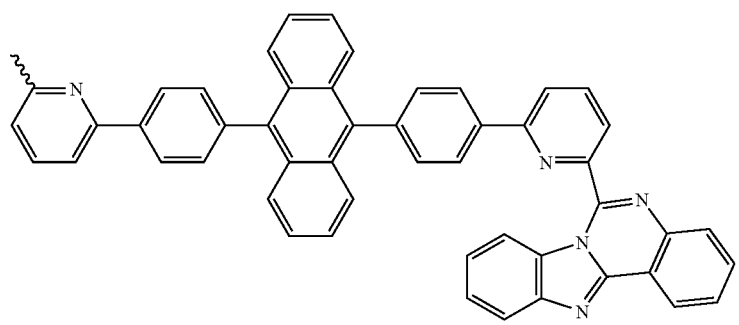 |
| 1-2-65 | 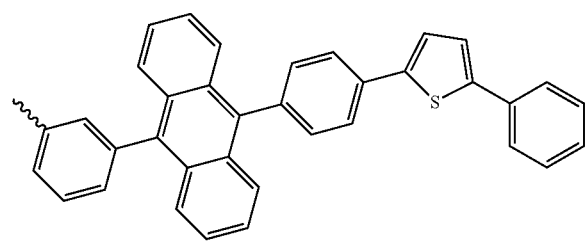 |
| 1-2-66 | 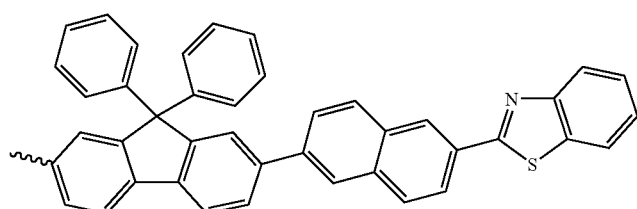 |

TABLE 1-continued
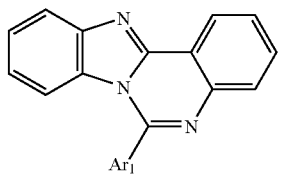
| No. | Ar1 |
|---|---|
| 1-2-67 | 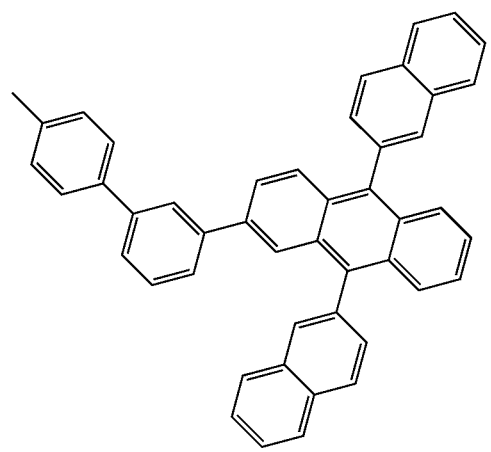 |
| 1-2-68 | 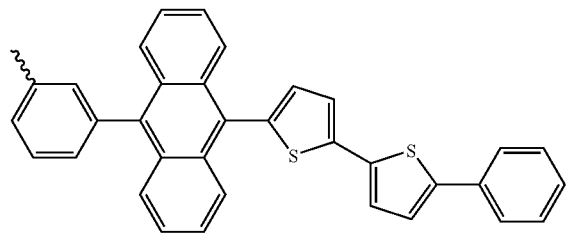 |
| 1-2-69 | 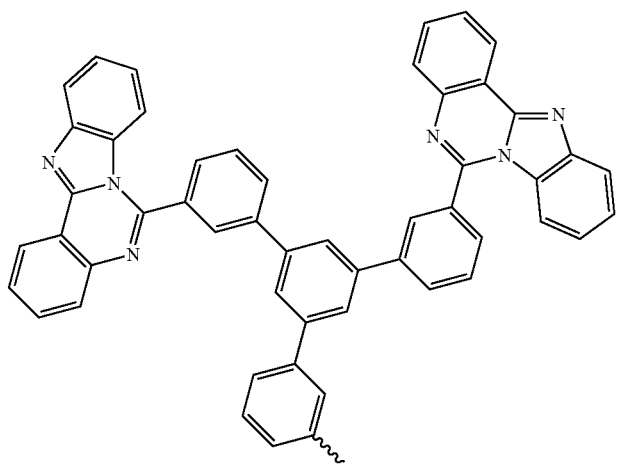 |
| 1-3-1 | 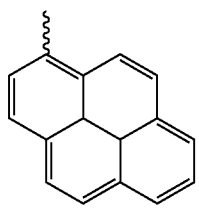 |

TABLE 1-continued
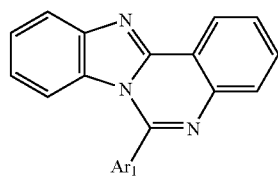
| No. | Ar1 |
|---|---|
| 1-3-2 | 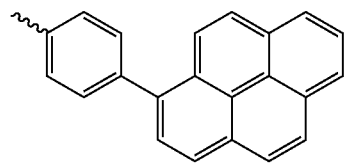 |
| 1-3-3 | 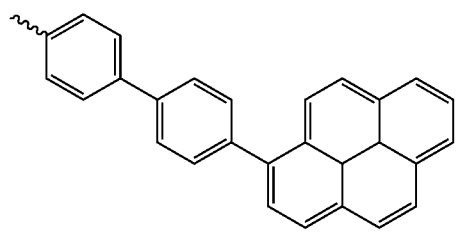 |
| 1-3-4 | 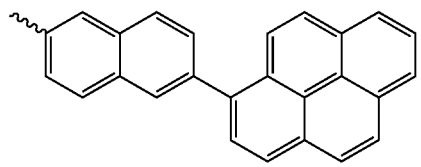 |
| 1-3-5 | 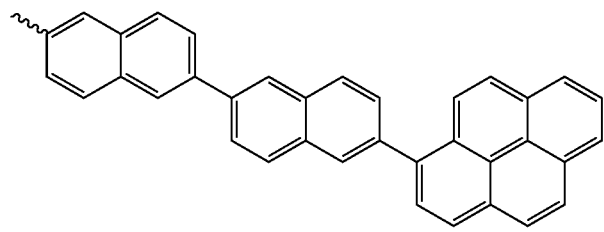 |
| 1-3-6 | 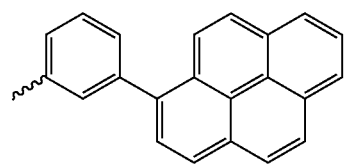 |
| 1-3-7 | 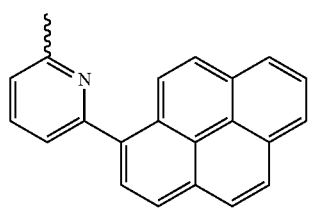 |
| 1-3-8 | 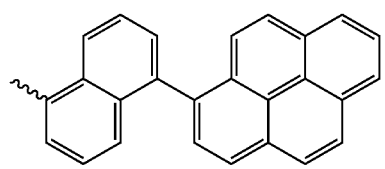 |

TABLE 1-continued
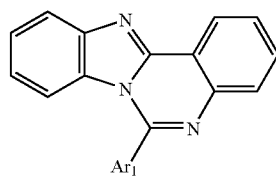
| No. | Ar1 |
|---|---|
| 1-3-9 | 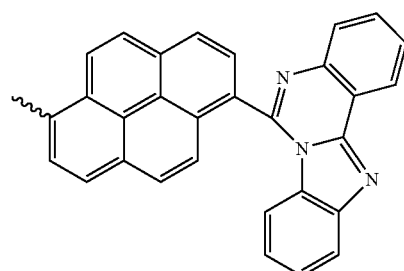 |
| 1-3-10 | 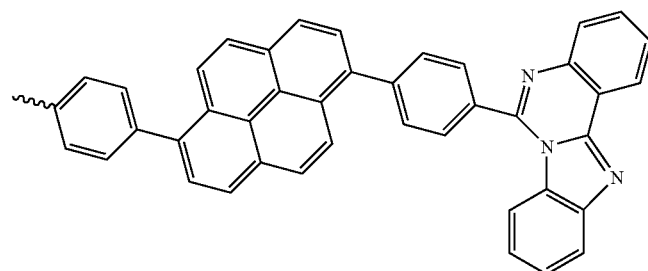 |
| 1-3-11 | 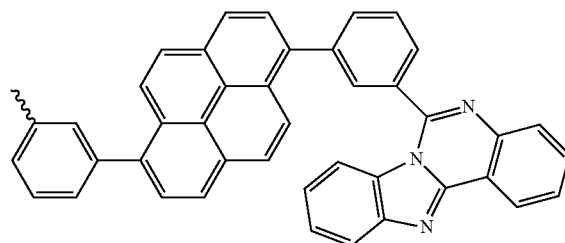 |
| 1-3-12 | 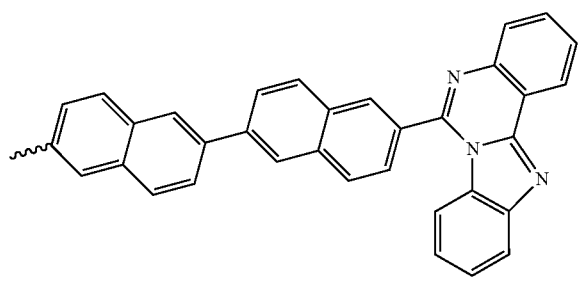 |
| 1-3-13 | 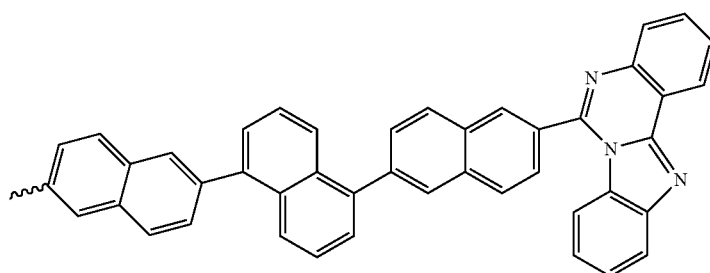 |

TABLE 1-continued
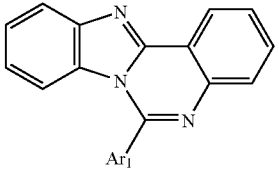
| No. | Ar1 |
|---|---|
| 1-3-14 | 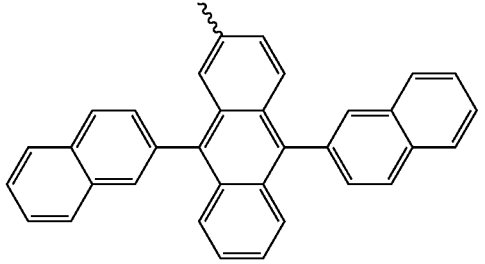 |
| 1-3-15 | |
| 1-3-16 | 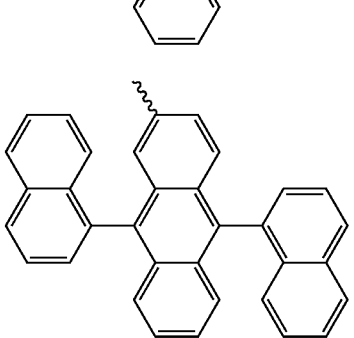 |
| 1-3-17 | 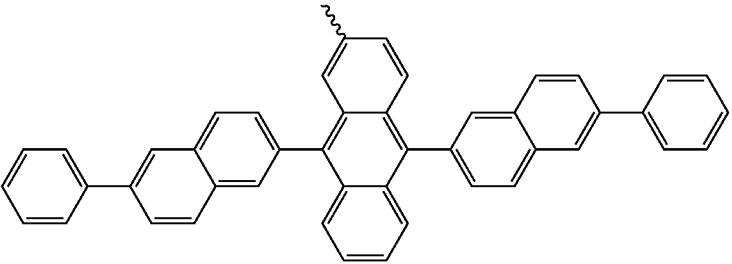 |
| 1-3-18 | 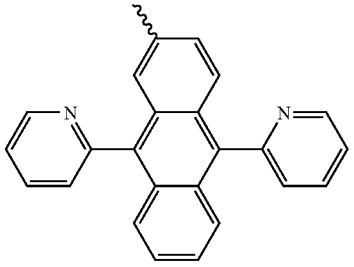 |

TABLE 1-continued
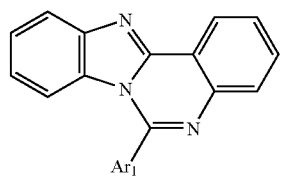
| No. | Ar1 |
|---|---|
| 1-3-19 | 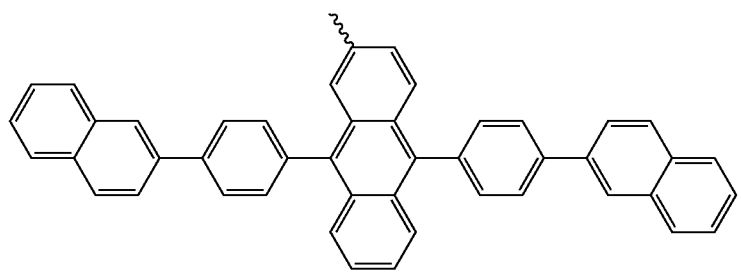 |
| 1-3-20 | 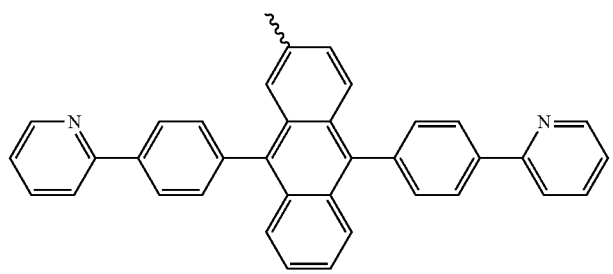 |
| 1-3-21 | 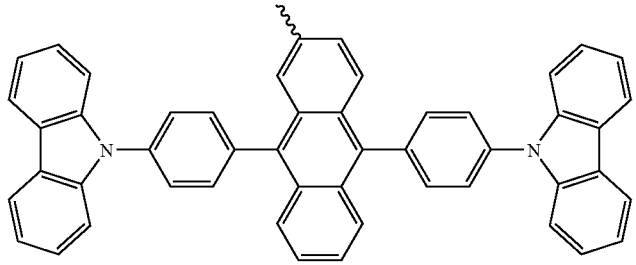 |
| 1-3-22 | 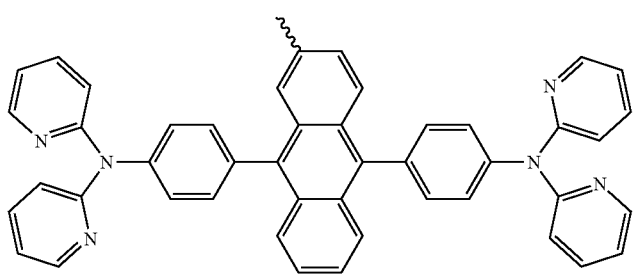 |
| 1-3-23 | 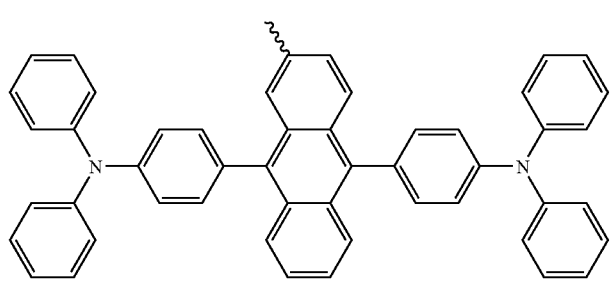 |

TABLE 1-continued
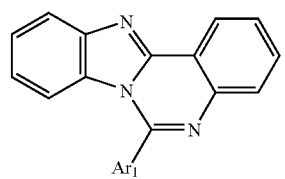
| No. | Ar1 |
|---|---|
| 1-3-24 | 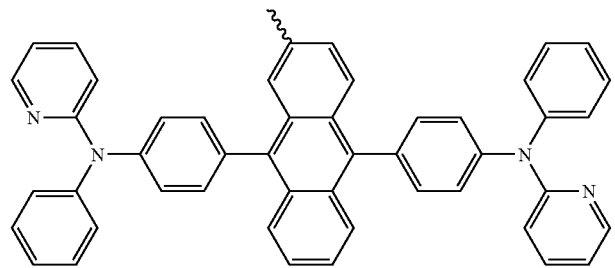 |
| 1-3-25 | 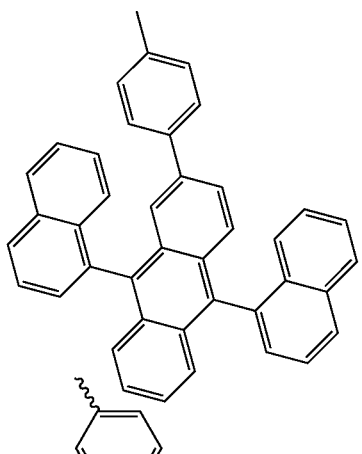 |
| 1-3-26 | 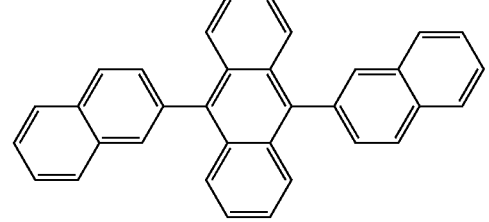 |
| 1-3-27 | 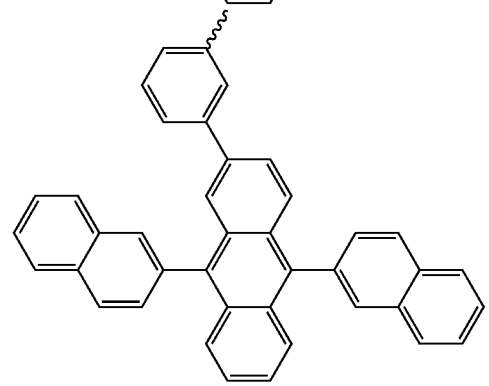 |

TABLE 1-continued
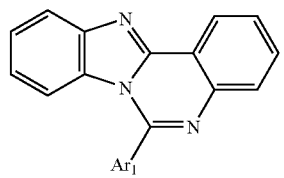
| No. | Ar1 |
|---|---|
| 1-3-28 | 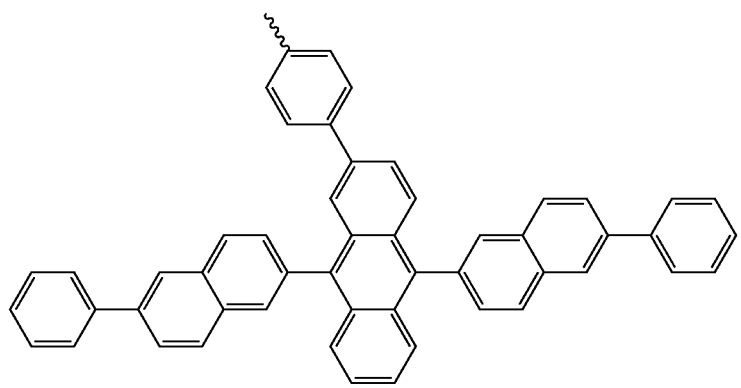 |
| 1-3-29 | 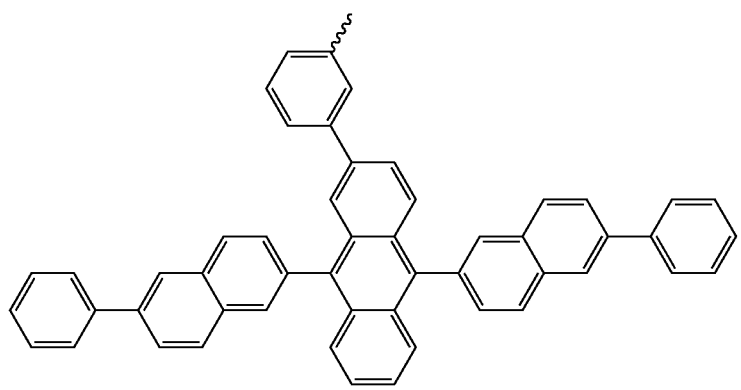 |
| 1-3-30 | 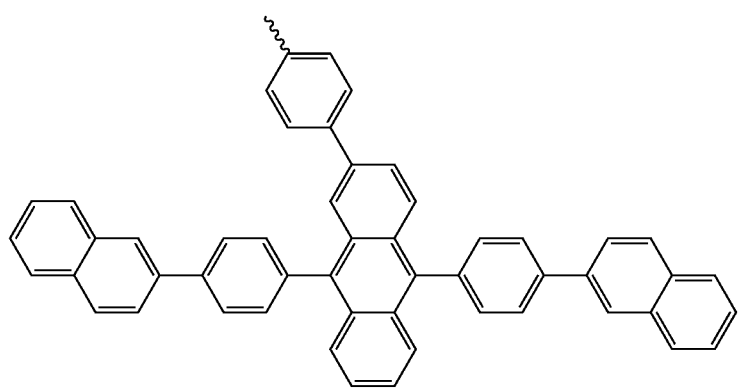 |

TABLE 1-continued
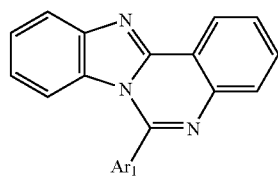
| No. | Ar1 |
|---|---|
| 1-3-31 | 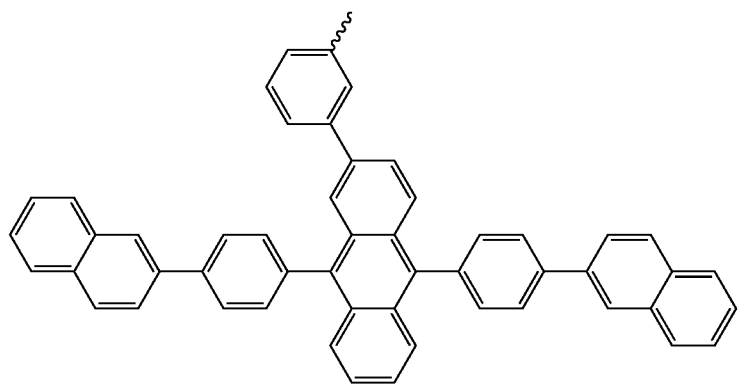 |
| 1-3-32 | 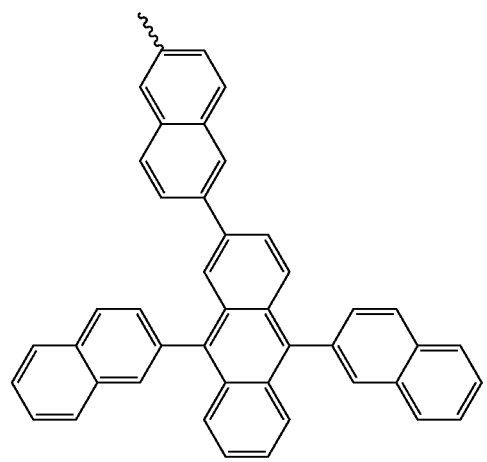 |
| 1-3-33 | 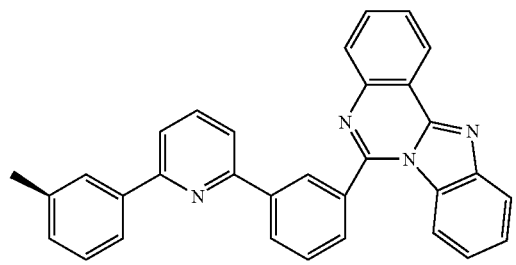 |
| 1-3-34 | 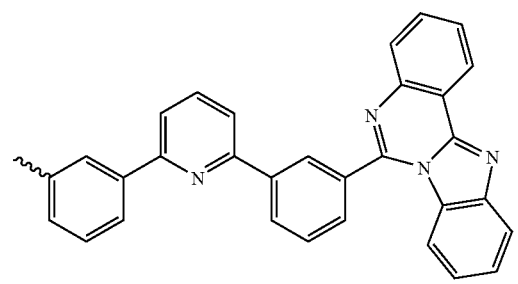 |

TABLE 1-continued
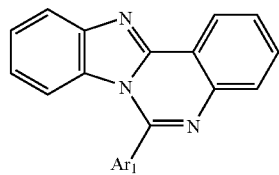
| No. | Ar1 |
|---|---|
| 1-3-35 | 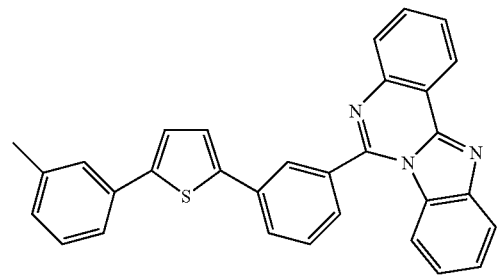 |
| 1-3-36 | |
| 1-3-37 | 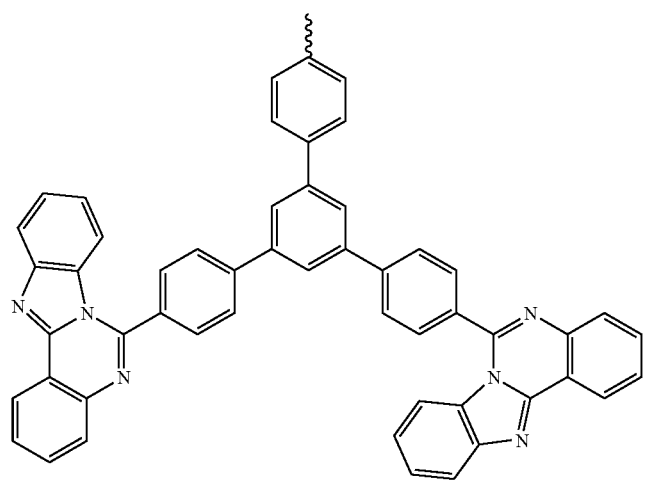 |
| 1-3-38 | 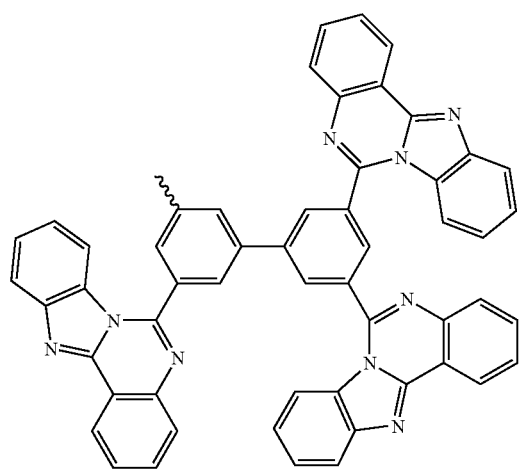 |

TABLE 1-continued
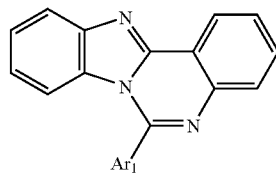
| No. | Ar1 |
|---|---|
| 1-3-39 | 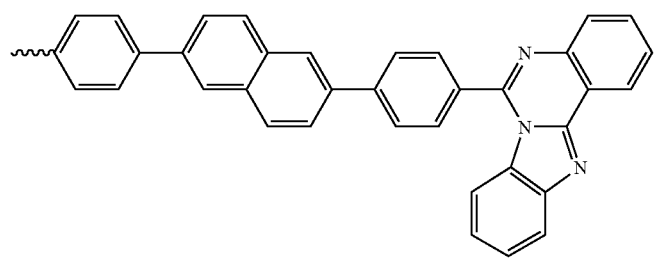 |
| 1-3-40 | 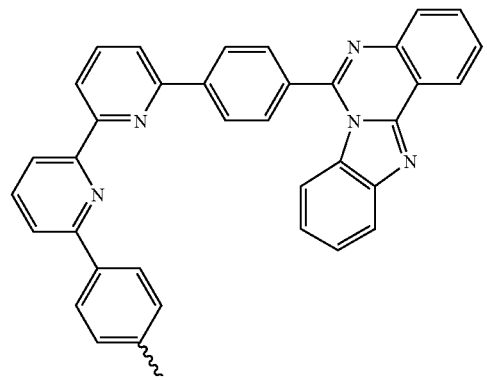 |
| 1-3-41 | 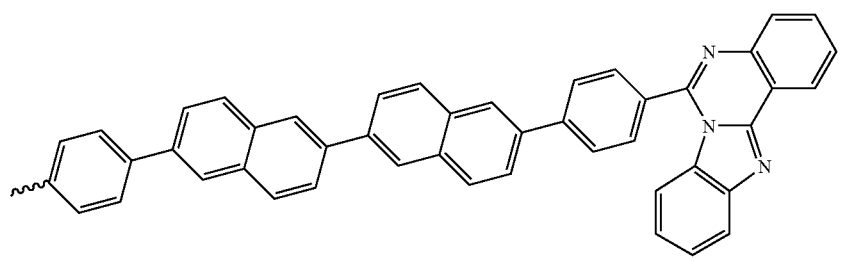 |
| 1-3-42 | 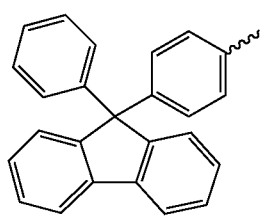 |
| 1-3-43 | 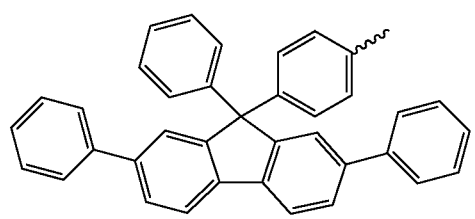 |

TABLE 1-continued

| No. | Ar1 |
|---|---|
| 1-3-44 | |
| 1-3-45 | |
| 1-3-46 | |
| 1-3-47 | |
| 1-3-48 | |
| 1-3-49 | |

TABLE 1-continued
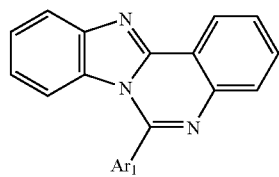
| No. | Ar1 |
|---|---|
| 1-3-50 | |
| 1-3-51 | |
| 1-3-52 | |
| 1-3-53 | |
| 1-3-54 | |

TABLE 1-continued
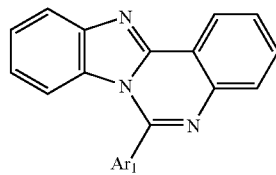
| No. | Ar1 |
|---|---|
| 1-3-55 | 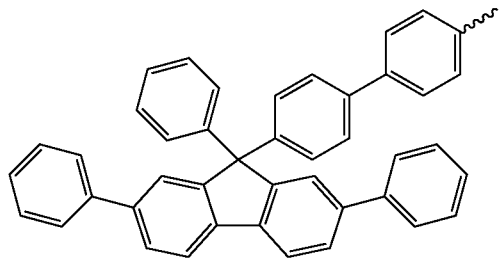 |
| 1-3-56 | 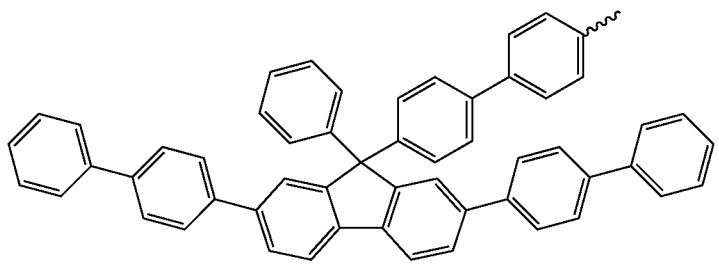 |
| 1-3-57 | 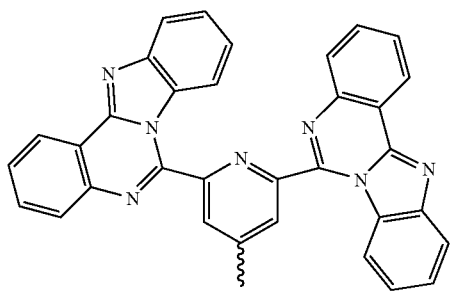 |
| 1-3-58 | 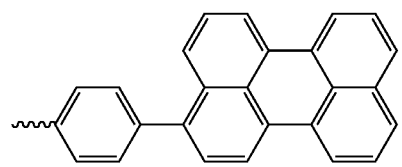 |
| 1-3-59 | 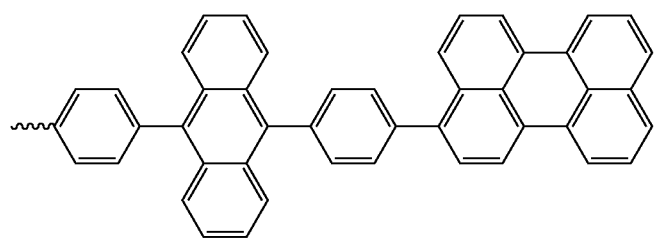 |

TABLE 1-continued
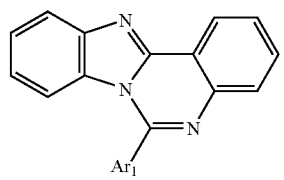
| No. | Ar1 |
|---|---|
| 1-3-60 | 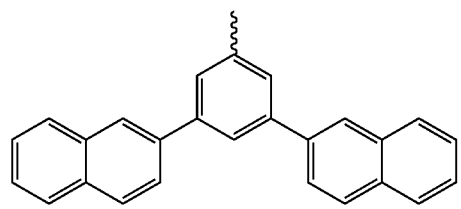 |
| 1-3-61 | 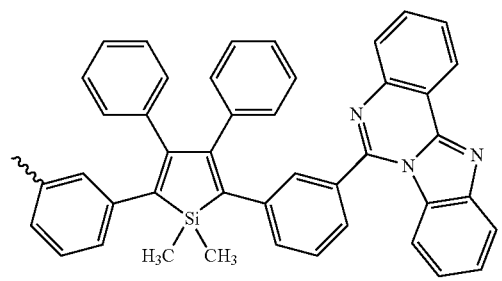 |
| 1-3-62 | 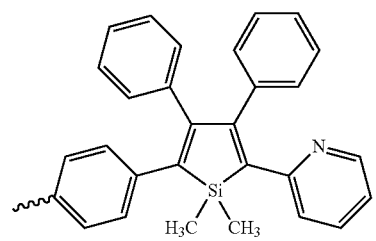 |
| 1-3-63 | 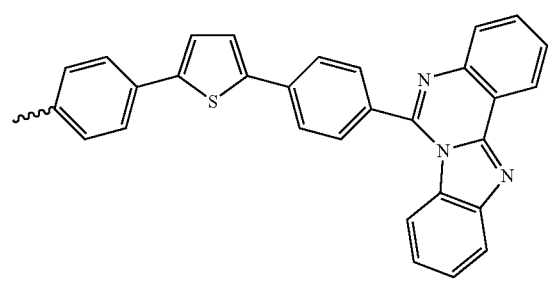 |
| 1-3-64 | 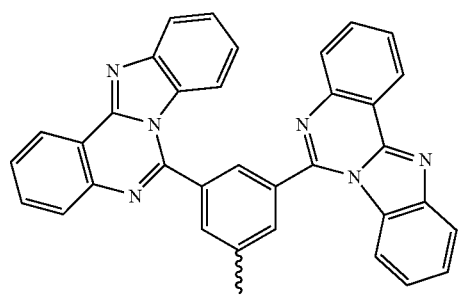 |

TABLE 1-continued
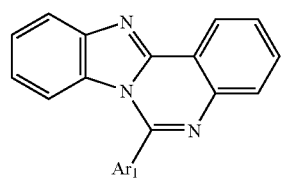
| No. | Ar1 |
|---|---|
| 1-3-65 | 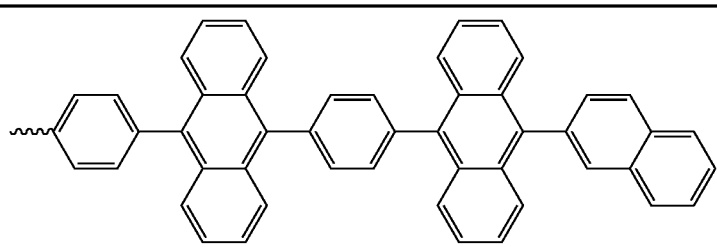 |
| 1-3-66 | 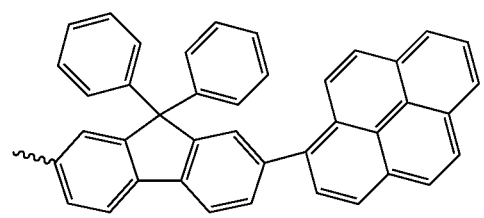 |
| 1-3-67 | 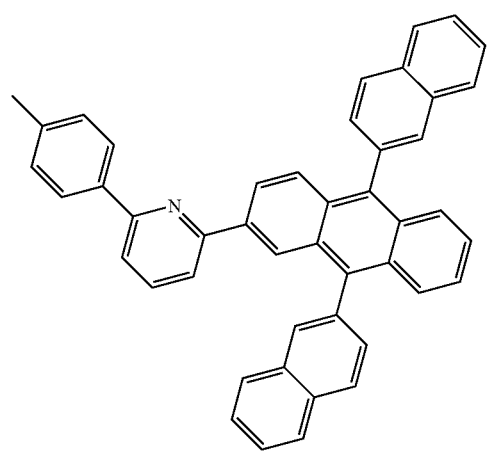 |
| 1-3-68 | 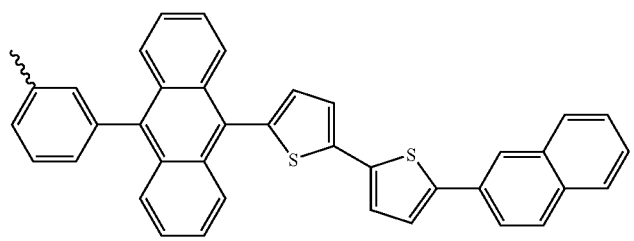 |
| 1-3-69 | 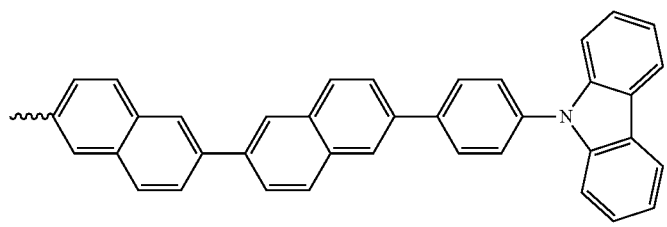 |

In addition, the structures of the formula 1 include the compounds of the following structural formulas, but not limited thereto.
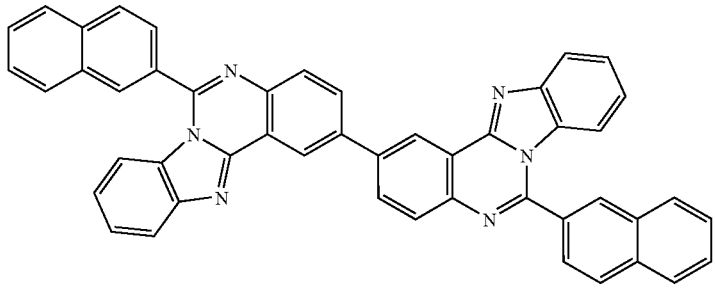
[compound 1-4-1]
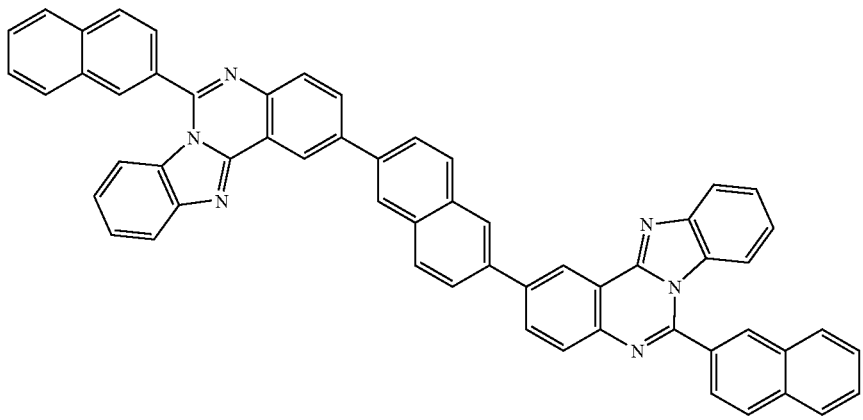
[compound 1-4-2]
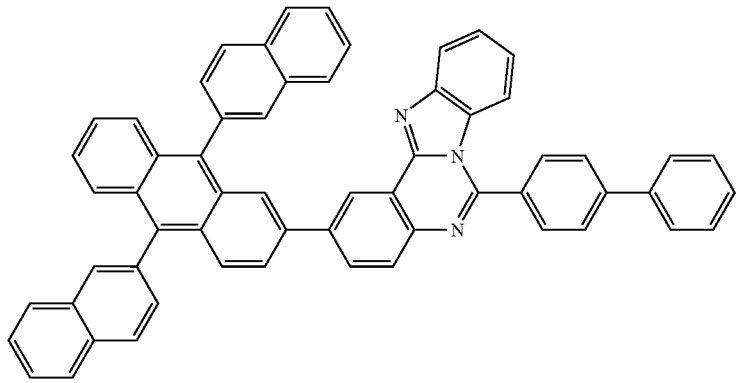
[compound 1-4-3]
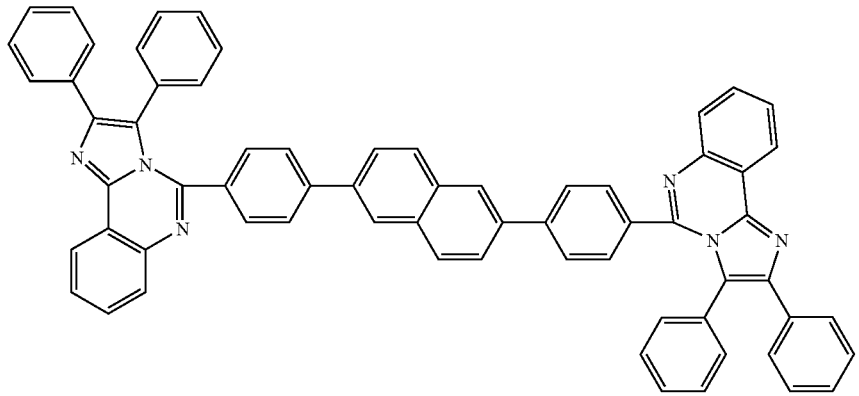
[compound 1-4-4]

[compound 1-4-5]
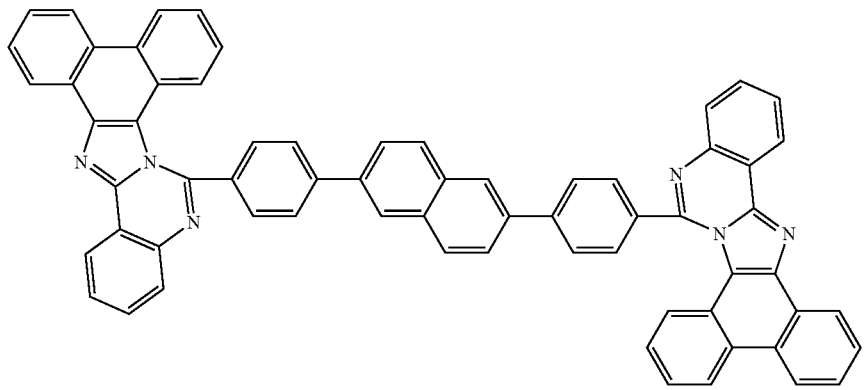
[compound 1-4-6]
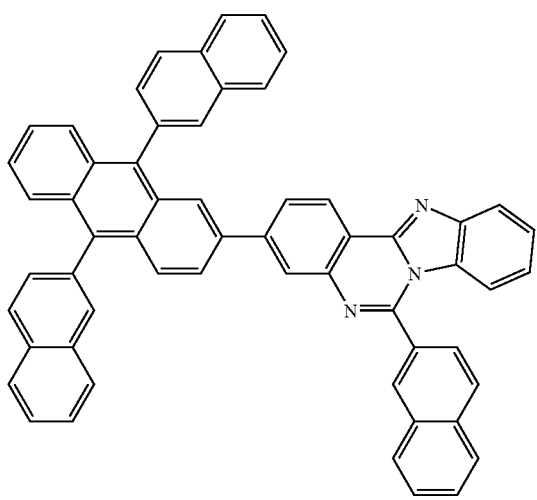
[compouond 1-4-7]
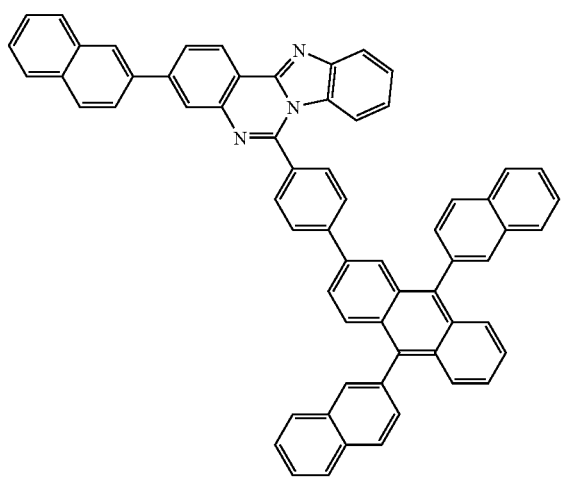
[compound 1-4-8]
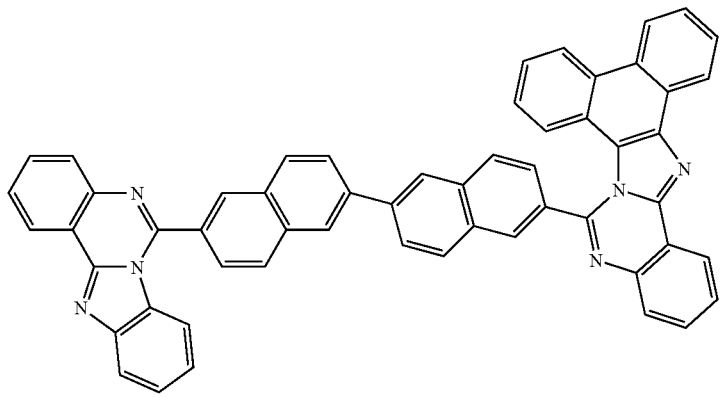
[compound 1-4-9]
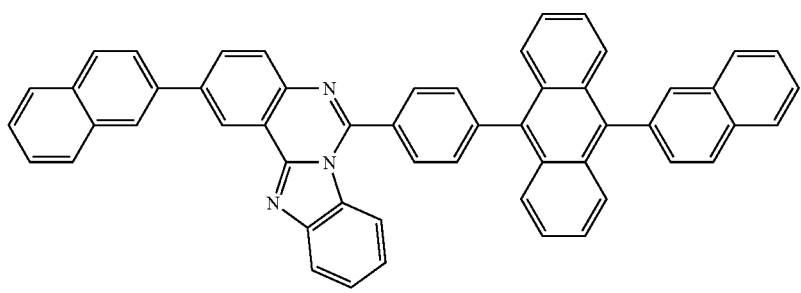

[compound 1-4-10]
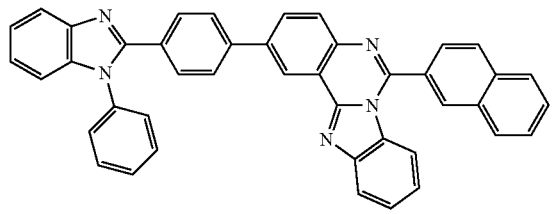
[compound 1-4-11]
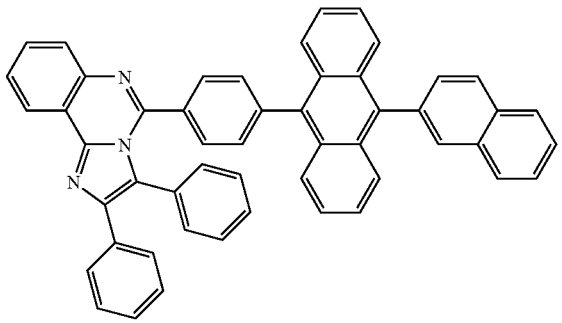
[compound 1-4-12]
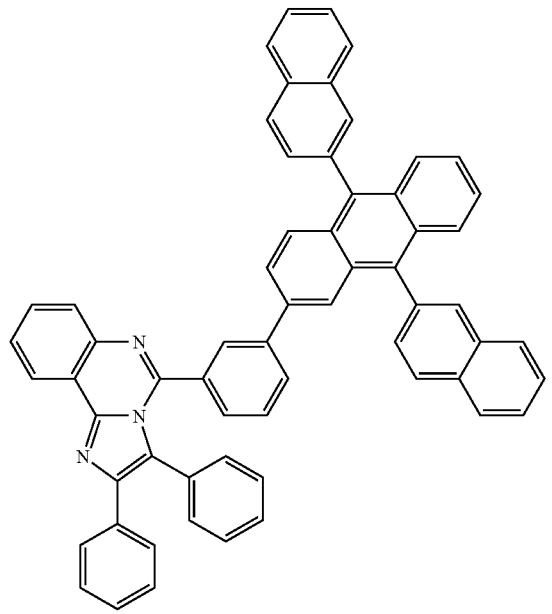
[compound 1-4-13]
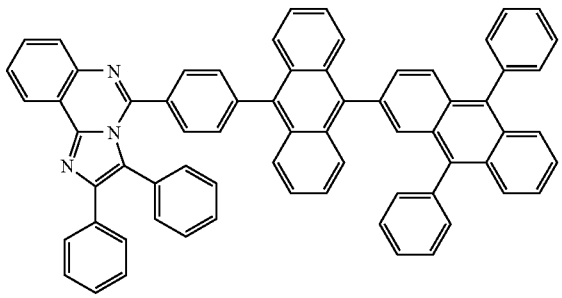
[compound 1-4-14]
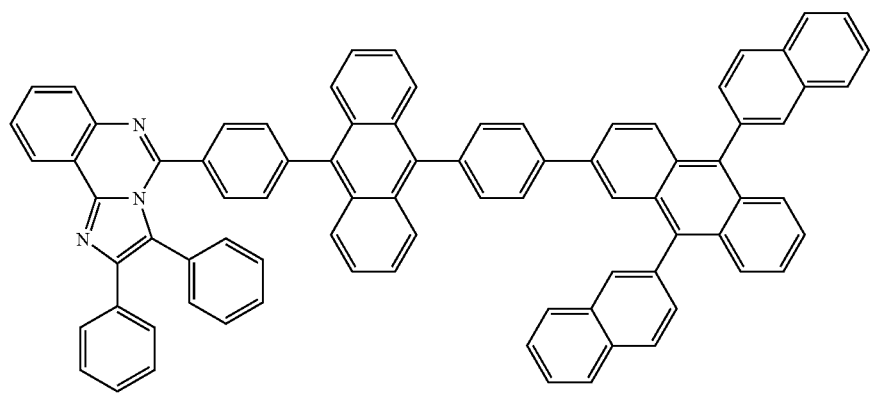

[compound 1-4-15]
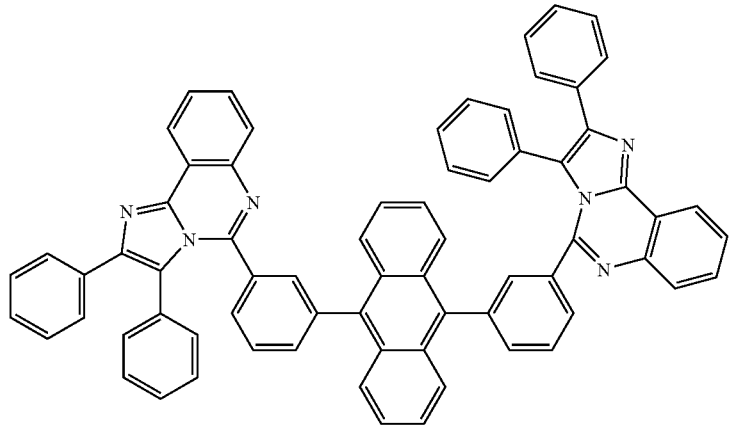
[compound 1-4-16]
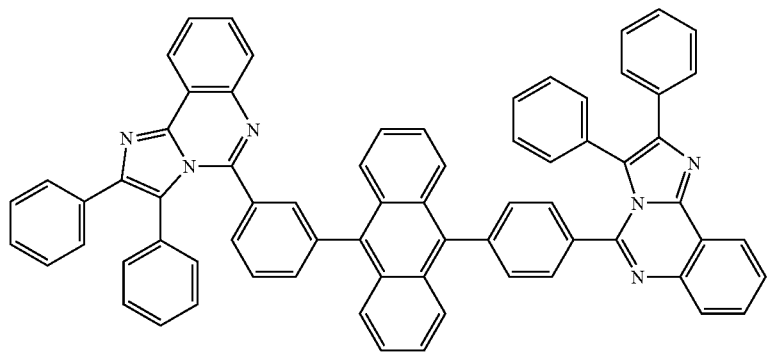
[compound 1-4-17]
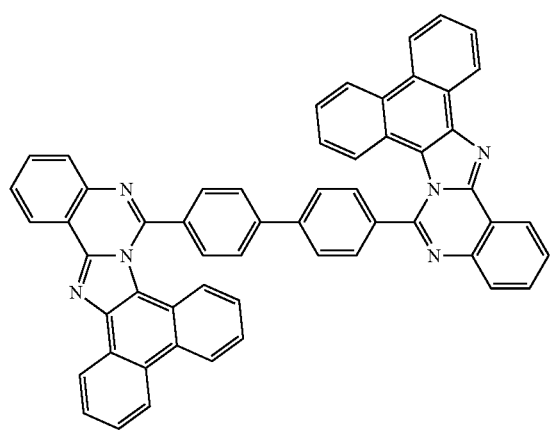
[compound 1-4-18]
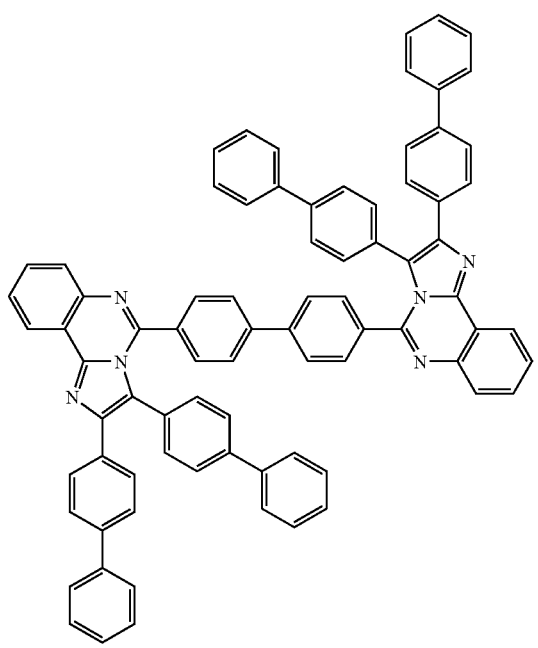

-continued
[compound 1-4-19]
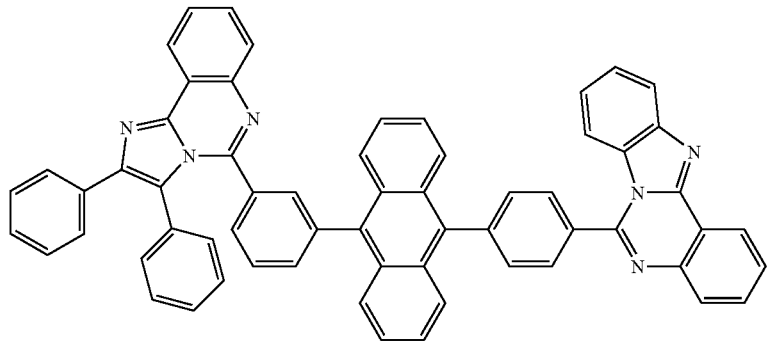
[compound 1-4-20]
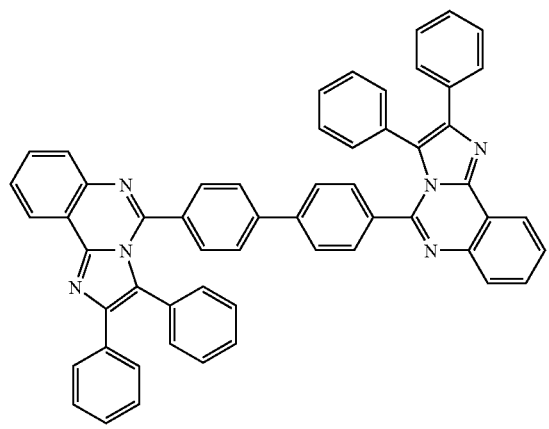
[compound 1-4-21]
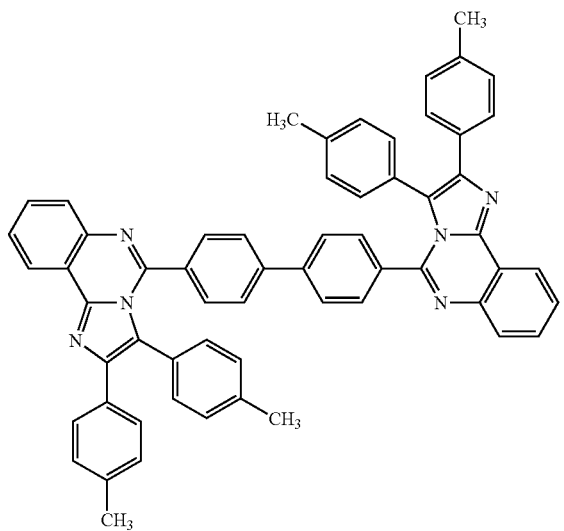
[compound 1-4-22]
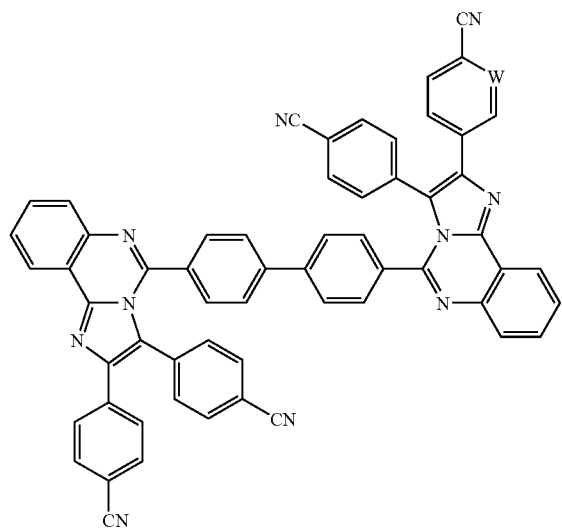
[compound 1-4-23]
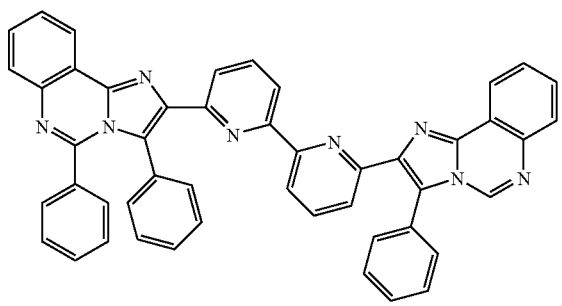

[compound 1-4-24]
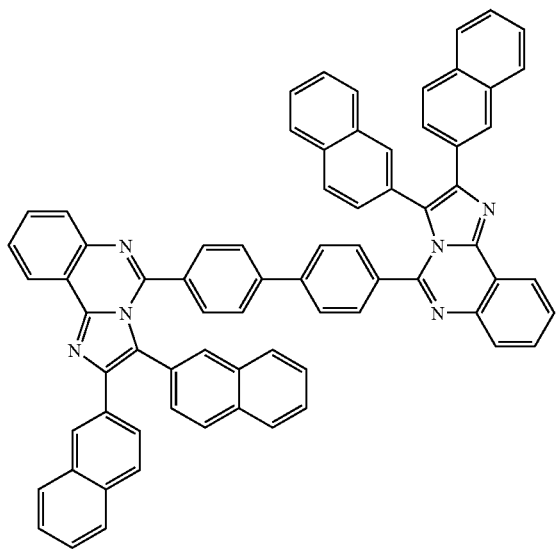
[compound 1-4-25]
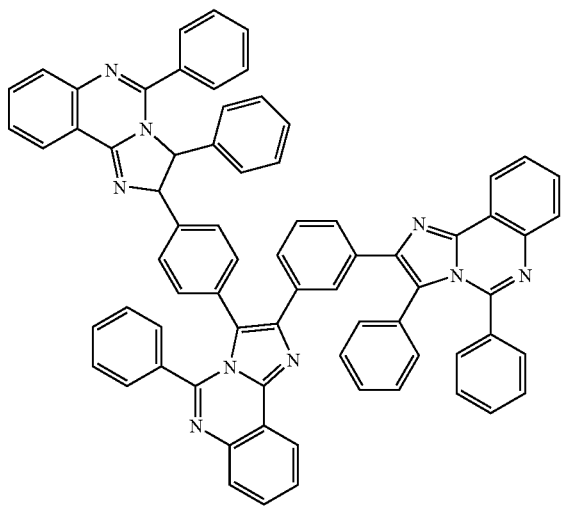
[compound 1-4-26]
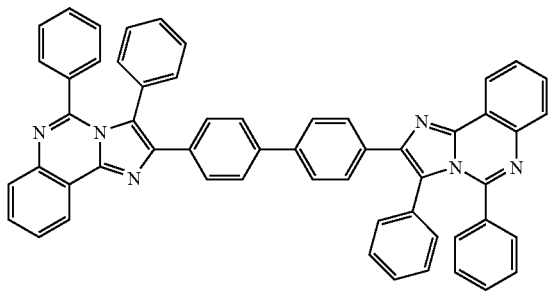
[compound 1-4-27]
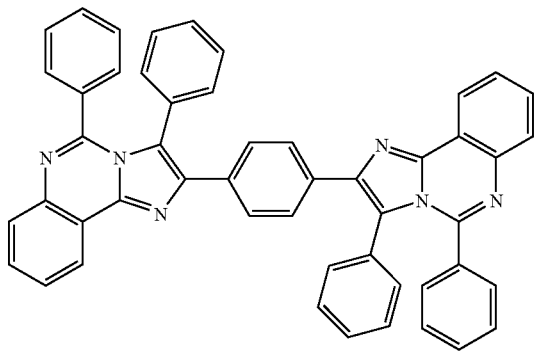
[compound 1-4-28]
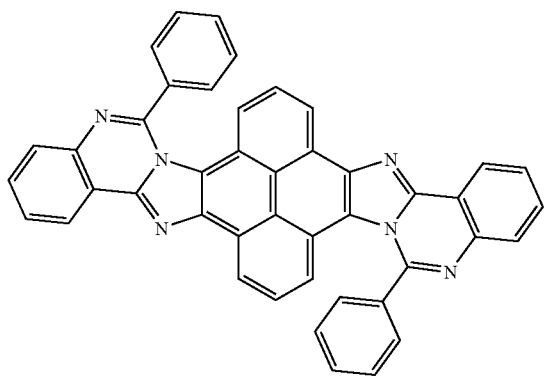
[compound 1-4-29]
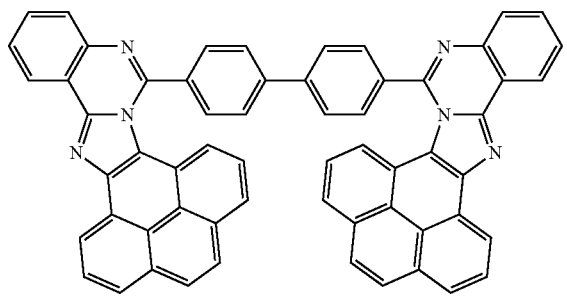

[compound 1-4-30]
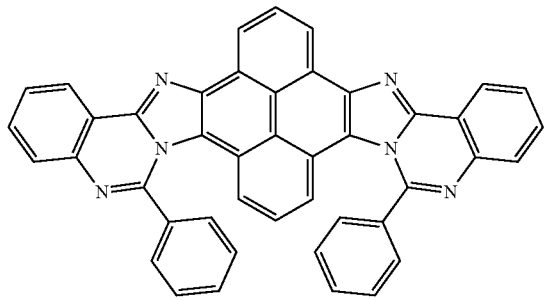
[compound 1-4-31]
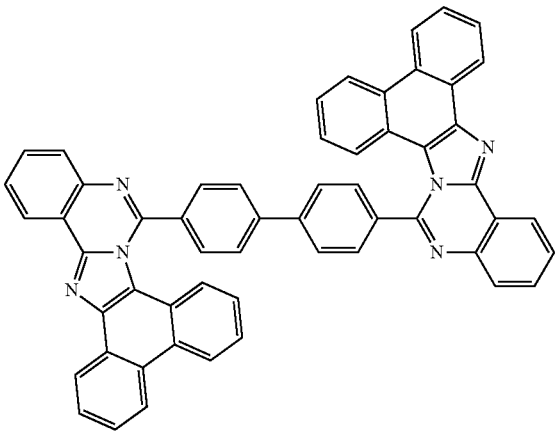
[compound 1-4-32]
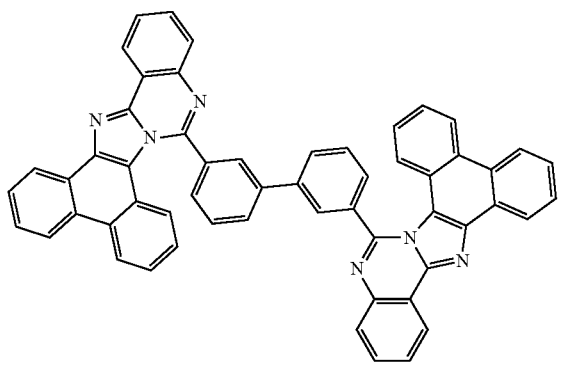
[compound 1-4-33]
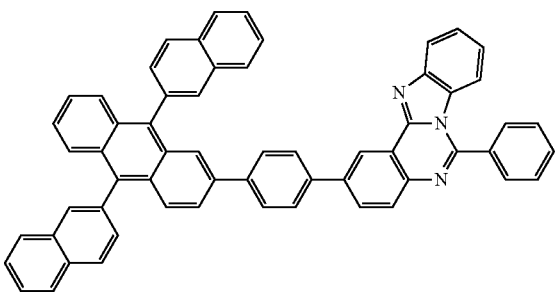
[compound 1-4-34]
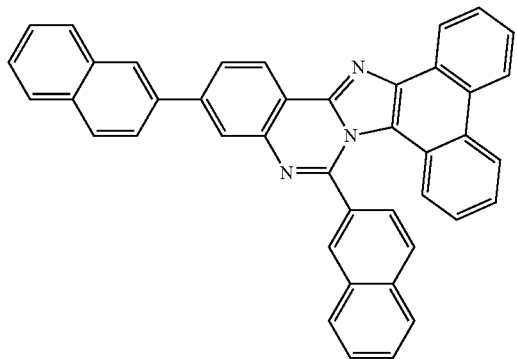
[compound 1-4-35]
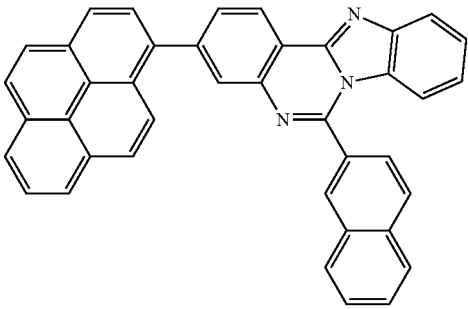

[compound 1-4-36]
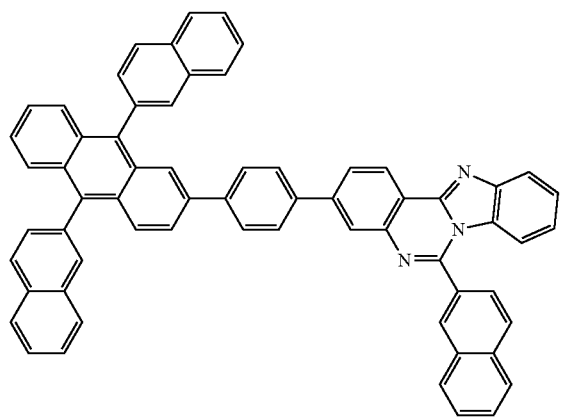
[compound 1-4-37]
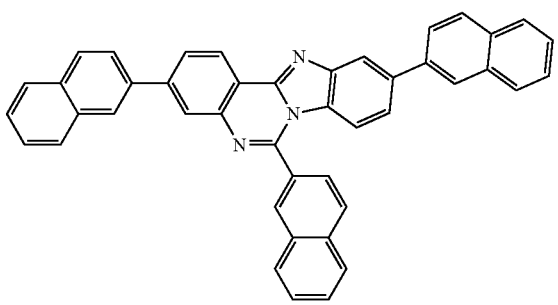
[compound 1-4-38]
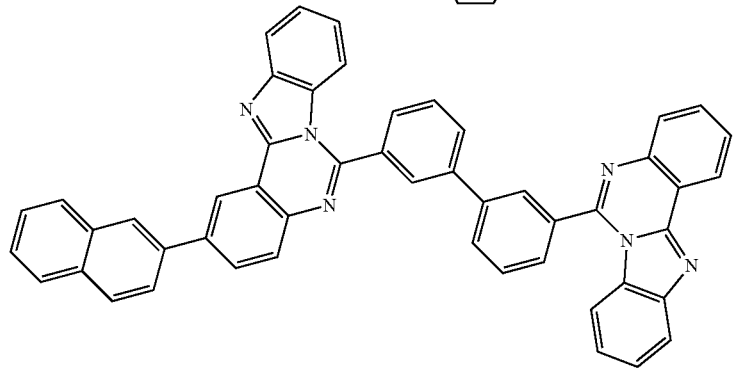
[compound 1-4-39]
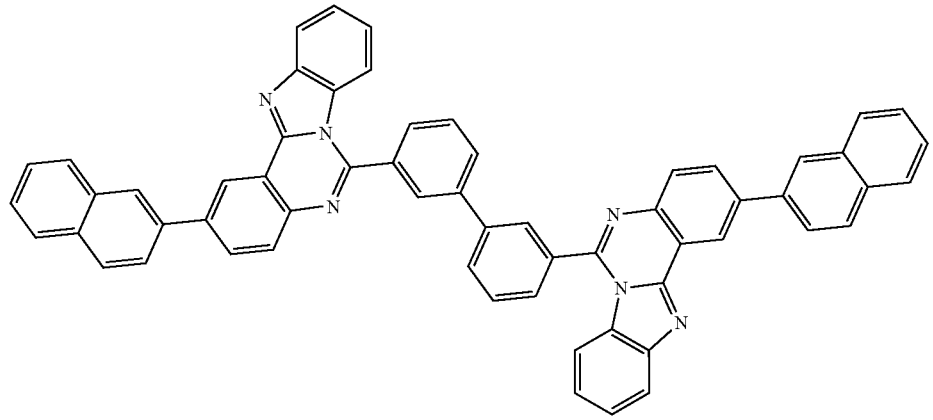
[compound 1-4-40]
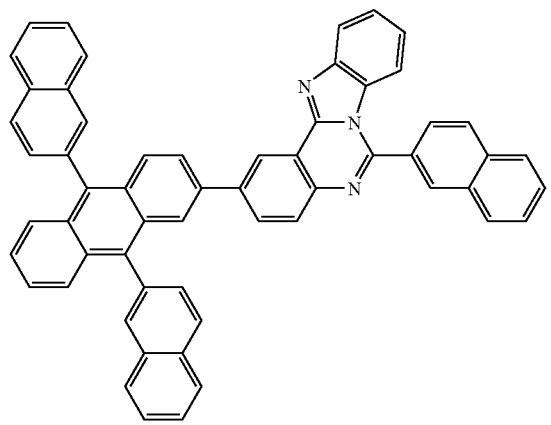
[compound 1-4-41]
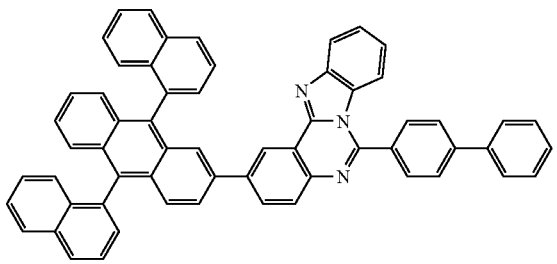

-continued
[compound 1-4-42]
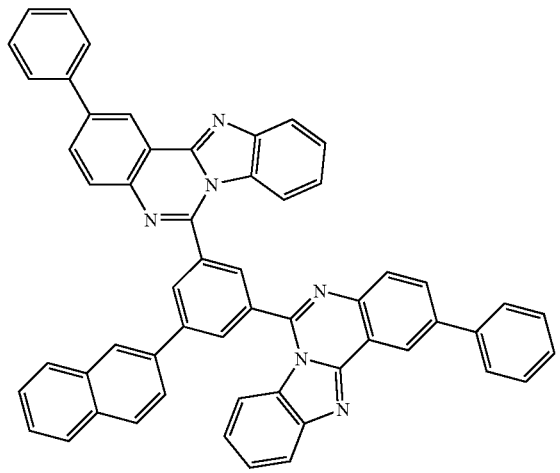
[compound 1-4-43]
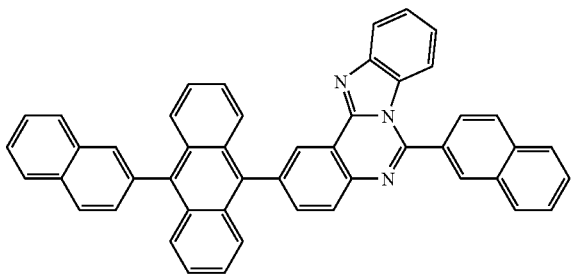
[compound 1-4-44]
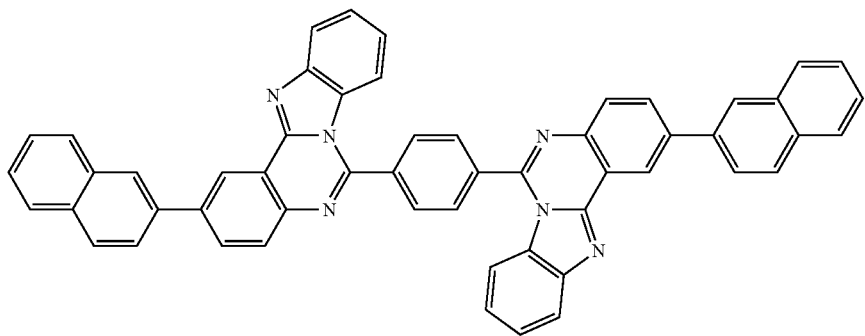
[compound 1-4-45]
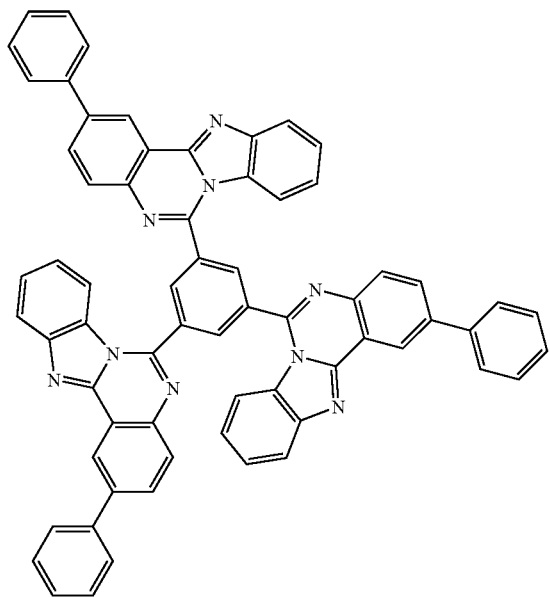
[compound A]
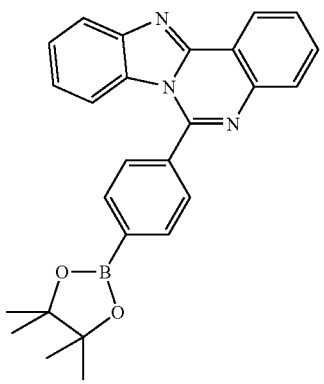

-continued

[compound B]

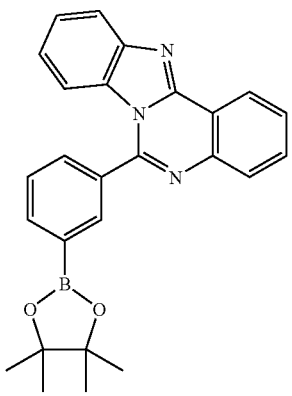

[compound D]

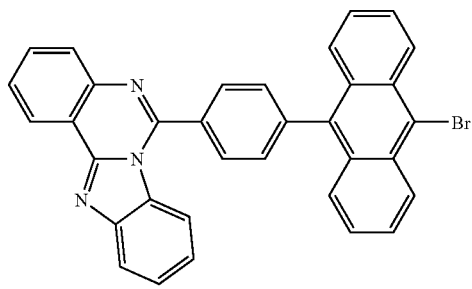

[compound E]

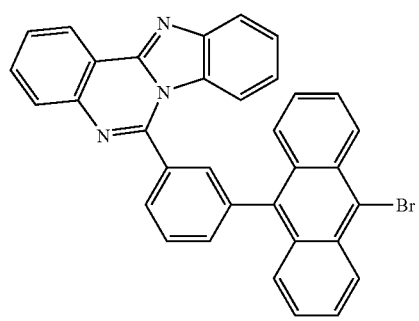

[compound M-1]

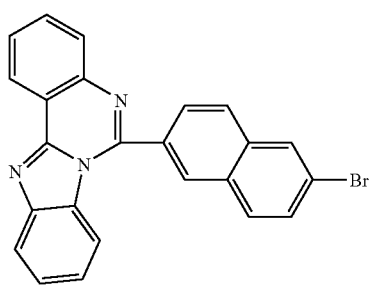

[compound M]

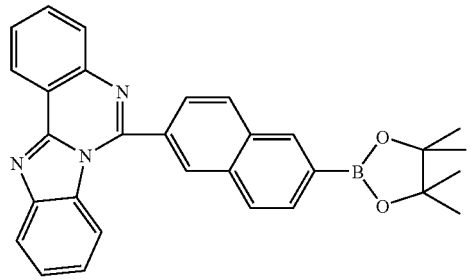

[compound F]

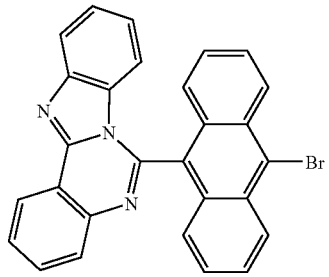

Further, the present invention provides a process for preparing the imidazoquinazoline derivative represented by the formula 1.

The process for preparing the imidazoquinazoline derivative according to the present invention can be carried out using the compound in which in the formula 1, R1 and R2 are not linked to the ring, and the compound in which in the formula 1, R1 and R2 are linked to the ring.

Firstly, in the case of the compound in which in the formula 1, R1 and R2 are not linked to the ring, the process for preparing the imidazoquinazoline derivative according to the present invention comprises the steps of:

1) reacting a 2-nitrobenzaldehyde compound (II) and a 1,2-diketone compound (III) with an ammonium acetate salt or formamide to prepare a 2-(2-nitrophenyl)imidazole derivative (IV), 2) subjecting the 2-(2-nitrophenyl)imidazole derivative (IV) as prepared in the step 1) to reaction using a palladium catalyst to prepare a 2-(2-aminophenyl)imidazole derivative (V), and 3) reacting 2-(2-aminophenyl)imidazole derivative (V) as prepared in the step 2) with an aldehyde compound (Ar1CHO) to prepare a compound (I), the process being represented by the following reaction scheme 1:

[Reaction Scheme 1]

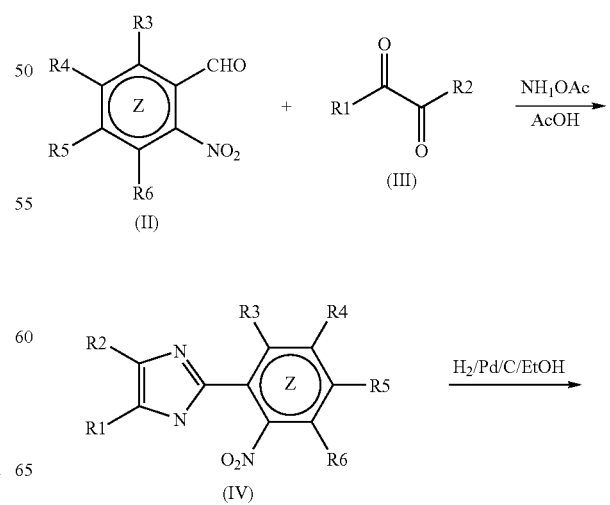

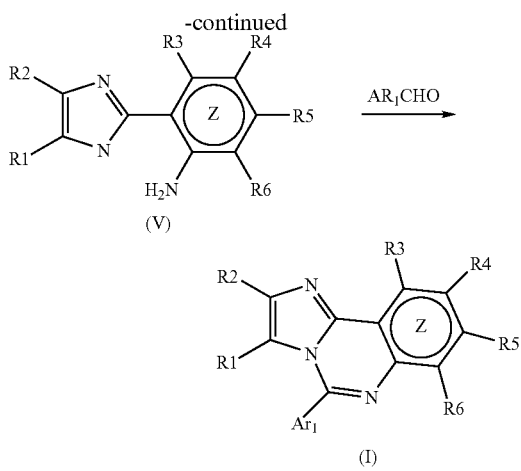

In the Reaction Scheme 1, R1 to R6, Ar1, and Z are each as defined in the formula 1.

Secondly, in the case of the compound in which in the formula 1, R1 and R2 are linked to the ring, the process for preparing the imidazoquinazoline derivative according to the present invention comprises the step of heating a 2-(2-aminophenyl)benzimidazole compound (VI) and an aldehyde compound (Ar1CHO) under stirring in an organic solvent to prepare a compound (I-1), and the process is represented by the following reaction scheme 2.

The organic solvent is preferably nitrobenzene or dimethylacetamide (DMAC), toluene, acetonitrile, acetic acid, ethanol, THF, or the like.

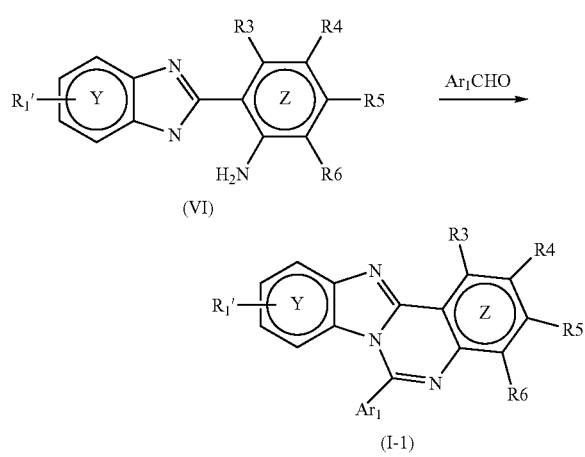

In the Reaction Scheme 2, R3 to R6, Ar1, and Z are each as defined in the formula 1, and R1_ is also same as defined for R1 in the formula 1.

The present invention also provides an organic electronic device using the imidazoquinazoline derivative of the formula 1.

The organic electronic device of the present invention can be prepared by a usual method and materials for preparing an organic electronic device, except that the above-described compounds are used to form at least one organic material layer.

Hereinbelow, the organic light emitting device will be exemplified.

The compound of the formula 1 can be used for an organic material layer in the organic light emitting device due to its structural specificity.

In one embodiment of the present invention, the organic light emitting device can have a structure comprising a first electrode, a second electrode, and an organic material layer interposed therebetween, and can be prepared by a usual method and materials for preparing an organic electronic device, except that the above-described compound according to the present inventions are used in at least one layer of the organic material layers in the organic light emitting device. The organic material layer in the organic light emitting device of the present invention may be a monolayer structure comprising a single layer, or a multilayer structure comprising two or more layers including a light emitting layer. If the organic material layer in the organic light emitting device of the present invention has a multilayer structure, it can has a structure in which a hole injecting layer, a hole transporting layer, a light emitting layer, an electron transporting layer, and the like are laminated. However, the structure of the organic light emitting device is not limited thereto, and it can further include a fewer number of organic materials layer. In such the multilayer structure of organic material layer, the compound of the formula 1 can be contained in a hole injecting and transporting layer, a hole transporting and light emitting layer, an electron transporting and light emitting layer, and the like.

For example, the structure of the organic light emitting device of the present invention can be those as shown FIGS. 1 to 4, but not limited thereto.

FIG. 1 illustrates a structure of an organic light emitting device in which an anode (102), a light emitting layer (105) and a cathode (107) are sequentially laminated on a substrate (101). In this structure, the compound of the formula 1 can be contained in the light emitting layer (105).

FIG. 2 illustrates a structure of an organic light emitting device in which an anode (102), a hole injecting/hole transporting, and light emitting layer (105), an electron transporting layer (106) and a cathode (107) are sequentially laminated on a substrate (101). In this structure, the compound of the formula 1 can be contained in the hole injecting/hole transporting, and light emitting layer (105).

FIG. 3 illustrates a structure of an organic light emitting device in which a substrate (101), an anode (102), a hole injecting layer (103), a hole transporting and light emitting layer (105), an electron transporting layer (106) and a cathode (107) are sequentially laminated. In this structure, the compound of the formula 1 can be contained in the hole injecting/hole transporting, and light emitting layer (105).

FIG. 4 illustrates a structure of an organic light emitting device in which a substrate (101), an anode (102), a hole injecting layer (103), a hole transporting layer (104), an electron transporting and light emitting layer (105) and a cathode (107) are sequentially laminated. In this structure, the compound of the formula 1 can be contained in the electron transporting and light emitting layer (105).

For example, the organic light emitting device according to the present invention can be prepared by depositing a metal, a metal oxide having conductivity or an alloy thereof on a substrate using a PVD (physical vapor deposition) process such as sputtering and e-beam evaporation to form an anode; forming an organic material layer comprising a hole injecting layer, a hole transporting layer, a light emitting layer and an electron transporting layer on the anode; and depositing a material, which can be used as a cathode, thereon. Alternatively, an organic light emitting device can be prepared by sequentially depositing a cathode material, an organic material layer, and an anode material on a substrate.

The organic material layer may be of a multilayer structure containing a hole injecting layer, a hole transporting layer, a light emitting layer, an electron transporting layer, and the like, but not limited thereto, and may be of a monolayer structure. Further, the organic material layer can be produced to have a fewer number of layers, by using a variety of polymeric materials, by means of a solvent process rather than a deposit process, such as spin coating, dip coating, doctor blading, screen printing, ink jet printing, and heat transfer processes.

The anode material is usually preferable which has a large work function to facilitate hole injection to an organic material layer. Specific examples of the anode material which can be used in the present invention include metals such as vanadium, chromium, copper, zinc and gold, or an alloy thereof; metal oxides such as zinc oxide, indium oxide, indium-tin oxide (ITO), and indium zinc oxide (IZO); a combination of a metal and an oxide such as ZnO:Al and $SnO_2$:Sb; conductive polymers such as poly(3-methylthiophene), poly[3,4-(ethylene-1,2-dioxy)thiophene] (PEDT), polypyrrole and polyaniline, but not limited thereto.

The cathode material is usually preferable which has a small work function to facilitate electron injection to an organic material layer. Specific examples of the cathode material include metals such as magnesium, calcium, sodium, potassium, titanium, indium, yttrium, lithium, gadolinium, aluminum, silver, tin and lead, or an alloy thereof; multilayer structure materials such as LiF/Al and $LiO_2$/Al, but not limited thereto.

The hole injecting material is preferable which facilitates hole injection from an anode at low voltage and of which the HOMO (highest occupied molecular orbital) is located between the work function of the anode materials and the HOMO level of its neighboring organic material layer. Specific examples of the hole injecting material include organic materials of metal porphyrin, oligothiophene and arylamine series, organic materials of hexanitrile hexaazatriphenylene and quinacridone series, organic materials of perylene series, and conductive polymers of anthraquinone, polyaniline, and polythiophene series, but are not limited thereto.

The hole transporting material is preferable which can transfer holes from the anode or the hole injecting layer toward the light emitting layer and has high hole mobility. Specific examples thereof include organic materials of arylamine series, conductive polymers and block copolymers having both conjugated portions and non-conjugated portions, but are not limited thereto.

The light emitting material is preferable which is capable of emitting visible light by accepting and recombining holes from the hole transporting layer and electrons from the electron transporting layer, and has high quantum efficiency for fluorescence and phosphorescence. Specific examples thereof include 8-hydroxyquinoline aluminum complex ($Alq_3$); compounds of carbazole series; dimerized styryl compounds; BAlq; 10-hydroxybenzoquinoline-metal compounds; compounds of benzoxazole, benzthiazole and benzimidazole series; polymers of poly(p-phenylenevinylene) (PPV) series; spiro compounds; and compounds of polyfluorene and rubrene series, but are not limited thereto.

The electron transporting material is suitably a material having high electron mobility, which can transfer electrons from the cathode to the light emitting layer. Specific examples thereof include an Al complex of a 8-hydroxyquinoline; complexes including $Alq_3$; organic radical compounds; and hydroxyflavone-metal complexes, but are not limited thereto.

The organic light emitting device according to the invention may be of a front-side, back-side or double-sided light emission according to the materials used.

The compound according to the invention can function in an organic electronic device including an organic solar cell, an organic photoconductor and an organic transistor, according to a principle similar to that applied to the organic light emitting device.

MODE FOR INVENTION

Hereinafter, preferable Examples are provided for the purpose of making the present invention more understandable. As such, Examples are provided for illustrating the Examples, but the scope of the invention is not limited thereto.

PREPARATION EXAMPLE 1

Preparation of Compound A 1-1. Preparation of Compound A-1

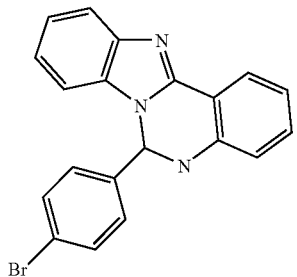

2-(2-aminophenyl)benzimidazole (4.18 g, 20.0 mmol) and 4-bromobenzaldehyde (4.07 g, 22.0 mmol) are dissolved in 50 mL of nitrobenzene, and then the solution was heated under stirring for 20 hours. The reaction temperature was cooled to room temperature, and filtered to obtain a yellow solid, and the solid was washed with ethylether and dried to prepare a compound A-1 (5.1 g, yield 67.8%).
MS $[M+H]^+$=376

1-2. Preparation of Compound A-2

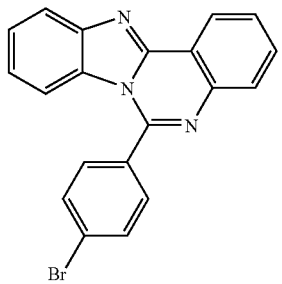

To the compound A-1 (5.1 g, 13.6 mmol) as prepared in the 1-1 step, were added $KMnO_4$ (2.3 g, 0.15 mmol) and 100 mL of THF, and the mixture was stirred at normal temperature for 12 hours. The reaction solution was filtered with Celite to remove a solid compound. To the resultant, were added 100 mL of $H_2O$ and 50 mL of ethylether, and an organic material layer was separated out and dried over anhydrous magnesium sulfate. The organic solvent was distilled off in vacuo to obtain a solid, and the solid was washed with ethanol, filtered and dried to prepare a compound A-2 (4.5 g, yield 89%).

MS [M+H]$^+$=374

1-3. Preparation of Compound A

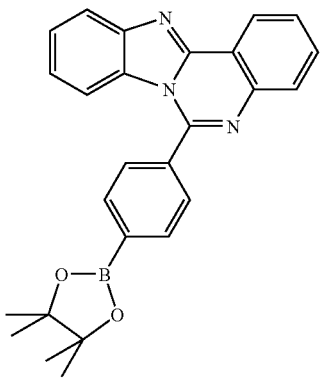

The compound A-2 (4.5 g, 12.0 mmol) as prepared in Preparation Example 1-2, bis(pinacolato)diboron (3.66 g, 14.4 mmol) and potassium acetate (3.54 g, 36 mmol) were suspended in dioxane (100 mL). To the suspension, was added palladium(diphenyl phosphinoferrocene)chloride (0.29 g, 3 mol). The mixture was stirred at 80 for about 8 hours, and then cooled to room temperature. The mixture was diluted with water (100 mL), and extracted by dichloromethane (3×50 mL). The organic extract was dried over magnesium sulfate, and concentrated in vacuo. The resultant was crystallized from ethylether and hexane, dried and filtered to prepare a compound A (3.13 g, 92).

MS [M+H]$^+$=422

PREPARATION EXAMPLE 2

Preparation of Compound B 2-1. Preparation of Compound B-1

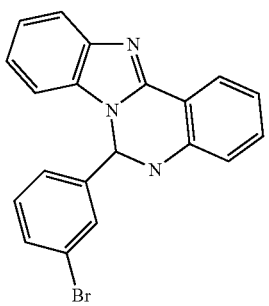

A compound B-1 was prepared in the same manner as in Preparation Example 1-1, except that in Preparation Example 1-1,3-bromobenzaldehyde was used instead of 4-bromobenzaldehyde.

MS [M+H]$^+$=376

2-2. Preparation of Compound B-2

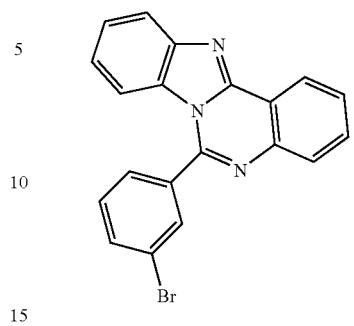

A compound B-2 was prepared in the same manner as in Preparation Example 1-2, except that in Preparation Example 1-2, the compound B-1 as prepared in the 2-1 step was used instead of the compound A-1.

MS [M+H]$^+$=374

2-3. Preparation of Compound B

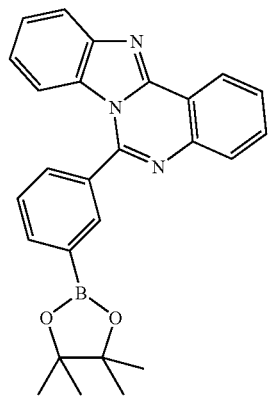

A compound B was prepared in the same manner as in Preparation Example 1-3, except that in Preparation Example 1-3, the compound B-2 as prepared in the 2-2 step was used instead of the compound A-2.

MS [M+H]$^+$=422

PREPARATION EXAMPLE 3

Preparation of Compound C 3-1. Preparation of Compound C-1

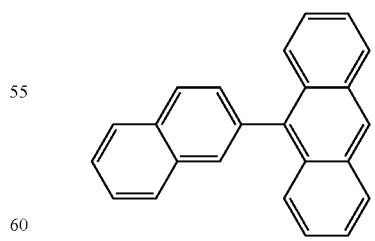

9-Bromoanthracene (2.57 g, 10.00 mmol), 2-naphthyl boric acid (1.80 g, 12.65 mmol) and sodium carbonate (2.34 g, 22.1 mmol) were suspended in a mixture of toluene (20 mL), ethanol (3 mL) and water (10 mL). To the suspension, was added tetrakis(triphenylphosphine)palladium (0.25 g, 0.22 mmol). The mixture was stirred under reflux for about 24 hours, and then the refluxed mixture was cooled to room temperature. The organic layer was separated and washed with water, and the aqueous layer was extracted by chloroform. The organic extract was dried over magnesium sulfate, and concentrated in vacuo to prepare a 9-(2-naphthyl)anthracene compound C-1 (2.55 g, yield 84).

MS [M+H]$^+$=305

3-2. Preparation of Compound C

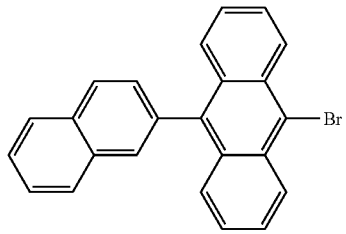

To a solution of 9-(2-naphthyl)anthracene (1.89 g, 6.24 mmol) as prepared in the 3-1 step in dry CCl$_4$ (60 ml), was added dropwise bromine (0.32 mL, 6.24 mmol) at 0. The reaction mixture was stirred at room temperature for about 3 hours, and saturated sodium bicarbonate solution was added thereto. The organic layer was separated, and the aqueous layer was extracted by chloroform. The combined organic extract was dried over magnesium sulfate, and concentrated in vacuo. The resultant was purified by column chromatography (THF/hexane=1/4), and recrystallized from ethanol to prepare a 9-bromo-10-(2-naphthyl)anthracene compound C (1.08 g, yield 45).

MS [M+H]$^+$=383

PREPARATION EXAMPLE 4

Preparation of Compound D 4-1. Preparation of Compound D-1

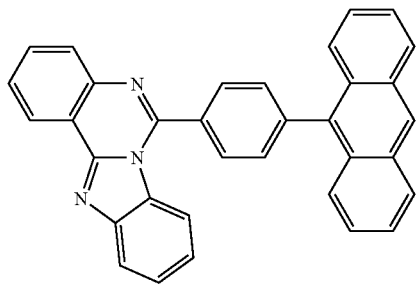

A compound D-1 was prepared in the same manner as in Preparation Example 3-1, except that in Preparation Example 3-1, the compound A as prepared in 1-3 was used instead of 2-naphthyl boric acid.

MS [M+H]$^+$=472

4-2. Preparation of Compound D

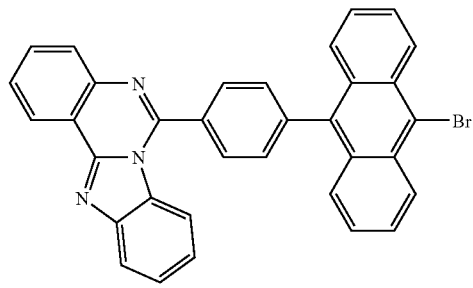

To the compound D-1 (4.7 g, 9.97 mmol) as prepared in the 4-1, was added 80 mL of DMF, the mixture was stirred, and at normal temperature, NBS (N-bromosuccinimide, 1.95 g, 10.96 mmol) was added dropwise at normal temperature. The reaction mixture was stirred at room temperature for about 3 hours, and the resulting white solid was filtered, washed with water and ethanol, and dried to prepare a compound D (3.6 g, yield 64).

MS [M+H]$^+$=550

PREPARATION EXAMPLE 5

Preparation of Compound E 5-1. Preparation of Compound E-1

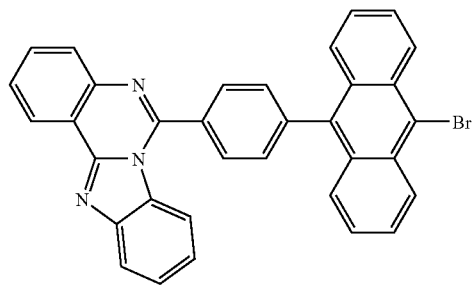

A compound E-1 was prepared in the same manner as in Preparation Example 3-1, except that in Preparation Example 3-1, the compound B as prepared in 2-3 was used instead of 2-naphthyl boric acid.

MS [M+H]$^+$=472

5-2. Preparation of Compound E

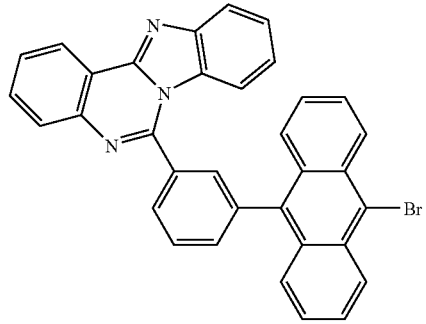

To the compound E-1 (4.7 g, 9.97 mmol) as prepared in the 5-1 step, 80 mL of DMF was added, the mixture was stirred at normal temperature, and NBS (N-bromosuccinimide, 1.95 g, 10.96 mmol) was added thereto. The reaction mixture was stirred at room temperature for about 3 hours, and the resulting white solid was filtered, washed with water and ethanol, and dried to prepare a compound E (4.2 g, yield 76.5).
MS [M+H]$^+$=550

PREPARATION EXAMPLE 6

Preparation of Compound F 6-1. Preparation of Compound F-1

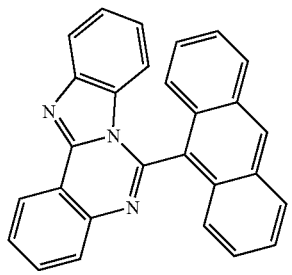

A compound F-1 was prepared in the same manner as in Preparation Example 1-1, except that in Preparation Example 1-1, 9-anthracenecarboxaldehyde was used instead of 4-bromobenzaldehyde.
MS [M+H]$^+$=396

6-2. Preparation of Compound F

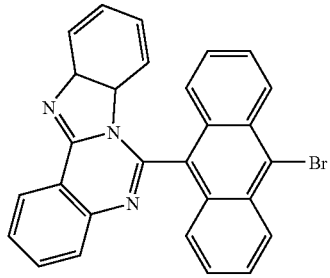

A compound F was prepared in the same manner as in Preparation Example 4-2, except that in Preparation Example 4-2, the compound F-1 as prepared in Preparation Example 6-1 was used instead of the compound D-1.
MS [M+H]$^+$=474

PREPARATION EXAMPLE 7

Preparation of Compound G

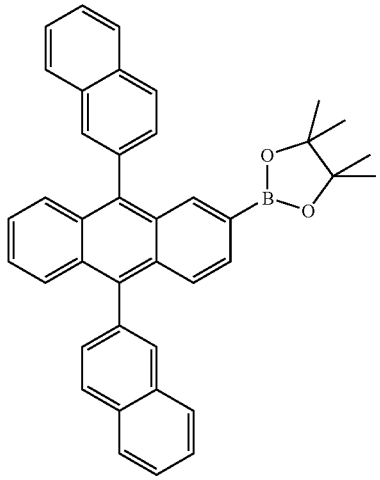

2-bromo-9,10-dinaphthyl anthracene (5.00 g, 9.82 mmol), bis(pinacolato)diboron (2.75 g, 10.9 mmol) and potassium acetate (2.89 g, 29.4 mmol) were suspended in dioxane (50 mL). To the suspension, was added palladium(diphenyl phosphinoferrocene)chloride (0.24 g, 3 mol). The mixture was stirred at 80 for about 6 hours, and then cooled to room temperature. The mixture was diluted with water (50 mL), and extracted by dichloromethane (3×50 mL). The organic extract was dried over magnesium sulfate, and concentrated in vacuo. The product was washed with ethanol, and dried in vacuo to prepare a 9,10-dinaphthyl anthracenyl-2-boronate compound G (5.46 g, 92).

MS [M+H]$^+$=557

PREPARATION EXAMPLE 8

Preparation of Compound H 8-1. Preparation of Compound H-1

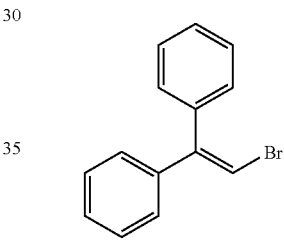

A solution of diphenyl ethylene (7.8 g, 43.3 mmol) in 100 mL of CCl$_4$ was maintained at −15, and then bromine (Br$_2$, 2.45 mL, 47.6 mmol) was slowly added dropwise. 10 g of the well-dried silica gel was added to the reaction product, and then the mixture was stirred at 80 for 1 hour. The reaction product was cooled to normal temperature, and then purified by column chromatography to prepare a compound H-1 (10.7 g, yield 95) having a bromo group introduced thereto.

MS: [M+H]$^+$=259

8-2. Preparation of Compound H

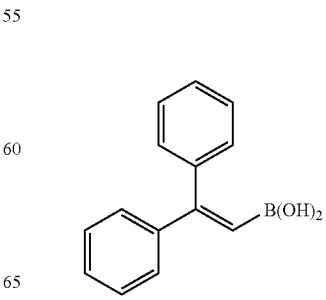

To a solution of the compound H-1 (10.7 g, 41.3 mmol) as prepared in Preparation Example 8-1 in dry THF (50 mL), was added dropwise n-BuLi (61.9 mmol, in 24.8 mL of a 2.5 M hexane solution) at −78 under nitrogen atmosphere. The mixture was stirred about 1 hours, and to the mixture was added dropwise trimethylborate (14 mL, 123.9 mmol) at −78. After about 30 minutes, the cooling vessel was removed, and the mixture was stirred at room temperature for about 3 hours. To the mixture, was added 1 N HCl (200 mL), and the resultant was extracted by ethyl acetate. The organic material layer was dried over magnesium sulfate, and concentrated in vacuo. A crude product was slurrified in petroleum ether, suction-filtered, and dried to prepare a compound H (4.0 g, yield 43).

PREPARATION EXAMPLE 9

Preparation of Compound I 9-1. Preparation of Compound I-1

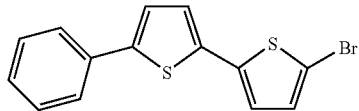

5,5'-Dibromo-2,2'-dithiophene (5.00 g, 15.4 mmol), phenyl boronic acid (2.07 g, 17.0 mmol) and sodium carbonate (4.90 g, 46.3 mmol) were suspended in a mixture of toluene (30 mL) and water (15 mL). To the suspension, was added tetrakis(triphenylphosphine)palladium (0.50 g, 0.46 mmol). The mixture was stirred under reflux for about 24 hours. The refluxed mixture was cooled to room temperature, and extracted by chloroform. The organic extract was dried over magnesium sulfate, and concentrated in vacuo. The resultant was purified by column chromatography (n-hexane) to prepare a compound I-1 (2.80 g, yield 56.6%).

MS: $[M+H]^+=321$ 9-2. Preparation of Compound I

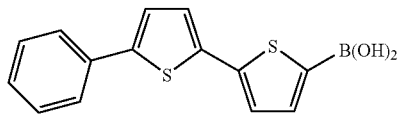

A compound I was prepared in the same manner as in Preparation Example 8-2, except that in Preparation Example 8-2, the compound I-1 as prepared in Preparation Example 9-1 was used instead of the compound H-1.

PREPARATION EXAMPLE 10

Preparation of Compound J 10-1. Preparation of Compound J-1

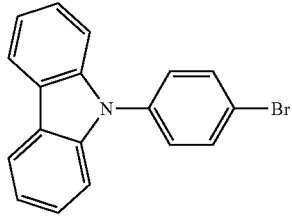

Carbazole (3.3 g, 20 mmol), 1-bromo-4-iodobenzene (3.0 mL, 24 mmol), potassium carbonate ($K_2CO_3$, 5.6 g, 40 mmol), copper iodide (CuI, 1.9 g, 1.0 mmol), and 50 mL of xylene were refluxed under nitrogen atmosphere. The resultant was cooled to normal temperature, and the product was extracted by ethyl acetate, the moisture was removed over anhydrous magnesium sulfate ($MgSO_4$), and the solvent was removed under reduced pressure. The resultant was passed through as silica gel using a hexane solvent to obtain a compound, and the solvent was removed under reduced pressure. The resultant was dried in vacuo to prepare a white solid compound J-1 (1.6 g, 25% yield).

MS: $[M+H]^+=322$.

10-2. Preparation of Compound J

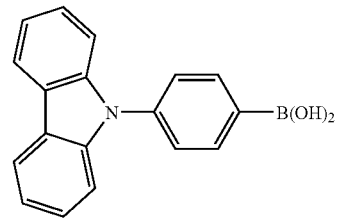

A compound J was prepared in the same manner as in Preparation Example 8-2, except that in Preparation Example 8-2, the compound J-1 as prepared in Preparation Example 10-1 was used instead of the compound H-1.

PREPARATION EXAMPLE 11

Preparation of Compound K 11-1. Preparation of Compound K-1

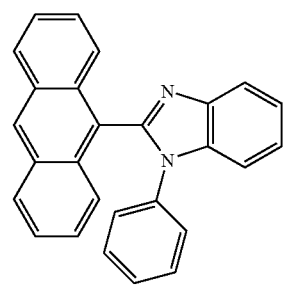

9-Anthracenecarboxaldehyde (3.3 g, 15.9 mmol) and N-phenyl-1,2-diaminobenzene (2.93 g, 15.9 mmol) were added to a mixed solution of 60 mL of toluene and 20 ml of acetic acid. The mixture was stirred at 160° C. for 12 hours, and cooled to normal temperature. The solvent was distilled off in vacuo, and the resultant was purified by column chromatography to prepare a compound K-1 (4.6 g, yield 78%).

MS: $[M+H]^+=371$

11-2. Preparation of Compound K

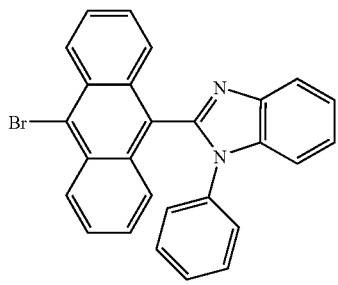

A compound K was prepared in the same manner as in Preparation Example 4-2, except that in Preparation Example 4-2, the compound K-1 as prepared in Preparation Example 11-1 was used instead of the compound D-1.

MS: [M+H]$^+$=449

PREPARATION EXAMPLE 12

Preparation of Compound L

12-1. Preparation of Compound L-1

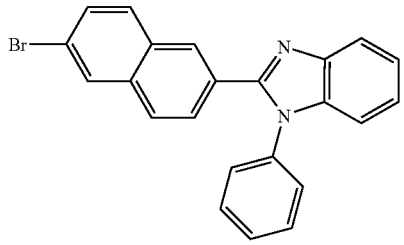

To 6-bromo-2-naphthoic acid (5.0 g, 20 mmol), were added 20 mL of thionyl chloride (SOCl$_2$), and dimethylformamide (DMF, 1 mL), and the mixture was heated under stirring for 4 hours. An excessive amount of thionyl chloride (SOCl$_2$) is distilled off in vacuo, and to the reaction mixture, were added 20 mL of N-methylpyrrolidine (NMP), and N-phenyl-1,2-diamino benzene (3.7 g, 20 mmol). The mixture was stirred at 160° C. for 12 hours, and cooled to normal temperature, and an excessive amount of water was added thereto to form a solid. The solid was filtered, washed with water and then ethanol, and dried to prepare a compound L-1 (6.2 g, yield 78%).

MS [M+H]$^+$=399

12-2. Preparation of Compound L-2

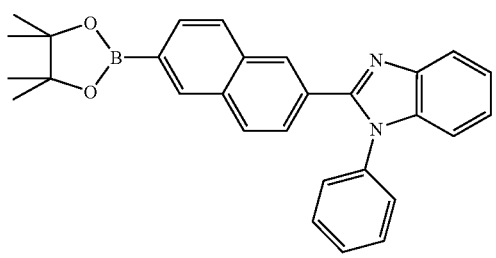

A compound L-2 was prepared in the same manner as in Preparation Example 7, except that in Preparation Example 7, the compound L-1 as prepared in Preparation Example 12-1 was used instead of 2-bromo-9,10-dinaphthyl anthracene.

MS [M+H]$^+$=446

12-3. Preparation of Compound L-3

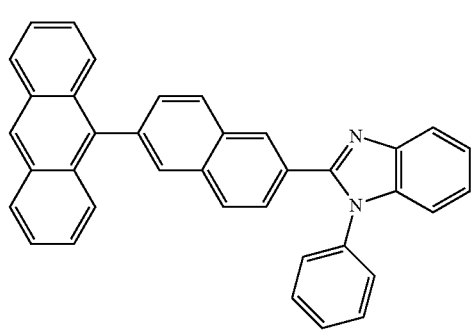

A compound L-3 was prepared in the same manner as in Preparation Example 3-1, except that in Preparation Example 3-1, the compound L-2 as prepared in Preparation Example 12-2 was used instead of 2-naphthyl boric acid.

MS [M+H]$^+$=497

12-4. Preparation of Compound L

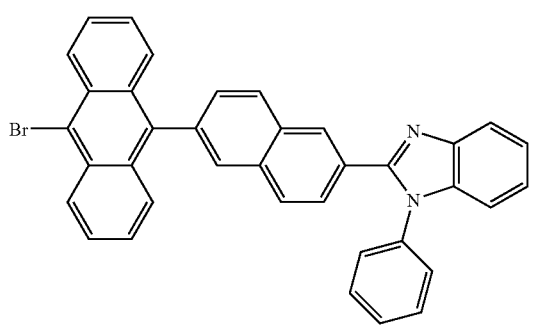

A compound L was prepared in the same manner as in Preparation Example 4-2, except that in Preparation Example 4-2, the compound L-3 as prepared in Preparation Example 12-3 was used instead of the compound D-1.

MS [M+H]$^+$=575

PREPARATION EXAMPLE 13

Preparation of Compound M

13-1. Preparation of Compound M-1

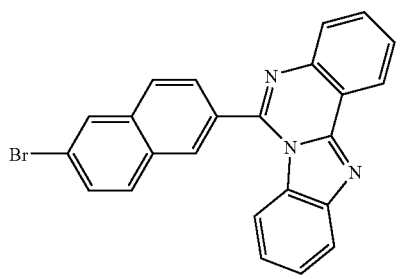

A compound M-1 was prepared in the same manner as in Preparation Example 1-1, except that in Preparation Example 1-1, 2-bromo-6-naphthaldehyde was used instead of 4-bromobenzaldehyde.

MS [M+H]$^+$=424

13-2. Preparation of Compound M

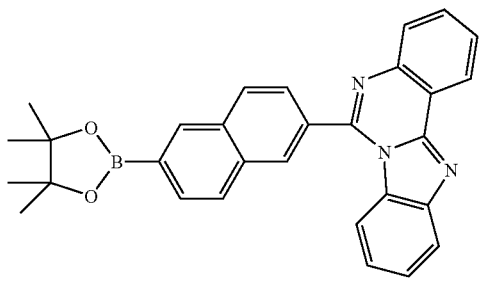

A compound M was prepared in the same manner as in Preparation Example 1-3, except that in Preparation Example 1-3, the compound M-1 as prepared in the 13-1 step was used instead of the compound A-2.

MS [M+H]$^+$=472

EXAMPLE 1

Preparation of Compound 1-2-24

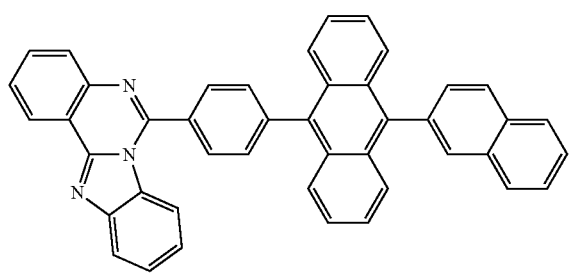

9-Bromo-10-(2-naphthyl)anthracene compound (3.83 g, 10 mmol), the compound A (5.06 g, 12 mmol) as prepared in Preparation Example 1, and sodium carbonate (2.76 g, 20 mmol) were suspended in a mixture of tetrahydrofuran (120 mL) and water (50 mL). Tetrakis(triphenylphosphine)palladium (0.06 g, 0.05 mmol) was added to the suspension. The mixture was stirred under reflux for about 24 hours, and then cooled to room temperature. The organic layer was separated, and the aqueous layer was extracted by tetrahydrofuran. The combined organic extract was dried over magnesium sulfate, and concentrated in vacuo. The resultant was purified with THF/EtOH to prepare a compound 1-2-24 (4.0 g, yield 67%).

MS [M+H]$^+$=598

EXAMPLE 2

Preparation of Compound 1-2-25

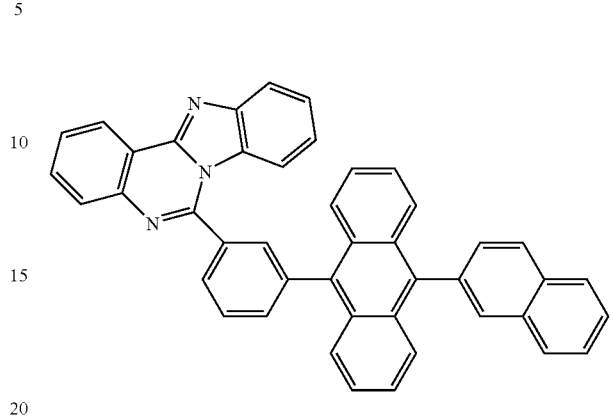

A compound 1-2-25 (1.9 g, yield 61%) was prepared in the same manner as in Example 1, except that in the preparation method of Example 1, 9-Bromo-10-(2-naphthyl)anthracene compound (3.83 g, 10 mmol) and the compound B (4.2 g, 10 mmol) as prepared in Preparation Example 2 instead of the compound A as prepared in Preparation Example 1 were used.

MS [M+H]$^+$=598

EXAMPLE 3

Preparation of Compound 1-2-62

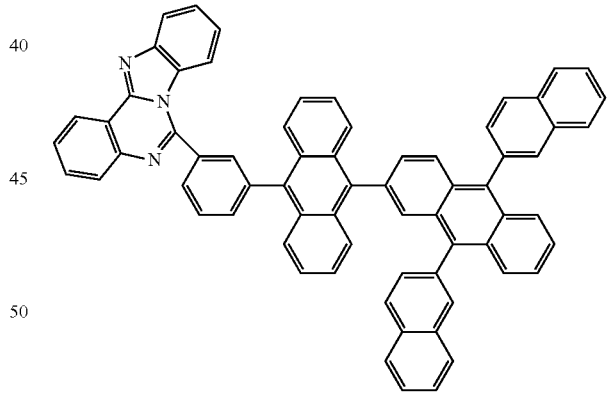

The compound E (3.00 g, 5.4 mmol) as prepared in Preparation Example 5, the compound G (3.3 g, 5.9 mmol) as prepared in Preparation Example 7, and sodium carbonate (1.5 g, 10.8 mmol) were suspended in a mixture of tetrahydrofuran (70 mL) and water (30 mL). To the suspension, was added tetrakis(triphenylphosphine)palladium (0.03 g, 0.025 mmol). The mixture was stirred under reflux for about 24 hours, and then the refluxed mixture was cooled to room temperature. The organic layer was separated, and the aqueous layer was extracted by tetrahydrofuran. The organic extract was dried over magnesium sulfate, concentrated in vacuo, and purified with THF/EtOH to prepare a compound 1-2-62 (2.4 g, yield 49%).

MS [M+H]⁺=900

EXAMPLE 4

Preparation of Compound 1-1-41

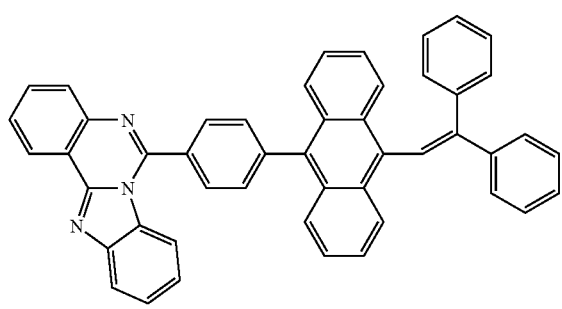

A compound 1-1-41 (2.35 g, yield 67%) was prepared in the same manner as in Example 3, except that in the preparation method of Example 3, the compound E (3.00 g, 5.4 mmol) as prepared in Preparation Example 5 and the compound H (1.8 g, 8.1 mmol) as prepared in Preparation Example 8 instead of the compound G as prepared in Preparation Example 7 were used.

MS [M+H]⁺=650

EXAMPLE 5

Preparation of Compound 1-2-68

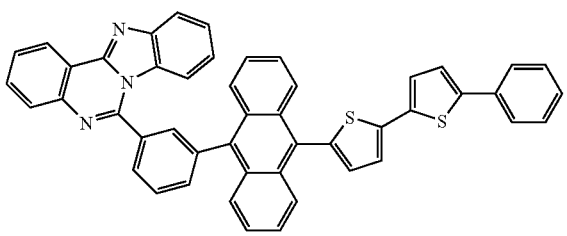

A compound 1-2-68 (1.8 g, yield 47%) was prepared in the same manner as in Example 3, except that in the preparation method of Example 3, the compound E (3.00 g, 5.4 mmol) as prepared in Preparation Example 5 and the compound 1 (2.3 g, 8.1 mmol) as prepared in Preparation Example 9 instead of the compound G as prepared in Preparation Example 7 was used.

MS [M+H]⁺=712

EXAMPLE 6

Preparation of Compound 1-1-2

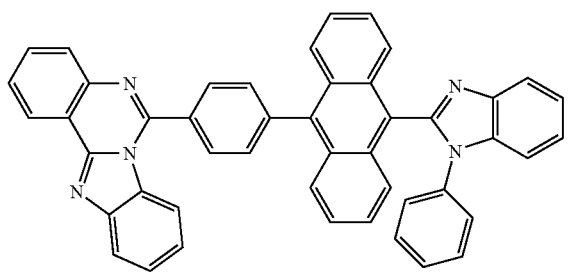

A compound 1-1-2 (5.8 g, yield 87%) was prepared in the same manner as in Example 1, except that in the preparation method of Example 1, the compound A (4.2 g, 10.0 mmol) as prepared in Preparation Example 1 and the compound K (4.5 g, 10.0 mmol) as prepared in Preparation Example 11 were used.

MS [M+H]⁺=664

EXAMPLE 7

Preparation of Compound 1-1-15

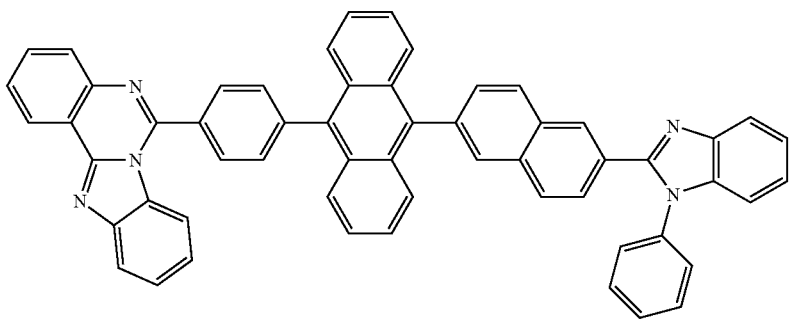

A compound 1-1-15 (5.8 g, yield 87%) was prepared in the same manner as in Example 1, except that in the preparation method of Example 1, the compound A (4.2 g, 10.0 mmol) as prepared in Preparation Example 1 and the compound L (5.7 g, 10.0 mmol) as prepared in Preparation Example 12 were used.

MS [M+H]$^+$=790

EXAMPLE 8

Preparation of Compound 1-2-35

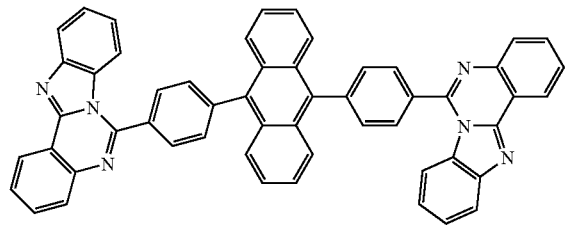

9,10-Dibromoanthracene compound (3.36 g, 10.00 mmol), the compound A (9.92 g, 23.56 mmol) as prepared in Preparation Example 1, and sodium carbonate (5.4 g, 39.28 mmol) were suspended in a mixture of tetrahydrofuran (120 mL) and water (50 mL). To the suspension, was added tetrakis(triphenylphosphine)palladium (0.06 g, 0.05 mmol). The mixture was stirred under reflux for about 18 hours, and then cooled to room temperature. The formed solid was filtered, dried, and then purified by column chromatography to prepare a compound 1-2-35 (3.9 g, yield 51%).

MS [M+H]$^+$=765

EXAMPLE 9

Preparation of Compound 1-2-36

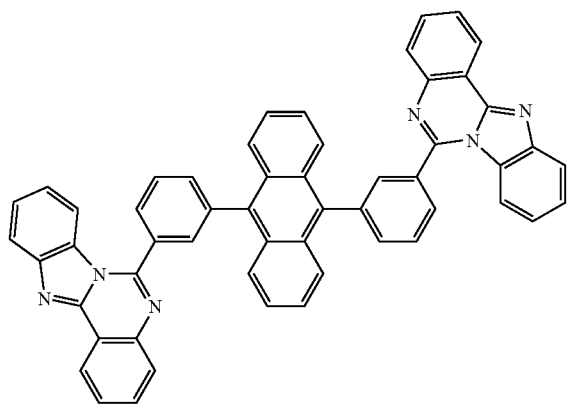

A compound 1-2-36 (4.3 g, yield 56%) was prepared in the same manner as in Example 8, except that in the preparation method of Example 8, the compound B (4.2 g, 10.0 mmol) as prepared in Preparation Example 2 was used instead of the compound A as prepared in Preparation Example 1.

MS [M+H]$^+$=765

EXAMPLE 10

Preparation of Compound 1-2-37

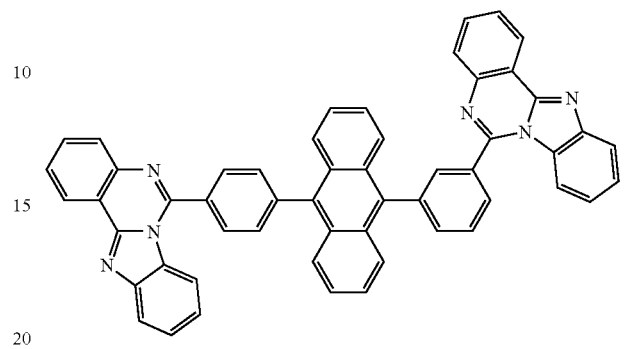

A compound 1-2-37 (6.0 g, yield 78%) was prepared in the same manner as in Example 1, except that in the preparation method of Example 1, the compound A (4.2 g, 10.0 mmol) as prepared in Preparation Example 1 and the compound E (5.5 g, 10.0 mmol) as prepared in Preparation Example 5 were used.

MS [M+H]$^+$=765

EXAMPLE 11

Preparation of Compound 1-2-34

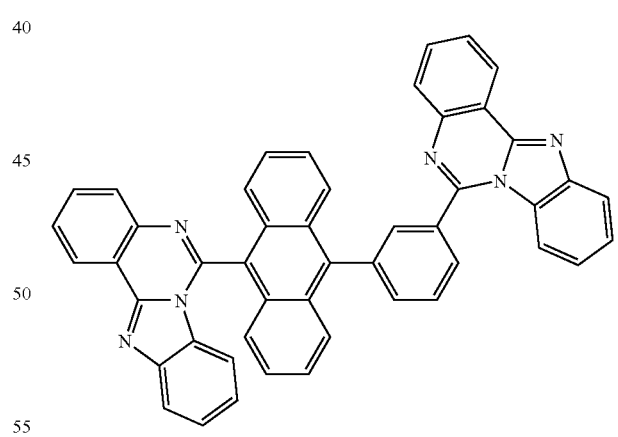

A compound 1-2-34 (4.5 g, yield 65%) was prepared in the same manner as in Example 1, except that in the preparation method of Example 1, the compound F (4.7 g, 10.0 mmol) as prepared in Preparation Example 6 and the compound B (4.2 g, 10.0 mmol) as prepared in Preparation Example 2 were used respectively instead of the 9-bromo-10-(2-naphthyl)anthracene compound and the compound A as prepared in Preparation Example 1.

MS [M+H]$^+$=689

EXAMPLE 12

Preparation of Compound 1-3-26

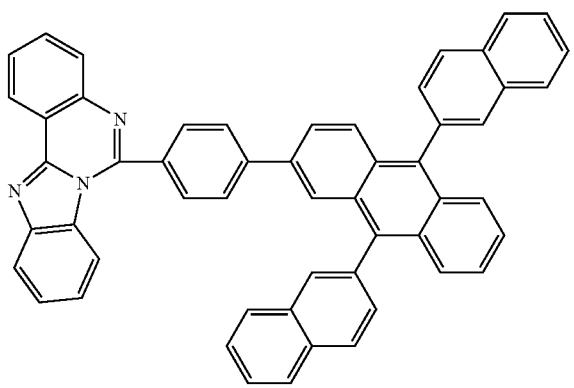

2-Bromo-9,10-di(2-naphthyl)anthracene compound (5.00 g, 9.82 mmol), the compound A (4.96 g, 11.78 mmol) as prepared in Preparation Example 1, and sodium carbonate (2.7 g, 19.64 mmol) were suspended in a mixture of tetrahydrofuran (120 mL), and water (50 mL). To the suspension, was added tetrakis(triphenylphosphine)palladium (0.06 g, 0.05 mmol). The mixture was stirred under reflux for about 24 hours, and then cooled to room temperature. The organic layer was separated, and the aqueous layer was extracted by tetrahydrofuran. The combined organic extract was dried over magnesium sulfate, and concentrated in vacuo. The resultant was purified with THF/EtOH to prepare a compound 1-3-26 (4.9 g, yield 68.9%).

MS $[M+H]^+=724$

EXAMPLE 13

Preparation of Compound 1-3-27

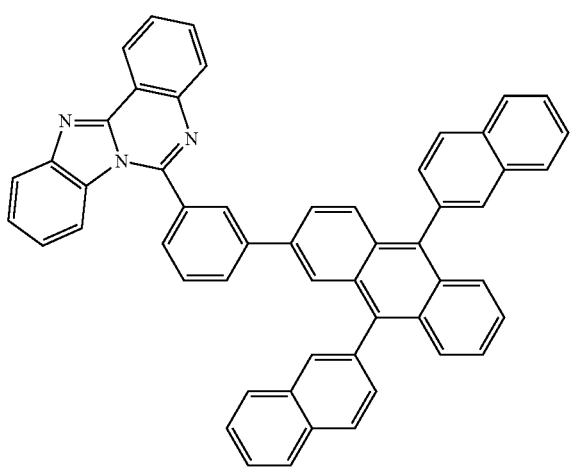

A compound 1-3-27 (5.2 g, yield 72%) was prepared in the same manner as in Example 12, except that in Example 12, the compound B (4.2 g, 10.0 mmol) as prepared in Preparation Example 2 were used instead of the compound A.

MS $[M+H]^+=724$

EXAMPLE 14

Preparation of Compound 1-3-32

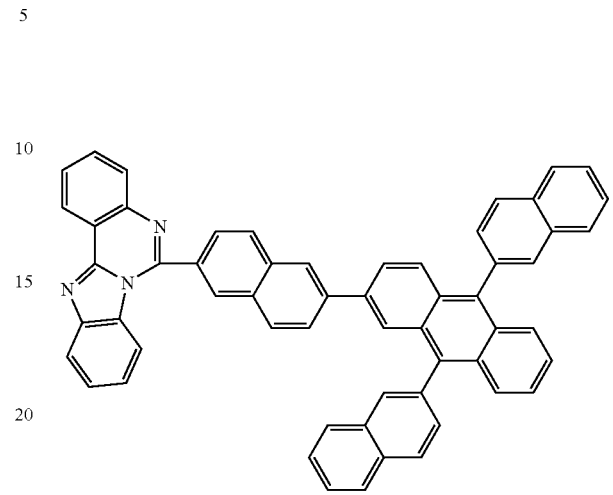

A compound 1-3-32 (3.6 g, yield 46%) was prepared in the same manner as in Example 1, except that in the preparation method of Example 1, 2-bromo-9,10-di(2-naphthyl)anthracene compound (5.1 g, 10.0 mmol), and the compound M (4.7 g, 10.0 mmol) as prepared in Preparation Example 13 were used respectively instead of the 9-bromo-10-(2-naphthyl)anthracene compound and the compound A as prepared in Preparation Example 1.

MS $[M+H]^+=774$

EXAMPLE 15

Preparation of Compound 1-3-12

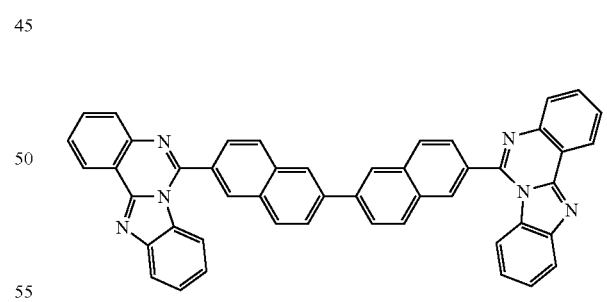

A compound 1-3-12 (3.9 g, yield 56%) was prepared in the same manner as in Example 1, except that in the preparation method of Example 1, the compound M-1 (4.2 g, 10.0 mmol) as prepared in Preparation Example 13-1, and the compound M (4.7 g, 10.0 mmol) as prepared in Preparation Example 13-2 were used respectively instead of the 9-bromo-10-(2-naphthyl)anthracene compound and the compound A as prepared in Preparation Example 1.

MS $[M+H]^+=689$

EXAMPLE 16

Preparation of Compound 1-2-39

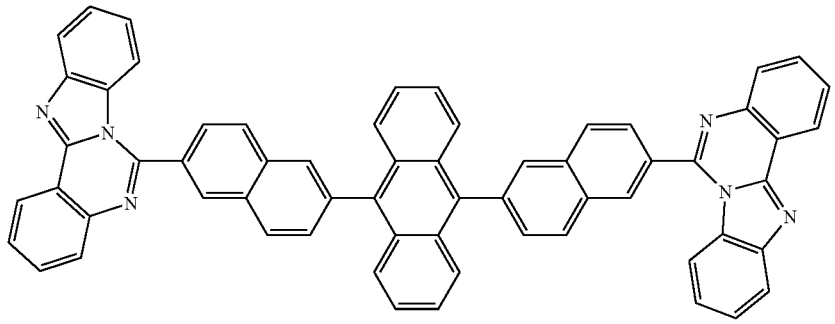

A compound 1-2-39 (4.7 g, yield 54%) was prepared in the same manner as in Example 1, except that in the preparation method of Example 1, 9,10-dibromoanthracene compound (3.4 g, 10.0 mmol), and the compound M (4.7 g, 10.0 mmol) as prepared in Preparation Example 13 were used respectively instead of the 9-bromo-10-(2-naphthyl)anthracene compound and the compound A as prepared in Preparation Example 1.

MS [M+H]$^+$=865

EXAMPLE 17

Preparation of Compound 1-1-51

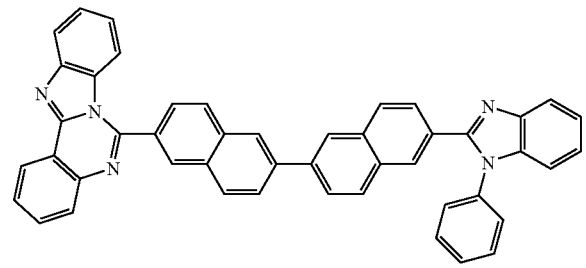

A compound 1-1-51 (4.4 g, yield 67%) was prepared in the same manner as in Example 1, except that in the preparation method of Example 1, the compound L-1 (4.0 g, 10.0 mmol) as prepared in Preparation Example 12, and the compound M (4.7 g, 10.0 mmol) as prepared in Preparation Example 13 were used respectively instead of the 9-bromo-10-(2-naphthyl)anthracene compound and the compound A as prepared in Preparation Example 1.

MS [M+H]$^+$=664

EXAMPLE 18

Preparation of Compound 1-2-8

[Compound 18-1]

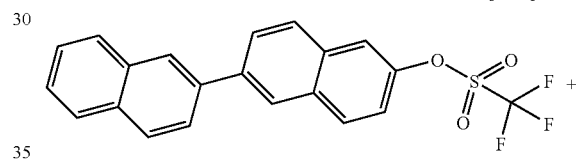

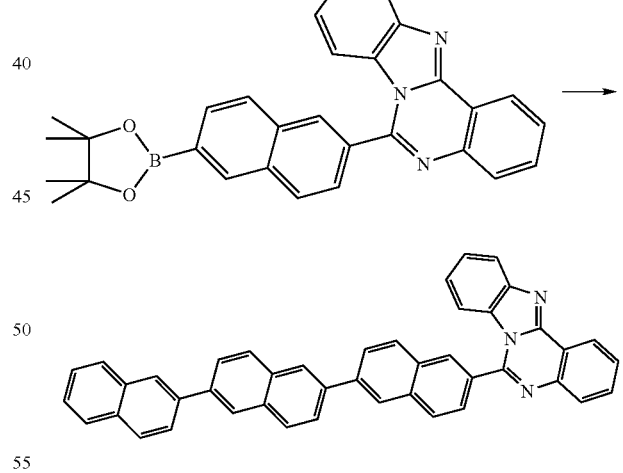

A compound 1-2-8 (5.3 g, yield 88%) was prepared in the same manner as in Example 1, except that in the preparation method of Example 1, the compound 18-1 (4.0 g, 10.0 mmol) in the above reaction scheme, and the compound M (4.7 g, 10.0 mmol) as prepared in Preparation Example 13 were used respectively instead of the 9-bromo-10-(2-naphthyl)anthracene compound and the compound A as prepared in Preparation Example 1.

MS [M+H]$^+$=598

EXAMPLE 19

Preparation of Compound 1-2-48

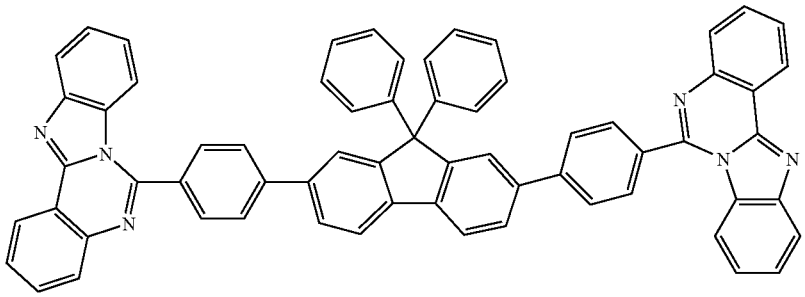

A compound 1-2-48 (5.9 g, yield 65%) was prepared in the same manner as in Example 1, except that in the preparation method of Example 1, 4,4'-dibromo-9,9'-diphenyl fluorene compound (4.8 g, 10.0 mmol) instead of the 9-bromo-10-(2-naphthyl)anthracene compound and the compound A (4.2 g, 10.0 mmol) as prepared in Preparation Example 1 was used.

MS $[M+H]^+=905$

EXAMPLE 20

Preparation of Compound 1-2-69

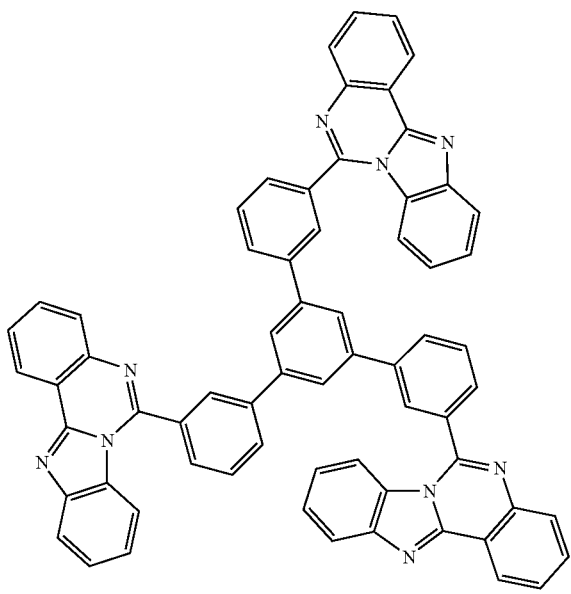

A compound 1-2-69 (3.3 g, yield 34%) was prepared in the same manner as in Example 1, except that in the preparation method of Example 1, 1,3,5-tribromobenzene compound (3.1 g, 10.0 mmol) and the compound B (16.9 g, 40.0 mmol) as prepared in Preparation Example 2 were used instead of the 9-bromo-10-(2-naphthyl)anthracene compound.

MS $[M+H]^+=958$

EXAMPLE 21

Preparation of Compound 1-3-64

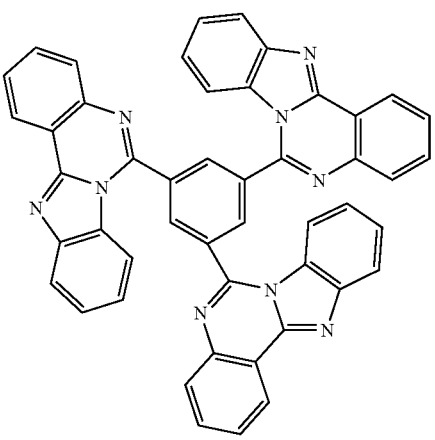

To 1,3,5-benzenetricarbonyltrichloride (1.3 g, 4.9 mmol) was added 60 mL of N-methylpyrrolidine (NMP), and stirred. 2-(2-aminophenyl)benzimidazole (6.0 g, 16.2 mmol) was added thereto. The mixture was heated for stirring at 180° C. for 18 hours, and NMP was distilled off in vacuo. The resultant was dissolved in CHCl$_3$, and the solution was passed through a silica gel layer to remove the solvent. The resultant was stirred with ethanol to prepare a white solid compound 1-3-64 (0.45 g, yield 12.6%).

MS $[M+H]^+=730$

EXAMPLE 22

Preparation of Compound 1-3-1

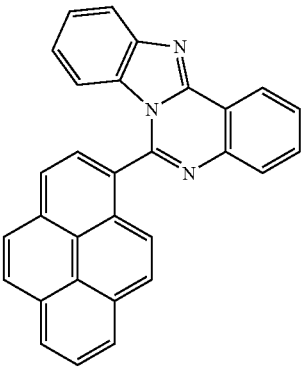

A compound 1-3-1 (3.5 g, yield 84%) was prepared in the same manner as in Example 1, except that in the preparation method of Example 1, 1-formylpyrene (2.3 g, 10 mmol) was used instead of 4-bromobenzaldehyde.
MS [M+H]$^+$=420

EXAMPLE 23

Preparation of Compound 1-3-2

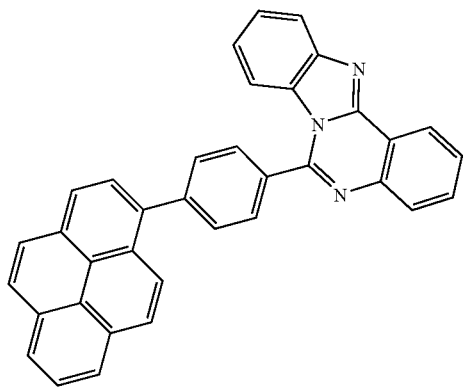

A compound 1-3-2 (3.8 g, yield 76%) was prepared in the same manner as in Example 1, except that in the preparation method of Example 1, 1-bromopyrenecompound (2.8 g, 10.0 mmol) and the compound A (4.2 g, 10.0 mmol) as prepared in Preparation Example 1 were used instead of the 9-bromo-10-(2-naphthyl)anthracene compound.

MS [M+H]$^+$=496

EXAMPLE 24

Preparation of Compound 1-3-5

[Compound 24-1]

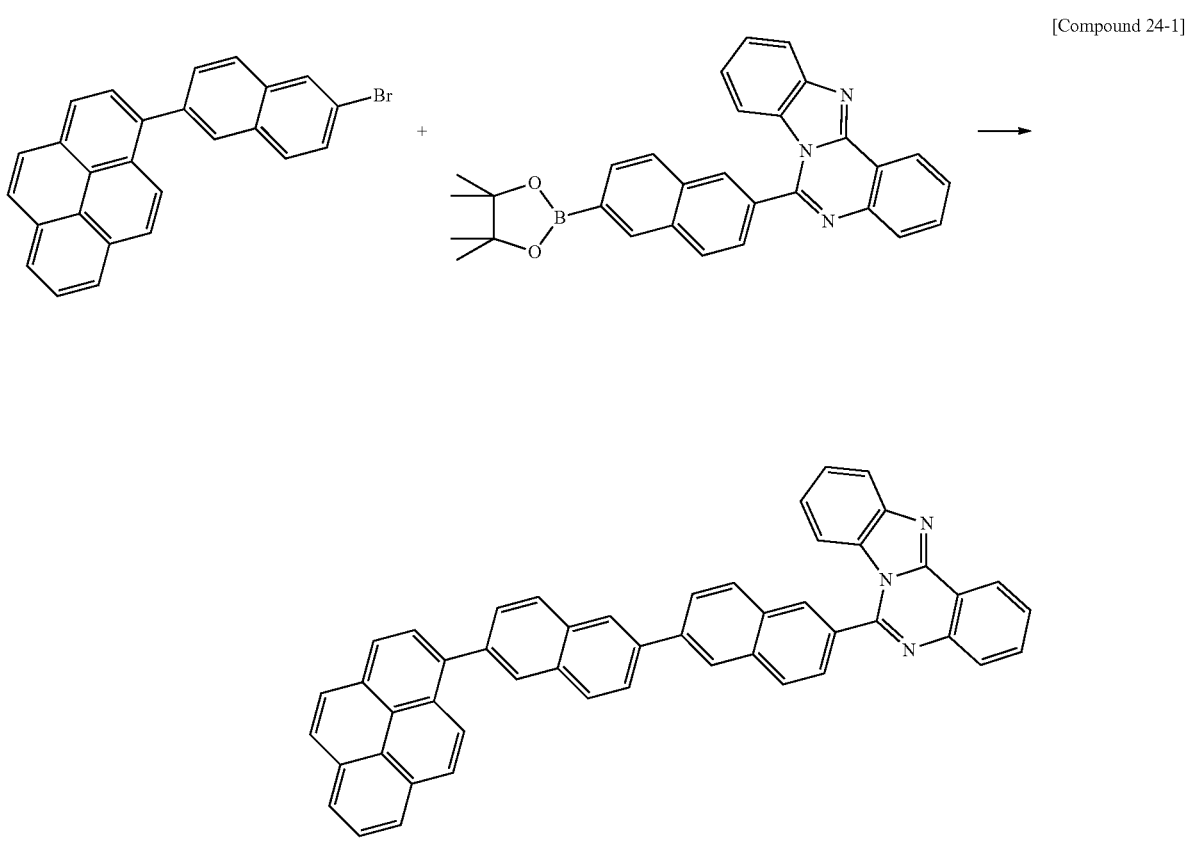

A compound 1-3-5 (4.5 g, yield 67%) was prepared in the same manner as in Example 1, except that in the preparation method of Example 1, the compound 24-1 (4.1 g, 10.0 mmol) and the compound M (4.7 g, 10.0 mmol) as prepared in Preparation Example 13 were used respectively instead of the 9-bromo-10-(2-naphthyl)anthracene compound and the compound A as prepared in Preparation Example 1.

MS [M+H]$^+$=672

EXAMPLE 25

Preparation of Compound 1-2-44

[Compound 25-1]

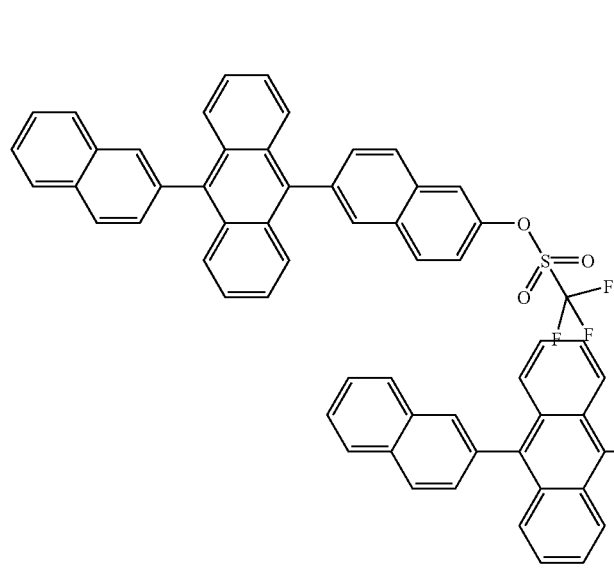
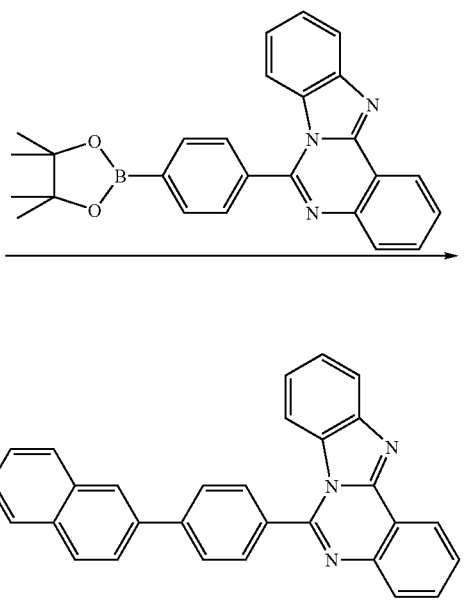

A compound 1-2-44 (3.3 g, yield 88%) was prepared in the same manner as in Example 1, except that in the preparation method of Example 1, the compound 25-1 (3.0 g, 5.2 mmol) in the above reaction scheme instead of the 9-bromo-10-(2-naphthyl)anthracene compound and the compound A (2.2 g, 5.2 mmol) as prepared in Preparation Example 1 were used.

MS [M+H]$^+$=729

EXAMPLE 26

Preparation of Compound 1-3-65

[Compound 26-1]

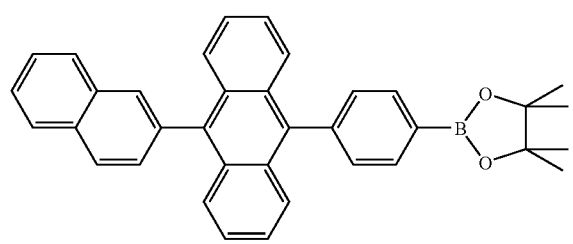
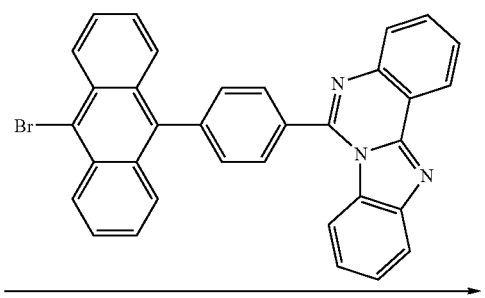

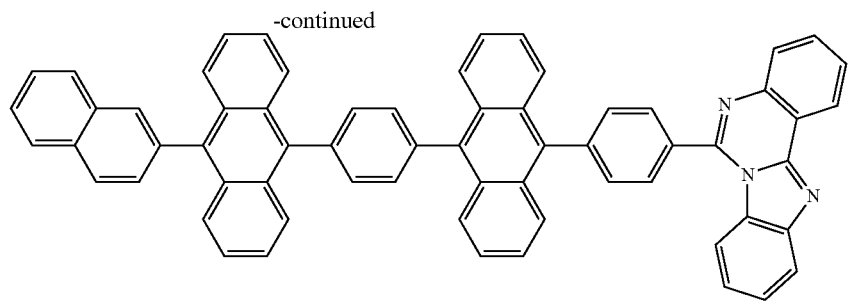

A compound 1-3-65 (2.6 g, yield 62%) was prepared in the same manner as in Example 1, except that in the preparation method of Example 1, the compound 26-1 (2.5 g, 5.0 mmol) in the above reaction scheme and the compound D (2.7 g, 4.9 mmol) as prepared in Preparation Example 4 were used respectively instead of the 9-bromo-10-(2-naphthyl)anthracene compound and the compound A as prepared in Preparation Example 1.

MS [M+H]$^+$=850

EXPERIMENTAL EXAMPLE 1

A glass substrate on which a thin film of ITO (indium tin oxide) was coated to a thickness of 1500 Å was immersed in distilled water having a detergent dissolved therein to wash the substrate with ultrasonic waves. At this time, the detergent was a product commercially available from Fisher Co. and the distilled water was distilled water which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was carried out by using solvents such as isopropyl alcohol, acetone and methanol. The substrate was dried, and then transported to a plasma washing machine. Using an oxygen plasma, the substrate was washed for 5 minutes and then transported to a vacuum depositing machine.

On the ITO transparent electrode thus prepared, hexanitrile hexaazatriphenylene was coated to thicknesses of 500 Å by thermal vacuum deposition to form a hole injecting layer. NPB (400 Å) as a hole transporting material was vacuum deposited, and then an Alq$_3$ compound was vacuum deposited to thicknesses of 300 Å for a light emitting layer.

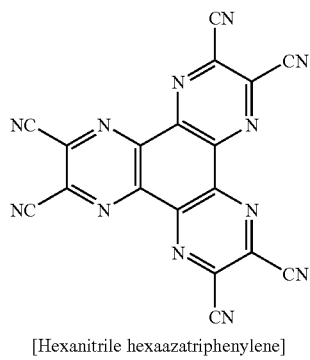

[Hexanitrile hexaazatriphenylene]

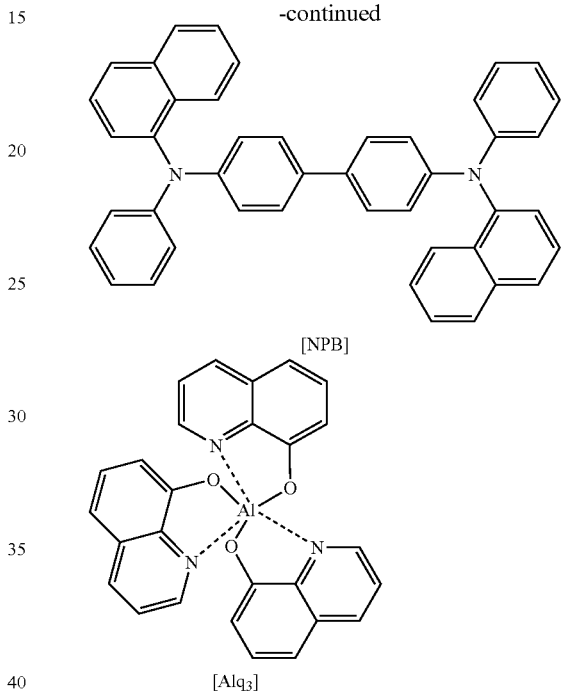

[NPB]

[Alq$_3$]

The compound 1-2-24 as prepared in Example 1 was vacuum deposited on the light emitting layer to thickness of 200 Å to form an electron injecting and transporting layer. Lithium fluoride (LiF) and aluminum were sequentially deposited on the electron injecting and transporting layer to thicknesses of 12 Å and 2000 Å respectively, to form a cathode.

In the above process, the deposition rate of the organic material was maintained at 1 Å/sec and the deposition rate of lithium fluoride was maintained at 0.2 Å/sec and the deposition rate of aluminum was maintained at 3 to 7 Å/sec, respectively.

The results of the testing the organic light emitting devices which prepared by using respective compound for an electron injecting and transporting layer as in the Experimental Example 1, are shown in Table 2.

TABLE 2

| Compound | | Voltage (V @ 100 mA/cm$^2$) | Brightness (cd/A @ 100 mA/cm$^2$) |
|---|---|---|---|
| Comparative Example 1 | Alq$_3$ | 8.7 | 4.7 |
| Experimental Example 1 | 1-2-24 | 7.9 | 5.2 |

TABLE 2-continued

| Compound | Voltage (V @ 100 mA/cm$^2$) | Brightness (cd/A @ 100 mA/cm$^2$) |
|---|---|---|
| Experimental Example 2 | 1-2-25 | 7.6 | 6.2 |
| Experimental Example 3 | 1-2-62 | 8.6 | 5.3 |
| Experimental Example 4 | 1-3-26 | 7.1 | 5.5 |
| Experimental Example 5 | 1-3-27 | 6.9 | 5.7 |
| Experimental Example 6 | 1-3-32 | 7.1 | 4.2 |
| Experimental Example 7 | 1-2-8 | 8.3 | 6.2 |
| Experimental Example 8 | 1-2-48 | 7.4 | 5.8 |
| Experimental Example 9 | 1-3-1 | 9.8 | 4.9 |
| Experimental Example 10 | 1-3-2 | 9.0 | 6.0 |
| Experimental Example 11 | 1-3-5 | 9.4 | 6.4 |
| Experimental Example 12 | 1-3-65 | 7.2 | 5.4 |

The following Experimental Example 13 describes an example wherein the organic light emitting device was tested as an light emiting layer.

EXPERIMENTAL EXAMPLE 13

On the ITO electrode as prepared as in Experimental Example 1, hexanitrile hexaazatriphenylene (500 Å, 4,4'-bis [N-(1-naphthyl)-N-phenylamino]biphenyl (NPB) (400 Å), the compound 1-2-25 (200 Å) as prepared in Example 2, and Alq$_3$ (300 Å) were sequentially coated by thermal vacuum deposition, to form a hole injecting layer, a hole transporting layer, a light emitting layer, an electron transporting layer and an electron injecting layer in this order. lithium fluoride (LiF) (12 Å) and aluminum (2000 Å) was deposited thereon to form a cathode, and then to prepare an organic light emitting device.

When a forward electric field of 5.2 V was applied to the organic light emitting device as prepared above, blue light emission was observed with x=0.21 and y=0.32 based on the 1931 CIE color coordinate at a current density of 50 mA/cm$^2$. When a forward electric field of 7.3 V was applied, blue light emission of 4.3 cd/A was observed at a current density of 100 mA/cm$^2$.

The invention claimed is:
1. An imidazoquinazoline derivative represented by the following formula 1:

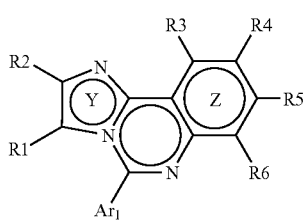

[Formula 1]

wherein R1 and R2 may be each independently the same as or different from each other, a hydrogen atom; a $C_1$ to $C_{30}$ alkyl group which is unsubstituted or substituted with at least one group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; a $C_3$ to $C_{30}$ cycloalkyl group which is unsubstituted or substituted with at least one group selected from the group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; a $C_5$ to $C_{30}$ aryl group which is unsubstituted or substituted with at least one group selected from the group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; or a $C_2$ to $C_{30}$ heteroaryl group which is unsubstituted or substituted with at least one group selected from the group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group, and are bonded with an adjacent group to form an aliphatic, aromatic, aliphatic hetero-, or aromatic hetero-condensed ring, or to form a spiro bond;

R3 to R6 may be each independently the same as or different from each other, and each are a hydrogen atom; a $C_1$ to $C_{12}$ alkoxy group which is unsubstituted or substituted with at least one group selected from the group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; a $C_1$ to $C_{12}$ alkylthioxy group which is unsubstituted or substituted with at least one group selected from the group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; a $C_1$ to $C_{30}$ alkylamine group which is unsubstituted or substituted with at least one group selected from the group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; a $C_5$ to $C_{30}$ arylamine group which is unsubstituted or substituted with at least one group selected from the group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; a $C_5$ to $C_{30}$ aryl group which is unsubstituted or substituted with at least one group selected from the group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; a $C_2$ to $C_{30}$ heteroaryl group which is unsubstituted or substituted with at least one group selected from the group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; a silicone group which is unsubstituted or substituted with at least one group selected from the group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; a boron group which is unsubstituted or substituted with at least one group selected from the group consisting of a halogen atom, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; an amino group; a nitrile group; a nitro group; a halogen group; an amide group; or an ester group, and are bonded with an adjacent group to form an aliphatic, aromatic, aliphatic hetero-, or aromatic hetero-condensed ring, or to form a spiro bond;

Ar1 is a $C_5$ to $C_{30}$ aryl group which is unsubstituted or substituted with at least one group selected from the group consisting of a halogen, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; or a $C_2$ to $C_{30}$ heteroaryl group which is unsubstituted or substituted with at least one group selected from the group consisting of a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group;

when Ar1 is a $C_5$ to $C_{30}$ aryl group which is unsubstituted, at least one of R4 and R5 is a $C_5$ to $C_{30}$ aryl group which is unsubstituted or substituted with at least one group selected from the group consisting of a $C_5$ to $C_{30}$ aryl group, and a $C_2$ to $C_{30}$ heteroaryl group; or a $C_2$ to $C_{30}$ heteroaryl group which is unsubstituted or substituted with at least one group selected from the group consisting of a $C_5$ to $C_{30}$ aryl group, and a $C_2$ to $C_{30}$ heteroaryl group;

Y is a heteroaryl group in which at least one ring-constituting carbon atoms is further substituted with nitrogen atom(s); and Z is an aryl group, or a heteroaryl group in which at least one ring-constituting carbon atoms is further substituted with nitrogen atom(s).

2. The imidazoquinazoline derivative according to claim 1, wherein the compound of the formula 1 is selected from the group consisting of

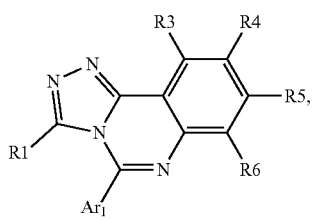

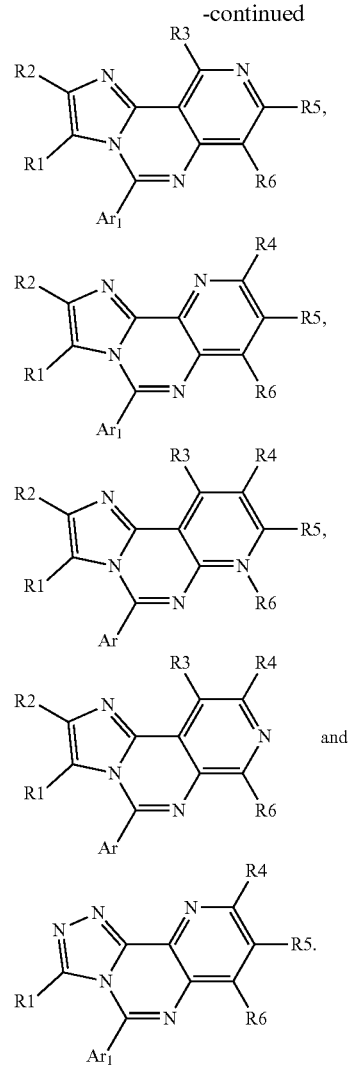

3. The imidazoquinazoline derivative according to claim 1, wherein in the formula 1, R1 and R2 may be each independently the same as or different from each other and each are a phenyl group, a biphenyl group, a naphthyl group, a pyridinyl group, or a methyl- or nitrile-substituted phenyl group.

4. The imidazoquinazoline derivative according to claim 1, wherein in the formula 1, R1 and R2 are bonded with an adjacent group to form an aliphatic, aromatic, aliphatic hetero-, or aromatic hetero-condensed ring, or to form a spiro bond.

5. The imidazoquinazoline derivative according to claim 1, wherein the compound of the formula 1 is selected from the group consisting of

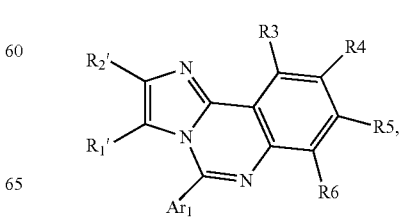

-continued
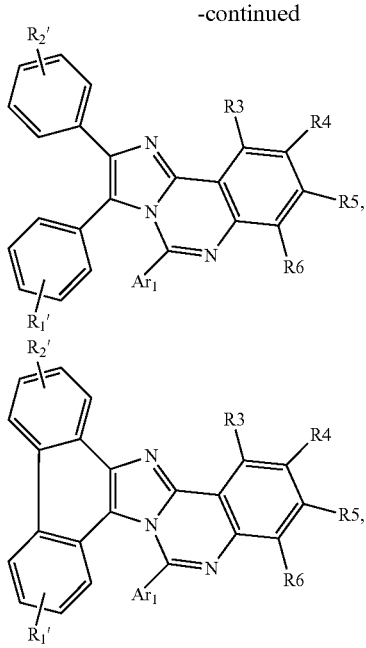
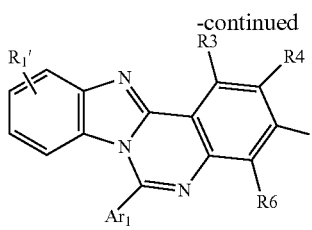
and
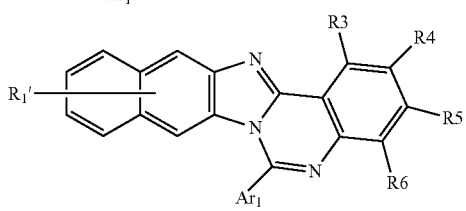
wherein R3 to R6, and Ar1 are as defined for the formula 1, and $R_1'$ and $R_2'$ are same as defined for R1 and R2 in the formula 1.
6. The imidazoquinazoline derivative according to claim 1, wherein the compound of the formula 1 is selected from the group consisting of the compounds of the following structural formulae:
TABLE 1
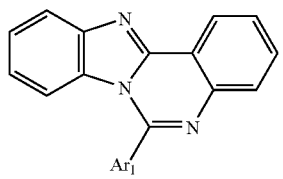
| No. | Ar1 |
|---|---|
| 1-1-1 | 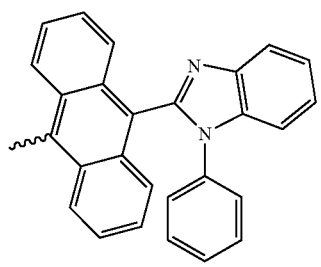 |
| 1-1-2 | 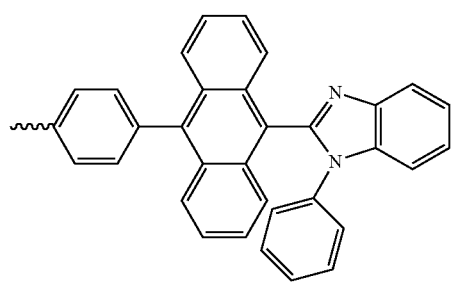 |

TABLE 1-continued

| No. | Ar1 |
|---|---|
| 1-1-3 | |
| 1-1-4 | |
| 1-1-5 | |
| 1-1-6 | |
| 1-1-7 | |

TABLE 1-continued
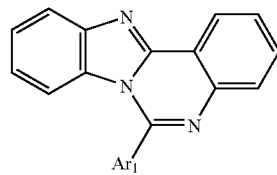
| No. | Ar1 |
|---|---|
| 1-1-8 | 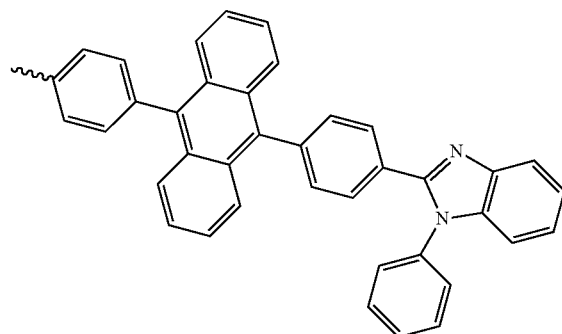 |
| 1-1-9 | 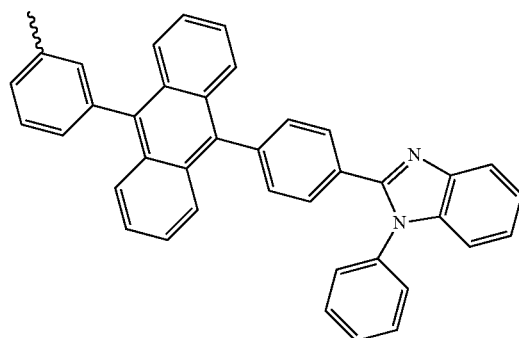 |
| 1-1-10 | 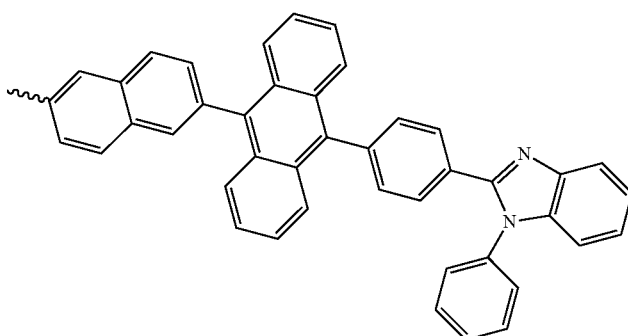 |
| 1-1-11 | 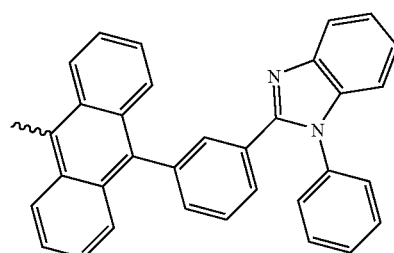 |

TABLE 1-continued
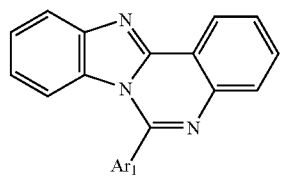
| No. | Ar1 |
|---|---|
| 1-1-12 | 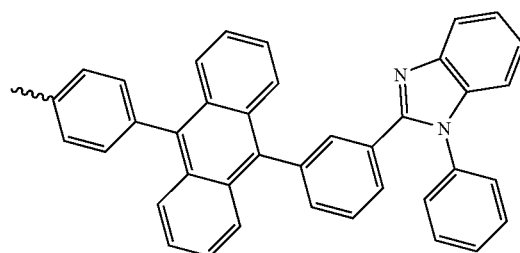 |
| 1-1-13 | 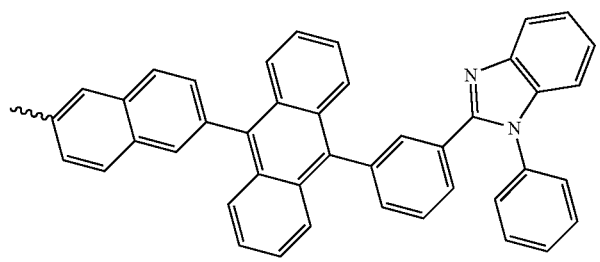 |
| 1-1-14 | 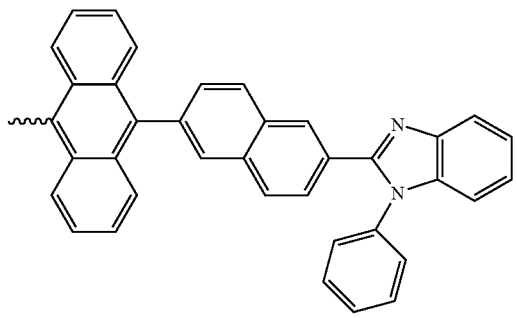 |
| 1-1-15 | 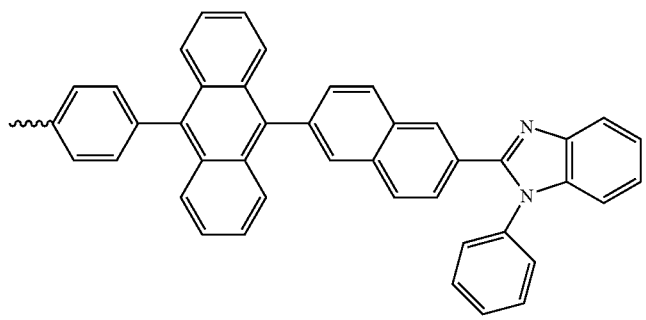 |

TABLE 1-continued
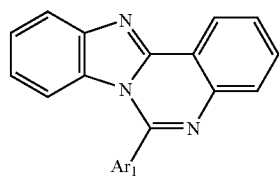
| No. | Ar1 |
|---|---|
| 1-1-16 | 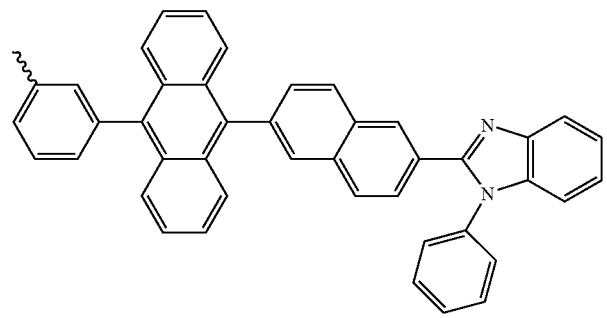 |
| 1-1-17 | 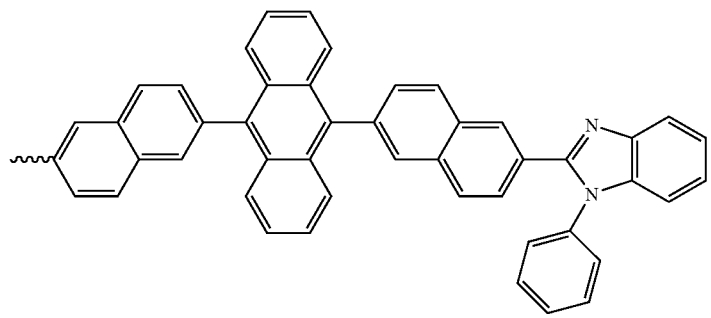 |
| 1-1-18 | 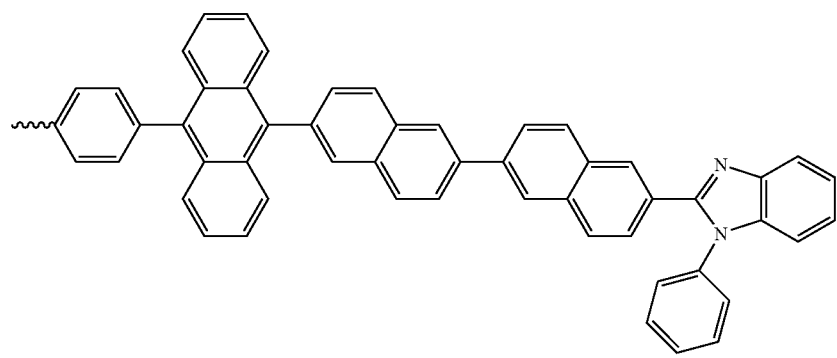 |
| 1-1-19 | 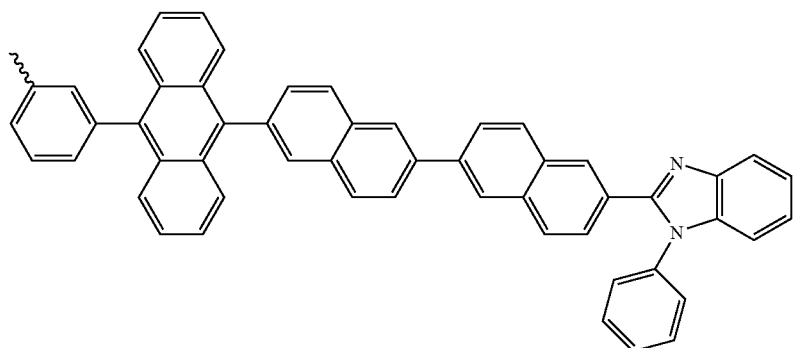 |

TABLE 1-continued
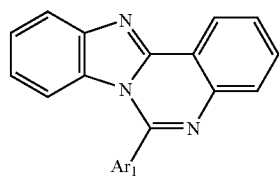
| No. | Ar1 |
|---|---|
| 1-1-20 | 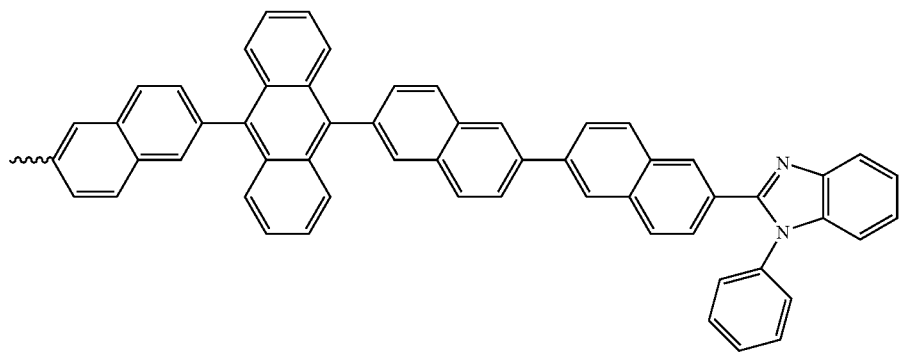 |
| 1-1-21 | 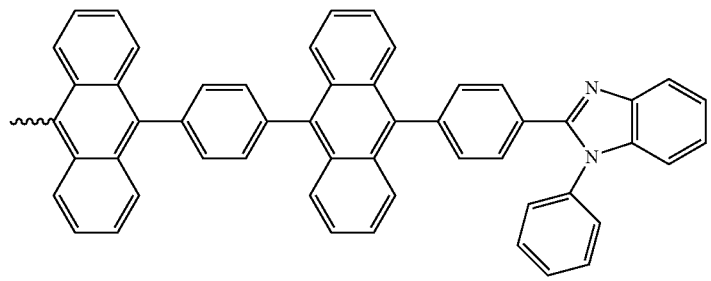 |
| 1-1-22 | 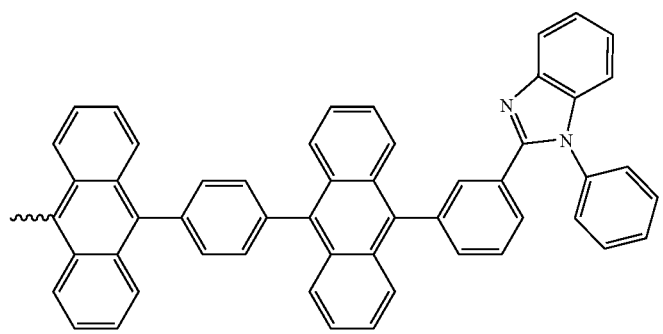 |
| 1-1-23 | 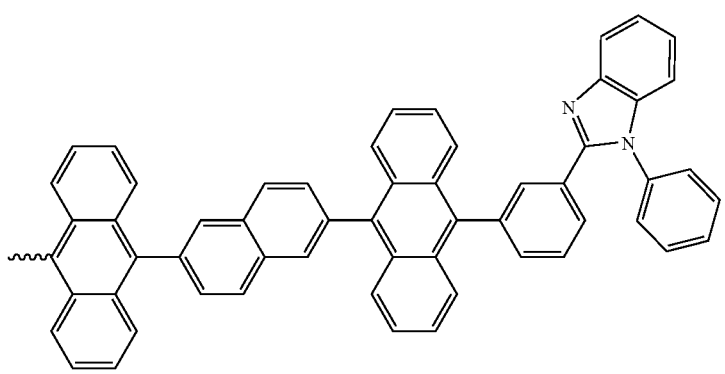 |

TABLE 1-continued
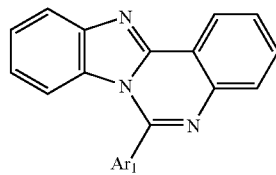
| No. | Ar1 |
| --- | --- |
| 1-1-24 | 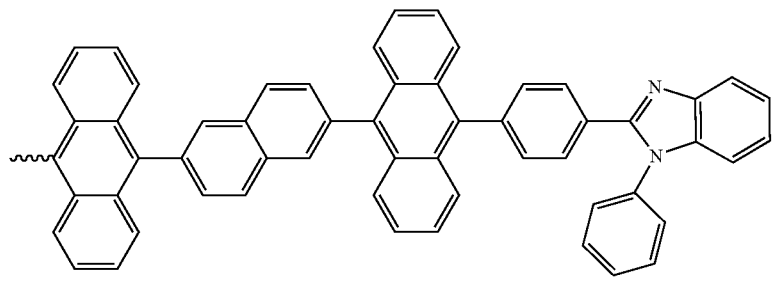 |
| 1-1-25 | 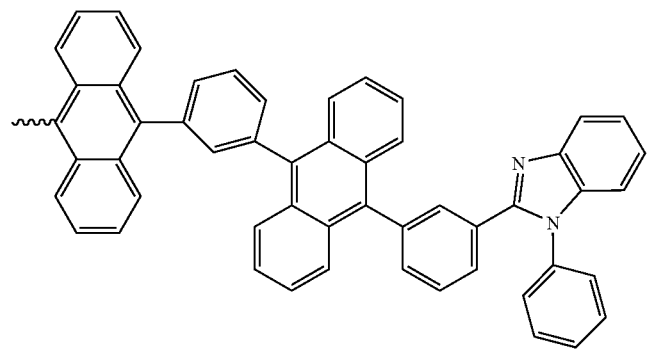 |
| 1-1-26 | 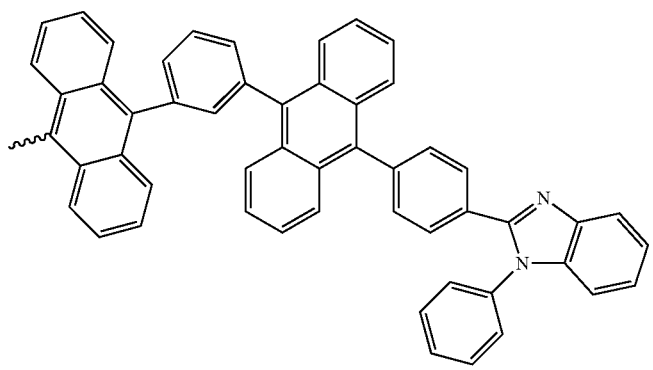 |
| 1-1-27 | 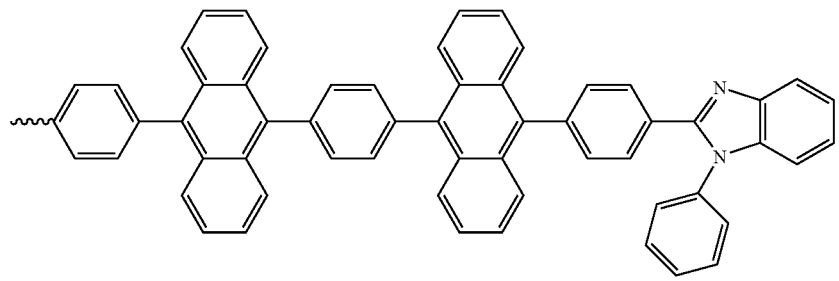 |

TABLE 1-continued
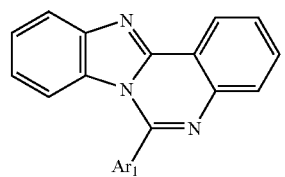
| No. | Ar1 |
|---|---|
| 1-1-28 | 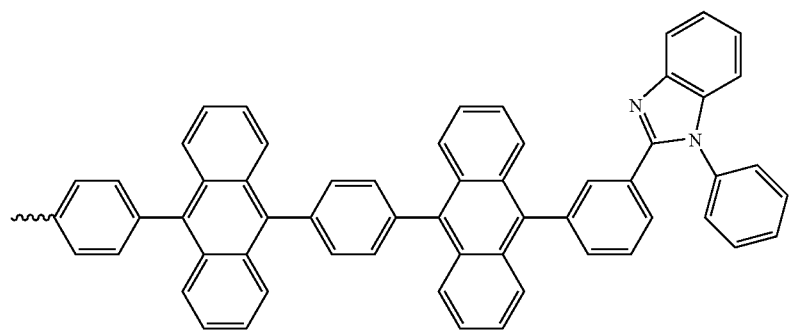 |
| 1-1-29 | 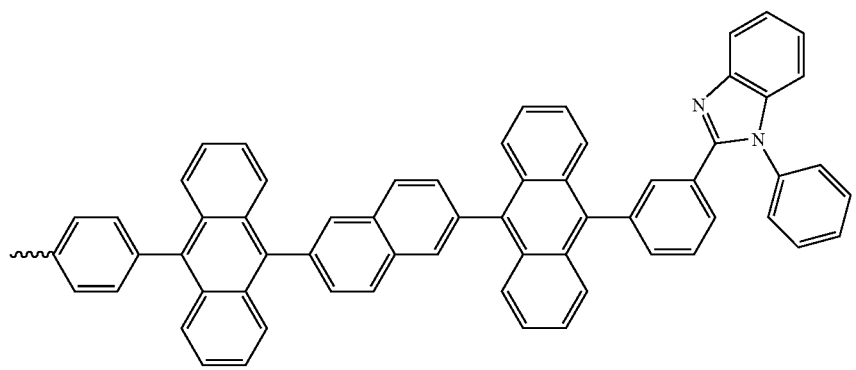 |
| 1-1-30 | 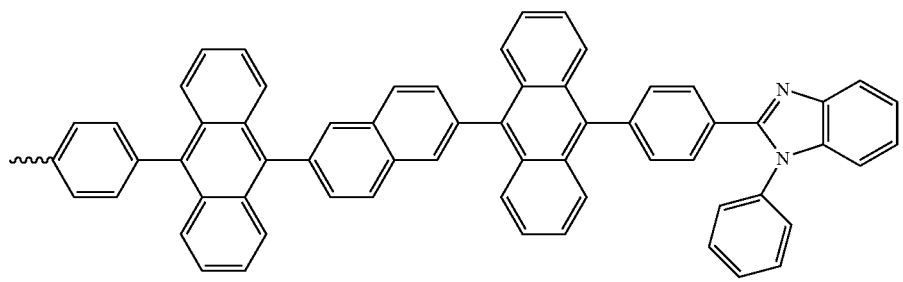 |
| 1-1-31 | 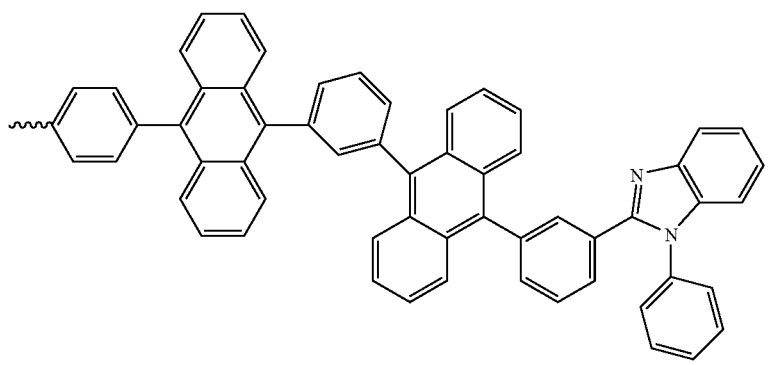 |

TABLE 1-continued
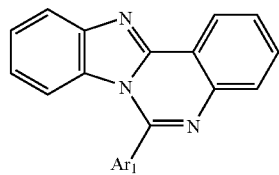
| No. | Ar1 |
|---|---|
| 1-1-32 | 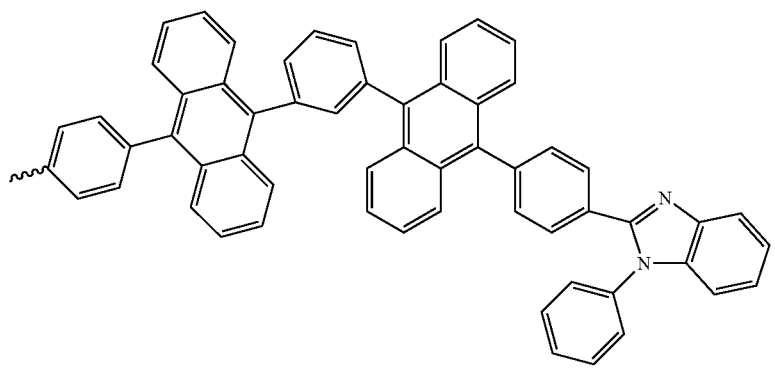 |
| 1-1-33 | 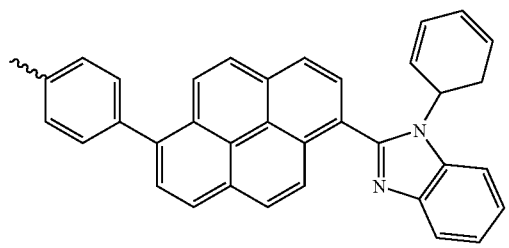 |
| 1-1-34 | 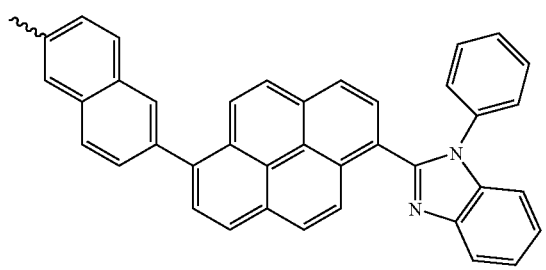 |
| 1-1-35 | 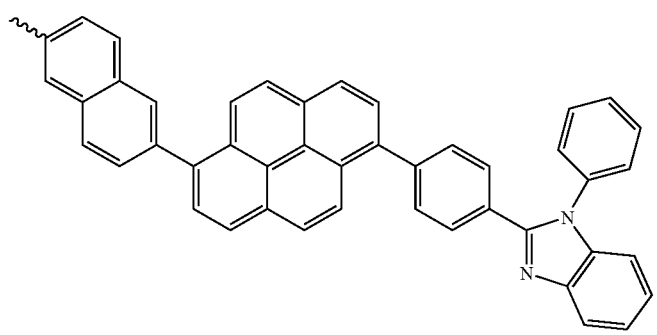 |

TABLE 1-continued
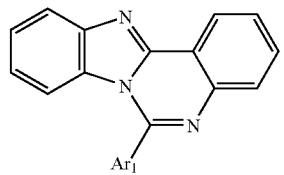
| No. | Ar1 |
|---|---|
| 1-1-36 | 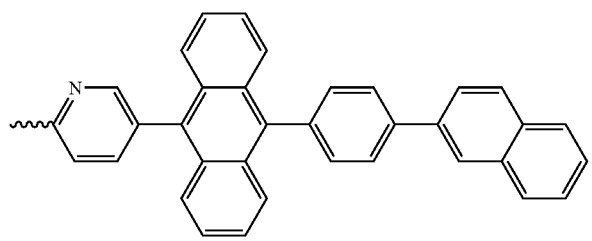 |
| 1-1-37 | 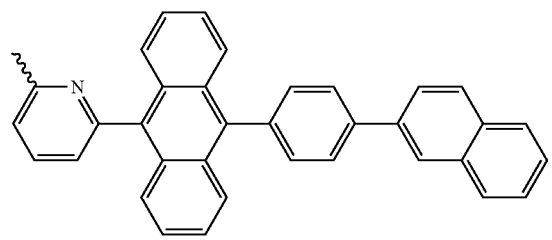 |
| 1-1-38 | 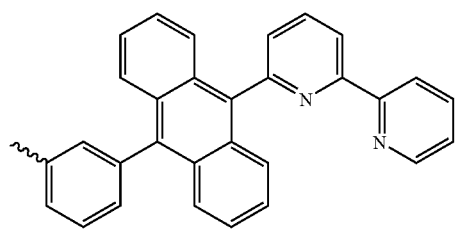 |
| 1-1-39 | 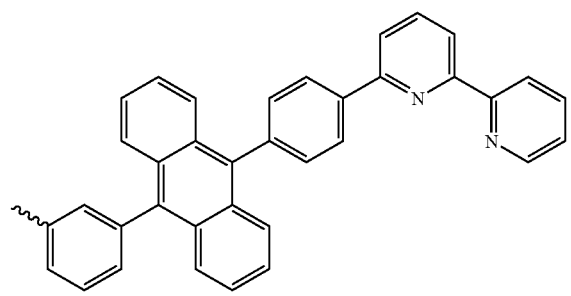 |
| 1-1-40 | 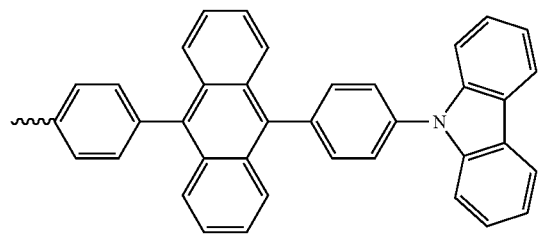 |

TABLE 1-continued
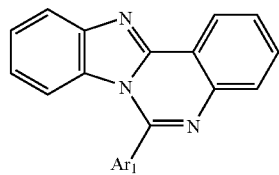
| No. | Ar1 |
|---|---|
| 1-1-41 | 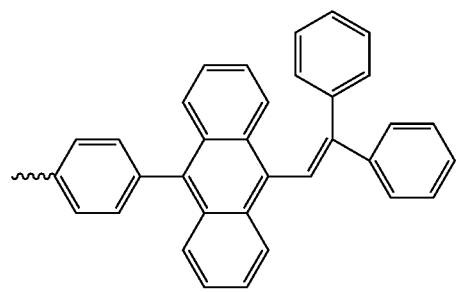 |
| 1-1-42 | 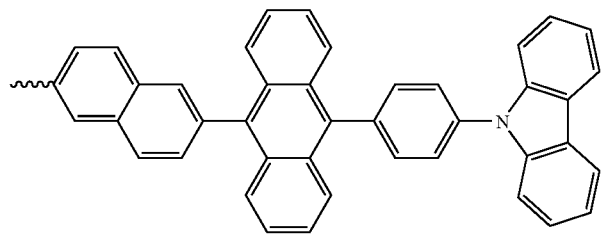 |
| 1-1-43 | 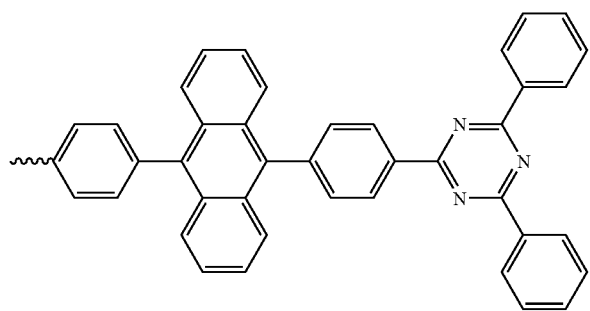 |
| 1-1-44 | 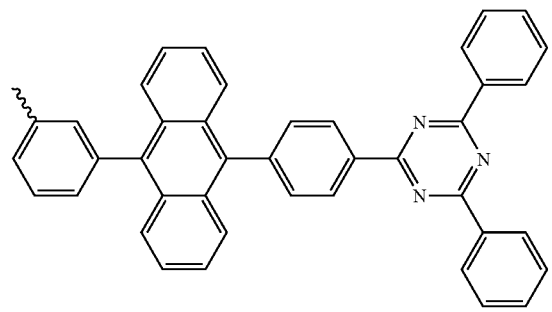 |

TABLE 1-continued
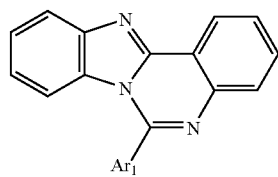
| No. | Ar1 |
|---|---|
| 1-1-45 | 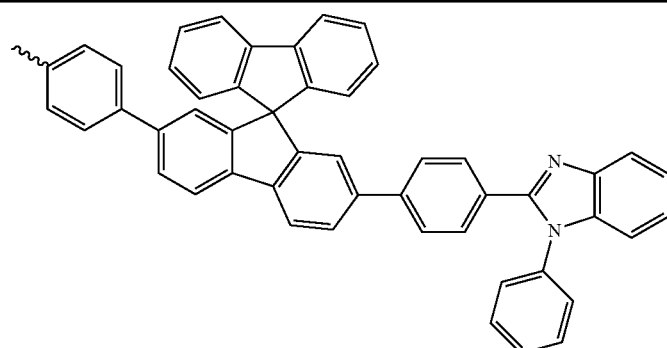 |
| 1-1-46 | 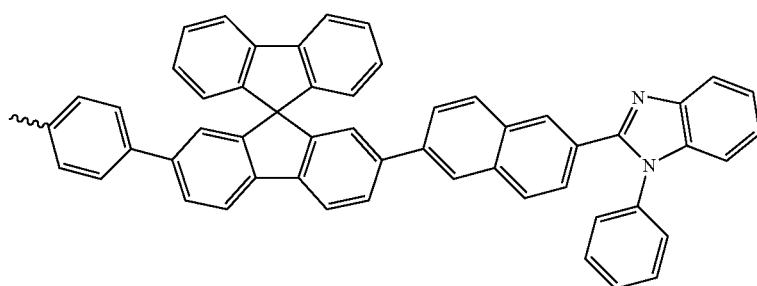 |
| 1-1-47 | 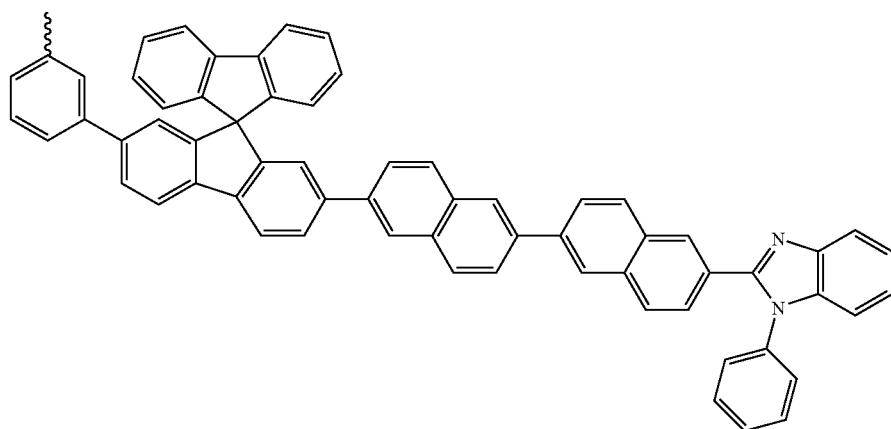 |
| 1-1-48 | 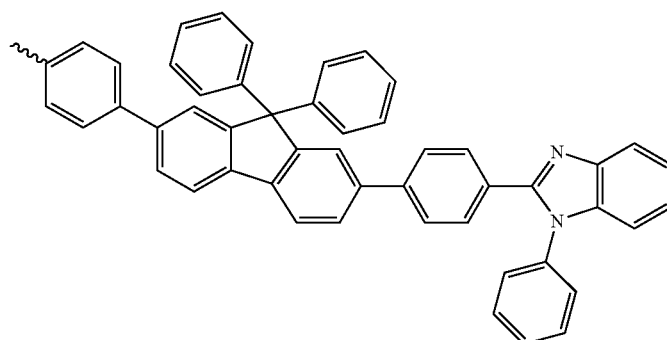 |

TABLE 1-continued
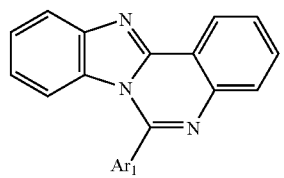
| No. | Ar1 |
|---|---|
| 1-1-49 | 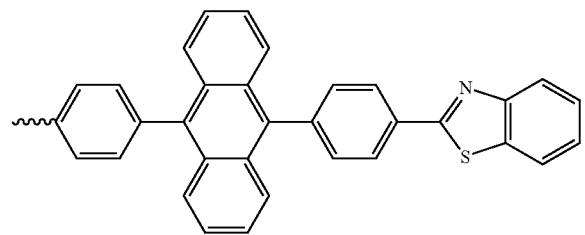 |
| 1-1-50 | 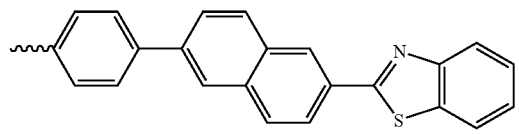 |
| 1-1-51 | 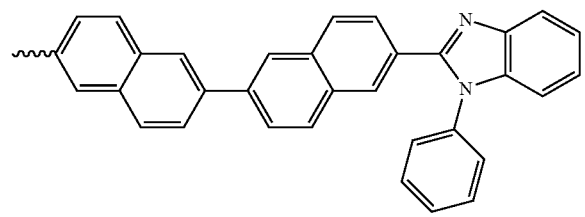 |
| 1-1-52 | 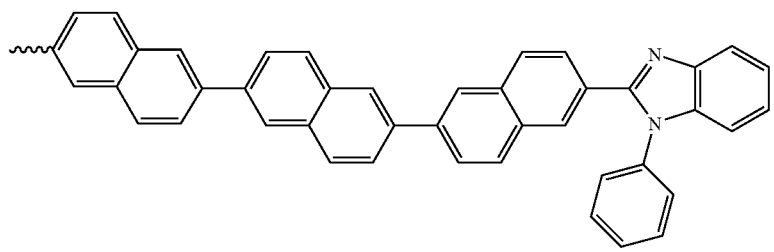 |
| 1-1-53 | 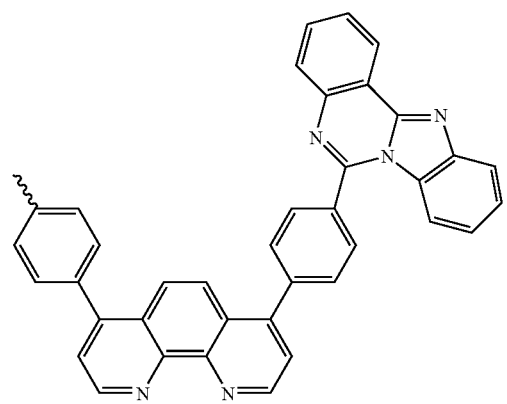 |

TABLE 1-continued
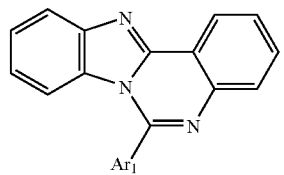
| No. | Ar1 |
|---|---|
| 1-1-54 | |
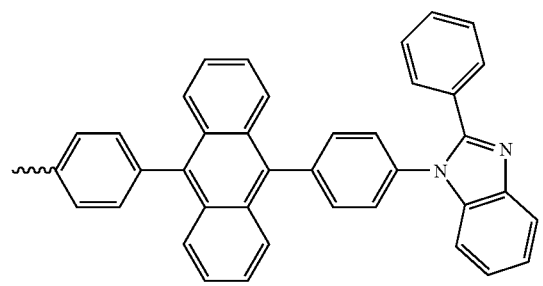
1-1-55
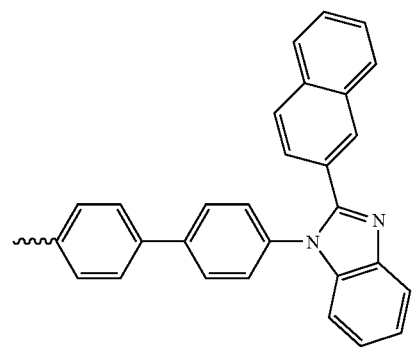
1-1-56
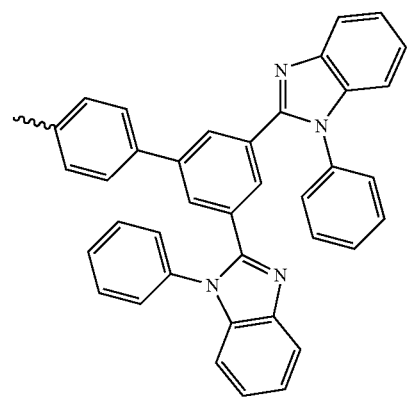

TABLE 1-continued
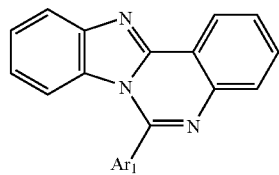
| No. | Ar1 |
|---|---|
| 1-1-57 | 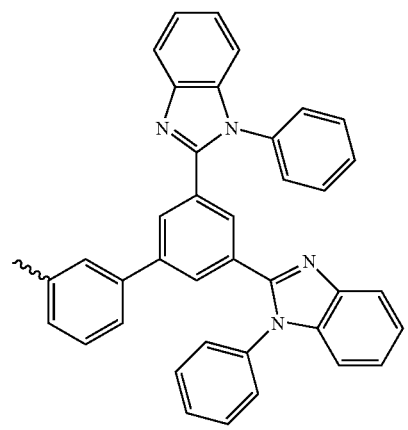 |
| 1-1-58 | 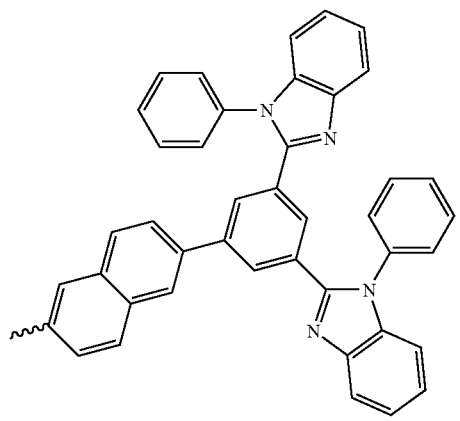 |
| 1-1-59 | 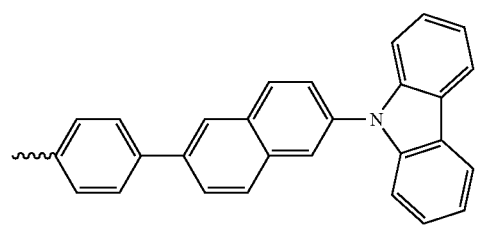 |

TABLE 1-continued
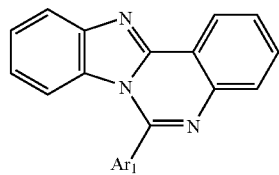
| No. | Ar1 |
|---|---|
| 1-1-60 | |
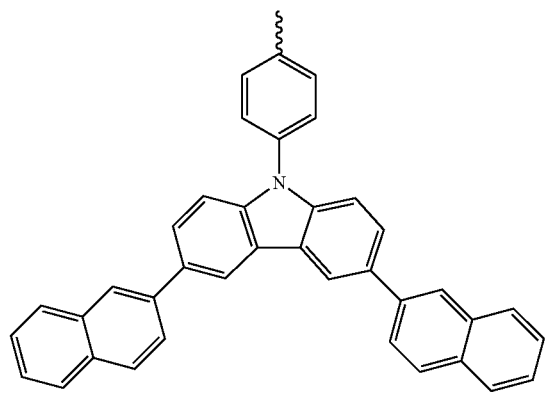
1-1-61
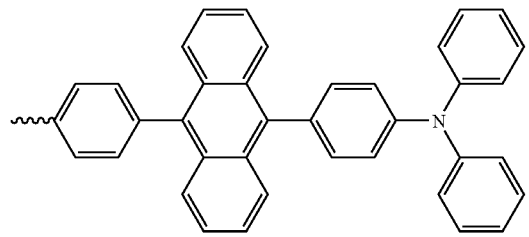
1-1-62
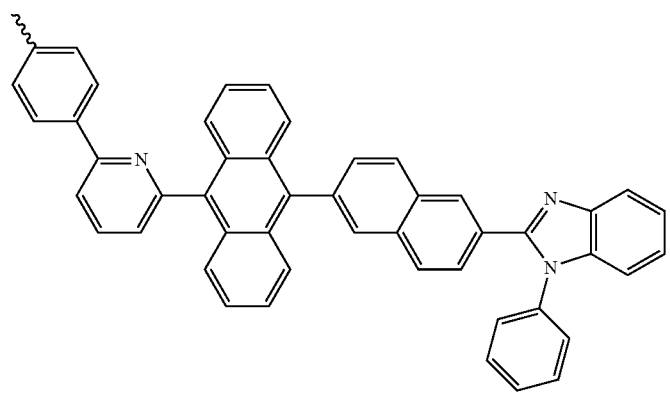

TABLE 1-continued
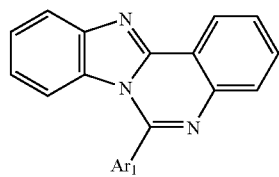
| No. | Ar1 |
|---|---|
| 1-1-63 | 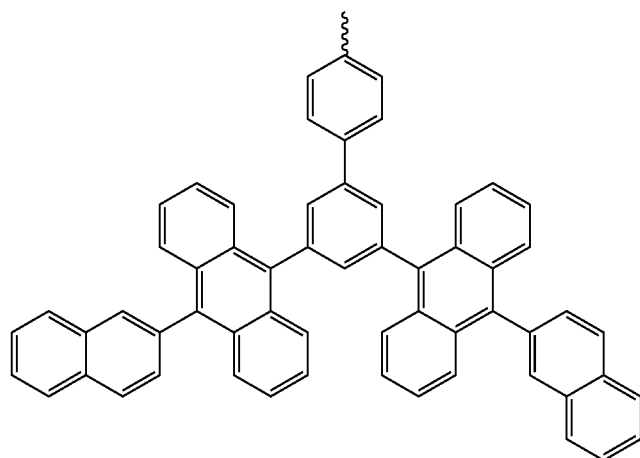 |
| 1-1-64 | 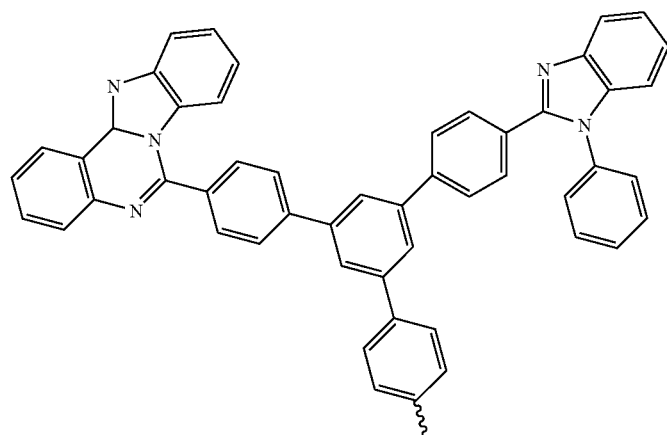 |
| 1-1-65 | 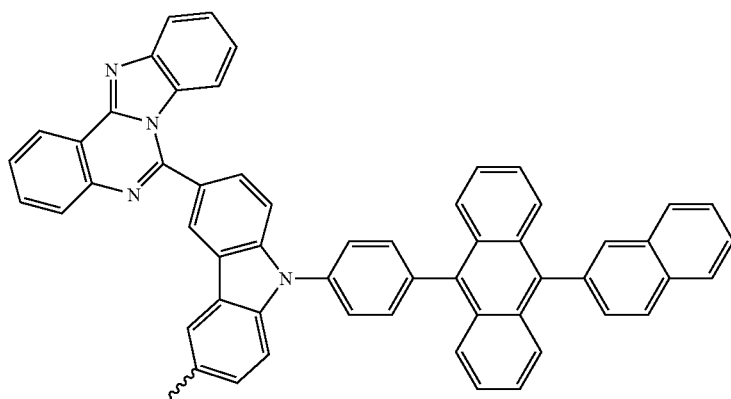 |

TABLE 1-continued
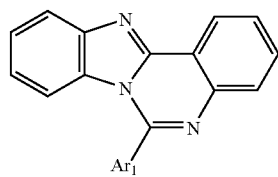
| No. | Ar1 |
|---|---|
| 1-1-66 | 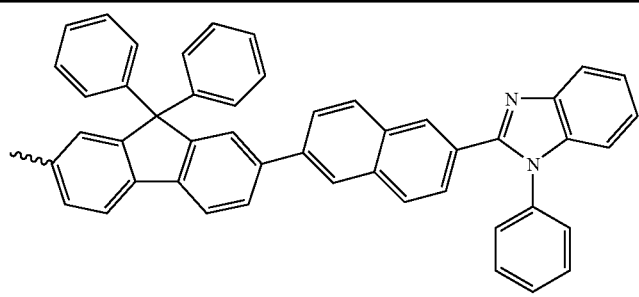 |
| 1-1-67 | 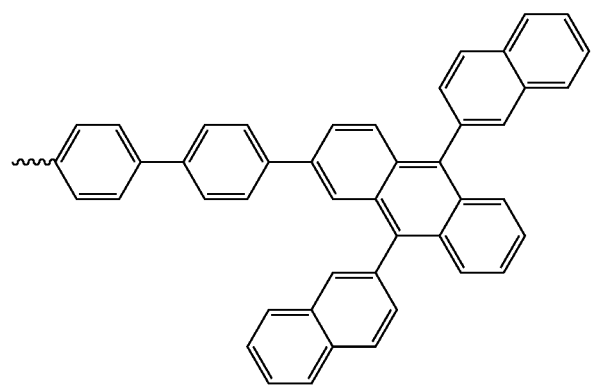 |
| 1-1-68 | 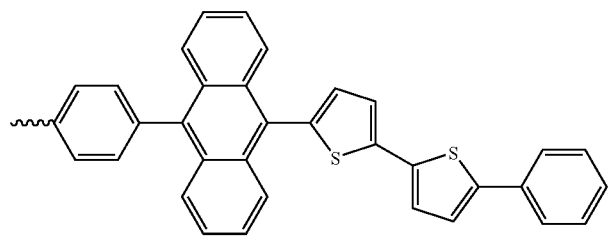 |
| 1-1-69 | 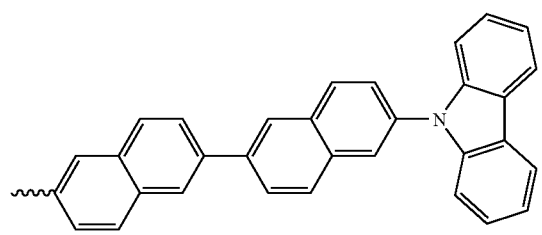 |
| 1-2-1 | 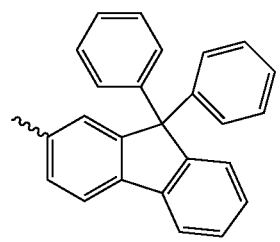 |

TABLE 1-continued
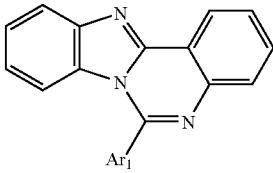
| No. | Ar1 |
|---|---|
| 1-2-2 | 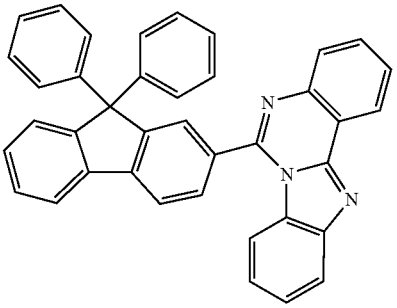 |
| 1-2-3 | 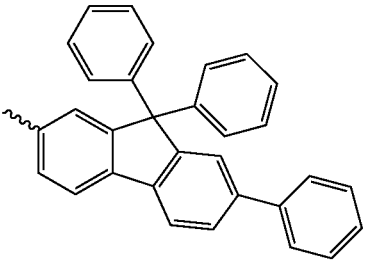 |
| 1-2-4 | 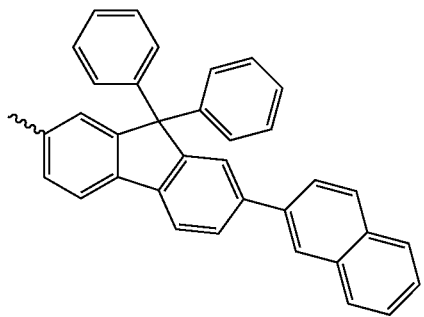 |
| 1-2-5 | 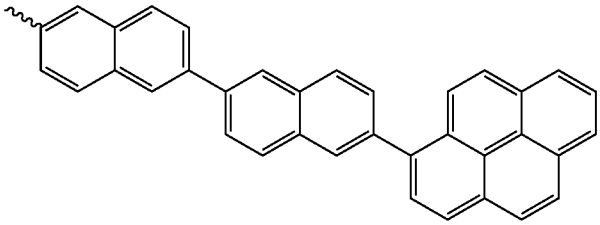 |
| 1-2-6 | 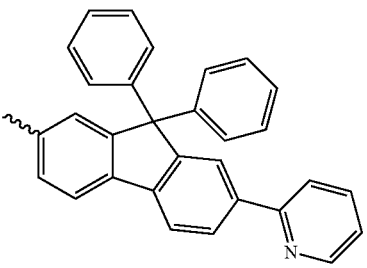 |

TABLE 1-continued
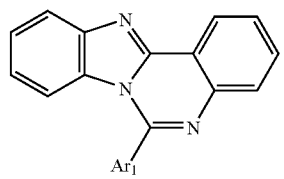
| No. | Ar1 |
|---|---|
| 1-2-7 | 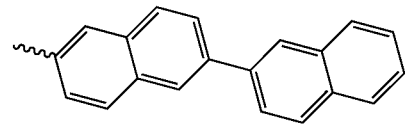 |
| 1-2-8 | 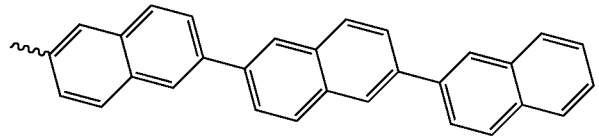 |
| 1-2-9 | 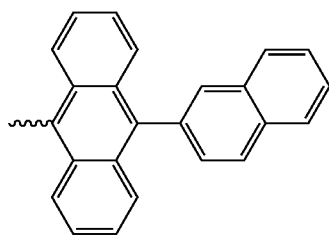 |
| 1-2-10 | 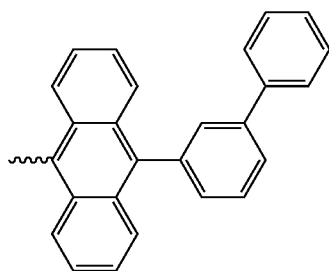 |
| 1-2-11 | 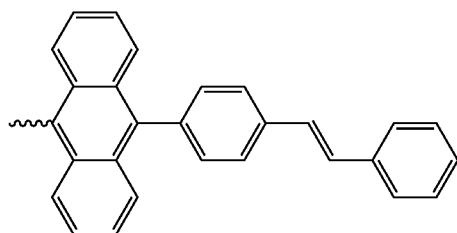 |
| 1-2-12 | 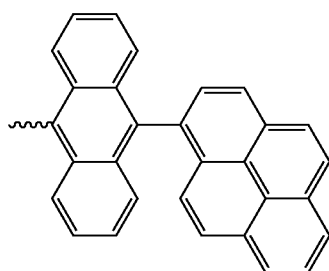 |

TABLE 1-continued
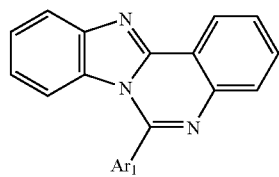
| No. | Ar1 |
|---|---|
| 1-2-13 | 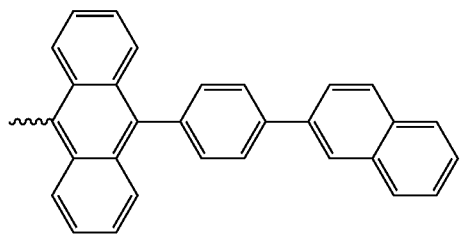 |
| 1-2-14 | 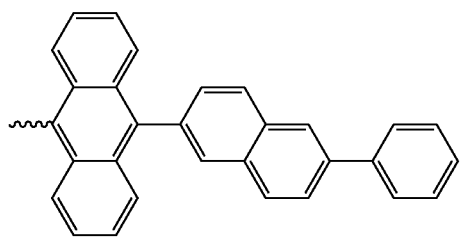 |
| 1-2-15 | 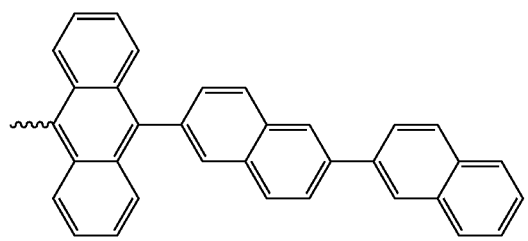 |
| 1-2-16 | 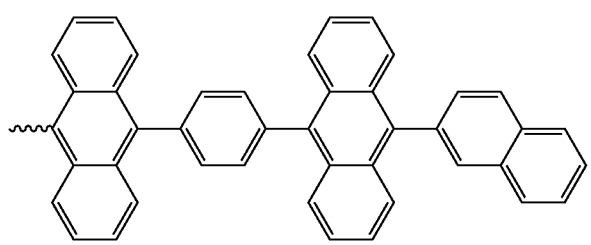 |
| 1-2-17 | 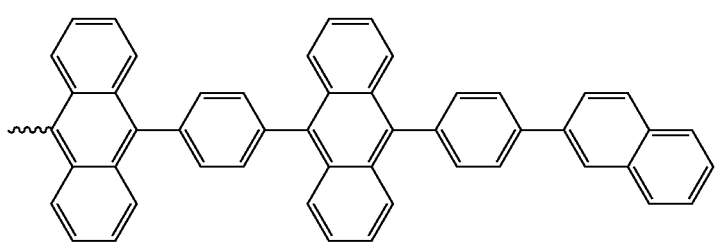 |

TABLE 1-continued
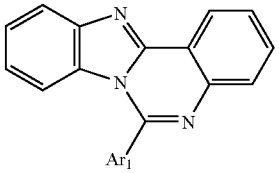
| No. | Ar1 |
|---|---|
| 1-2-18 | 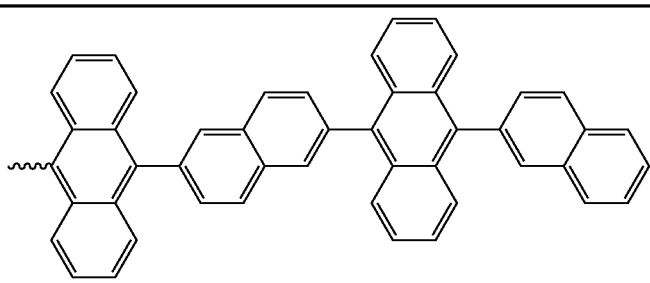 |
| 1-2-19 | 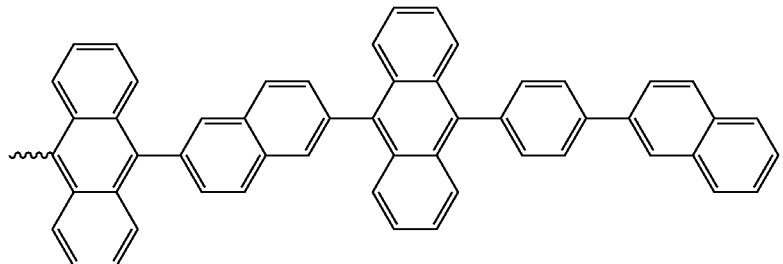 |
| 1-2-20 | 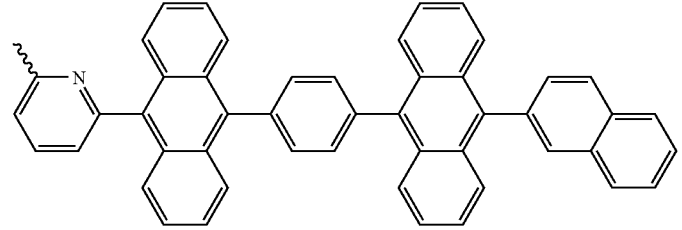 |
| 1-2-21 | 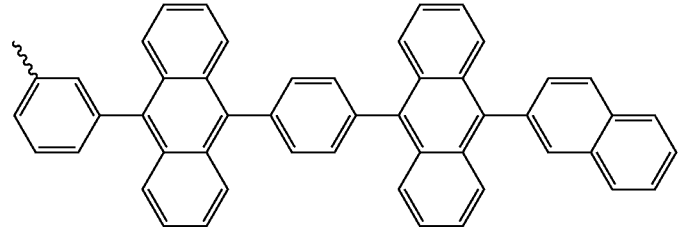 |
| 1-2-22 | 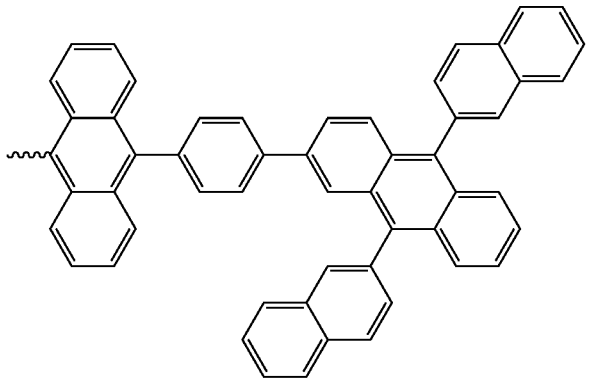 |

TABLE 1-continued

| No. | Ar1 |
|---|---|
| 1-2-23 | |
| 1-2-24 | |
| 1-2-25 | |
| 1-2-26 | |
| 1-2-27 | |

TABLE 1-continued
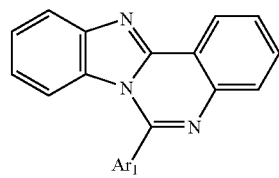
| No. | Ar1 |
|---|---|
| 1-2-28 | 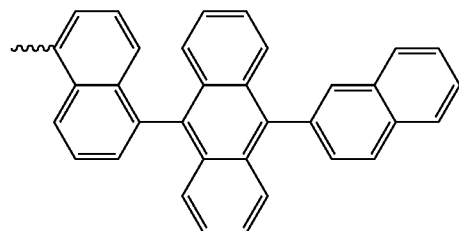 |
| 1-2-29 | 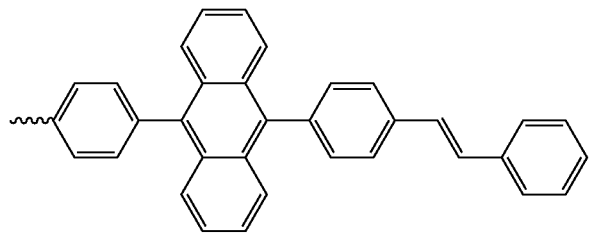 |
| 1-2-30 | 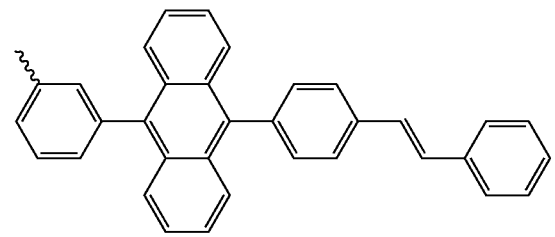 |
| 1-2-31 | 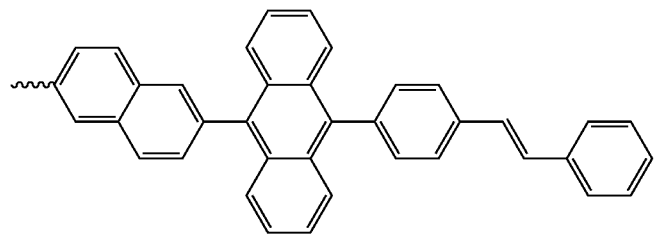 |
| 1-2-32 | 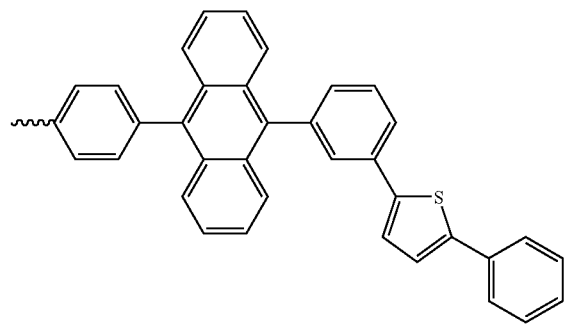 |

TABLE 1-continued
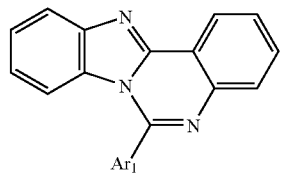
| No. | Ar1 |
|---|---|
| 1-2-33 | 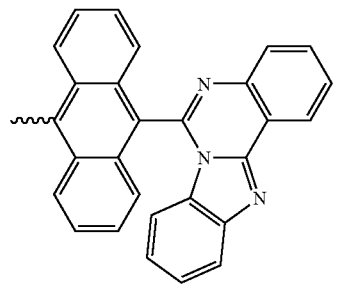 |
| 1-2-34 | 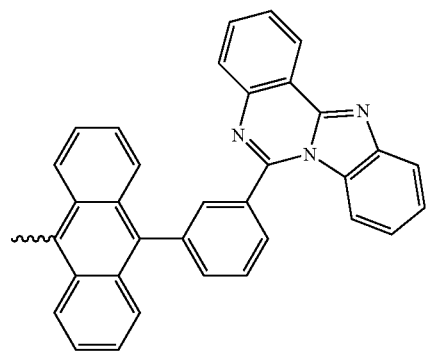 |
| 1-2-35 | 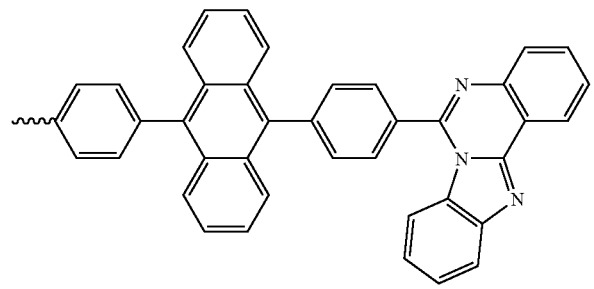 |
| 1-2-36 | 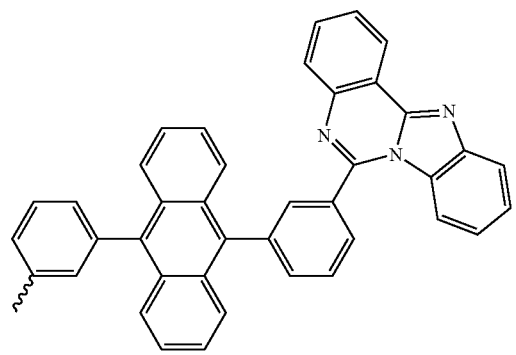 |

TABLE 1-continued

| No. | Ar1 |
|---|---|
| 1-2-37 | |
| 1-2-38 | |
| 1-2-39 | |
| 1-2-40 | |
| 1-2-41 | |

TABLE 1-continued
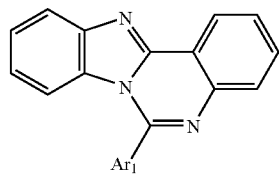
| No. | Ar1 |
|---|---|
| 1-2-42 | 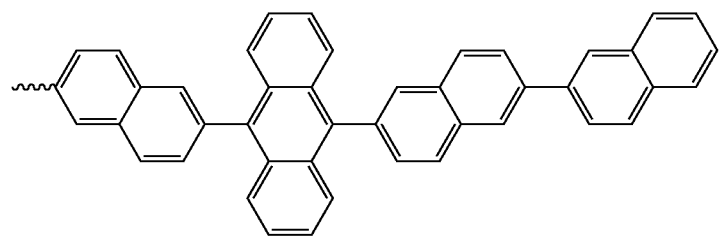 |
| 1-2-43 | 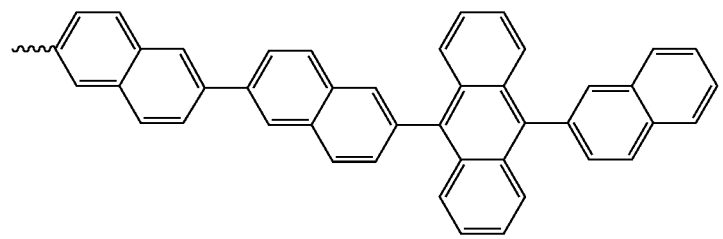 |
| 1-2-44 | 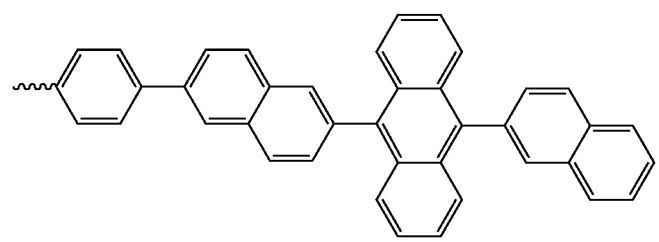 |
| 1-2-45 | 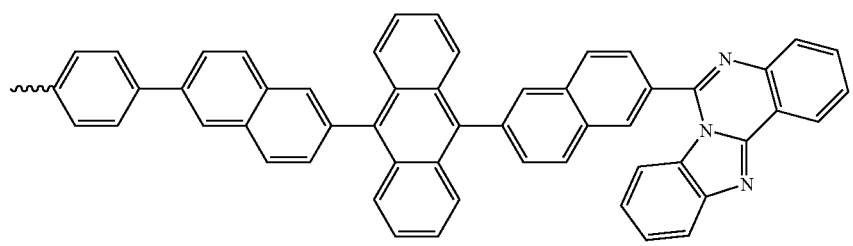 |
| 1-2-46 | 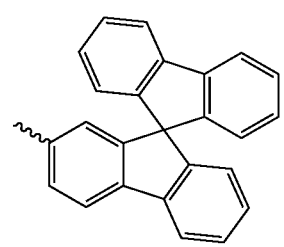 |

TABLE 1-continued

| No. | Ar1 |
|---|---|
| 1-2-47 | |
| 1-2-48 | |
| 1-2-49 | |
| 1-2-50 | |
| 1-2-51 | |

TABLE 1-continued

| No. | Ar1 |
|---|---|
| 1-2-52 | |
| 1-2-53 | |
| 1-2-54 | |
| 1-2-55 | |
| 1-2-56 | |

TABLE 1-continued
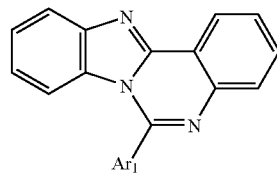
| No. | Ar1 |
|---|---|
| 1-2-57 | 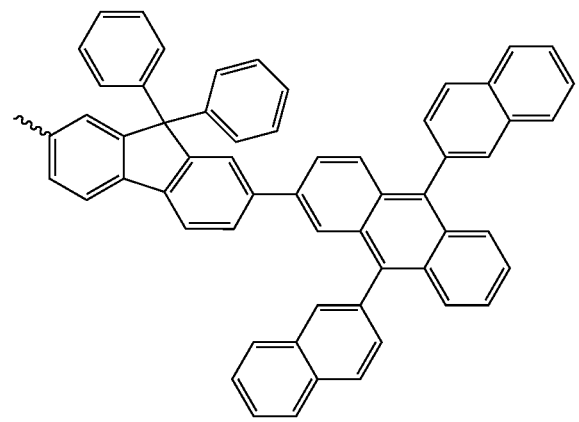 |
| 1-2-58 | 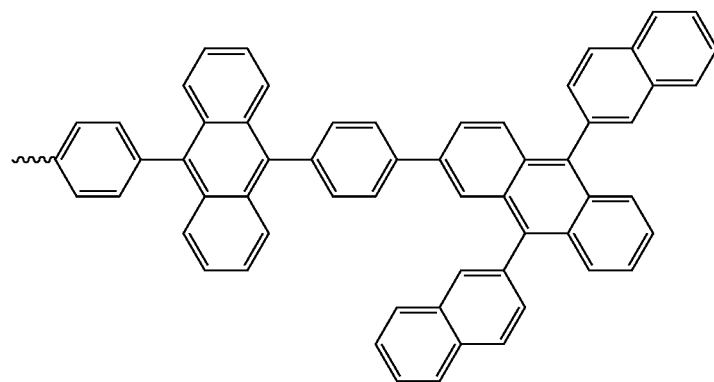 |
| 1-2-59 | 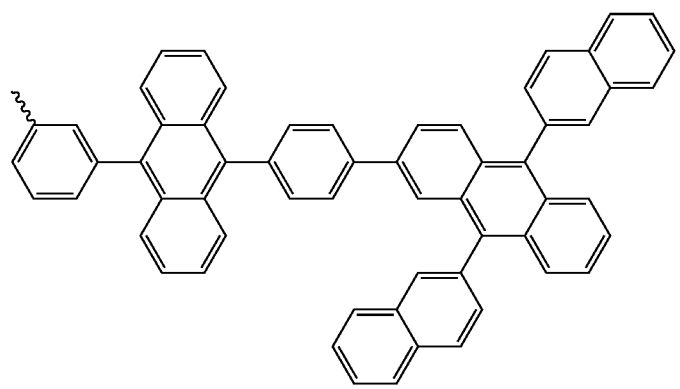 |

TABLE 1-continued
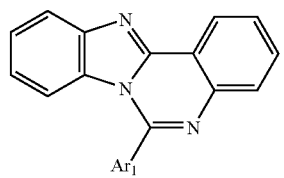
| No. | Ar1 |
|---|---|
| 1-2-60 | 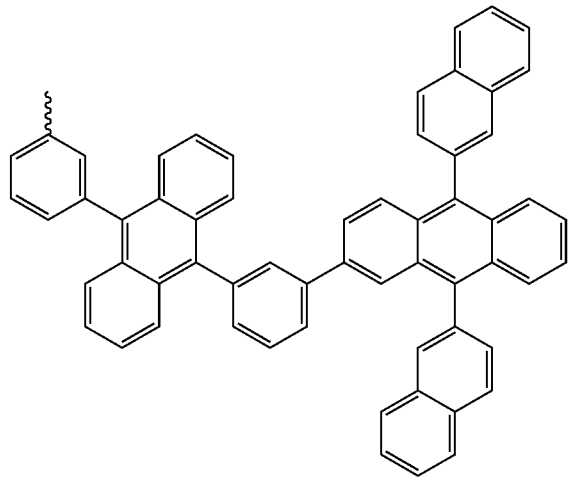 |
| 1-2-61 | 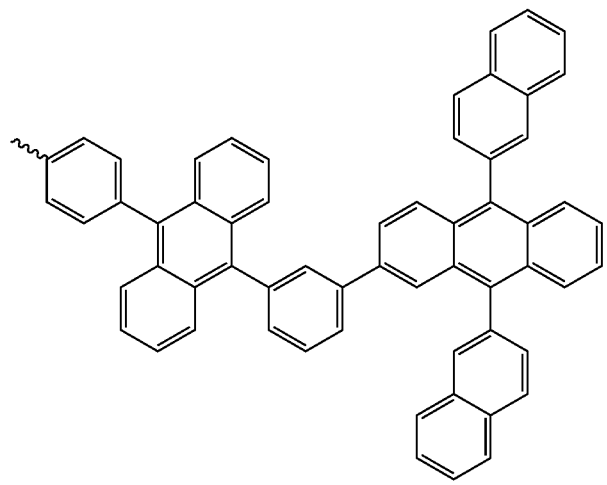 |
| 1-2-62 | 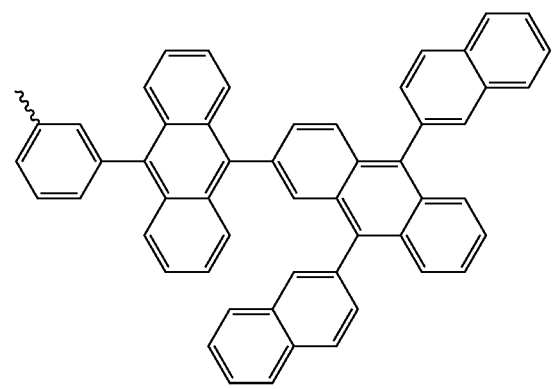 |

TABLE 1-continued
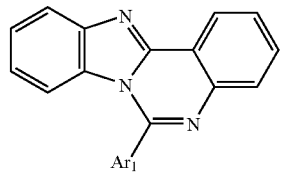
| No. | Ar1 |
| --- | --- |
| 1-2-63 | 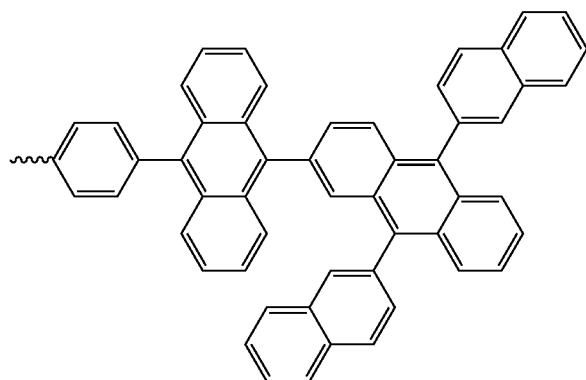 |
| 1-2-64 | 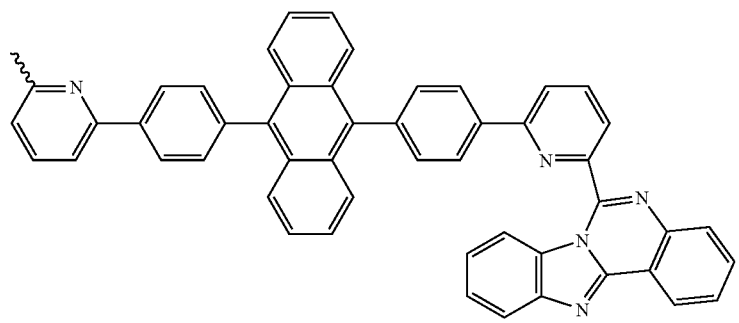 |
| 1-2-65 | 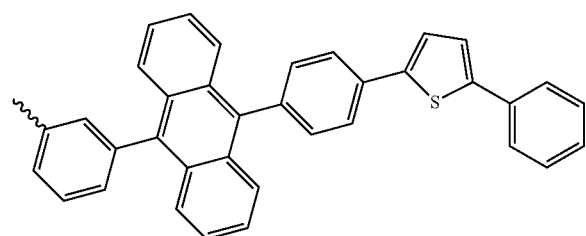 |
| 1-2-66 | 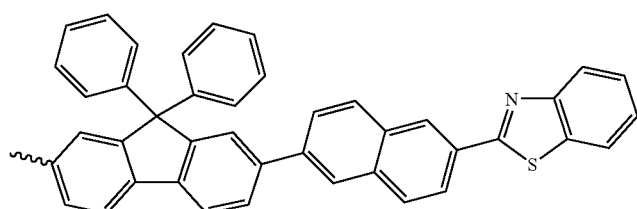 |

TABLE 1-continued
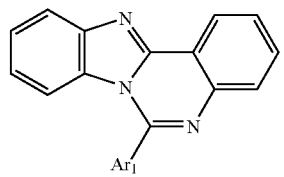
| No. | Ar1 |
|---|---|
| 1-2-67 | 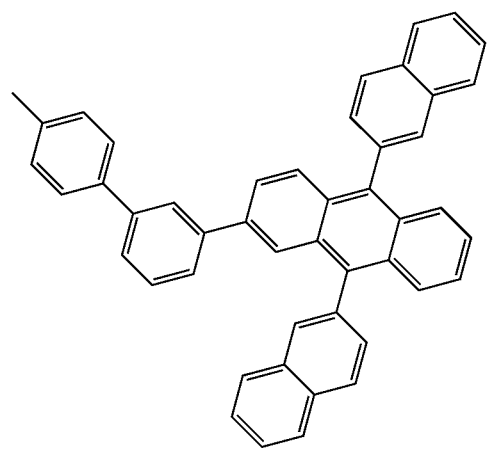 |
| 1-2-68 | 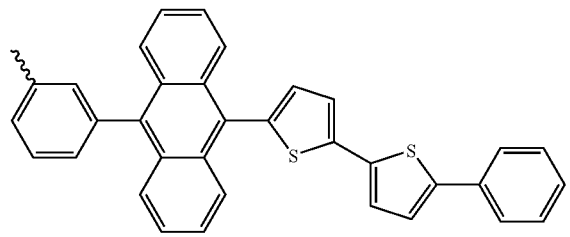 |
| 1-2-69 | 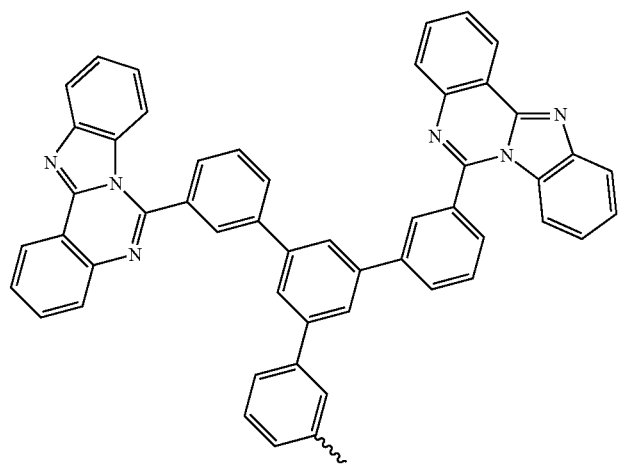 |
| 1-3-1 | 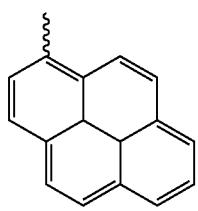 |

TABLE 1-continued
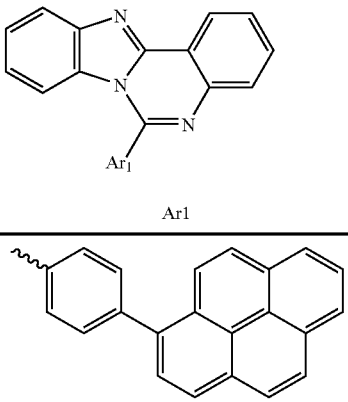
| No. | Ar1 |
| --- | --- |
| 1-3-2 | 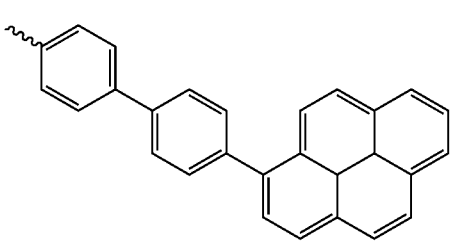 |
| 1-3-3 | 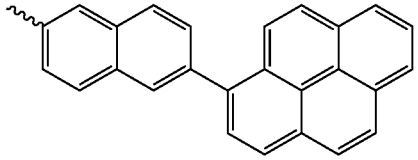 |
| 1-3-4 | 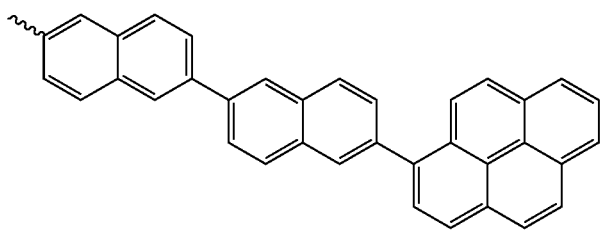 |
| 1-3-5 | 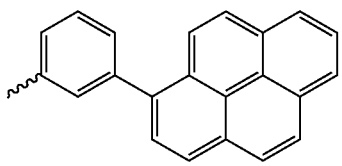 |
| 1-3-6 | 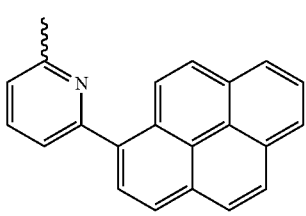 |
| 1-3-7 | 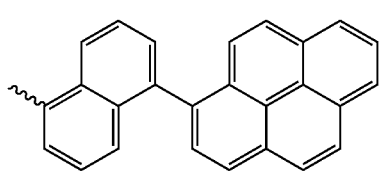 |
| 1-3-8 | |

TABLE 1-continued
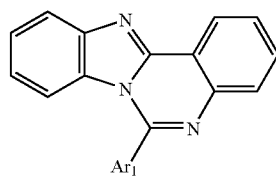
| No. | Ar1 |
|---|---|
| 1-3-9 | 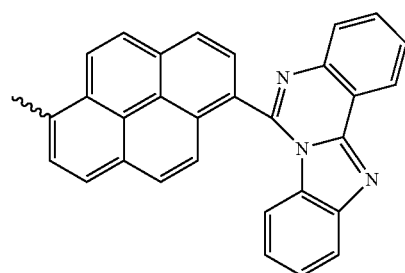 |
| 1-3-10 | 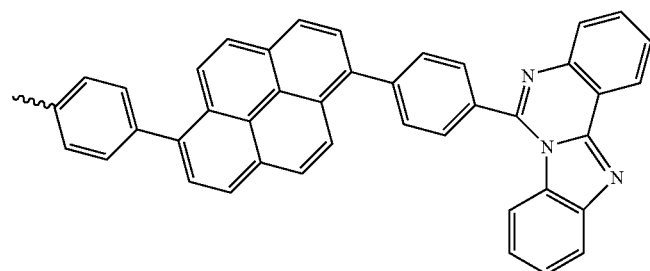 |
| 1-3-11 | 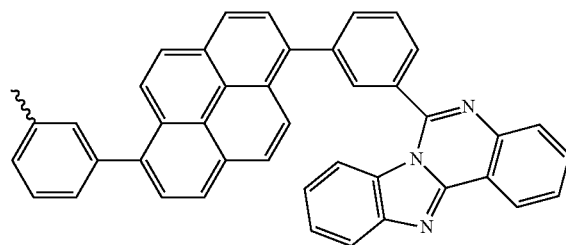 |
| 1-3-12 | 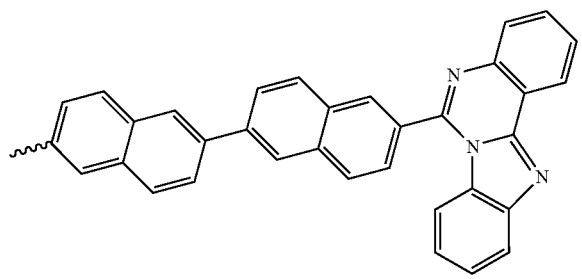 |
| 1-3-13 | 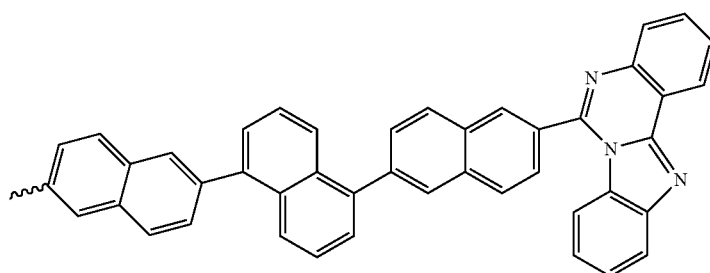 |

TABLE 1-continued

| No. | Ar1 |
|---|---|
| 1-3-14 | |
| 1-3-15 | |
| 1-3-16 | |
| 1-3-17 | |
| 1-3-18 | |

TABLE 1-continued
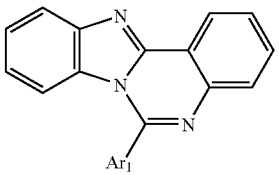
| No. | Ar1 |
|---|---|
| 1-3-19 | 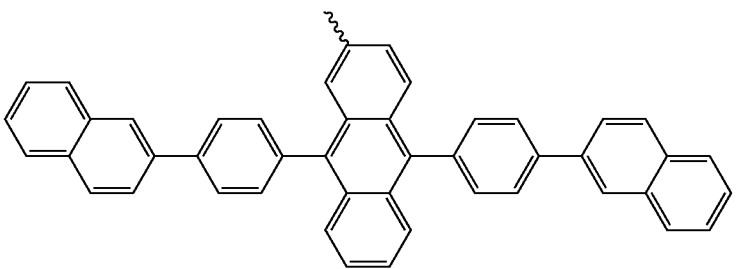 |
| 1-3-20 | 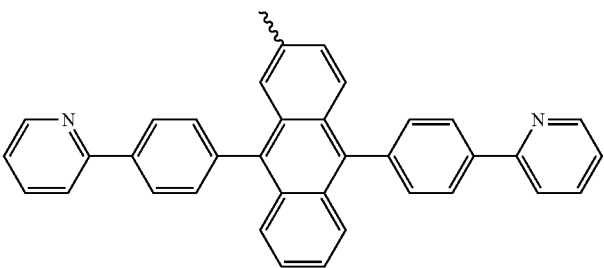 |
| 1-3-21 | 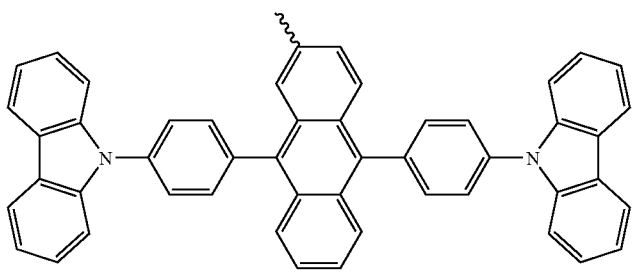 |
| 1-3-22 | 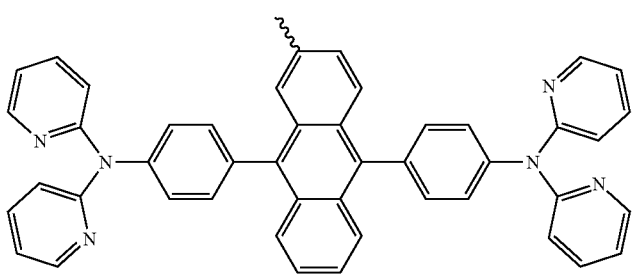 |
| 1-3-23 | 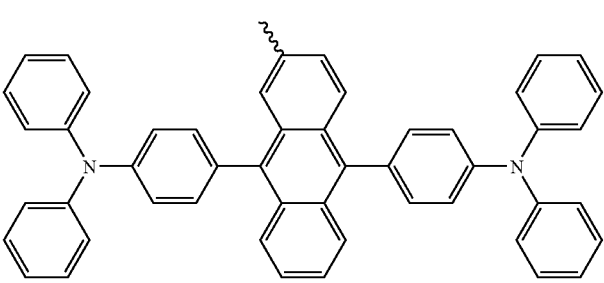 |

TABLE 1-continued
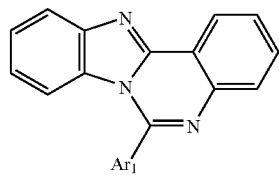
| No. | Ar1 |
|---|---|
| 1-3-24 | 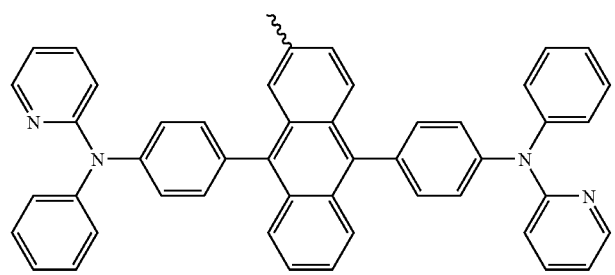 |
| 1-3-25 | 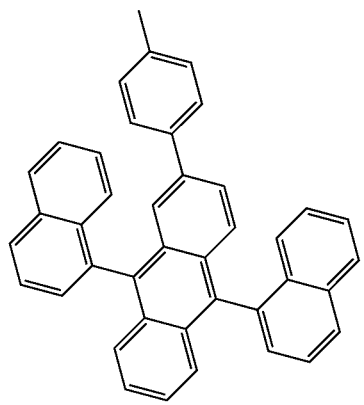 |
| 1-3-26 | 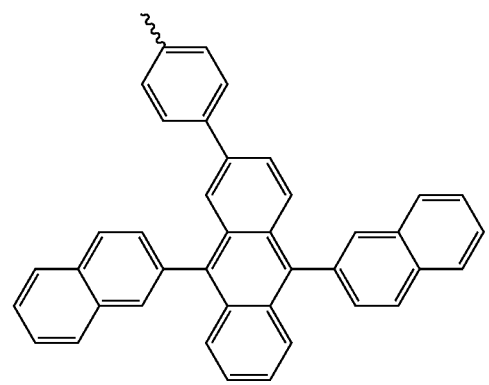 |

TABLE 1-continued
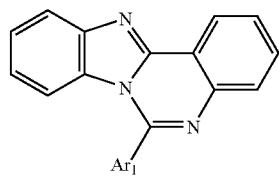
| No. | Ar1 |
|---|---|
1-3-27
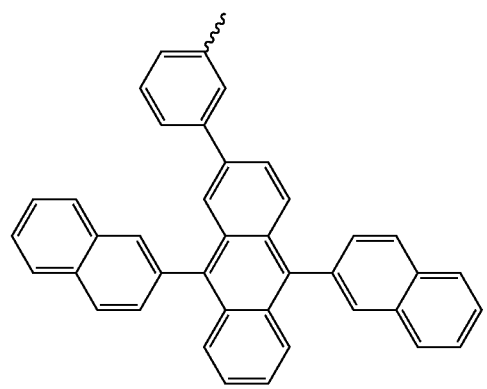
1-3-28
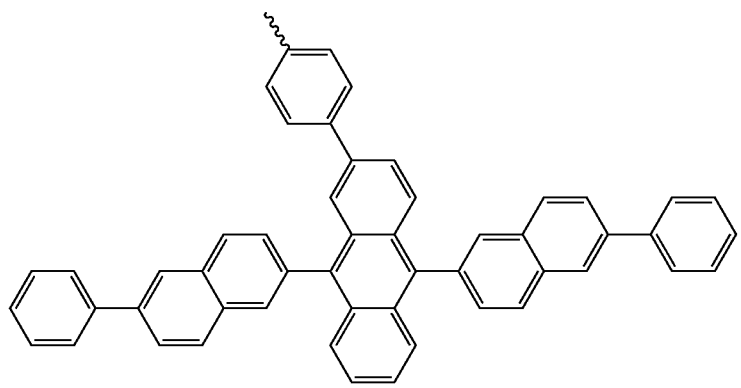
1-3-29
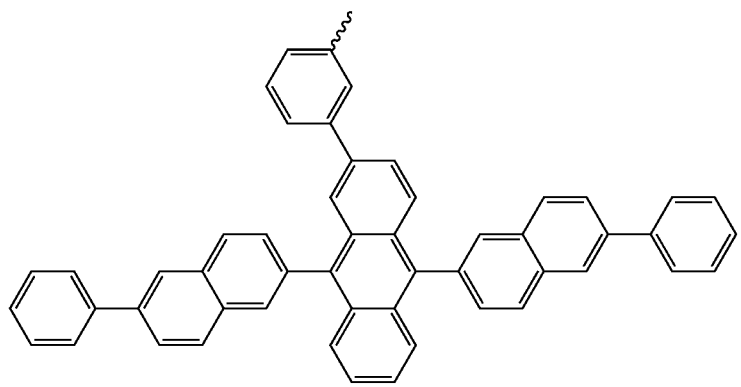

TABLE 1-continued
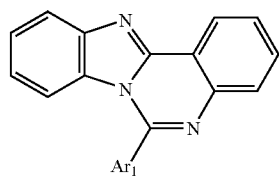
| No. | Ar1 |
|---|---|
| 1-3-30 | 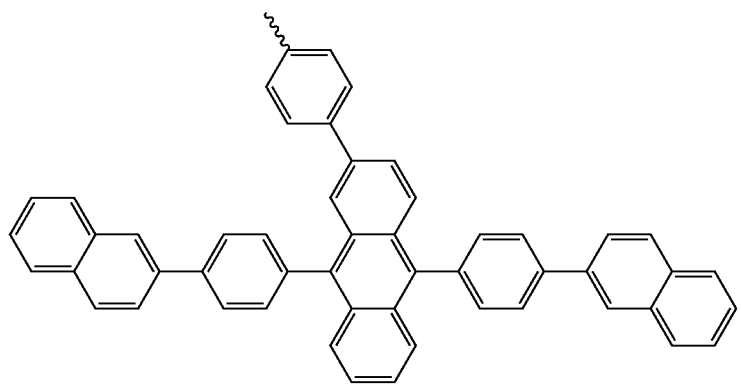 |
| 1-3-31 | 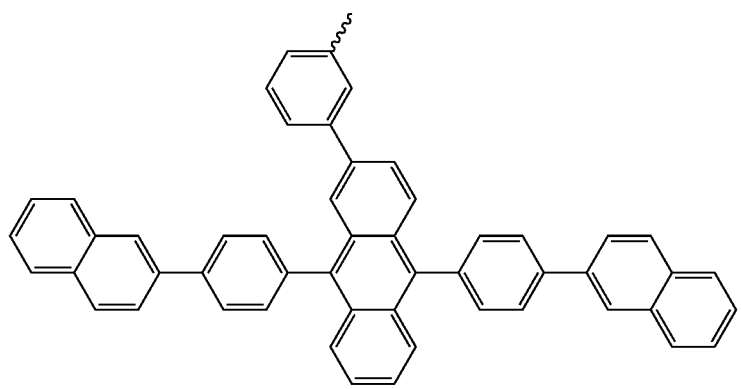 |
| 1-3-32 | 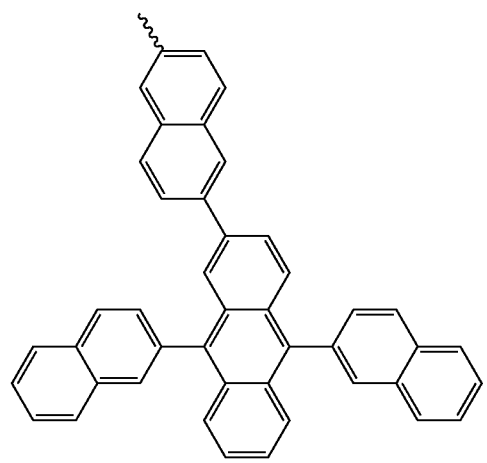 |

TABLE 1-continued
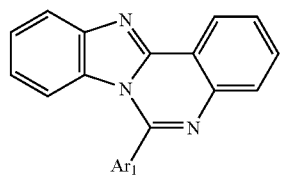
| No. | Ar1 |
|---|---|
| 1-3-33 | 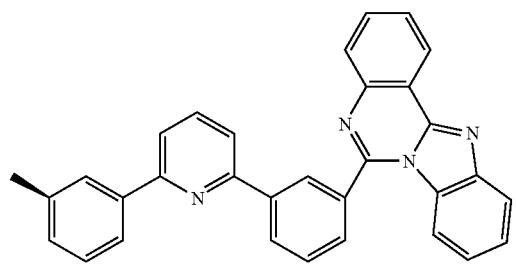 |
| 1-3-34 | 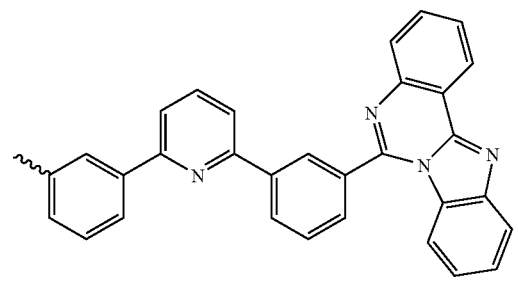 |
| 1-3-35 | 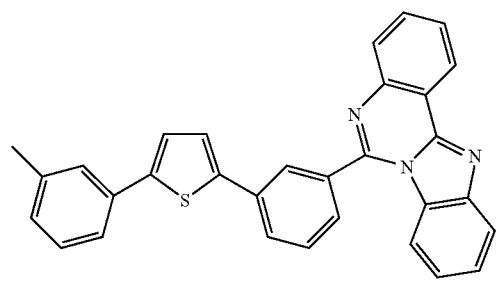 |
| 1-3-36 | |
| 1-3-37 | 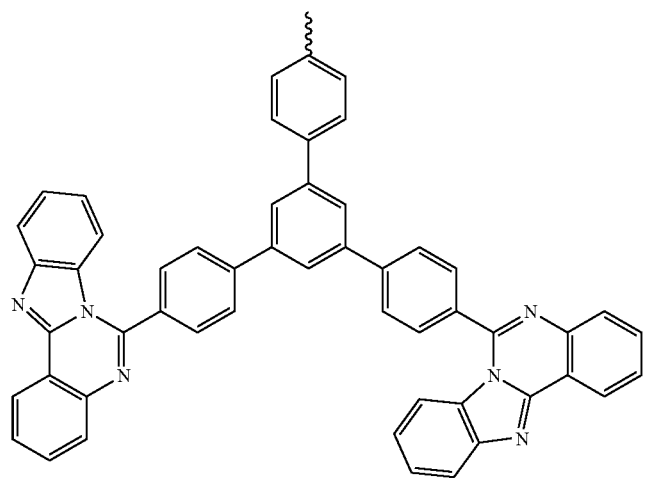 |

TABLE 1-continued

| No. | Ar1 |
|---|---|
| 1-3-38 | |
| 1-3-39 | |
| 1-3-40 | |
| 1-3-41 | |

TABLE 1-continued
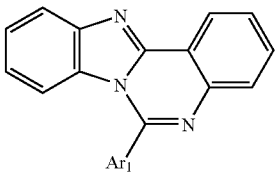
| No. | Ar1 |
|---|---|
| 1-3-42 | 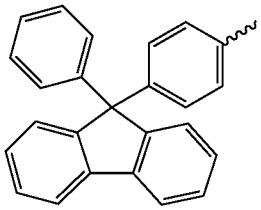 |
| 1-3-43 | 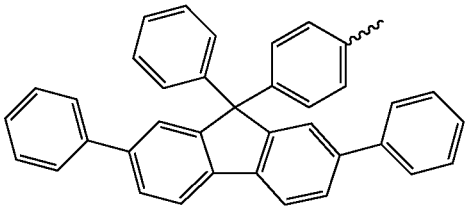 |
| 1-3-44 | 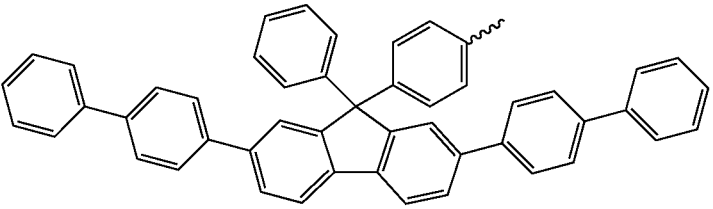 |
| 1-3-45 | 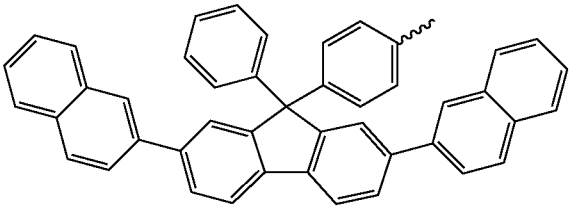 |
| 1-3-46 | 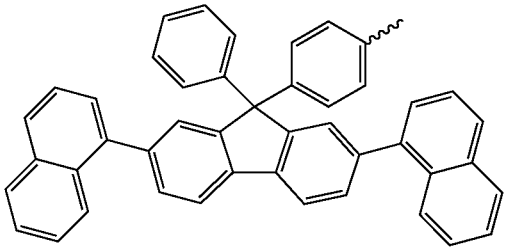 |
| 1-3-47 | 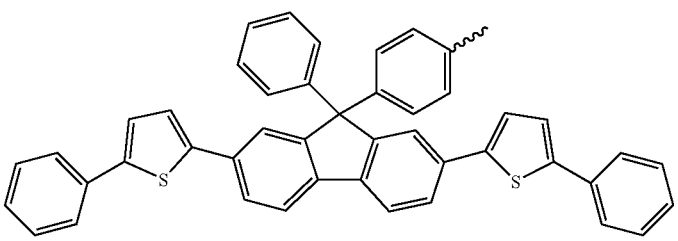 |

TABLE 1-continued

| No. | Ar1 |
|---|---|
| 1-3-48 | |
| 1-3-49 | |
| 1-3-50 | |
| 1-3-51 | |
| 1-3-52 | |
| 1-3-53 | |

TABLE 1-continued
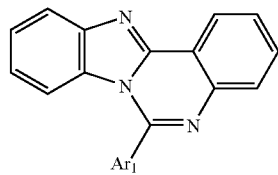
| No. | Ar1 |
|---|---|
| 1-3-54 | 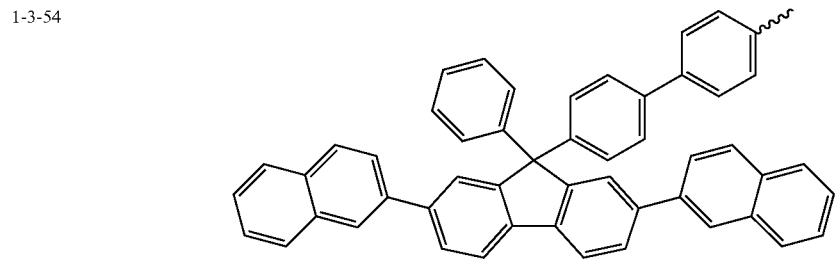 |
| 1-3-55 | 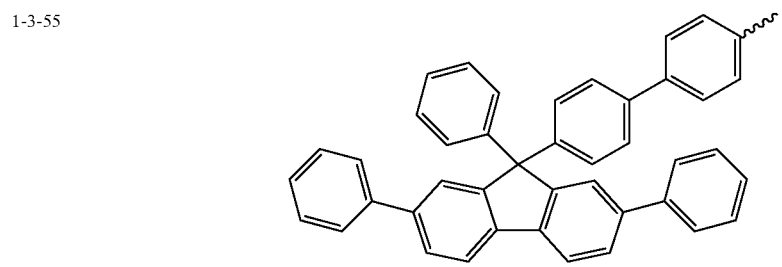 |
| 1-3-56 | 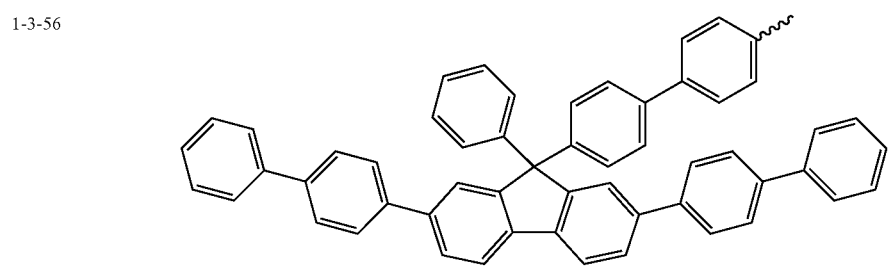 |
| 1-3-57 | 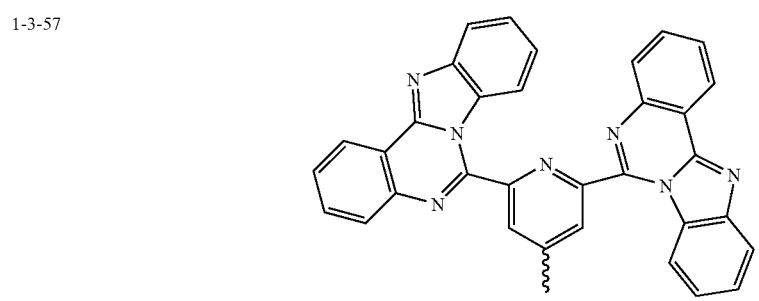 |
| 1-3-58 | 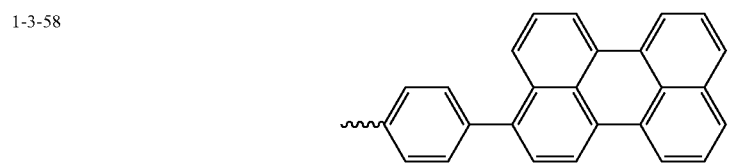 |

TABLE 1-continued
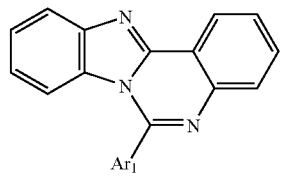
| No. | Ar1 |
|---|---|
| 1-3-59 | 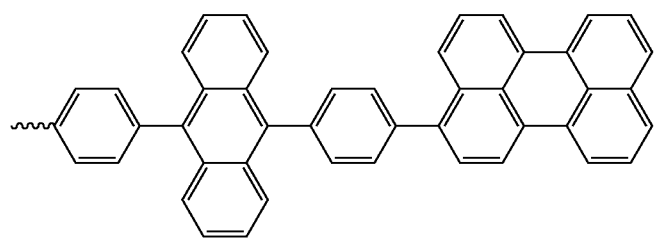 |
| 1-3-60 | 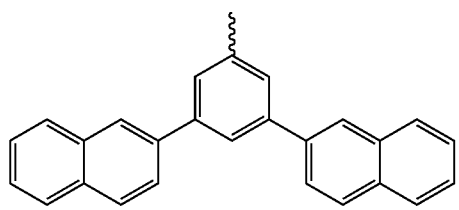 |
| 1-3-61 | 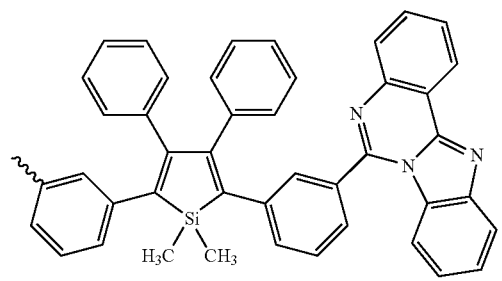 |
| 1-3-62 | 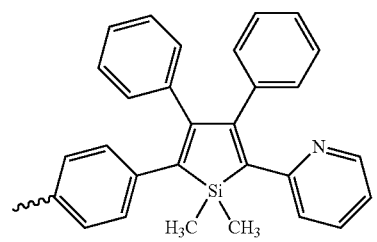 |
| 1-3-63 | 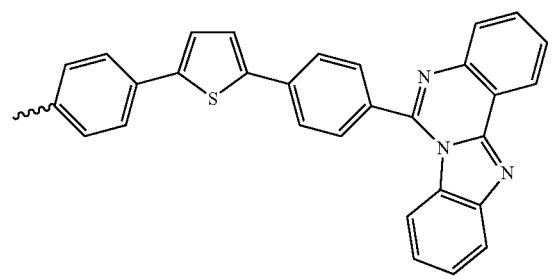 |

TABLE 1-continued
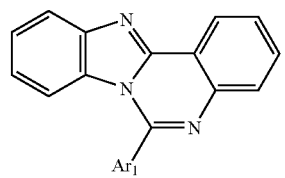
| No. | Ar1 |
|---|---|
| 1-3-64 | 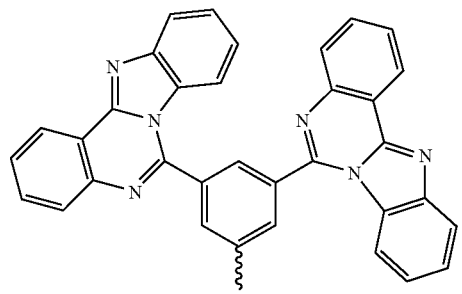 |
| 1-3-65 | 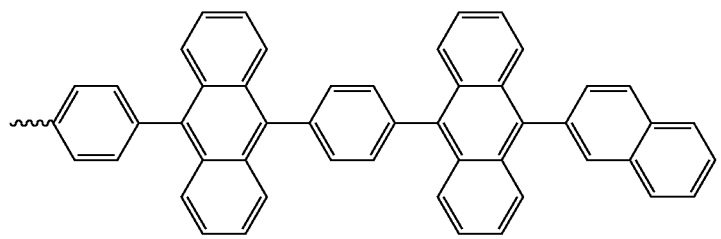 |
| 1-3-66 | 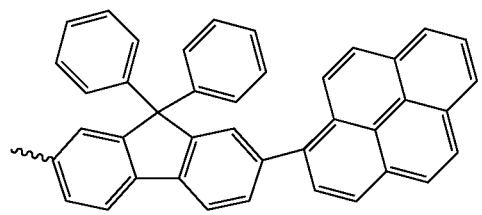 |
| 1-3-67 | 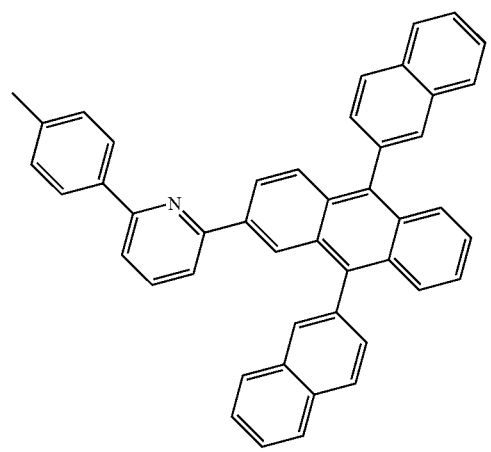 |

TABLE 1-continued
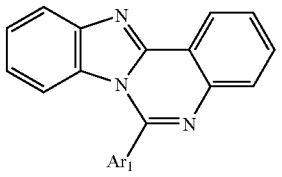
| No. | Ar1 |
|---|---|
| 1-3-68 | 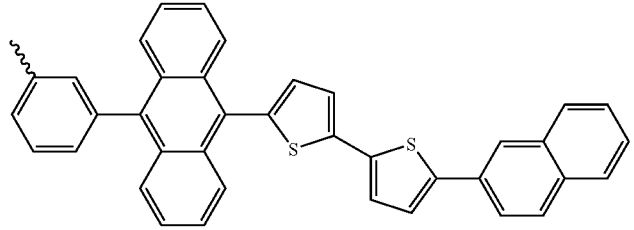 |
| 1-3-69 | 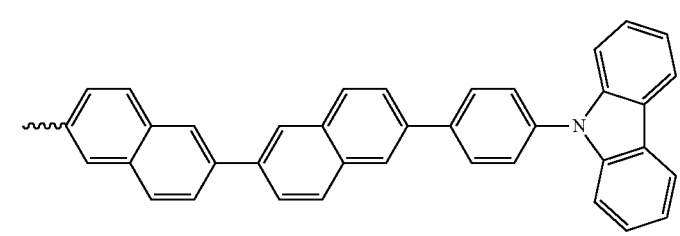 |
7. The imidazoquinazoline derivative according to claim 1, wherein the compound of the formula 1 is selected from the group consisting of
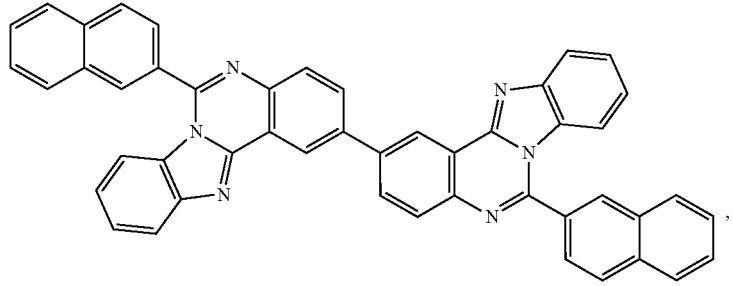
[compound 1-4-1]
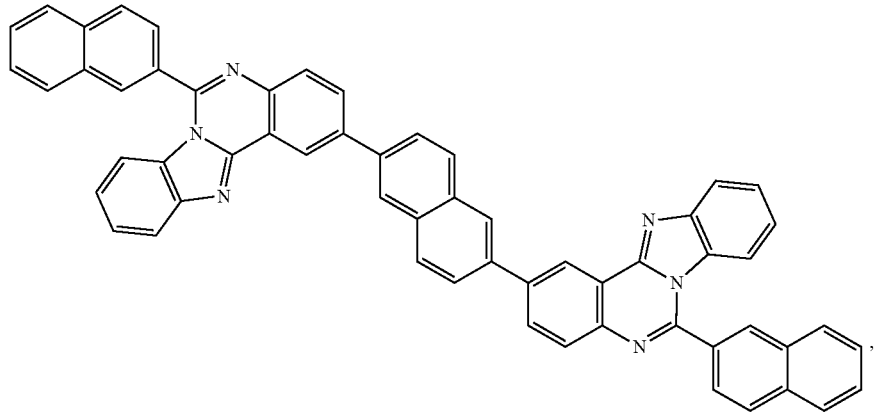
[compound 1-4-2]

[compound 1-4-3]
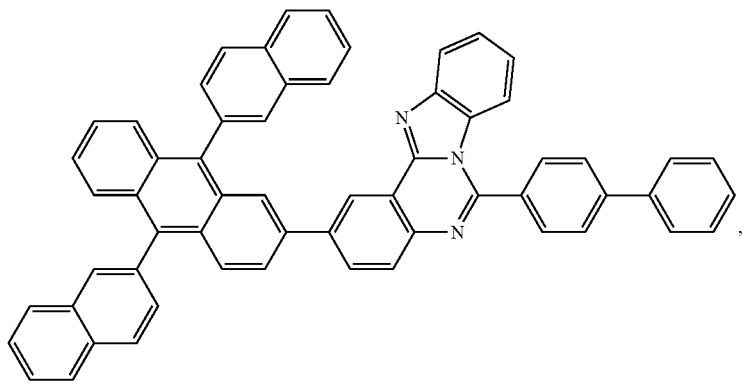
[compound 1-4-4]
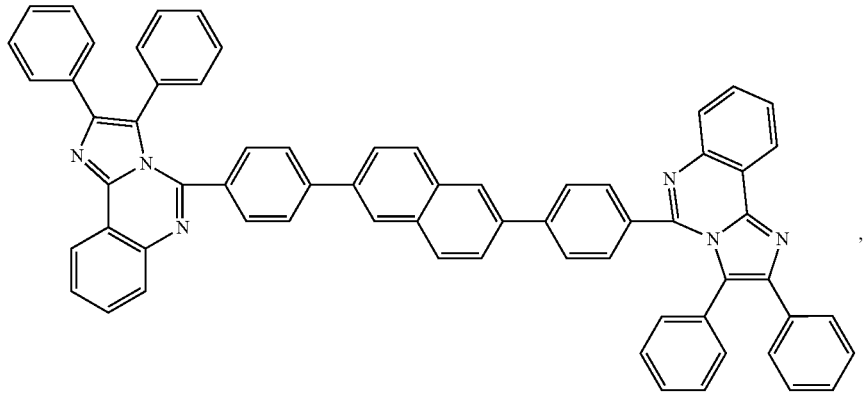
[compound 1-4-5]
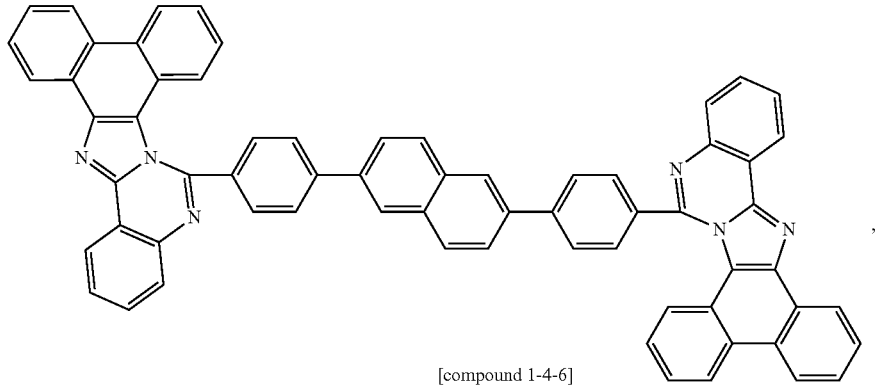
[compound 1-4-6]
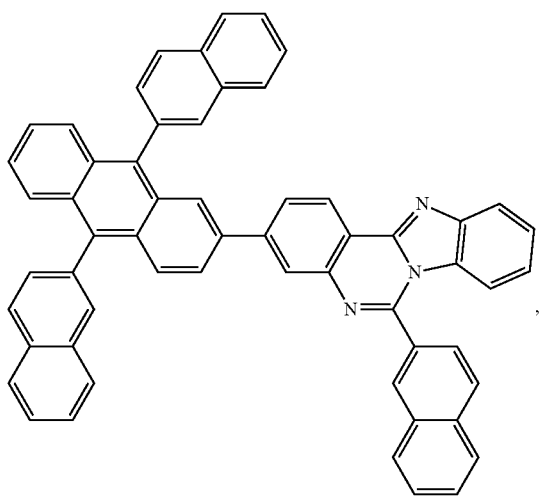
[compouond 1-4-7]
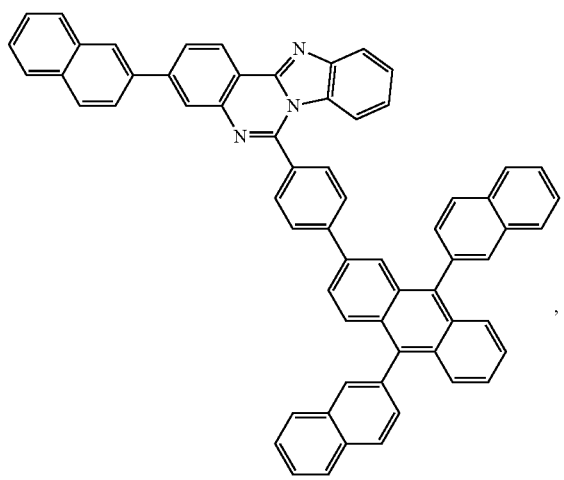

[compound 1-4-8]
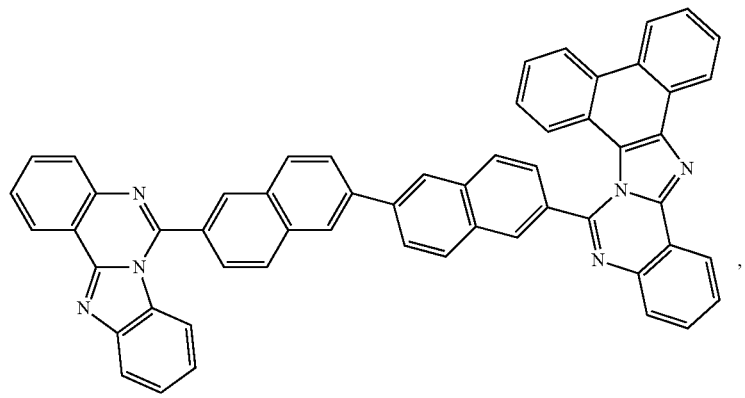
[compound 1-4-9]
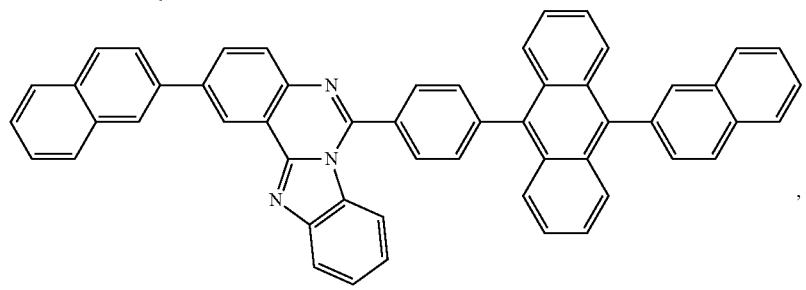
[compound 1-4-10]
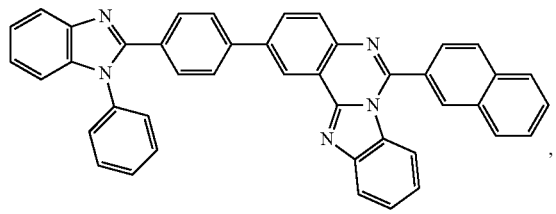
[compound 1-4-11]
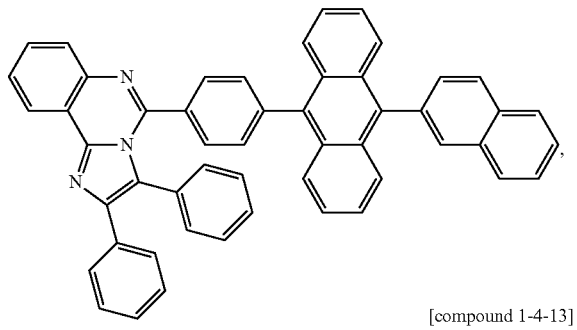
[compound 1-4-12]
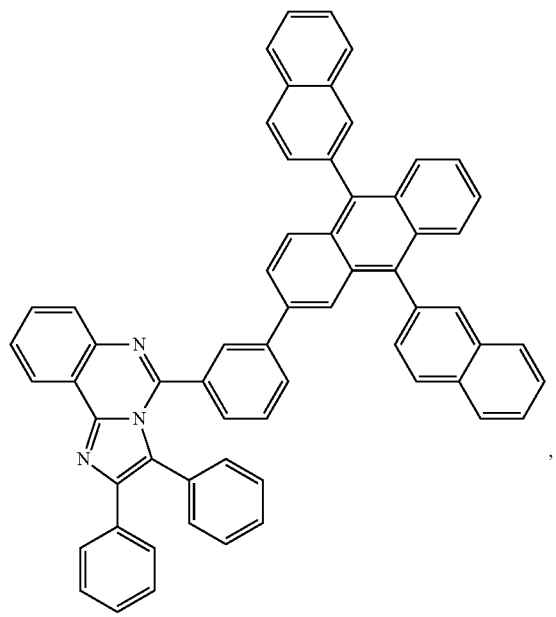
[compound 1-4-13]
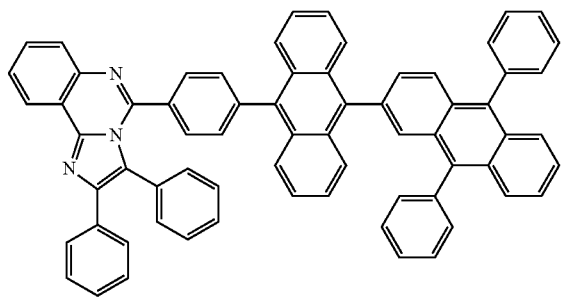

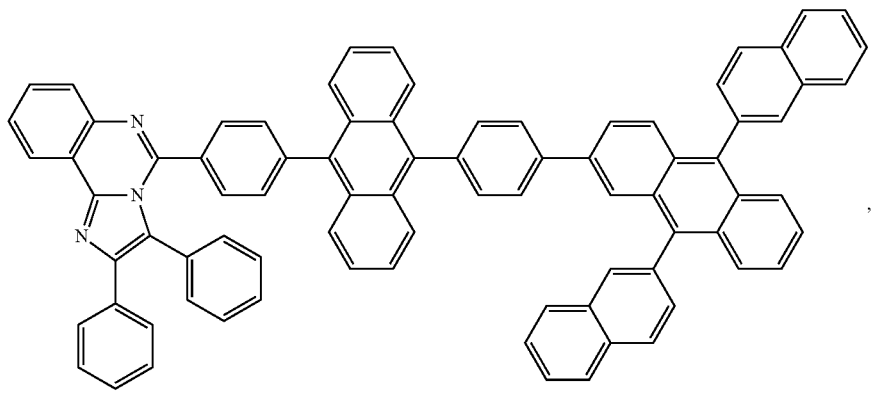
[compound 1-4-14]
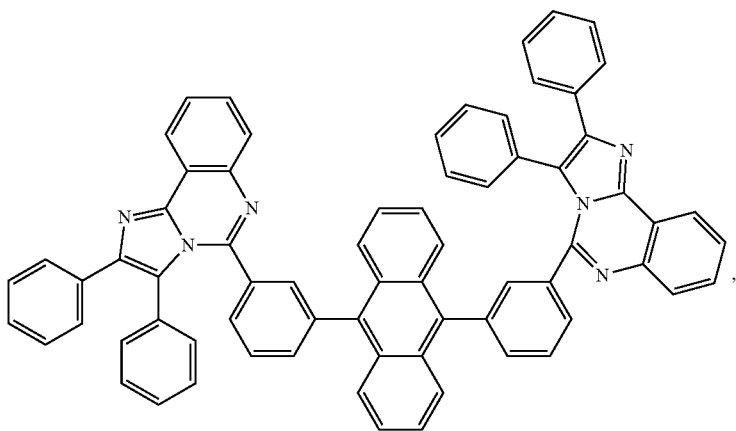
[compound 1-4-15]
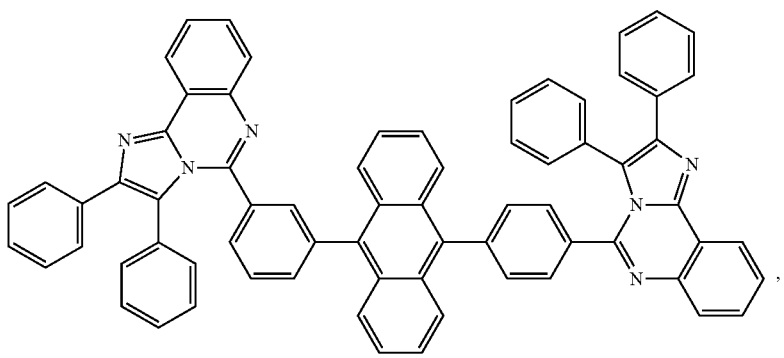
[compound 1-4-16]

[compound 1-4-17]
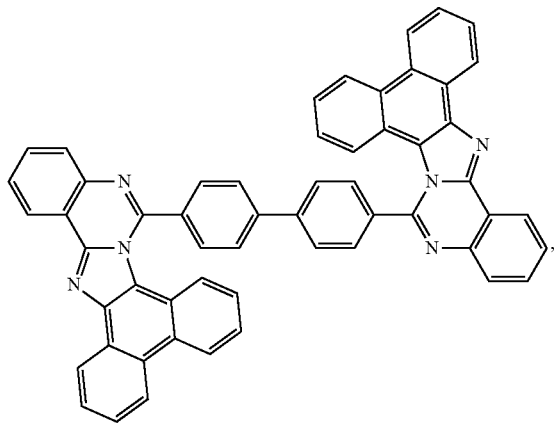
[compound 1-4-18]
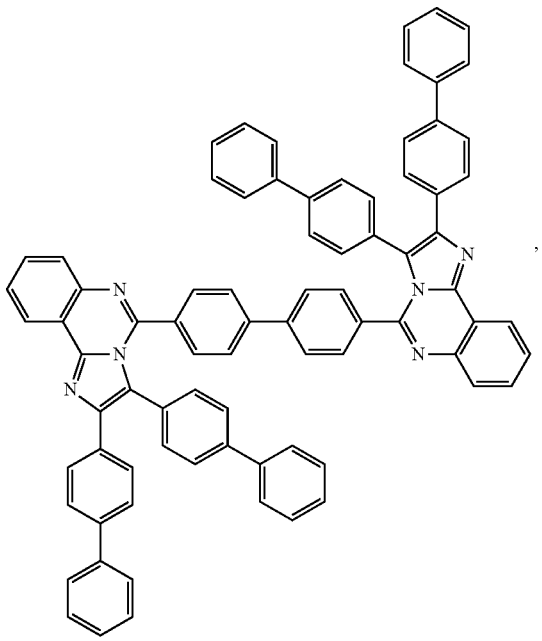
[compound 1-4-19]
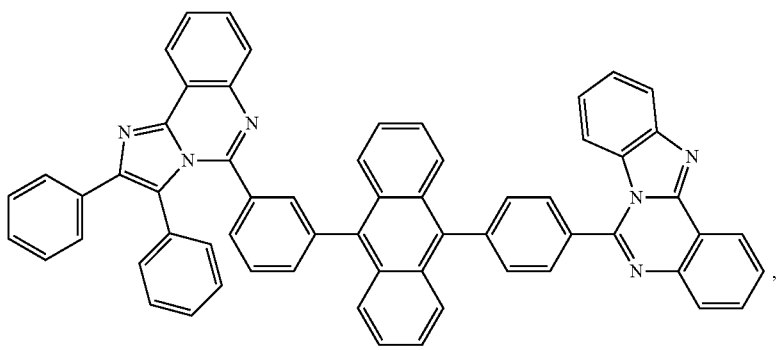
[compound 1-4-20]
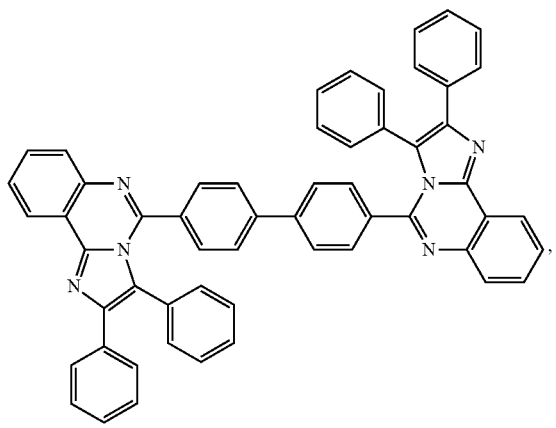
[compound 1-4-21]
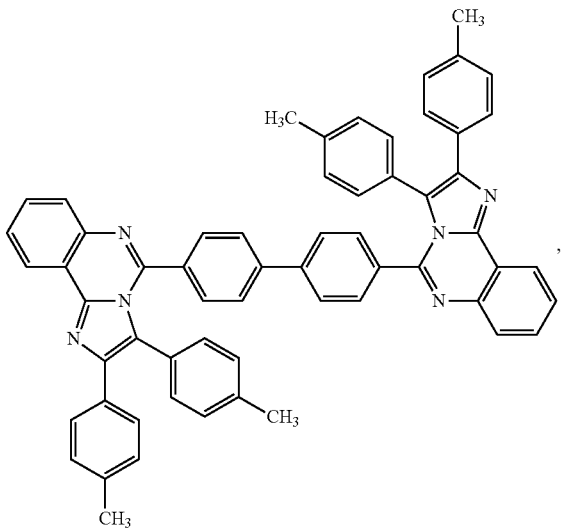

[compound 1-4-22]
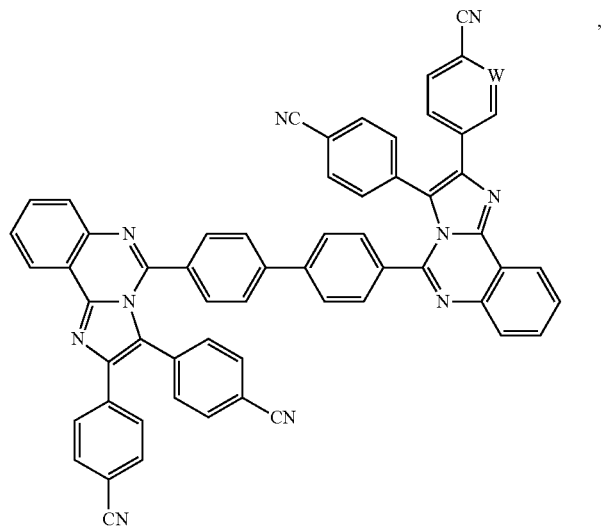
[compound 1-4-24]
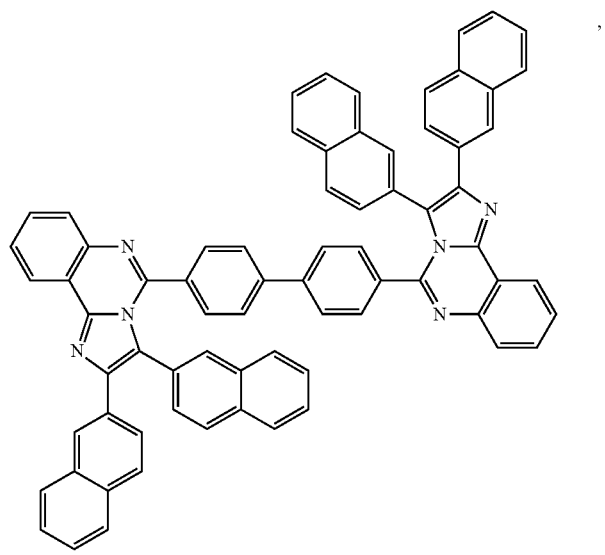
[compound 1-4-29]
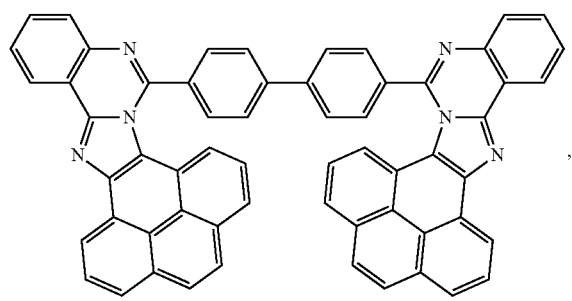

[compound 1-4-28]
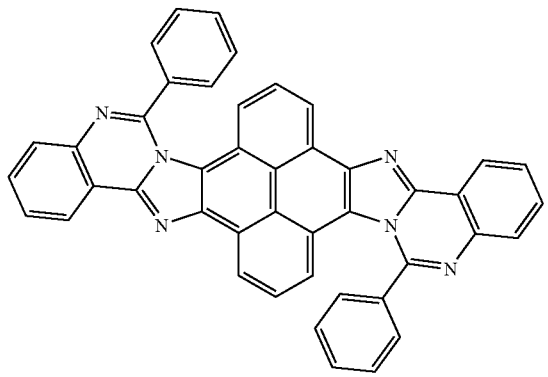
[compound 1-4-29]
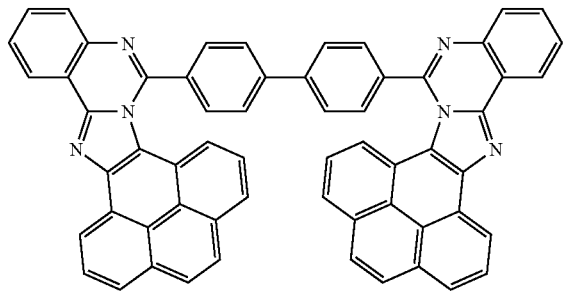
[compound 1-4-31]
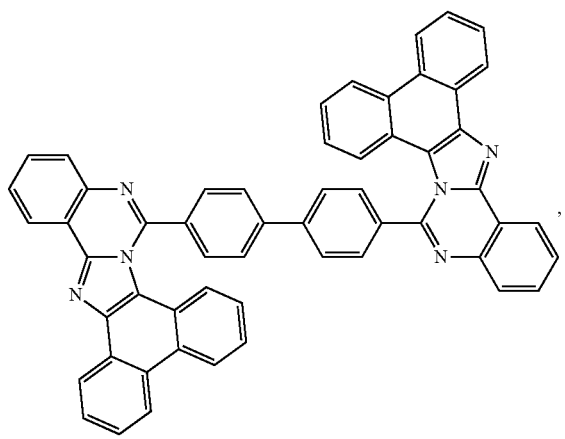
[compound 1-4-32]
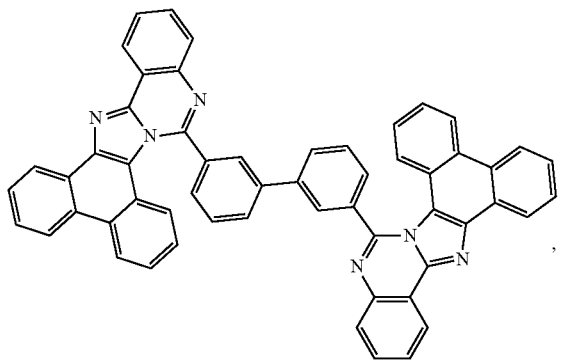
[compound 1-4-33]
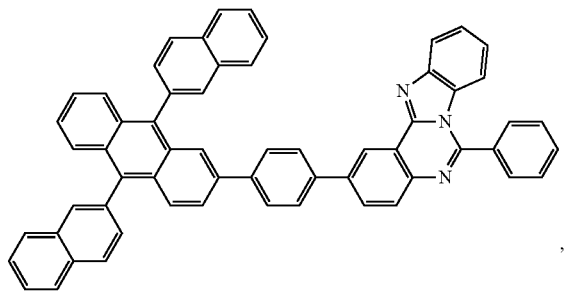
[compound 1-4-34]
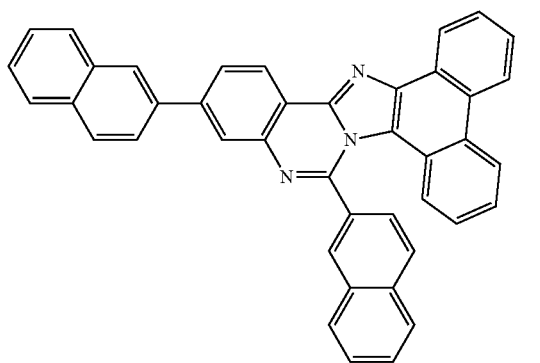
[compound 1-4-35]
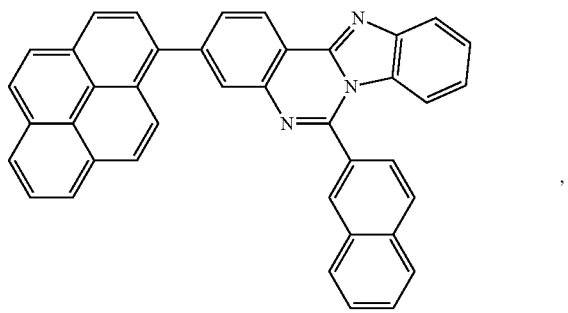

-continued
[compound 1-4-36]
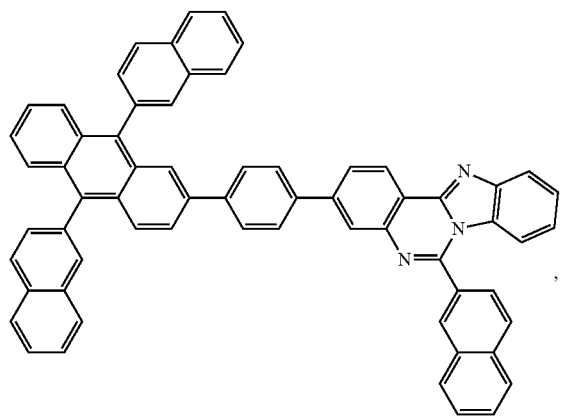
[compound 1-4-37]
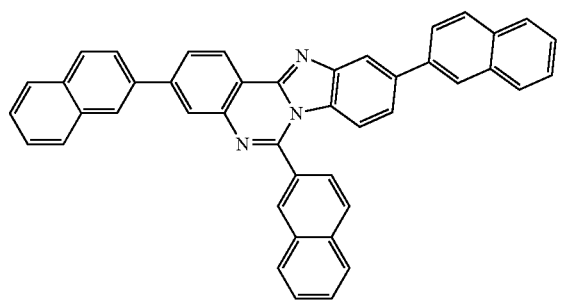
[compound 1-4-38]
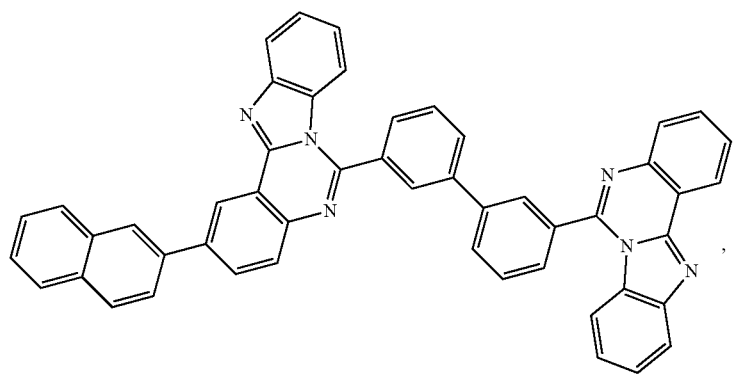
[compound 1-4-39]
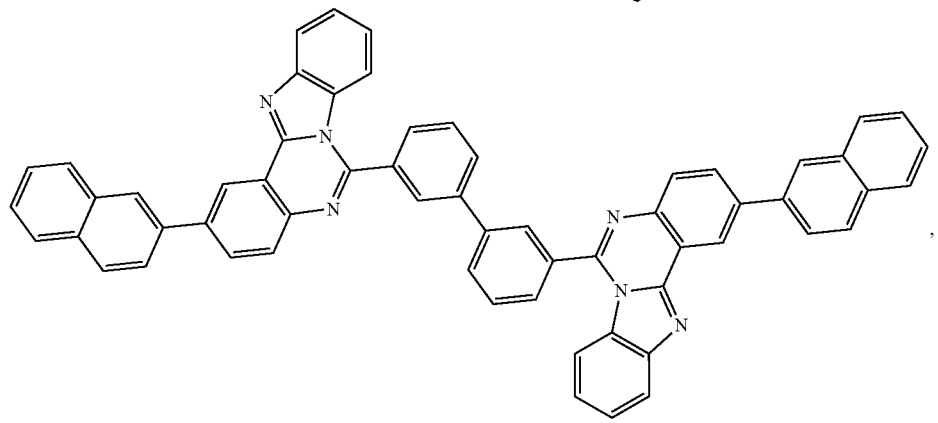
[compound 1-4-40]
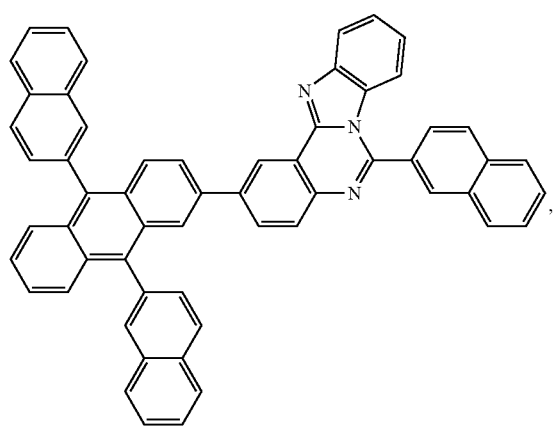
[compound 1-4-41]
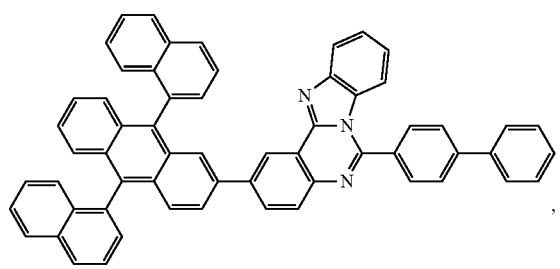

[compound 1-4-42]
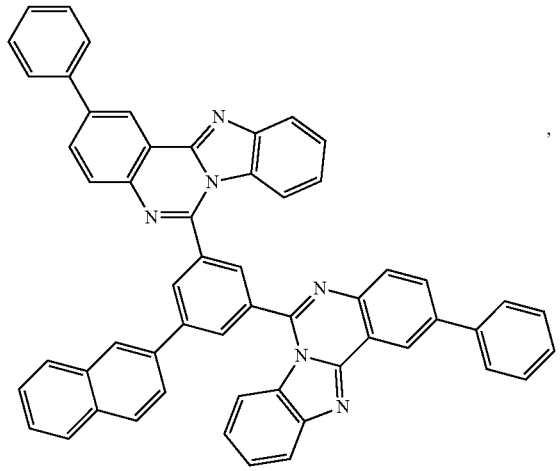
[compound 1-4-43]
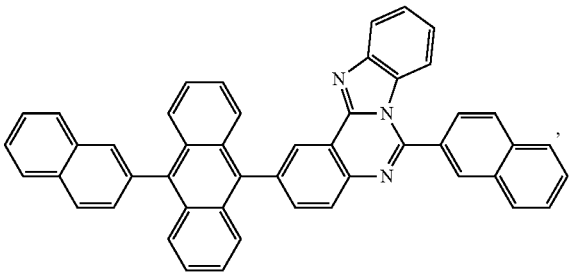
[compound 1-4-44]
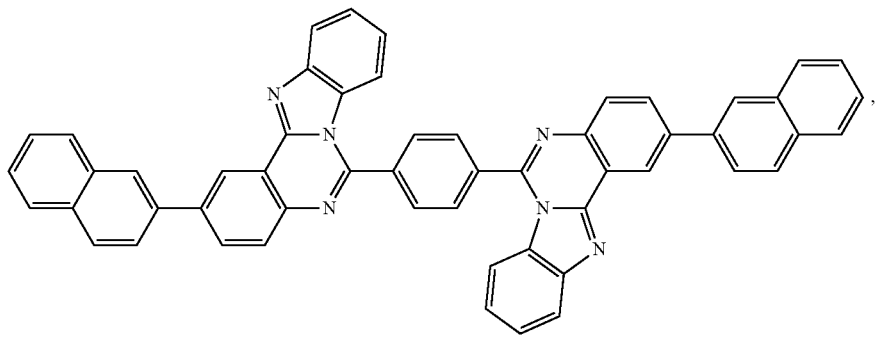
[compound 1-4-45]
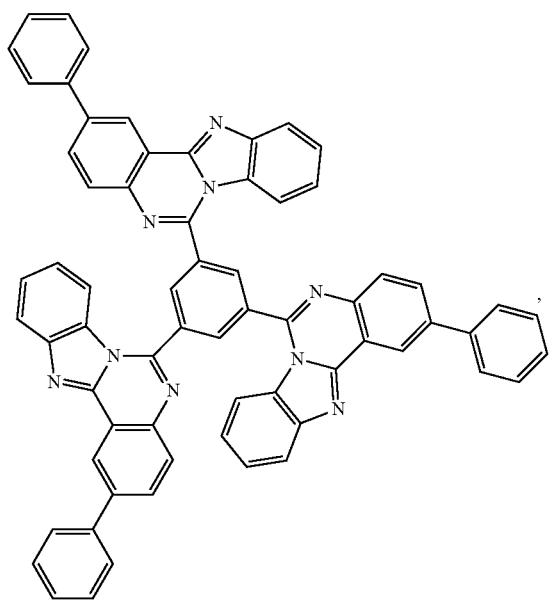
[compound A]
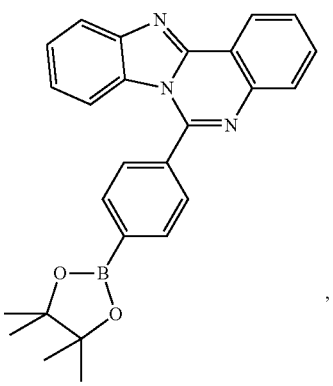

-continued

[compound B]

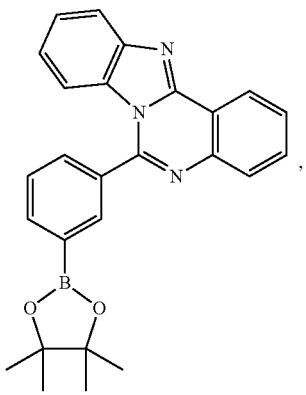

[compound D]

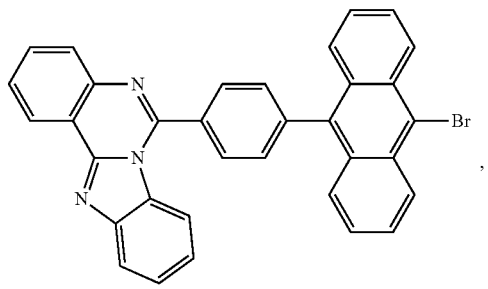

[compound E]

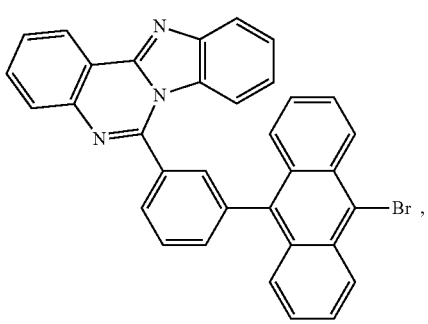

[compound M-1]

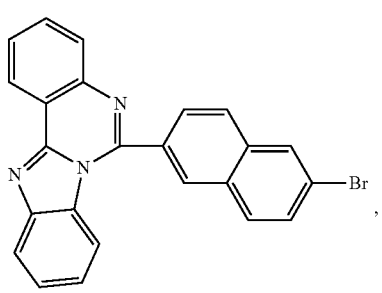

[compound M]

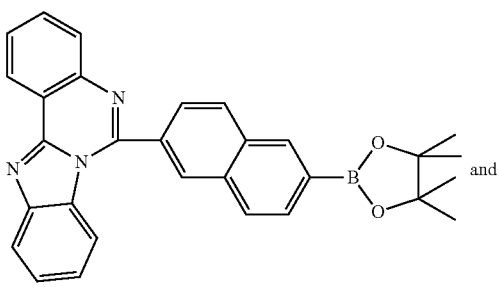

[compound F]

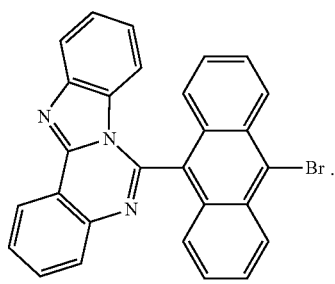

and

8. A process for preparing the imidazoquinazoline derivative according to claim 1, comprising the steps of:

1) reacting a 2-nitrobenzaldehyde compound (II) and a 1,2-diketone compound (III) with an ammonium acetate salt or formamide to prepare a 2-(2-nitrophenyl)imidazole derivative (IV), 2) subjecting the 2-(2-nitrophenyl)imidazole derivative (IV) as prepared in the step 1) to reaction using a palladium catalyst to prepare a 2-(2-aminophenyl)imidazole derivative (V), and 3) reacting 2-(2-aminophenyl)imidazole derivative (V) as prepared in the step 2) with an aldehyde compound (Ar1CHO) to prepare a compound (I), the process being represented by the following reaction scheme 1:

[Reaction Scheme 1]

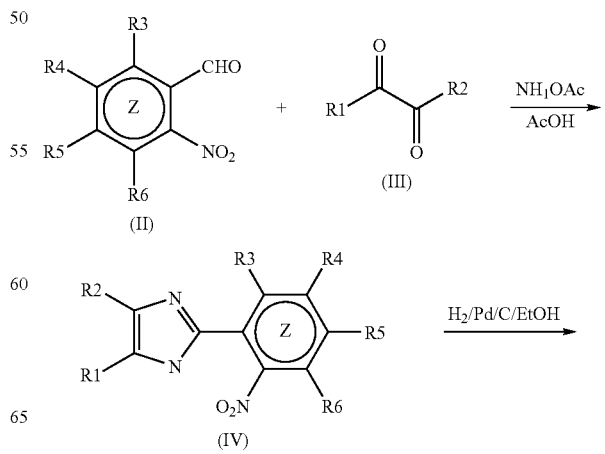

-continued

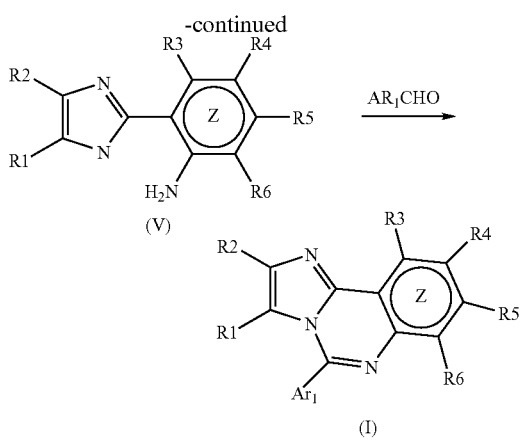

wherein R1 to R6, Ar1, and Z are each as defined in the formula 1.

9. A process for preparing the imidazoquinazoline derivative according to claim 1, comprising the step of heating a 2-(2-aminophenyl)benzimidazole compound (VI) and an aldehyde compound (Ar1CHO) under stirring in an organic solvent to prepare a compound (I-1), the process being represented by the following reaction scheme 2:

[Reaction Scheme 2]

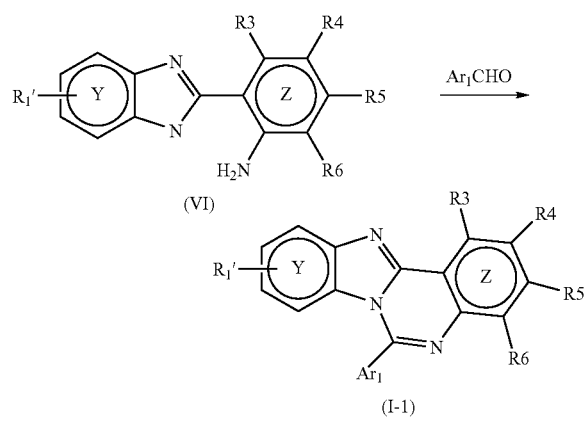

wherein R3 to R6, Ar1, and Z are each as defined in the formula 1, and $R_{1\_}$ is also as defined for R1 in the formula 1.

10. An organic electronic device comprising a first electrode, a second electrode, and one or more organic material layers interposed therebetween, wherein at least one layer of the one or more organic material layers comprises the compound according to any one of claims 1 to 5.

11. An organic electronic device comprising a first electrode, a second electrode, and one or more organic material layers interposed therebetween, wherein the one or more organic material layers comprise a hole injecting layer and a hole transporting layer, wherein at least the hole injecting layer and the hole transporting layer comprise the compound according to any one of claims 1 to 5.

12. An organic electronic device comprising a first electrode, a second electrode, and one or more organic material layers interposed therebetween, wherein the one or more organic material layers comprise at least a light emitting layer, wherein the light emitting layer comprises the compound according to any one of claims 1 to 5.

13. An organic electronic device comprising a first electrode, a second electrode, and one or more organic material layers interposed therebetween, wherein the one or more organic material layers comprise an electron transporting layer, wherein the electron transporting layer comprises the compound according to any one of claims 1 to 5.

14. The organic electronic device according to claim 10, wherein the organic electronic device is selected from the group consisting of an organic light emitting device, an organic photovoltaic cell, an organic photo conductor (OPC) and an organic transistor.

* * * * *